(12) United States Patent
Jaffrey et al.

(10) Patent No.: US 9,664,676 B2
(45) Date of Patent: May 30, 2017

(54) RNA SEQUENCES THAT INDUCE FLUORESCENCE OF SMALL MOLECULE FLUOROPHORES

(71) Applicant: Cornell University, Ithaca, NY (US)

(72) Inventors: Samie R. Jaffrey, New York, NY (US); Rita L. Strack, Jersey City, NJ (US); Grigory Filonov, New York, NY (US); Wenjiao Song, Poughkeepsie, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/480,130

(22) Filed: Sep. 8, 2014

(65) Prior Publication Data
US 2015/0141282 A1 May 21, 2015

Related U.S. Application Data

(60) Provisional application No. 61/874,819, filed on Sep. 6, 2013.

(51) Int. Cl.
*C12N 15/11* (2006.01)
*G01N 33/53* (2006.01)
*C12N 15/115* (2010.01)

(52) U.S. Cl.
CPC ....... *G01N 33/5308* (2013.01); *C12N 15/115* (2013.01); *C12N 2310/16* (2013.01); *C12N 2310/51* (2013.01); *C12N 2320/10* (2013.01)

(58) Field of Classification Search
CPC .................. C12N 15/115; G01N 33/5308
See application file for complete search history.

(56) References Cited

U.S. PATENT DOCUMENTS

| 6,458,559 B1 | 10/2002 | Shi et al. |
| 6,766,183 B2 | 7/2004 | Walsh et al. |
| 7,125,660 B2 | 10/2006 | Stanton et al. |
| 2002/0111358 A1 | 8/2002 | Nishiyama et al. |
| 2003/0211516 A1 | 11/2003 | Davis |
| 2004/0138227 A1 | 7/2004 | Nishiyama et al. |
| 2006/0172320 A1 | 8/2006 | Stojanovic |
| 2011/0189663 A1* | 8/2011 | Cotterchio ........... C12Q 1/6886 435/6.11 |
| 2012/0252699 A1 | 10/2012 | Jaffrey et al. |
| 2014/0220560 A1 | 8/2014 | Jaffrey et al. |

FOREIGN PATENT DOCUMENTS

| EP | 0422900 A2 | 10/1990 |
| FR | 2919608 A1 | 1/2007 |
| JP | 2006-178325 | 7/2006 |
| WO | 2007147159 A2 | 12/2007 |
| WO | 2010096584 A1 | 8/2010 |
| WO | 2013016694 A1 | 1/2013 |

OTHER PUBLICATIONS

Szent-Gyorgyi et al., "Fluorogen-Activating Single-Chain Antibodies for Imaging Cell Surface Proteins," Nat. Biotechnol. 26(2):235-240 (2008).
Babendure et al., "Aptamers Switch on Fluorescence of Triphenylmethane Dyes," J. Am. Chem. Soc. 14716-14717 (2003).
Pakhomov et al., "GFP Family: Structural Insights into Spectral Tuning," Chem. Biol. Rev. 755-764 (2008).
Bellobono et al., "Kinetics of Base-Catalysed Condensation of 5-Methylfuran-2(3H)-one with 2-Hydroxybenzaldehyed," J. Chem. Soc. Perkin Trans. Phys. Org. Chem. 15:1773-1776 (1975).
Bourotte et al., "Fluorophores Related to the Green Fluorescent Protein," Tetrahedron Lett. 45:6343-6348 (2004).
Supplementary Search Report and Written Opinion for EP Patent Application No. 10744308.7 (mailed Dec. 5, 2012).
Yarmoluk et al., "Interaction of Cyanine Dyes with Nucleic Acids—XXVII: Synthesis and Spectral Properties of Novel Homodi- and Homotrimeric Monomethine Cyanine Dyes," Dyes and Pigments 50:21-28 (2001).
Dong et al., "Isomerization in Fluorescent Protein Chromophores Involves Addition/Elimination," J. Am. Chem. Soc. 130:14096-14098 (2008).
Lotfy Aly et al., "Intercalating Nucleic Acids with Insertion of 5-[(Pyren-1-yl)methylidene]hydantoin-Substituted Butane-1,2-diol," Helvetica Chimica Acta 88:3137-3144 (2005).
Narang et al., "CXXXV.—Studies in Chemotherapy (Antimalarials). Part I. A Derivative of Glyoxalinoquinoline," J. Chem. Soc. p. 976 (Jan. 1, 1931).
Petersen et al., "Synthesis and Characterization of Model Compounds for the Neutral Green Fluorescent Protein Chromophore," Synthesis 23:3635-3638 (2007).
Socher et al., "FIT Probes: Peptide Nucleic Acid Probes with a Fluorescent Base Surrogate Enable Real-Time DNA Quantification and Single Nucleotide Polymorphism Discovery," Analyt. Biochem. 375:318-330 (2008).
Stafforst et al., "Synthesis of Alaninyl and N-(2-Aminoethyl)glycinyl Amino Acid Derivatives Containing the Green Fluorescent Protein Chromophore in their Side Chains for Incorporation into Peptides and Peptide Nucleic Acids," Eur. J. Org. Chem. 899-911 (2007).
Ajmera et al. "CNS-Depressant and Anticonvulsant Activities of 1-Substituted Phenyl (Aryl)-2-Methyl-4 (3,4,5, Trimethoxybenzylidene)-5-Imidazolones," Drugs Expt Clin Res 6(3):171-176 (1980).
Nichols et al. "Serotoin Receptors," Chem Rev 108:1614-1641 (2008).
He et al. "Synthesis and Spectroscopic Studies of Model Red Fluorescent Protein Chromophores," Organic Letters 4(9):1523-1526 (2002).

(Continued)

*Primary Examiner* — Brian Whiteman
(74) *Attorney, Agent, or Firm* — LeClairRyan, a Professional Corporation

(57) ABSTRACT

The present invention relates to novel nucleic acid molecules, called aptamers, that bind specifically to a small molecule fluorophore and thereby enhance the fluorescence signal of the fluorophore upon exposure to radiation of suitable wavelength. Molecular complexes formed between the novel fluorophores, novel nucleic acid molecules, and their target molecules are described, and the use of multivalent aptamer constructs as fluorescent sensors for target molecules of interest are also described.

16 Claims, 32 Drawing Sheets

(56) References Cited

OTHER PUBLICATIONS

You et al. "Fluorophores Related to the Green Fluorescent Protein and Their Use in Optoelectronic Devices," Advanced Materials 12(22):1678-1681 (2000).
Badr et al. "Synthesis of 1,2-Disubstituted 4-Benzylidene-2-Imidazolin-5-ones and their Thione Derivatives," Indian Jour of Chem 18B(3):240-242 (1979) (Abstract only).
Grate et al. "Laser-mediated, Site-specific Inactivation of RNA Transcripts," Proc Natl Acad Sci USA 96:6131-6136 (1999).
Lerestif et al. "Cycloaddition with Stabilized Imidates as Potential Azomethines Ylides : A New Route to 2-Imidazoline and 4-Yliden-5-Imidazolinone," Tetrahedron Letters 34(29):4639-4642 (1993).
Stanlis et al., "Single-strand DNA Aptamers as Probes for Protein Localization in Cells," J. Histochem Cytochem. 51(6):797-808 (2003).
Stojanovic et al., "Modular Aptameric Sensors," JACS 126:9266-9270 (2004).
PCT International Search Report and Written Opinion for PCT/US10/24622 (mailed Jul. 30, 2010).
PCT International Search Report and Written Opinion for corresponding application No. PCT/US12/48701 (mailed Jan. 23, 2013).

* cited by examiner

FIG. 16A

Negative control: none transfected HEK293T cells

HEK293T transfected with pAV U6+27-tRNA-aptamer plasmid

FIG. 18 a. tBroccoli

GCCCGGATAGCTCAGTCGGTAGAGCAGCGGCCGGACGGTCCGGGTCAAATTGGTGTGTGTAGTA
GAGTGTGGGCTCGCGGGTTCAAGTCCCTGTTCGGGCGCCA

*FIG. 22A* b. tRNA-Broccoli-c-diGMP sensorm

GCCCGGATAGCTCAGTCGGTAGAGCAGCGGCCGGACGGTCGGGTACGCAGGGCAACCATTCGAA
AGAGTGGGACAAGCCTGGGCTAAACGAAGACATGGTAGGGTAGGTAGCCGGTACGGATAGTA
GAGTGTGGGCTCGCGGGTTCAAGTCCCTGTTCGGGCGCCA

*FIG. 22B* c. tdBroccoli

GCCCGGATAGCTCAGTCGGTAGAGCAGCGGCCGGACGGTCGGGTCCTCGACGGTCCGGGTCGAG
ATATTGGTATCTGTGTAGATGTGGGCTCGCGGGTCCA
GGGTTCAAGTCCCTGTTCGGGCGCCA

*FIG. 22C*

RNA SEQUENCES THAT INDUCE FLUORESCENCE OF SMALL MOLECULE FLUOROPHORES

This application claims the benefit of U.S. Provisional Patent Application Ser. No. 61/874,819, filed Sep. 6, 2013, which is hereby incorporated by reference in its entirety.

This invention was made with government support under grant numbers NINDS R01NS064516, R01 NS064516, R01 EB010249, and F32 GM106683 awarded by the National Institutes of Health. The U.S. government has certain rights in the invention.

FIELD OF THE INVENTION

The present invention relates nucleic acid molecules (aptamers) that bind specifically to small molecule fluorophores, molecular complexes containing the aptamers and fluorophores, and their use for in vitro or in vivo monitoring of the activity, trafficking or localization, degradation, or quantification of various molecules. The present invention also relates to methods and uses for such complexes, as well as kits for practicing those methods.

BACKGROUND OF THE INVENTION

RNA used to be considered a simple and straightforward molecule in cells. The three major classes of RNA, i.e., transfer RNA, ribosomal RNA, and messenger RNA (mRNA), have generally not been thought to be subjected to regulation by signaling pathways, or to have major roles in disease processes. However, a rapidly emerging concept over the past few years is that transcription and other cell signaling pathways are regulated by a diverse array of noncoding RNAs, such as microRNAs, termini-associated RNAs (Han et al., "Promoter-associated RNA Is Required for RNA-directed Transcriptional Gene Silencing in Human Cells," *Proc. Natl. Acad. Sci. U.S.A.* 104:12422-12427 (2007)), and other noncoding RNAs. Additionally, mRNA is no longer viewed as a simple intermediate between DNA and protein, but instead is now known to be subjected to wide range of post-transcriptional processing events, including diverse types of splicing reactions, nonsense-mediated decay, RNA editing, exo- and endonucleolytic degradation, polyadenylation, and deadenylation. Another intriguing aspect of RNA biology is the finding that trinucleotide repeat-containing mRNAs exert specific gain-of-function toxicities associated with their accumulation at certain intracellular sites (Ranum et al., "Myotonic Dystrophy: RNA Pathogenesis Comes Into Focus," *Am. J. Hum. Genet.* 74:793 (2004)). In addition to these different regulatory pathways, recent studies indicate that RNAs traffic through different parts of the cell during RNA maturation. For example, nascent RNA transcripts are likely trafficked to specific intracellular sites in the nucleus for processing events, such as splicing, nonsense-mediated decay, or for packaging into transport granules. After nuclear export, some RNAs have been localized to RNA-enriched intracellular structures including RNA granules, stress granules, and processing bodies (P-bodies) (Kiebler et al., "Neuronal RNA Granules: Movers and Makers," *Neuron* 51:685-690 (2006)). The diversity of these RNA regulatory mechanisms makes it clear that RNA is regulated by a complex and intricate network of regulatory mechanisms and intracellular structures that have a critical role in gene expression.

RNA is increasingly being utilized for various biotechnology applications, including as sensors (Breaker, "Engineered Allosteric Ribozymes as Biosensor Components," *Curr. Opin. Biotech.* 13:31 (2002); Cho et al., "Applications of Aptamers as Sensors," *Annu. Rev. Anal. Chem.* 2:241 (2009)), nanodevices (Sherman and Seeman, "Design of Minimally Strained Nucleic Acid Nanotubes," *Biophys. J.* 90:4546 (2006); Win et al., "Frameworks for Programming Biological Function through RNA Parts and Devices," *Chem. Biol.* 16:298 (2009)), catalysts (Joyce, "Directed Evolution of Nucleic Acid Enzymes," *Annu. Rev. Biochem.* 73: 791 (2004); Lincoln and Joyce, "Self-sustained Replication of an RNA Enzyme," *Science* 323:1229 (2009)), protein inhibitors (Lee et al., "Aptamer Therapeutics Advance," *Curr. Opin. Chem. Biol.* 10:282 (2006)), and in the development of supramolecular structures (Chworos et al., "Building Programmable Jigsaw Puzzles with RNA," *Science* 306:2068 (2004); Dirks et al., "Paradigms for Computational Nucleic Acid Design," *Nucleic Acids Res.* 32:1392 (2004); Levy-Nissenbaum et al., "Nanotechnology and Aptamers: Applications in Drug Delivery," *Trends Biotechnol.* 26:442 (2008)). The ability to confer GFP-like functionality to RNA will facilitate molecular studies of RNA and advance various RNA-based applications.

Although PCT Application Publ. No. WO 2010/096584 to Jaffrey and Paige describes a number of RNA aptamers that bind to conditionally fluorescent molecules derived from the chromophore of green fluorescent protein, and their use, for example, in cellular imaging and RNA trafficking, there continues to be a need for improved aptamers and aptamer-fluorophore complexes to enhance the generation of aptamer-based small molecule sensors as well as in vitro and in vivo monitoring of RNA molecules.

The present invention is directed to overcoming these and other deficiencies in the art.

SUMMARY OF THE INVENTION

A first aspect of the invention relates to a nucleic acid molecule that includes a first domain that binds specifically to a conditionally fluorescent fluorophore, wherein binding of the nucleic acid molecule to the fluorophore substantially enhances fluorescence of the fluorophore upon exposure to radiation of suitable wavelength. This nucleic acid molecule includes RNA, DNA, and/or modified nucleic acids. A plurality of these nucleic acid molecules can be linked together in tandem, optionally separated by a linker, to form multimeric nucleic acid molecules.

In one embodiment, the nucleic acid molecule comprises the nucleotide sequence of SEQ ID NO: 2 or 73, or a portion thereof sufficient to allow for binding to the fluorophore molecule to induce fluorescence thereof. The fluorophore can be, among others, those of formula (I) as identified herein, as exemplified by 4-(3,5-difluoro-4-hydroxybenzylidene)-1,2-dimethyl-imidazol-5-one ("DFHBI") and (Z)-4-(3,5-difluoro-4-hydroxybenzylidene)-2-methyl-1-(2,2,2-trifluoroethyl)-1H-imidazol-5(4H)-one ("DFHBI-1T").

In another embodiment, the nucleic acid molecule comprises the nucleotide sequence of SEQ ID NO: 75 or 74, or a portion thereof sufficient to allow for binding to the fluorophore molecule to induce fluorescence thereof. The fluorophore can be, among others, those of formula (I) as identified herein, as exemplified by DFHBI and DFHBI-1T.

In another embodiment, the nucleic acid molecule comprises the nucleotide sequence of SEQ ID NO: 76, or a portion thereof sufficient to allow for binding to the fluorophore molecule to induce fluorescence thereof. The fluorophore can be, among others, those of formula (I) as identified herein, as exemplified by DFHBI, DFHBI-1T, and 4-(3,5- difluoro-4-hydroxybenzylidene)-1-methyl-5-oxo-4,5-di-hydro-1H-imidazole-2-carbaldehyde oxime ("DFHO").

In another embodiment, the nucleic acid molecule comprises the nucleotide sequence of SEQ ID NO: 77, or a portion thereof sufficient to allow for binding to the fluorophore molecule to induce fluorescence thereof. The fluorophore can be, among others, those of formula (I) as identified herein, as exemplified by DFHBI, DFHBI-1T, and DFHO.

A second aspect of the invention relates to a fusion RNA molecule that includes an RNA molecule according to the first aspect of the invention. By way of example, the fused RNA molecule can be a hybridization probe, another RNA aptamer, or a non-aptamer RNA molecule that binds to a protein of interest.

A third aspect of the invention relates to a nucleic acid molecule according to the first aspect of the invention, which also includes an analyte-binding domain that comprises a nucleotide sequence that adopts a conformation to allow the second domain to bind specifically to an analyte. According to one embodiment, the first domain binds to the fluorophore only after the second domain binds to the analyte.

A fourth aspect of the present invention relates to a detection array that includes a plurality of nucleic acid molecules according to the first or second aspect of the invention each tethered to a discrete location on a surface of the array.

An fifth aspect of the invention relates to a molecular complex that includes a nucleic acid molecule according to the first or second aspect of the invention and a fluorophore molecule specifically bound to the nucleic acid molecule, wherein the fluorophore has substantially enhanced fluorescence (in comparison to the fluorophore prior to specific binding) upon exposure to radiation of suitable wavelength.

A sixth aspect of the invention relates to a molecular complex that includes a nucleic acid molecule according to the third aspect of the invention, a fluorophore molecule specifically bound to the nucleic acid molecule, and an analyte specifically bound to the nucleic acid molecule, wherein the fluorophore has substantially enhanced fluorescence (in comparison to the fluorophore prior to specific binding) upon exposure to radiation of suitable wavelength.

A seventh aspect of the invention relates to a host cell or organism that includes a molecular complex according to the fifth or sixth aspects of the invention.

An eighth aspect of the invention relates to a kit that includes one or more conditionally fluorescent fluorophores and one or more nucleic acid molecules according to the first, second, or third aspects of the invention.

A ninth aspect of the invention relates to a DNA construct that includes a first region that encodes an RNA molecule according to the first, second, or third aspects of the invention. The constructed DNA molecule can be in the form of an isolated transgene or an expression vector that includes appropriate regulatory sequences to allow for expression of the encoded RNA molecules.

A tenth aspect of the invention relates to a DNA construct of the ninth aspect of the invention, which includes an intron positioned within the first region, whereby the excision of the intron from a transcript of the constructed DNA molecule affords the RNA molecule. The constructed DNA molecule can be in the form of an isolated transgene or an expression vector (i.e., that include appropriate regulatory sequences to allow for expression of the encoded RNA molecules).

An eleventh aspect of the invention relates to a DNA construct that includes a first region that encodes an RNA molecule according to the first or second aspects of the invention and a second region that is linked to the first region, the second region encoding an RNA transcript of interest, whereby transcription of the constructed DNA molecule forms an RNA molecule that includes the RNA transcript of interest joined to the RNA molecule that binds specifically to a fluorophore. The constructed DNA molecule can be in the form of an isolated transgene or an expression vector (i.e., that include appropriate regulatory sequences to allow for expression of the encoded RNA molecules).

A twelfth aspect of the invention relates to a transgenic host cell that includes a DNA construct according to the ninth, tenth, or eleventh aspects of the invention.

A thirteenth aspect of the invention relates to an empty genetic construct that can be used to prepare a DNA construct according to the eleventh aspect of the invention. The genetic construct includes a promoter sequence operably linked to a first DNA sequence that encodes one or more RNA molecule according to the first or second aspect of the invention and a second DNA sequence that contains one or more enzymatic cleavage sites. This aspect of the invention also includes kits that contain the empty genetic construction, and which can be used to prepare the DNA construct according to the thirteenth aspect of the invention.

A fourteenth aspect of the invention relates to a method of detecting a target molecule that includes: first exposing a nucleic acid molecule according to the third aspect of the invention (where the first domain binds to the fluorophore only after the second domain binds to the target molecule) to a medium suspected to contain the target molecule under conditions effective to allow the second domain to bind specifically to the target molecule, if present; and second exposing the nucleic acid molecule and medium to a fluorophore comprising a methyne bridge between a substituted aromatic ring system and a substituted imidazol(thi)one, oxazol(thi)one, pyrrolin(thi)one, or furan(thi)one ring under conditions effective to allow the first domain to bind specifically to the fluorophore after binding of the target molecule by the second domain, thereby inducing the fluorophore to adopt a conformation that exhibits enhanced fluorescent emissions; and exciting the fluorophore with radiation of appropriate wavelength and detecting fluorescence by the fluorophore, whereby the detection of fluorescence emissions by the fluorophore indicates binding of the nucleic acid molecule to the target molecule.

A fifteenth aspect of the invention relates to a method of determining location of a target molecule that includes: forming a molecular complex according to the fifth or sixth aspects of the invention; exciting the fluorophore with radiation of appropriate wavelength; and detecting fluorescence by the fluorophore, whereby fluorescence by the fluorophore identifies presence of the target molecule.

A sixteenth aspect of the invention relates to a method of measuring transcription by a promoter of interest in a cell, where the method includes: introducing into a cell a DNA construct according to the ninth aspect of the invention; introducing into the cell a fluorophore in a substantially non-fluorescent form; introducing an agent that modulates transcription of the DNA construct into the cell; and detecting fluorescence by the fluorophore within the cell, whereby the level of fluorescence correlates with the level of transcription for the DNA construct and the effect of the agent in modulating the level of transcription.

A seventeenth aspect of the invention relates to a method of measuring transcription by a promoter of interest, where the method includes: introducing into a cell a DNA construct according to the ninth aspect of the invention and an agent that modulates transcription of the DNA construct; recovering RNA transcripts from the cell; introducing a fluorophore in a substantially non-fluorescent form to the recovered RNA transcripts; and detecting fluorescence by the fluorophore, whereby the level of fluorescence correlates with the level of transcription by the DNA construct and the effect of the agent in modulating the level of transcription.

An eighteenth aspect of the invention relates to a method of monitoring RNA that includes: introducing into a cell a first DNA construct according to the eleventh aspect of the invention; and introducing into the cell a first fluorophore having a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the RNA molecule encoded by the DNA construct to enhance fluorescence emissions by the first fluorophore; exposing the cell to radiation of a wavelength suitable to induce fluorescence emissions by the first fluorophore that is bound by the first domain or a FRET partner; and measuring the fluorescent emissions of the first fluorophore or the FRET partner to monitor the RNA transcript. This aspect is particularly useful for monitoring the location, degradation (over time), and for quantitating the RNA transcript (i.e., based on the level of fluorescence). Moreover, simultaneous monitoring of two or more RNA transcripts is possible.

A nineteenth aspect of the invention relates to a method of monitoring a target molecule in a cell that includes: introducing into a cell a nucleic acid molecule according to the third aspect of the invention (where the first domain binds to the fluorophore only after the second domain binds to the target molecule), wherein the second domain binds the target molecule; introducing into the cell a first fluorophore having a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the nucleic acid molecule to enhance fluorescence emissions by the first fluorophore; exposing the cell to radiation of a wavelength suitable to induce fluorescence emissions by the first fluorophore that is bound by the nucleic acid molecule or a FRET partner; and measuring the fluorescent emissions of the first fluorophore or the FRET partner to monitor the target molecule. This aspect is particularly useful for monitoring the location, degradation (over time), and for quantitating the target molecule (i.e., based on the level of fluorescence). Moreover, simultaneous monitoring of two or more target molecules is possible.

A twentieth aspect of the invention relates to a method of monitoring a target molecule in a cell that includes: introducing into a cell a gene encoding the nucleic acid molecule according to the third aspect of the invention (where the first domain binds to the fluorophore only after the second domain binds to the target molecule), wherein the second domain binds the target molecule; introducing into the cell a first fluorophore having a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the nucleic acid molecule to enhance fluorescence emissions by the first fluorophore; exposing the cell to radiation of a wavelength suitable to induce fluorescence emissions by the first fluorophore that is bound by the nucleic acid molecule or a FRET partner; and measuring the fluorescent emissions of the first fluorophore or the FRET partner to monitor the target molecule. This aspect is particularly useful for monitoring the location, degradation (over time), and for quantitating the target molecule (i.e., based on the level of fluorescence). Moreover, simultaneous monitoring of two or more target molecules is possible.

A twenty-first aspect of the invention relates to a method of screening an agent that modifies gene expression, which includes: introducing a transgene into a cell under conditions suitable to cause transcription of the gene, the transcript comprising an RNA molecule according to the second aspect of the invention; exposing the cell to an agent; introducing into the cell a fluorophore having a methyne bridge between a substituted aromatic ring system and a substituted imidazol(thi)one, oxazol(thi)one, pyrrolin(thi)one, or furan(thi)one ring, wherein the fluorophore is bound specifically by the first domain of the RNA molecule to enhance fluorescence emissions by the fluorophore; exposing the cell to radiation of a wavelength suitable to induce fluorescence emissions by the fluorophore that is bound by the RNA molecule or a FRET partner; and measuring the fluorescent emissions of the fluorophore or the FRET partner, whereby a reduction or absence of fluorescent emissions, relative to an otherwise identical control cell that is not exposed to the agent, indicates that the agent inhibits expression of the transgene, and an increase of fluorescent emissions, relative to an otherwise identical control cell that is not exposed to the agent, indicates that the agent increases expression of the transgene.

A twenty-second aspect of the invention relates to a method of screening an agent that modifies RNA splicing, which includes: introducing into a cell a transgene comprising a DNA construct according to the tenth aspect of the invention, wherein transcription of the transgene affords a transcript comprising an intron positioned between first and second portions of the RNA molecule; exposing the cell to an agent; introducing into the cell a fluorophore having a methyne bridge between a substituted aromatic ring system and a substituted imidazol(thi)one, oxazol(thi)one, pyrrolin(thi)one, or furan(thi)one ring, wherein the fluorophore is bound specifically by the first domain of the RNA molecule to enhance fluorescence emissions by the fluorophore; exposing the cell to radiation of a wavelength suitable to induce fluorescence emissions by the fluorophore that is bound by the RNA molecule or a FRET partner; and measuring the fluorescent emissions of the fluorophore or the FRET partner, whereby a reduction or absence of fluorescent emissions, relative to an otherwise identical control cell that is not exposed to the agent, indicates that the agent inhibits proper splicing of the transcript; and an increase of fluorescent emissions, relative to the otherwise identical control cell that is not exposed to the agent, indicates that the agent promotes proper splicing of the transcript.

A twenty-third aspect of the invention relates to method of screening an agent that modifies RNA splicing, which includes: providing a medium comprising an RNA transcript, a spliceosome comprising a splicing enzyme, an agent, and a fluorophore, wherein the RNA transcript comprises first and second exons having an intervening intron region, the first and second exons, upon excision of the intron, forming an RNA molecule according to the second aspect of the invention, wherein the fluorophore has a methyne bridge between a substituted aromatic ring system and a substituted imidazol(thi)one, oxazol(thi)one, pyrrolin(thi)one, or furan(thi)one ring, and wherein the fluorophore is bound specifically by the first domain of the RNA molecule to enhance fluorescence emissions by the fluorophore; exposing the medium to radiation of a wavelength suitable to induce fluorescence emissions by the fluorophore that is bound by the RNA molecule or a FRET partner; and measuring the fluorescent emissions of the fluorophore or the FRET partner, whereby a reduction or absence of fluorescent emissions, relative to an otherwise identical medium that lacks the agent, indicates that the agent inhibits proper splicing of the transcript; and an increase of fluorescent emissions, relative to the otherwise identical medium that lacks the agent indicates that the agent promotes proper splicing of the transcript.

A twenty-fourth aspect of the invention relates to a method of screening an agent for activity against a target molecule. The method includes the steps of introducing into a cell a nucleic acid molecule according to the third aspect of the invention (where the first domain binds to the fluorophore only after the second domain binds to the target molecule), wherein the second domain binds a target molecule; introducing into the cell a first fluorophore comprising a methyne bridge between a substituted aromatic ring system and a substituted imidazol(thi)one, oxazol(thi)one, pyrrolin(thi)one, or furan(thi)one ring, wherein the first fluorophore is bound specifically by the first domain of the nucleic acid molecule to enhance fluorescence emissions by the first fluorophore; exposing the cell to radiation of a wavelength suitable to induce fluorescence emissions by the first fluorophore that is bound by the nucleic acid molecule or a FRET partner; and measuring the fluorescent emissions of the first fluorophore or the FRET partner, wherein the a difference in the fluorescent emissions by the fluorophore or FRET partner, relative to an otherwise identical cell that lacks the agent, indicates that the agent modifies the activity of the target molecule.

A twenty-fifth aspect of the invention relates to a method of identifying nucleic acid molecules capable of binding to a target molecule, which method includes: providing a pool of nucleic acid molecules that each comprise a first domain comprising a nucleic acid molecule according to the first aspect of the invention, which binds specifically to a fluorophore having a methyne bridge between a substituted aromatic ring system and a substituted imidazol(thi)one, oxazol(thi)one, pyrrolin(thi)one, or furan(thi)one ring, and a second domain that comprises a random sequence, and only after binding of the second domain to the target molecule is first domain capable of binding specifically to the fluorophore; exposing the pool of nucleic acid molecule to a target molecule and the fluorophore, whereby fluorescence emissions by the fluorophore are enhanced by the binding of the first domain to the fluorophore; illuminating the fluorophore with light of a wavelength suitable to induce fluorescence emissions by the fluorophore that is bound by the first domain molecule; and measuring the fluorescent emissions of the fluorophore, whereby detection of fluorescence by the fluorophore indicates that the second domain of the nucleic acid molecule binds to the target molecule.

A twenty-sixth aspect of the invention relates to a method for screening a nucleic acid aptamer for in vivo activity in inducing fluorescence of a conditionally selective fluorophore. The method includes introducing a conditionally selective fluorophore into a plurality of recombinant host cells that each express a nucleic acid aptamer of a library; and sorting the plurality of recombinant host cells, based on the presence or absence of host cell fluorescence caused by the conditionally selective fluorophore, using a flow cytometer.

A twenty-seventh aspect of the invention relates to a method for detecting nucleic acid molecules. The method includes separating nucleic acid molecules on a gel; exposing the separated nucleic acid molecules to a fluorophore having a methyne bridge between a substituted aromatic ring system and a substituted imidazol(thi)one, oxazol(thi)one, pyrrolin(thi)one, or furan(thi)one ring; illuminating the gel with light of a wavelength suitable to induce fluorescence emissions by the fluorophore that is bound by a nucleic acid molecule; and detecting the fluorescent emissions of the fluorophore, whereby detection of fluorescence by the fluorophore detects the location of the nucleic acid molecule on the gel.

Additional aspects of the invention include new fluorophores according to formula I and new nucleic acid aptamers that bind to these fluorophores to induce their fluorescence, as well as the use thereof these to form molecular complexes. The use of these materials and genetic constructs encoding the aptamers is also contemplated here, including all of the methods described herein.

The examples of the present invention demonstrate the development of improved nucleic acid molecules that bind to various conditionally fluorescent fluorophores. These aptamers are optimized for proper folding and retention of their binding activity in vivo. Optimization of in vivo folding was assisted through the use of a SELEX-FACS procedure whereby whole cells that express a particular aptamer of interest are utilized to assess whether a conditionally fluorescent fluorophore exhibits fluorescence in the presence of a particular aptamer expressed in vivo. Fluorescent cells are sorted by flow cytometry and recovered; if desired, further rounds of SELEX-FACS sorting can be performed to enhance aptamer properties.

The aptamer/fluorophore complexes of the invention are useful for a wide variety of purposes, both in vitro and in vivo, including monitoring the location or degradation of RNA molecules in vivo, monitoring and quantifying the amount of a target molecule in an in vitro or in vivo system. Importantly, the fluorophores are non-toxic, unlike many prior art dyes. The detection procedures can be implemented using existing optical detection devices and is amenable to high-throughput microarrays or drug screening. Moreover, the generation of RNA-based small molecule sensors demonstrates that it is possible to vastly increase the number molecules that can be detected in cells beyond what is possible using current protein-based FRET sensors. The present invention provides a rapid, simple, and general approach to obtain sensors for any small molecule. These sensors should immediately find use as simple fluorometric reagents to measure small molecules, thereby simplifying assays, and permitting high-throughput fluorescence-based screens.

BRIEF DESCRIPTION OF THE DRAWINGS

FIG. 1A shows micrographs of COS-7 cells expressing $(CGG)_{60}$-Spinach (Spinach), $(CGG)_{60}$-Spinach2 (Spinach2) and mCherry-hSam68 in the presence of DFHBI as well as of cells expressing $(CGG)_{60}$-Spinach2 and mCherry-hSam68 in the absence of DFHBI (Spinach2, no DFHBI). Nuclei were stained using Hoechst. Scale bar, 10 µm. FIG. 1B illustrates the secondary structure of Spinach (SEQ ID NO: 1) and Spinach2 (SEQ ID NO: 2). Spinach is predicted to form one stem and three stem-loops. Stem 1 and stem-loop 3 (boxed) were mutated to generate Spinach2.

FIG. 2A shows the fluorescence signal from 1 µM of indicated RNAs and 10 µM DFHBI, measured at 25° C. and normalized to Spinach fluorescence. FIG. 2B shows the results of folding assay.

AU, arbitrary units. FIG. 2C illustrates the percentage folded values of Spinach and derivatives at 25° C. and 37° C. FIG. 2D represents the fluorescence signal from 1 µM of Spinach and Spinach2 RNA with indicated flanking sequence and 10 µM DFHBI, measured at 25° C. and normalized to Spinach fluorescence. Dash indicates no flanking sequence. Error bars, s.e.m. for three independent replicates.

FIG. 3A demonstrates the thermostability of Spinach and Spinach2 in the presence of DFHBI, measured from 20° C. to 60° C. Shown are representative data (dots) from three independent experiments along with the best-fit curve from fitting with the Boltzmann sigmoidal equation (line). Dashed lines correspond to half-maximal fluorescence signal. FIG. 3B represents the fluorescence signal from *E. coli* expressing Spinach or Spinach2, normalized to Spinach signal at 25° C. Error bars, s.e.m. for three independent experiments. FIG. 3C shows Spinach and Spinach2 expression in *E. coli*, normalized to expression of 16S RNA. Total RNA from samples used in fluorescence measurements was subjected to reverse transcription followed by qRT-PCR. Error bars, s.e.m. for three independent replicates. FIG. 3D illustrates fluorescence excitation spectra of Spinach and Spinach2 measured from 300 nm to 500 nm, with emission recorded at 510±10 nm. FIG. 3E shows emission spectra of Spinach and Spinach2. Fluorescence was excited with 420±10 nm light and emission was recorded from 450 nm to 600 nm. In FIGS. 3D,E spectra were normalized to maximal signal and represent average values for three independent measurements.

FIG. 4A shows fluorescence images of HEK293T cells expressing 5S RNA tagged with either Spinach or Spinach2 under the control of the 5S promoter. Cells were incubated with 20 µM DFHBI and imaged with a 1-s exposure time. Scale bar, 10 µm. FIG. 4B shows the brightness for cells labeled with either 5S-Spinach or 5S-Spinach2, normalized for area. 5S-Spinach signal was normalized to 1. 5S-Spinach2 was 3.2-fold brighter than Spinach. Error bars, s.e.m. for 20 cells per condition. FIG. 4C are fluorescence images of HeLa cells expressing either Spinach-7SK or Spinach2-7SK under the control of the CMV promoter. Cells were cotransfected with SC35-mCherry, which labels nuclear speckles. Cells were incubated with 20 µM DFHBI and imaged for 200 ms. Scale bar, 10 µm.

FIG. 5A shows micrographs of COS-7 cells transiently transfected with a CGG-Spinach2 vector, 2 h later incubated with imaging medium containing DFHBI and imaged every 20 min over 6 h. Time 0 indicates the first frame that displayed fluorescence above background. White arrowheads mark small foci formed de novo; red and blue asterisks mark merging foci. FIG. 5B illustrates images of a cell 24 h after transfection with the CGG-Spinach2 vector undergoing mitosis in imaging medium containing DFHBI. FIG. 5C shows images of a cell containing $(CGG)_{60}$-Spinach2 aggregates after treatment with 1 µg/ml actinomycin D. FIG. 5D shows the percentage of nuclei that contain foci 0, 24 and 48 h after treatment with doxycycline in cells containing $(CGG)_{60}$-Spinach2 expressed using a TET-off expression system. Error bars, s.e.m. for three independent replicates in which 100 DsRed-positive cells were counted for each treatment. FIG. 5E shows images of representative nuclei from cells expressing $(CGG)_{60}$-Spinach2 0 h and 48 h after doxycycline addition. Scale bars, 10 µm. Images are representative of 50 analyzed cells (FIGS. 5A, 5C, 5E).

FIG. 6A shows the presence of nuclear foci in COS-7 cells expressing $(CGG)_{60}$-Spinach2, treated with vehicle, 20 µM 1a or 5 µM tautomycin. After 24 h, 100 DsRed-positive cells were analyzed for the presence of nuclear foci for each condition. 94±1.4%, 25±4.9% and 12±4.2% of nuclei contained foci with vehicle, 1a, and tautomycin, respectively. Error bars, s.e.m. for three independent experiments. FIG. 6B illustrates images representative of 100 COS-7 cells (per treatment) expressing (CGG) $_{60}$-Spinach2 after 24 h of treatment with vehicle, 1a and tautomycin. Images show nuclei labeled using Hoechst, fluorescence signal from Spinach2 and fluorescence signal from DsRed-Max, a transfection control. FIG. 6C shows images of COS-7 cells expressing $(CGG)_{60}$-Spinach2, incubated with vehicle, 20 µM 1a or 5 µM tautomycin and imaged over 2 h after drug treatment. Scale bars, 10 µm.

FIG. 7A is a schematic representation of the combined SELEX-FACS approach. SELEX is performed using a random library containing ~$10^{14}$ RNAs. When the RNA pool begins to exhibit fluorescence upon incubation with the fluorophore, the RNAs are reverse-transcribed and cloned into a bacterial expression plasmid. The library is transformed into *E. coli* and the transformants are screened by FACS in the presence of DFHBI. This screening approach markedly reduces the time required for identification of RNA-fluorophore complexes and selects RNAs based exclusively based on their in vivo fluorescence. FIG. 7B is a FACS dot plot showing the fluorescence distribution of *E. coli* transformed with a library containing the RNA pool from round 6 of SELEX. In this experiment, *E. coli* expressing the SELEX round 6 RNA library (yellow population) was pre-incubated with 40 µM DFHBI fluorophore and then sorted using the indicated gate. The position of each dot reflects RNA fluorescence (x-axis) and the overall expression level of the plasmid indicated by the far-red fluorescence of eqFP670 (y-axis). *E. coli* expressing either Spinach (green) or no aptamer (grey) were used as controls. As can be seen, a fraction of the library-expressing bacteria exhibit fluorescence comparable to that seen in Spinach-expressing *E. coli*. FIG. 7C illustrates the screening of aptamer-expressing *E. coli* on DFHBI-agar plates. FACS isolated cells were plated on LB-agar plates. The next day resulted colonies were induced with IPTG and the dishes were treated with DFHBI to a final concentration of 1 mM and 40 µM, respectively. The plates were imaged using a BioRad ChemiDoc MP imager 4 h later. Fluorescence of the RNA-DFHBI complexes in the colonies was detected using ex=470±30 nm; em=532±28 nm. The expression of eqFP670 was detected using ex=630±30 nm, em=697±55 nm. The resulting images were processed in Fiji (Schindelin et al., "Fiji—An Open Source Platform for Biological Image Analysis," *Nat Methods.*; 9(7):676-682 (2013), which is hereby incorporated by reference in its entirety) to normalize green fluorescence to the far-red fluorescence to control for variations in colony size and expression level. A heat map representation of the normalized image facilitates identification of the most promising mutants (numbered). FIG. 7D illustrates the identification of colonies with highest normalized fluorescence. Shown are the colonies that exhibited the highest fluorescence after normalization for eqFP670 expression. Clone 29-1 was chosen for further optimization based on its marginally higher brightness in bacteria. Error bars indicate SD (n=3).

FIG. 9A is a schematic representation of the fluorescent RNA aptamers directed evolution approach. FIG. 9B is a FACS dot plot of 29-1-T2 doped library in bacteria. Bacterial cells expressing this library or positive and negative control were pre-incubated with 40 mM 1T dye and then FACS sorted. Negative bacterial population is dark grey (behind yellow), doped library expressing bacteria is yellow, 29-1 expressing cells, used as a positive control, are dark green. Again, bacterial cells having the brightest fluorescent signal were isolated based on the gate presented. This time dot plot is presented as green fluorescence vs. side scatter, the latter was also used to exclude those negative cells which are bright owing to their increased size. FIG. 9C is a bar graph of the normalized brightness of bacterial colonies of the winning clones in comparison with the original 29-1 and short 29-1-T2. To assess sorted mutants performance in vivo, mutants were expressed in bacterial cells and the fluorescent signal of bacterial colonies growing on agar dish supplemented with 40 µM of DFHBI-1T was measured. Empty vector expressing cells along with 29-1 and 29-1-0 expressing ones were used as controls. This data demonstrates successful restoration of the truncated aptamers brightness as evidenced by very similar signal of 29-1-3 compared to 29-1 aptamer. Error bars indicated SD (n=3). FIG. 9D is an alignment of the sequences of the brightest mutants from the doped T2 library screening with the variable and proposed conserved regions highlighted. Parent aptamer 29-1-T2 (SEQ ID NO: 4) is the original sequence subjected to doping. Green—conservative bases (or equivalent substitutions) participating in base pairing. Blue—conservative bases in bulges. Yellow—highly variable terminal stem with stabilized tetraloops in bold. Non colored bases are mutations which prevent otherwise conservative base pairing or which are substitutions in conservative bulges. Clones 2-5, 7, and 9 are SEQ ID NOS: 5-10, respectively.

FIG. 11A illustrates the mFold predicted secondary structure of dimeric Broccoli (dBroccoli, SEQ ID NO: 12). For simplicity no tRNA scaffold is drawn. Green color indicates individual Broccoli units, yellow denotes connector stem. FIG. 11B illustrates that dimeric Broccoli in tRNA scaffold (tdBroccoli) is almost twice brighter than Broccoli in tRNA (tBroccoli). To compare tBroccoli and tdBroccoli in vitro performance, tBroccoli and tdBroccoli were run on urea-Page, the urea was washed allowing the aptamers to fold in gel. The gel was then stained with DFHBI-1T to reveal specific aptamers' signal and finally with SYBR Gold to quantify RNA amount. FIG. 11C shows the calculation of the bands intensity from the gel on panel b demonstrates that tdBroccoli molecule is ~1.8 fold more fluorescent than the one of tBroccoli. Band fluorescence was normalized to molecular weight to account for different size of tBroccoli and tdBroccoli.

FIG. 12A shows the excitation and emission spectra of tBroccoli as measured for 20 µM RNA and 2 µM DFHBI-1T solution on a fluorometer. FIG. 12B illustrates the absorbance spectra of DFHBI-1T dye alone and in complex with tBroccoli RNA aptamer shows bathochromic shift similar to that observed for Spinach2 before. 50 µM of RNA was pre-incubated with 5 µM of the dye and the solution spectrum was recorder on spectrophotometer and compared to the spectrum of the fluorophore alone. FIG. 12C shows that the dissociation constant of tBroccoli is within a nanomolar range. To calculate dissociation constant titration of 50 nM RNA with increasing concentration of DFHBI-1T was performed; the resulting data points were then fitted with the curve based on the Hill equation. tBroccoli's KD is lower than the one of Spinach2. Error bars indicate SD (n=3). FIG. 12D illustrates the folding of tBroccoli in comparison to the one of tSpinach2 and in a different flanking sequences context. Spinach and Spinach2 data was taken from Examples 1-6 (see also Strack et al., "A Superfolding Spinach2 Reveals the Dynamic Nature of Trinucleotide Repeat-Containing RNA," *Nat Methods* 10(12):1219-24 (2013), which is hereby incorporated by reference in its entirety). FIG. 12E illustrates that the magnesium dependence of tBroccoli and tSpinach2 fluorescence reveals one of the key differences between these aptamers. To measure magnesium dependence 1 µM of RNA was mixed with 10 µM of DFHBI-1T and the fluorescence signal of the complex was measured at different concentrations of MgCl2. The signal at 1 mM MgCl2 for both aptamers was set to 100. Error bars indicated SD (n=3). FIG. 12F shows that the tBroccoli aptamer demonstrates higher thermostability compared to tSpinach2 aptamer. To measure temperature dependence of tBroccoli and tSpinach2 fluorescence fluorescent signal decay of 1 µM RNA and 10 µM of the dye solution was followed upon gradual temperature increasing.

FIG. 13A illustrate microphotographs of bacteria expressing tSpinach2, tBroccoli, tdBroccoli. Respective aptamers were expressed in *E. coli* and then bacterial cells were attached to poly-d-lysine coated glass-bottom dishes, pre-incubated with 200 µM DFHBI-1T dye and imaged under the fluorescent microscope. Scale bar, 2 µm. FIG. 13B illustrates the fluorescence signal from bacterial cells of FIG. 13A as measured in suspension on a plate reader. Signal from the media with the dye only was used as a background and subtracted. Error bars indicate SD (n=3). FIG. 13C illustrates that tBroccoli, tSpinach2 and tdBroccoli are expressed at similar level in bacterial cells. Total RNA from the cells from FIGS. 13A-B was fractionated on urea-PAGE and stained with DFHBI-1T and SYBR Gold. tBroccoli, tSpinach2 and tdBroccoli processed RNA bands are indicated with yellow arrows. Higher molecular weight bands are unprocessed transcripts. 5S indicated with the black arrow was used as a loading normalization control. FIG. 13D shows quantification of intensity of the SYBR Gold stained bands from FIG. 13C presented as bar graph. Sum of both processed and unprocessed RNA band intensity was normalized to aptamers length. Gel image processing was performed in Image Lab 5.0 software (BioRad). Error bars indicate SD (n=3).

FIG. 14A illustrates flow cytometry analysis of DFHBI-1T treated HEK293T cells transfected with plasmids expressing 5S rRNA fused to the aptamer in tRNA scaffold. 5S rRNA only expression was used as a negative control. mCherry protein expressed from another plasmid was used for assessing transfection efficiency. Transfected cells were analyzed in two channels: green (ex=488 nm; em=525±50 nm) and red (ex=561 nm and em=610±20). Where indicated, cells were also pre-treated with 5 mM $MgSO_4$. tSpinach2-induced fluorescence can only be observed upon magnesium treatment. FIG. 14B shows fluorescent microscopy microphotographs of the same cells analyzed on panel 14A. Cells were pre-treated with 20 μM DFHBI-1T and, where indicated, with 5 mM $MgSO_4$. Exposure time is 0.5 s. Scale bar, 10 μm. FIG. 14C shows that total RNA from the same transfected HEK293T cells was ran on urea-PAGE and stained with DFHBI-1T to reveal aptamers and then with SYBR Gold to stain all RNA and allow RNA quantification. tRNA-scaffolded aptamers appear to be processed (yellow arrows). The same gel also presents total RNA from HEK293T cells expressing 5S RNA rRNA fused to the aptamer without tRNA scaffold. No processing for such fusions was observed. Endogenous 5S rRNA is used as a loading control. FIG. 14D illustrates flow cytometry analysis of DFHBI-1T treated HEK293T cells transfected with plasmids expressing 5S RNA rRNA fused to the aptamer without tRNA scaffold. Again, mCherry expression was used for transfection efficiency normalization and cells were analyzed in two channels: green (ex=488 nm; em=525±50 nm) and red (ex=561 nm and em=610±20). 5S-Spinach2 expressing cells were also tested in presence of 5 mM $MgSO_4$. No Spinach2 fluorescence is observed without tRNA scaffold. FIG. 14E illustrates fluorescent microscopy microphotographs of HEK293T cells expressing 5S-Broccoli or 5S-dBroccoli. Cells were pre-treated with 20 μM DFHBI-1T. Exposure time is 0.5 s. Scale bar, 10 μm.

FIG. 15A illustrates the ability of aptamer 29-1 to turn on the fluorescence of DFHBI and DFHBI-IT. FIG. 15B is a representative dot plot of a FACS experiment in which aptamer sequences comprising the core sequence elements of Broccoli were expressed in bacterial (or mammalian) cells.

FIGS. 16A-D demonstrate that aptamers comprising core sequence elements are capable of binding to and switching on the fluorescence of DFHO. FIG. 16A is a DNA sequence alignment of parent aptamer 29-1 (SEQ ID NO: 13), indicated in bold, along with 7 representative mutant sequences of aptamer 29-1, SEQ ID NOS: 14-20 (from top to bottom). Core and variable regions are indicated. The only consistent mutations observed in the proposed core sequence is indicated by the asterisk. FIG. 16B illustrates the enhancement of DFHO fluorescence upon binding of Orange or Red aptamers. FIG. 16C illustrates the expression of the Orange aptamer in E. coli. FIG. 16D illustrates the expression of the Red aptamer in E. Coli.

FIG. 17A illustrates the ability of a parent aptamer to induce the fluorescence of DFHO. The baseline fluorescence of DFHO is increased upon addition of the parent aptamer. FIG. 17B illustrates the ability of aptamers to enhance fluorescence of DFHO. FIG. 17C is a DNA sequence alignment of a shortened core sequence (SEQ ID NO: 21) with 8 representative mutant sequences (from top-to-bottom, SEQ ID NOS: 22-29, respectively). Core and variable regions are indicated. FIG. 17D illustrates the expression of aptamers in living cells. Bacterial cells are shown in the top row. Mammalian cells (HEK293) are shown in the bottom row. Phase images are shown on the right. FIGS. 17E-H illustrate the use of aptamers to image promoter activity in cells using FACS. FIG. 17E shows a negative control experiment in bacterial cells. FIG. 17F shows the expression of an aptamer library in E. coli. FIG. 17G shows a negative control experiment in HEK293T cells. FIG. 17H shows an experiment in which HEK293T cells were transfected with pAV U6+27-tRNA-aptamer plasmid.

FIG. 18 illustrates the aligned DNA sequences of Spinach (DNA conversion of SEQ ID NO: 1), Spinach1.1 (SEQ ID NO: 30), Spinach1.2 (SEQ ID NO: 31), and Spinach2 (DNA conversion of SEQ ID NO: 2). Green shaded positions represent sites that were mutated to generate Spinach2 from Spinach1.2. Underlined regions correspond to the designated stem or stem loop.

FIG. 19A shows the alignment of three mutants from 29-n family (29-1, nts 2-100 of SEQ ID NO: 3 in DNA form; 29-2, SEQ ID NO: 33; 29-3, SEQ ID NO: 34), Spinach (DNA conversion of SEQ ID NO: 1), and two unrelated sequences which also exhibited fluorescence activation (30-1, SEQ ID NO: 35; 30-2, SEQ ID NO: 36). The expected sequence of an average library member (SEQ ID NO: 32) is shown above. Green indicates constant library regions used for PCR amplification. Blue indicates fixed region serving as a stable tetraloop facilitating folding. Interestingly, this region is missing in 29-1. Red indicates identical regions in Spinach and 29-n. Yellow indicates nucleotides which were variable in three 29 family mutants. FIG. 19B illustrates RNA structures predicted in mFold online software. Folds with the minimal energy were chosen for presentation. mFold predicted structure of Spinach was taken from FIG. 1B. Interestingly, despite substantial sequences similarity 29-1 (SEQ ID NO: 3) and Spinach (SEQ ID NO: 1) seem to have different predicted secondary structure, while 30-1 (SEQ ID NO: 35) and 30-2 (SEQ ID NO: 36) share structural, but not sequence, similarity with 29-1.

FIG. 20A shows that rational mutagenesis of 29-1-3 aptamer guides its final optimization. mFold prediction of the secondary structure of 29-1-3 fused with tRNA scaffold (SEQ ID NO: 37) with the tested regions marked. Red color indicates changes reducing fluorescence while green indicates fluorescence preserving mutations allowing structure optimization. FIG. 20B depicts the in vitro brightness of the mutants of 29-1-3 (1-16 on FIG. 20A) in comparison with 29-1-3 and 29-1. To test different mutations RNA was transcribed in vitro from the mutant DNA templates and measured their fluorescence on a plate reader in complex with excess of DFHBI-1T dye. All RNAs contain tRNA scaffold. FIG. 20C shows that the fluorescent brightness of the best aptamers selected in FIG. 20B measured in vivo confirms selection of final mutations and deletions. Several aptamers from FIG. 20B were expressed in bacterial cells and measured their fluorescent signal in colonies growing on DFHBI-1T supplemented LB-agar dish. 29-3-1 aptamer resulted as a combination of mutations and deletions 1 and 4 from FIG. 20A shows almost as strong signal as the parental 29-1 while being ~50 nt shorter. All aptamers tested were expressed in tRNA scaffold. Error bars indicate SD (n=3).

FIG. 22A illustrates the sequence of tBroccoli (SEQ ID NO: 38). FIG. 22B illustrates the sequence of Broccoli-based c-diGMP sensor (SEQ ID NO: 39). FIG. 22C illustrates the sequence of tdBroccoli (SEQ ID NO: 40). In FIGS. 22A-C: Green—Broccoli parts; Orange—transducer (in sensor) or connector and terminal stem-loop (in monomer and dimer) regions; Blue—c-diGMP sensor part; and tRNA scaffold is not colored.

DETAILED DESCRIPTION OF THE INVENTION

Figure 1A:
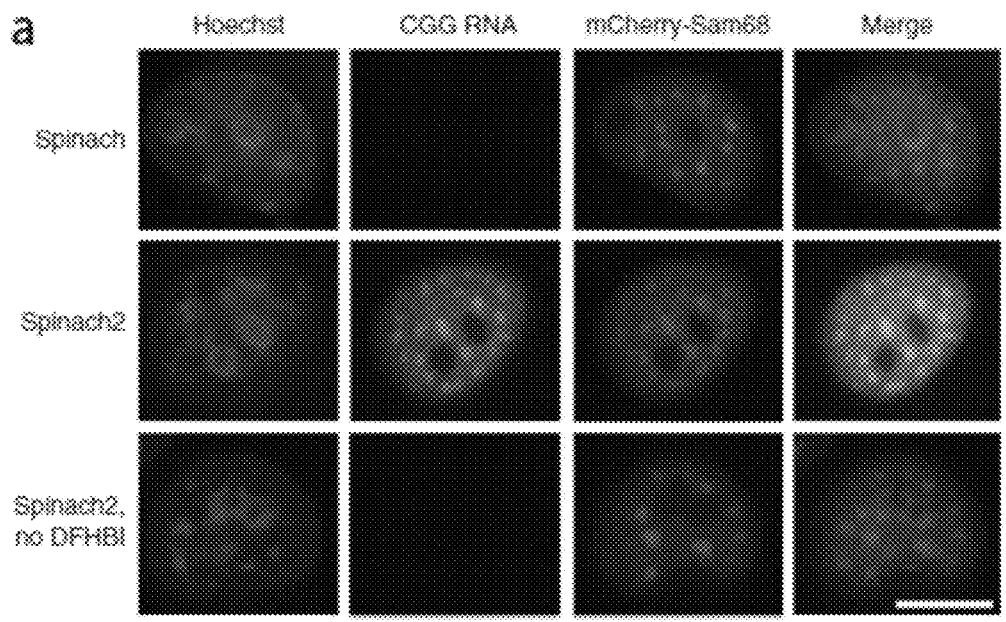
FIGS. 1A-B demonstrate that RNAs containing CGG-Spinach2 can be imaged in living cells.

The present invention relates to novel nucleic acid aptamers that can bind selectively to conditionally fluorescent molecules ("fluorophores") to enhance the fluorescence signal of the fluorophore upon exposure to radiation of suitable wavelength. Molecular complexes formed between the novel aptamers and fluorophores, and their target molecules are also discussed below, as are the uses of these novel materials.

Fluorophores and their Synthesis

The fluorophores recognized by the nucleic acid aptamers of the present invention include those that possess a methyne (also known as methine) bridge between a substituted aromatic ring system and a substituted imidazol(thi)one, oxazol(thi)one, pyrrolin(thi)one, or furan(thi)one ring Importantly, the methyne bridge contains a single carbon that is double-bonded to a ring carbon of the substituted imidazol(thi)one, oxazol(thi)one, pyrrolin(thi)one, or furan(thi)one ring. Thus, these conditionally fluorescent compounds are unlike cyanine dyes characterized by a polymethyne bridge.

The fluorophores used in the present invention are characterized by a low quantum yield at a desired wavelength in the absence of aptamer binding. In certain embodiments, the quantum yield of the fluorophore, in the absence of specific aptamer binding, is less than about 0.01, more preferably less than about 0.001, most preferably less than about 0.0001.

The fluorophores are substantially unable to exhibit increases in quantum yield upon binding or interaction with molecules other than the aptamer(s) that bind specifically to them. This includes other molecules in a cell or sample besides those aptamer molecules having a polynucleotide sequence that was selected for binding to the fluorophore.

The fluorophores are preferably water soluble, non-toxic, and cell permeable. Preferably, the fluorophore is soluble in an aqueous solution at a concentration of 0.1 µM, 1 µM, more preferably 10 µM, and most preferably 50 µM or higher. Preferably, incubating a cell with these concentrations of the fluorophore does not affect the viability of the cell. The fluorophores are preferably capable of migrating through a cell membrane or cell wall into the cytoplasm or periplasm of a cell by either active or passive diffusion. Preferably, the fluorophore is able to migrate through both the outer and inner membranes of gram-negative bacteria, the cell wall and membrane of gram-positive bacteria, both the cell wall and plasma membrane of plant cells, cell wall and membrane of fungi and molds (e.g. yeast), the capsid of viruses, the plasma membrane of an animal cell, and through the GI tract or endothelial cell membranes in animals.

As used herein, the terms "enhance the fluorescence signal" or "enhanced signal" (i.e., upon specific aptamer binding) refer to an increase in the quantum yield of the fluorophore when exposed to radiation of appropriate excitation wavelength, a shift in the emission maxima of the fluorescent signal (relative to the fluorophore emissions in ethanol glass or aqueous solution), an increase in the excitation coefficient, or two or more of these changes. The increase in quantum yield is preferably at least about 1.5-fold, more preferably at least about 5 to 10-fold, at least about 20 to 50-fold, more preferably at least about 100 to about 200-fold. Fold increases in quantum yield exceeding 500-fold and even 1000-fold have been achieved with the present invention.

The radiation used to excite the fluorophore may be derived from any suitable source, preferably any source that emits radiation within the visible spectrum or infrared spectrum. The radiation may be directly from a source of radiation (e.g., a light source) or indirectly from another fluorophore (e.g., a FRET donor fluorophore). The use of FRET pairs is discussed more fully hereinafter.

Preferred fluorophores that can be used in accordance with the present invention include those according to formula I below:

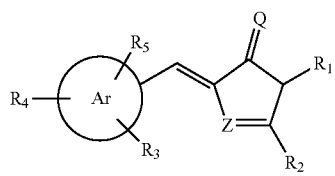

(I)

wherein,
Q is S or O,
Y is O or N,
Z is N or C($R_{10}$),
Ar is an aromatic or hetero-aromatic ring system comprising one or two rings;
$R_1$ is present when Y is N, and is a $C_{1-8}$ hydrocarbon or —$(CH_2)_n$—$R_6$ where n is an integer greater than or equal to 1;
$R_2$ is methyl, a mono-, di-, or tri-halo methyl, an aldoxime, an O-methyl-aldoxime, iminomethyl, carboxylic acid, thioic acid, (thio)amido, alkyl(thio)amido, unsubstituted or substituted phenyl with up to three substituents ($R_7$-$R_9$), (meth)acrylate, $C_{2-8}$ unsaturated hydrocarbon optionally terminated with an amine, amide, carboxylic acid, ester, enone, oxime, O-methyl-oxime, imine, nitromethane, nitrile, ketone, mono-, di-, tri-halo, nitro, cyano, acrylonitrile, acrylonitrile-enoate, acrylonitrile-carboxylate, acrylonitrile-amide, alkylester, or a second aromatic or hetero-aromatic ring;
$R_3$-$R_5$ are independently selected from H, hydroxy, alkyl, alkoxy, fluoro, chloro, bromo, a mono-, di-, or tri-halo alkoxy, amino, alkylamino, dialkylamino, (thio)amido, alkyl (thio)amido, alkylthio, cyano, mercapto, nitro, and mono-, di-, or tri-halo methyl, ketone, carboxylic acid, thioc acid, alkylester, a surface-reactive group, a solid surface, or a functional group that can be linked to a reactive group on the solid surface;
$R_6$ is H, hydroxy, alkyl, alkoxy, fluoro, chloro, bromo, a mono-, di-, or tri-halo alkoxy, amino, alkylamino, dialkylamino, (thio)amido, alkyl(thio)amido, alkylthio, cyano, mercapto, nitro, and mono-, di-, or tri-halo methyl, ketone, carboxylic acid, alkylester, a surface-reactive group, a solid surface, or a functional group that can be linked to a reactive group on the solid surface; and
$R_7$-$R_{10}$ are independently selected from H, hydroxy, alkyl, alkoxy, fluoro, chloro, bromo, amino, alkylamino, dialkylamino, (thio)amido, alkyl(thio)amido, alkylthio, cyano, mercapto, nitro, and mono-, di-, or tri-halo methyl, ketone, carboxylic acid, thioic acid, and alkylester.

As used in the preceding definitions, alkyl substituents are C1 to C6 alkyls, preferably methyl or ethyl groups. In the various substituents, an optional thio-derivative identified using, e.g., (thio)amido, is intended to encompass both amido and thioamido groups.

As used in the definition of $R_3$-$R_6$, the solid surface can be any solid surface, including glass, plastics, metals, semiconductor materials, ceramics, and natural or synthetic polymers (e.g., agarose, nitrocellulose). The solid surface can be an optically transparent material.

By surface-reactive group, it is intended that the group is a carboxylic acid (which can be modified by a carbodiimide to react with amines or alcohols), NHS ester, imidoester, PFP ester, p-nitrophenyl ester, hydroxymethyl phosphine, maleimide, haloacetyl group, haloacetamide group, vinyl sulfone, hydrazide, isocyanate, oxirane, epoxide, thiol, amine, alkyne, azide, anhydride, sulfonyl chloride, acyl chloride, ethylenimine, mixed disulfides, activated disulfides, or thiosulfinate. By functional group that can be linked to a reactive group on a solid surface, it is intended that the group is any reactive group, including without limitation, carboxyl, amine, sulfhydryl, aldehyde, hydroxyl, thiol, or any of the groups listed as suitable for the surface-reactive group.

The compounds of the invention also encompass salts, particularly phenolate salts.

Other known compounds within the scope of formula I include those where Ar is phenyl, Z and Y are both N, and either (i) $R_3$-$R_5$ are all H; (ii) $R_1$ and $R_2$ are methyl, $R_4$ and $R_5$ are H, and $R_3$ is hydroxy, methoxy, or dimethylamino; and (iii) $R_1$ is methyl, $R_4$ and $R_5$ are H, $R_3$ is hydroxy, and $R_2$ is a conjugated hydrocarbon chain. Other such compounds of formula I include those disclosed in He et al., "Synthesis and Spectroscopic Studies of Model Red Fluorescent Protein Chromophores," *Org. Lett.* 4(9):1523-26 (2002); You et al., "Fluorophores Related to the Green Fluorescent Protein and Their Use in Optoelectornic Devices," *Adv. Mater.* 12(22):1678-81 (2000); and Bourotte et al., "Fluorophores Related to the Green Fluorescent Protein," *Tetr. Lett.* 45:6343-6348 (2004), each of which is hereby incorporated by reference in its entirety). In certain embodiments, these previously known compounds are excluded from the scope of the invention.

Subclasses of these fluorophores, including oxazolithiones, pyrrolinthiones, imidazolithiones, and furanthiones, as well as those possessing an oxazolone ring, imidazolone ring, furanone ring, or pyrrolinone ring, are shown and/or described in PCT Application Publ. No. WO 2010/096584 to Jaffrey and Paige, which is hereby incorporated by reference in its entirety. In certain embodiments, these previously known compounds are excluded from the scope of the invention.

Further diversification of the compounds can be achieved by conversion of an $R_2$ methyl group in compounds of formula I into an aldehyde using selenium dioxide (with dioxane under reflux). The resulting aldehyde can be converted into a $C_{2-8}$ unsaturated hydrocarbon, preferably a conjugated hydrocarbon, using the Wittig reaction. Basically, the resulting aldehyde is reacted with a triphenyl phosphine (e.g., $Ph_3P{=}R_{10}$ where $R_{10}$ is the unsaturated hydrocarbon) in the presence of strong base. The unsaturated hydrocarbon that is present in the Wittig reactant is optionally terminated with any desired functional group, preferably an amine, amide, carboxylic acid, (meth)acrylate, ester, enone, oxime, O-methyl-oxime, imine, nitromethane, nitrile, ketone, mono-, di-, tri-halo, nitro, cyano, acrylonitrile, acrylonitrile-enoate, acrylonitrile-carboxylate, acrylonitrile-amide, or a second aromatic or hetero-aromatic ring. These reactants are commercially available or readily synthesized by persons of skill in the art. Alternatively, the resulting aldehyde can be reacted with hydroxylamine or methoxyamine derivative according to the procedure of Maly et al., "Combinatorial Target-guided Ligand Assembly: Identification of Potent Subtype-selective c-Src Inhibitors," *Proc. Natl. Acad. Sci. U.S.A.* 97(6): 2419-24 (2002), which is hereby incorporated by reference in its entirety) (see compounds of formulae Ma, Mb below). The aldehyde can also be reacted with nitromethane to form acrylonitro groups according to established protocols (see Muratore et al., "Enantioselective Bronsted Acid-catalyzed N-acyliminium Cyclization Cascades," *J. Am. Chem. Soc.* 131(31): 10796-7 (2009); Crowell and Peck, *J. Am. Chem. Soc.* 75:1075 (1953), each of which is hereby incorporated by reference in its entirety). Additionally, aldehydes can be reacted with nucleophilic cyano-containing molecules such as 2-cyanoacetamide, malononitrile methylcyanoacetate, cyano acetic acid, etc., in a Knoevenagel condensation reaction to produce acrylonitrile groups with different functional groups (Cope et al., *J. Am. Chem. Soc.* 63:3452 (1941), which is hereby incorporated by reference in its entirety).

Alternatively, the $R_2$ methyl can be replaced with a mono-, di-, or tri-halomethyl group. Halo-substituted acetamides are readily available, and are sufficiently reactive with the arylaldehydes.

In the compounds of formula I, Ar can be any single or multiple (including fused) ring structure, except as noted above when Ar is phenyl. Preferred Ar groups include substituted phenyl, naphthalenyl pyridinyl, pyrimidinyl, pyrrolyl, furanyl, benzofuranyl, thiophene-yl, benzothiophene-yl, thiazolyl, benzothiazolyl, imidizolyl, benzoimidizolyl, oxazolyl, benzoxazolyl, purinyl, indolyl, quinolinyl, chromonyl, or coumarinyl groups. The substituents of these Ar groups can be one or more of hydrogen, hydroxy, alkyl, alkoxy, fluoro, chloro, bromo, a mono-, di-, or tri-halo alkoxy, amino, alkylamino, dialkylamino, (thio)amido, alkyl (thio)amido, alkylthio, cyano, mercapto, nitro, and mono-, di-, or tri-halo alkyl, ketone, carboxylic acid, and thioc acid. The aromatic or hetero-aromatic group terminating the $R_2$ group can also be any one or the Ar groups identified above.

Other suitable subclasses of these compounds are the tri-substituted benzylidene imidazolones of formulae II, Ma, and Mb as described in PCT Application Publ. Nos. WO 2010/096584 and WO 2013/016694, both to Jaffrey et al., which are hereby incorporated by reference in their entirety.

Exemplary fluorophores identified in the above-referenced PCT Application Publ. Nos. WO 2010/096584 and WO 2013/016694 to Jaffrey et al. include, without limitation: 4-(3,4,5-trimethoxybenzylidene)-1,2-dimethyl-imidazol-5-one ("TMBI"); 4-(4-hydroxy-3,5-dimethoxybenzylidene)-1,2-dimethyl-imidazol-5-one ("DMHBI"); 4-(3,5-difluoro-4-hydroxybenzylidene)-1,2-dimethyl-imidazol-5-one ("DFHBI"); (E)-4-(3,5-difluoro-4-hydroxybenzylidene)-1-methyl-5-oxo-4,5-dihydro-1H-imidazole-2-carbaldehyde O-methyl oxime ("DFHBI-methyloxime"); 4-(3,5-dichloro-4-hydroxybenzylidene)-1,2-dimethyl-imidazol-5-one; 4-(3,5-dibromo-4-hydroxybenzylidene)-1,2-dimethyl-imidazol-5-one; 4-(2-hydroxybenzylidene)-1,2-dimethyl-imidazol-5-one ("o-HBI"); 4-(2-methoxybenzylidene)-1,2-dimethyl-imidazol-5-one; 4-(3-fluoro-4-hydroxy-5-methoxybenzylidene)-1,2-dimethyl-imidazol-5-one; 4-(4-(dimethylamino)benzylidene)-1,2-dimethyl-imidazol-5-one ("DMABI"); 4-(4-(t-butylthio)benzylidene)-1,2-dimethyl-imidazol-5-one; 4-(4-(methylthio)benzylidene)-1,2-dimethyl-imidazol-5-one; 4-(4-cyanobenzylidene)-1,2-dimethyl-imidazol-5-one; 4-(3,5-difluoro-4-acetate)benzylidene-1,2-dimethyl-imidazol-5-one; 4-(4-hydroxy-3-nitrobenzylidene)-1,2-dimethyl-imidazol-5-one; 4-(4-hydroxy-3-methoxy-5-nitrobenzylidene)-1,2-dimethyl-imidazol-5-one; 4-(4-methoxy-3-nitrobenzylidene)-1,2-dimethyl-imidazol-5-one; 4-(4-bromobenzylidene)-1,2-dimethyl-imidazol-5-one; 4-(4-chlorobenzylidene)-1,2-dimethyl-imidazol-5-one; 4-(4-hydroxybenzylidene)-1,2-dimethyl-imidazol-5-one ("p-HBI"); 4-((indol-7-yl)methylene)-1,2-dimethyl-imidazole-5-one; 4-((indol-3-yl)methylene)-1,2-dimethyl-imidazole-5-one; 4-((indol-3-yl)methylene)-1-methyl-2-phenyl-imidazole-5-one; 4-(4-hydroxy-3,5-dimethoxybenzylidene)-1-methyl-2-phenyl-imidazole-5-one; 4-(4-(dimethylamino)benzylidene)-1-methyl-2-phenyl-imidazole-5-one; 4-(4-hydroxybenzylidene)-2-acetyl-1-methyl-imidazole-5-one; 4-(4-hydroxybenzylidene)-1-methyl-2-prop-1-enyl-imidazole-5-one; 3-(4-(4-hydroxybenzylidene)-4,5-dihydro-1-methyl-5-oxo-imidazol-2-yl)acrylamide; 3-(4-(4-hydroxybenzylidene)-4,5-dihydro-1-methyl-5-oxo-imidazol-2-yl)acrylic acid; and methyl 3-(4-(4-hydroxybenzylidene)-4,5-dihydro-1-methyl-5-oxo-imidazol-2-yl)acrylate. Of these, DFHBI and DFHBI-methyloxime are particularly desirable because of their distinct emission maxima and high quantum yield.

Additional conditional fluorophores include, without limitation:

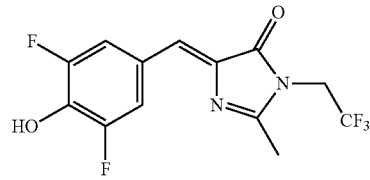 [SMILES: CC1=N/C(=C\c2cc(F)c(O)c(F)c2)C(=O)N1CC(F)(F)F]

(Z)-4-(3,5-difluoro-4-hydroxybenzylidene)-2-methyl-1-(2,2,2-trifluoroethyl)-1H-imidazol-5(4H)-one) ("DFHBI-1T")

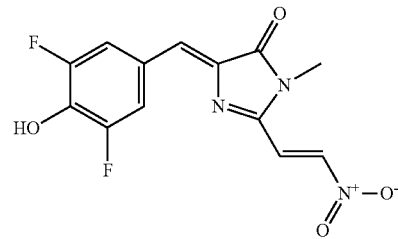 [SMILES: CN1C(=O)/C(=C/c2cc(F)c(O)c(F)c2)N=C1/C=C/[N+](=O)[O-]]

4-(3,5-difluoro-4-hydroxybenzylidene)-1-methyl-2-((E)-2-nitrovinyl)-1H-imidazol-5(4H)-one ("DFAN")

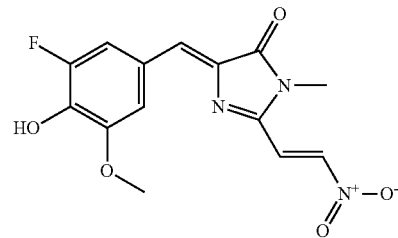 [SMILES: COc1cc(/C=C2N=C(/C=C/[N+](=O)[O-])N(C)C\2=O)cc(F)c1O]

4-(3-fluoro-4-hydroxy-5-methoxybenzylidene)-1-methyl-2-((E)-2-nitrovinyl)-1H-imidazol-5(4H)-one;

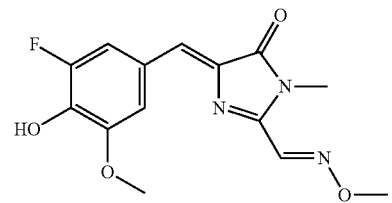 [SMILES: CO/N=C/C1=NC(=C\c2cc(F)c(O)c(OC)c2)/C(=O)N1C]

4-(3-fluoro-4-hydroxy-5-methoxybenzylidene)-1-methyl-5-oxo-4,5-dihydro-1H-imidazole-2-carbaldehyde O-methyl oxime;

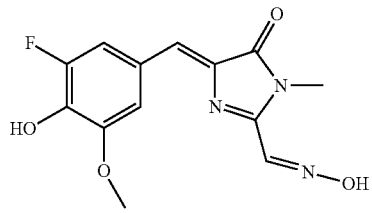 [SMILES: COc1cc(/C=C2\N=C(C=NO)N(C)C2=O)cc(F)c1O]

4-(3-fluoro-4-hydroxy-5-methoxybenzylidene)-1-methyl-5-oxo-4,5-dihydro-1H-imidazole-2-carbaldehyde oxime ("MFHO");

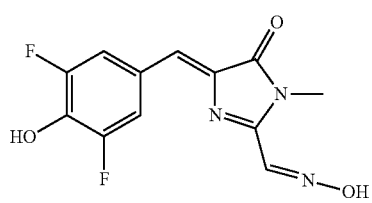 [SMILES: CN1C(=O)/C(=C/c2cc(F)c(O)c(F)c2)N=C1C=NO]

4-(3,5-difluoro-4-hydroxybenzylidene)-1-methyl-5-oxo-4,5-dihydro-1H-imidazole-2-carbaldehyde oxime ("DFHO");

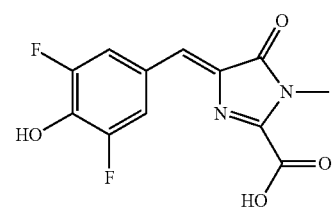 [SMILES: CN1C(=O)/C(=C/c2cc(F)c(O)c(F)c2)N=C1C(=O)O]

4-(3,5-difluoro-4-hydroxybenzylidene)-1-methyl-5-oxo-4,5-dihydro-1H-imidazole-2-carboxylic acid;

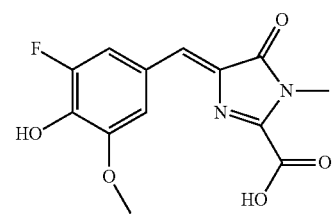 [SMILES: COc1cc(/C=C2\N=C(C(=O)O)N(C)C2=O)cc(F)c1O]

4-(3-fluoro-4-hydroxy-5-methoxybenzylidene)-1-methyl-5-oxo-4,5-dihydro-1H-imidazole-2-carboxylic acid;

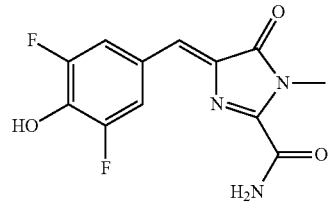 [SMILES: CN1C(=O)/C(=C/c2cc(F)c(O)c(F)c2)N=C1C(N)=O]

4-(3,5-difluoro-4-hydroxybenzylidene)-1-methyl-5-oxo-4,5-dihydro-1H-imidazole-2-carboxamide;

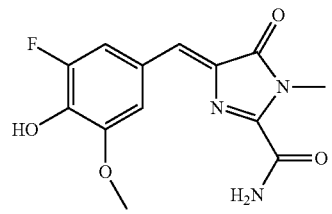

4-(3-fluoro-4-hydroxy-5-methoxybenzylidene)-1-methyl-5-oxo-4,5-dihydro-1H-imidazole-2-carboxamide;

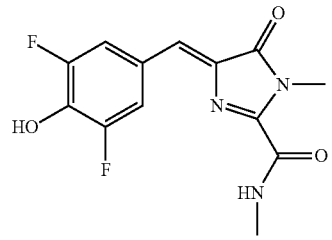 [SMILES: CNC(=O)C1=N/C(=C\c2cc(F)c(O)c(F)c2)C(=O)N1C]

4-(3,5-difluoro-4-hydroxybenzylidene)-N,1-dimethyl-5-oxo-4,5-dihydro-1H-imidazole-2-carboxamide;

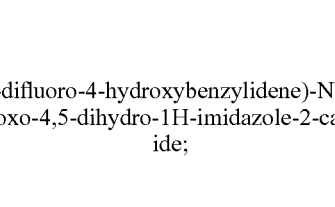

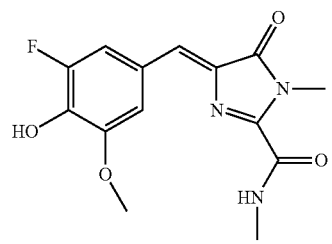 [SMILES: CNC(=O)C1=N/C(=C\c2cc(F)c(O)c(OC)c2)C(=O)N1C]

4-(3-fluoro-4-hydroxy-5-methoxybenzylidene)-N,1-dimethyl-5-oxo-4,5-dihydro-1H-imidazole-2-carboxamide;

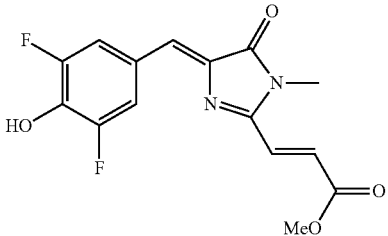

methyl 3-((Z)-4-(3,5-difluoro-4-hydroxybenzylidene)-1-methyl-5-oxo-4,5-dihydro-1H-imidazol-2-yl)acrylate ("DFAME");

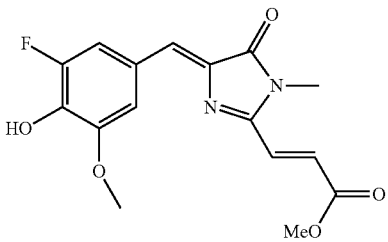 [SMILES: COC(=O)/C=C/C1=NC(=C\c2cc(F)c(O)c(OC)c2)/C(=O)N1C]

methyl 3-(4-(3-fluoro-4-hydroxy-5-methoxybenzylidene)-1-methyl-5-oxo-4,5-dihydro-1H-imidazol-2-yl)acrylate, and

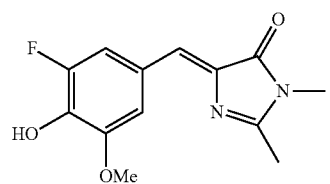 [SMILES: COc1cc(/C=C2\N=C(C)N(C)C2=O)cc(F)c1O]

4-(3-fluoro-4-hydroxy-5-methoxybenzylidene)-1,2-dimethyl-1H-imidazol-5(4H)-one ("MFHBI"). Of these, DFAN, DFAME, DFHO, MFHO, and MFHBI are particularly desirable because of their distinct emission maxima, relative to DFHBI, DFHBI-1T, and DFHBI-methyloxime, and their high quantum yield. DFHBI-1T is also desirable because of its improved properties relative to DFHBI.

If cell permeability is a problem for some fluorophores, then acylation of phenolic moieties should improve the cell permeability without impacting fluorophore activity, as these acyl moieties are rapidly cleaved by intracellular esterases (Carrigan et al., "The Engineering of Membrane-permeable Peptides," *Anal. Biochem.* 341:290-298 (2005), which is hereby incorporated by reference in its entirety). For fluorophores with low cell permeability, their O-acyl esters can be trivially made by reacting the fluorophores with the appropriate acid chloride, e.g., myristoyl, octanoyl, or butanoyl chloride. To the extent that these acyl moieties are not rapidly cleaved, these may in fact improve the fluorescence of the various RNA-fluorophore complexes.

Aptamers

The present invention also relates to nucleic acid molecules that are known in the art as aptamers. Aptamers are nucleic acid molecules characterized by a single-strand and having a secondary structure that may possess one or more stems (i.e., base-paired regions) as well as one or more non base-paired regions along the length of the stem. These non base-paired regions can be in the form of a bulge or loop (e.g., internal loop) along the length of the stem(s) and/or a loop at the end of the one or more stem(s) (e.g., hairpin loop). These nucleic acid aptamers possess specificity in binding to a particular target molecule, and they noncovalently bind their target molecule through an interaction such as an ion-ion force, dipole-dipole force, hydrogen bond, van der Waals force, electrostatic interaction, stacking interaction or any combination of these interactions.

Identifying suitable nucleic acid aptamers basically involves selecting aptamers that bind a particular target molecule with sufficiently high affinity (e.g., $K_d$<500 nM) and specificity from a pool or library of nucleic acids containing a random region of varying or predetermined length. For example, identifying suitable nucleic acid aptamers of the present invention can be carried out using an established in vitro selection and amplification scheme known as SELEX. The SELEX scheme is described in detail in U.S. Pat. No. 5,270,163 to Gold et al.; Ellington and Szostak, "In Vitro Selection of RNA Molecules that Bind Specific Ligands," *Nature* 346:818-822 (1990); and Tuerk and Gold, "Systematic Evolution of Ligands by Exponential Enrichment: RNA Ligands to Bacteriophage T4 DNA Polymerase," *Science* 249:505-510 (1990), each of which is hereby incorporated by reference in their entirety. An established template-primer system (Bartel et al., "HIV-1 Rev Regulation Involves Recognition of Non-Watson-Crick Base Pairs in Viral RNA," *Cell* 67:529-536 (1991), which is hereby incorporated by reference in its entirety) can be adapted to produce RNA molecules having a stretch of about 38-40 random bases sandwiched between 5' and 3' constant regions.

The synthetic oligonucleotide templates can be amplified by polymerase chain reaction ("PCR") and then transcribed to generate the original RNA pool. Assuming that ten percent of the RNA molecules are free of chemical lesions that prevent second-strand synthesis and transcription, this pool would contain more than $3\times10^{13}$ different sequences. Because filter binding is applicable for most protein targets, it can be used as the partitioning device, although other suitable schemes can be used. The selected primary RNA aptamers can be cloned into any conventional subcloning vector and sequenced using any variation of the dideoxy method. Next, the secondary structure of each primary RNA aptamer can be predicted by computer programs such as MulFold or mFOLD (Jaeger et al, "Improved Predictions of Secondary Structures for RNA," *Proc. Natl. Acad. Sci. U.S.A.* 86:7706-7710 (1989), and Zuker, "On Finding All Suboptimal Foldings of an RNA Molecule," *Science* 244: 48-52 (1989), each of which is hereby incorporated by reference in its entirety). Mutational studies can be conducted by preparing substitutions or deletions to map both binding sites on the RNA aptamer and its target molecule, as well as to further enhance aptamer binding affinity, as described in the accompanying Examples.

Aptamers generated from SELEX experiments can be optimized to produce second generation aptamers with improved properties (Eaton et al., "Post-SELEX Combinatorial Optimization of Aptamers," *Bioorg. Med. Chem.* 5:1087-1096 (1997), which is hereby incorporated by reference in its entirety). Through successive rounds of affinity maturation of a primary SELEX clone, it is possible to obtain aptamers that possess improved fluorescence and higher quantum yield characteristics than the original clone. Therefore, prior to using aptamers in cell-based experiments, each aptamer can be optimized using the following considerations:

Find the minimal aptamer sequence within the SELEX clone to identify the domain to subject to affinity maturation. This will lead to more desirable, smaller aptamers, which should be better for tagging RNAs with aptamers;

It is important to know if the aptamers are selective for their intended fluorophore or if they bind other fluorophores that are intended to bind to other aptamers. In dual color imaging experiments involving two RNA-fluorophore complexes, cross-reactive fluorophores would be problematic.

The fluorescence of the aptamer-fluorophore complexes may be optimized by affinity maturation. This may avoid unwanted interference or FRET.

Additionally, tagging the target molecule with multiple tandem aptamers rather than a single aptamer will increase the fluorescence of a tagged target molecule. Tagging of the aptamers should be possible without impacting the aptamer ability to bind specifically to a particular fluorophore or target molecule of interest.

If any cross-reactivity is observed, then a doped library can be prepared and subjected to "negative selection," also called "counter-SELEX." There is considerable precedent that documents the ability of negative selection to generate aptamers with high degrees of selectivity, even among closely related molecules (Tuerk et al., "Using the SELEX Combinatorial Chemistry Process to Find High Affinity Nucleic Acid Ligands to Target Molecules," *Methods Mol. Biol.* 67:219-230 (1997); Rink et al., "Creation of RNA Molecules that Recognize the Oxidative Lesion 7,8-dihydro-8-hydroxy-2'-deoxyguanosine (8-oxodG) in DNA," *Proc. Natl. Acad. Sci. U.S.A.* 95:11619-11624 (1998); Haller et al., "In vitro Selection of a 7-Methyl-guanosine Binding RNA that Inhibits Translation of Capped mRNA Molecules," *Proc. Natl. Acad. Sci. U.S.A.* 94:8521-8526 (1997); Edwards et al., "DNA-oligonucleotide Encapsulating Liposomes as a Secondary Signal Amplification Means," *Anal. Chem.* 79:1806-1815 (1997), each of which is hereby incorporated by reference in its entirety). To perform negative selection, RNAs bound to dye-agarose are subjected to a washing step in which the buffer contains other fluorophores. This results in the elution of aptamers that have undesirable cross-reactivity. The RNAs that remain bound to the agarose beads are then eluted with the fluorophore of interest, and amplified as in the classic SELEX procedure. This process is repeated until clones are generated which do not bind and activate the fluorescence of inappropriate fluorophores.

Optimization of aptamers can also be achieved during re-selection by using rigorous washing conditions in all steps, including the use of high temperature (37° C. or 45° C.) washing buffers, mild denaturants, and low salt and high salt washes, etc. Since the quantum yield may reflect the efficiency of the RNA to conformationally restrict the photoexcited fluorophores, RNA aptamers that bind more tightly to the fluorophore may improve the quantum yield, and thereby the fluorescence of the RNA-fluorophore complexes. The proposed stringent washing conditions are intended to select for aptamers that bind more tightly to the fluorophore, and thereby improve the quantum yield. An additional benefit of generating RNA aptamers that bind with higher affinity to the fluorophore is that lower concentrations of fluorophore will be needed for live-cell experiments, which may reduce potential off-target or cytotoxic effects of the fluorophore. Since most aptamers that bind to small molecules bind with modest affinity, i.e., a $K_d$ of >100 nM (Famulok et al., "Nucleic Acid Aptamers-from Selection in vitro to Applications in vivo," *Accounts Chem. Res.* 33:591-599 (2000), which is hereby incorporated by reference in its entirety), it is expected that this high affinity will not affect the resistance to photobleaching.

Another method to use during optimization is the use of a smaller bias during doping. For example, the library can be doped with a 2:1:1:1 ratio instead of 5:1:1:1. This will result in more library members being substantially different from the parent aptamer.

The SELEX procedure can also be modified so that an entire pool of aptamers with binding affinity can be identified by selectively partitioning the pool of aptamers. This procedure is described in U.S. Patent Application Publication No. 2004/0053310 to Shi et al., which is hereby incorporated by reference in its entirety.

Single stranded DNA aptamers have advantages for in vitro settings due to their ease of synthesis and greater stability. Recent studies have argued that proper buffer conditions and certain RNA sugar modifications can lead to highly stable RNAs (Osborne et al., "Aptamers as Therapeutic and Diagnostic Reagents: Problems and Prospects," *Curr. Opin. Chem. Biol.* 1:5-9 (1997); Faria et al., "Sugar Boost: When Ribose Modifications Improve Oligonucleotide Performance," *Curr. Opin. Mol. Ther.* 10:168-175 (2008), each of which is hereby incorporated by reference in its entirety). Additionally, microarrays of RNAs have been shown to be stable in the presence of tissue lysates when suitable RNAase inhibitors are added (Collett et al., "Functional RNA Microarrays for High-throughput Screening of Antiprotein Aptamers," *Anal. Biochem.* 338:113-123 (2005), which is hereby incorporated by reference in its entirety). Moreover, as part of the optimization and stabilization process, stabilizing hairpins can be added which markedly enhance aptamer levels in cells (Blind et al., "Cytoplasmic RNA Modulators of an Inside-out Signal-transduction Cascade," *Proc. Natl. Acad. Sci. U.S.A.* 96:3606-3610 (1999), which is hereby incorporated by reference in its entirety). Regardless, DNA aptamer sequences that switch on fluorophores of the invention would be inexpensive to synthesize and provide additional assurance of sensor stability in solution phase or microarray-based assays.

Another approach for optimization of the SELEX procedure, particularly with respect to the in vivo activity of aptamers in binding to an inducing fluorescence of conditionally fluorescent molecules of the type described herein, includes FACS sorting of recombinant cells that express the aptamer and exhibit fluorescence in the presence of both a properly folded aptamer and an appropriately selected conditionally fluorescent molecule. Briefly, SELEX is carried out until the RNA pool exhibits the capacity to bind to the conditional fluorophore of interest. At this point, the RNA pool is reverse transcribed and cloned into a bacterial expression plasmid to prepare an aptamer expression library. According to one embodiment, the aptamer is cloned so that it is transcribed fused to a suitable aptamer-folding scaffold, e.g., $tRNA^{Lys}_3$ (Ponchon et al., "Recombinant RNA Technology: the tRNA Scaffold," *Nat Methods* 4(7): 571-6 (2007); Paige et al, "RNA Mimics of Green Fluorescent Protein," *Science* 333(6042): 642-6 (2011); and Strack et al., "A Superfolding Spinach2 Reveals the Dynamic Nature of Trinucleotide Repeat-Containing RNA," *Nat Methods* 10(12):1219-24 (2013), which are hereby incorporated by reference in their entirety).

After transformation of the library into bacterial host cells and transcription induction, bacteria are then sorted by FACS in presence of the conditional fluorophore to identify those aptamers that exhibit the highest fluorescence. In certain embodiments, the plasmid may also contain a separate promoter for expressing a far-red fluorescent protein which allows the aptamer fluorescence to be normalized to cell volume. Sorted bacteria are recovered and grown on agar dishes and imaged in presence of the fluorophore. Plasmid DNA from the brightest colonies can be isolated, sequenced and transcribed into RNA for further characterization (see FIG. 7A). This process can be repeated for more than one round.

Overall, the protocol described above offers a rapid and efficient way to isolate fluorescent aptamers from the large initial random library.

SELEX can be performed as readily with DNA as with RNA (Breaker, "DNA Aptamers and DNA Enzymes," *Curr. Opin. Chem. Biol.* 1:26-31 (1997), which is hereby incorporated by reference in its entirety). The absence of a 2'-OH does not substantially impair the ability of DNA to fold or adopt structures. Indeed, SELEX has been used to identify DNAs that bind both small molecules and proteins, with structures that are reminiscent of RNA aptamers. Thus, DNA aptamers can be developed and subjected to analogous mutagenesis and truncation studies to identify entry points and analyte sensors as described herein.

As used herein, "nucleic acid" includes both DNA and RNA, in both D and L enantiomeric forms, as well as derivatives thereof (including, but not limited to, 2'-fluoro-, 2'-amino, 2'O-methyl, 5'iodo-, and 5'-bromo-modified polynucleotides). Nucleic acids containing modified nucleotides (Kubik et al., "Isolation and Characterization of 2'fluoro-, 2'amino-, and 2'fluoro-amino-modified RNA Ligands or Human IFN-gamma that Inhibit Receptor Binding," *J. Immunol.* 159:259-267 (1997); Pagratis et al., "Potent 2'-amino, and 2'-fluoro-2'-deoxy-ribonucleotide RNA Inhibitors of Keratinocyte Growth Factor," *Nat. Biotechnol.* 15:68-73 (1997), each which is hereby incorporated by reference in its entirety) and the L-nucleic acids (sometimes termed Spiegelmers®), enantiomeric to natural D-nucleic acids (Klussmann et al., "Mirror-image RNA that Binds D-adenosine," *Nat. Biotechnol.* 14:1112-1115 (1996) and Williams et al., "Bioactive and nuclease-resistant L-DNA Ligand of Vasopressin," *Proc. Natl. Acad. Sci. U.S.A.* 94:11285-11290 (1997), each which is hereby incorporated by reference in its entirety), and non-natural bases are used to enhance biostability. In addition, the sugar-phosphate backbone can be replaced with a peptide backbone, forming a peptide nucleic acid (PNA), other natural or non-natural sugars can be used (e.g., 2'-deoxyribose sugars), or phosphothioate or phosphodithioate can be used instead of phosphodiester bonds. The use of locked nucleic acids (LNA) is also contemplated.

According to one embodiment, the nucleic acid molecule includes a domain—an aptamer—that binds specifically to a fluorophore having a methyne bridge between a substituted aromatic ring system and a substituted imidazol(thi)one, oxazol(thi)one, pyrrolin(thi)one, or furan(thi)one ring. Preferably, the fluorophore is a compound according to any of formulae recited in PCT Application Publ. Nos. WO 2010/096584 and WO 2013/016694 to Jaffrey et al., which are briefly described above. These nucleic acid aptamers, upon binding to the fluorophore, induces the fluorophore to adopt a conformation whereby the fluorescent emission spectrum is substantially enhanced upon exposure to radiation of suitable wavelength.

According to one embodiment, a nucleic acid aptamer includes the nucleotide sequence of SEQ ID NO: 73 or SEQ ID NO: 2 below:

```
                                            SEQ ID NO: 73
AUGGUGAAGGACGGGUCCA-N-UUGUUGAGUAGAGUGUGAGCUCCGU,
``` where N at position 20 can be any single nucleotide base (A, U, G, or C) or an insertion of any length of various nucleotide bases, which may or may not conditionally alter the folding structure of nucleotides 1-19 and 21-45 of SEQ ID NO: 73 (see FIG. 1B); or

```
                                           (SEQ ID NO: 2)
GAUGUAACUGAAUGAAAUGGUGAAGGACGGGUCCAGUAGGCUGCUUCGGC

AGCCUACUUGUUGAGUAGAGUGUGAGCUCCGUAACUAGUUACAUC, (see FIG. 1B).
```

Both of these aptamer sequences can be preceded or followed by additional nucleotide sequences at their 5' and 3' ends that do not materially affect the relevant structure or binding activity. Both of these aptamers bind to DFHBI and DFHBI-1T to induce fluorescence in the green region of the visible spectrum.

According to another embodiment, a nucleic acid aptamer includes the nucleotide sequence of SEQ ID NO: 74 or SEQ ID NO: 75 below:

```
                                            SEQ ID NO: 74
GAGANGGUCGGGUCCAGN-N-GCUGUNGAGUAGAGUGUGGGCUC,
``` where N at each of positions 5, 18, and 25 can be any single nucleotide base (A, U, G, or C), and N at position 19 can be any single nucleotide base (A, U, G, or C) or an insertion of any length of various nucleotide bases, which may or may not conditionally alter the folding structure of nucleotides 1-18 and 20-42 of SEQ ID NO: 74 (see FIG. 10); or

```
                                            SEQ ID NO: 75
GAGACGGUCGGGUCCAGAUAUUCGUAUCUGUCGAGUAGAGUGUGGGCU
C, (see FIG. 10).
```

Both of these aptamer sequences can be preceded or followed by additional nucleotide sequences at their 5' and 3' ends that do not materially affect the relevant structure or binding activity. Both of these aptamers bind to DFHBI and DFHBI-1T to induce fluorescence in the green region of the visible spectrum.

According to yet another embodiment, a nucleic acid aptamer includes the nucleotide sequence of SEQ ID NO: 76 below:

```
                                            SEQ ID NO: 76
            CGANGAAGGAGGUCUNAGGAGGUCANNG,
``` where N at each of positions 4, 16, 26, and 27 can be any single nucleotide base (A, U, G, or C. These aptamer sequences can be preceded or followed by additional nucleotide sequences at their 5' and 3' ends that do not materially affect the relevant structure or binding activity. These aptamers bind to DFHO to induce fluorescence in the yellow region of the visible spectrum. According to one embodiment, the nucleic acid aptamer that induces fluorescence in the yellow region of the visible spectrum includes or is the nucleotide sequence of SEQ ID NO: 82 below:

```
                                            SEQ ID NO: 82
GGGAGACGCAACTGAATGGCGCGAAGAAGGAGGTCTGAGGAGGTCACTG
CGCCGGCAGTGGGGCGTCTCCC, .
```

According to a further embodiment, a nucleic acid aptamer includes the nucleotide sequence of SEQ ID NO: 78 below:

```
                                            SEQ ID NO: 78
     GAGACGGUCGGGUCCAG-N-CUGUUGAGUAGCGUGUGGGCUC,
``` where N at position 18 can be any single nucleotide base (A, U, G, or C) or an insertion of any length of various nucleotide bases, which may or may not conditionally alter the folding structure of nucleotides 1-17 and 20-40 of SEQ ID NO: 78. These aptamer sequences can be preceded or followed by additional nucleotide sequences at their 5' and 3' ends that do not materially affect the relevant structure or binding activity. These aptamers bind to DFHO to induce fluorescence in the orange region of the visible spectrum. According to one embodiment, the nucleic acid aptamer that induces fluorescence in the orange region of the visible spectrum includes or is the nucleotide sequence of SEQ ID NO: 83 below:

```
                                            SEQ ID NO: 83
GACGCAACTGAATGAAATtGTtAAGGAGACGGTCGGGTCCAGGTGCACAA
ATGTGGCCTGTTGAGTAGCGTGTGGGCTCCGTAACTAGTCGCGTC, .
```

According to a further embodiment, a nucleic acid aptamer includes the nucleotide sequence of SEQ ID NO: 79 below:

```
                                            SEQ ID NO: 79
     GAGACGGUCGGGUCCAG-N-CUGUUGAGUAGUGUGUGGGCUC,
``` where N at position 18 can be any single nucleotide base (A, U, G, or C) or an insertion of any length of various nucleotide bases, which may or may not conditionally alter the folding structure of nucleotides 1-17 and 20-40 of SEQ ID NO: 79. These aptamer sequences can be preceded or followed by additional nucleotide sequences at their 5' and 3' ends that do not materially affect the relevant structure or binding activity. These aptamers bind to DFHO to induce fluorescence in the red region of the visible spectrum. According to one embodiment, the nucleic acid aptamer that induces fluorescence in the red region of the visible spectrum includes or is the nucleotide sequence of SEQ ID NO: 84 below:

```
                                            SEQ ID NO: 84
GACGCAACTGAATGAAATGTTTTCGGAGACGGTCGGGTCCAGTCCCAA
CGATGTTGGCTGTTGAGTAGTGTGTGGGCTCCGTAACTAGTCGCGTC, .
```

The nucleic acid aptamers of the present invention include both monovalent aptamers that contain a single first domain for binding to the fluorophore, as well as multivalent aptamers that contain more than one aptamer domain.

According to one embodiment, the nucleic acid aptamer molecule can include a plurality of first domains for binding to multiple identical fluorophore compounds per molecule. These can be in the form of concatamers of a single type of aptamer that binds to a single fluorophore. Examples of these concatamers that are useful for expanding the fluorescent emissions per molecule include 2-mers, 4-mers, 8-mers, 12-mers, 16-mers, and 32-mers. In forming these concatamers, the plurality of aptamer domains can be separated by linker regions of a suitable length (e.g., about 30 to about 100 nts) that prevents steric or folding interference between the distinct aptamer domains, allowing each to properly fold and bind to their target fluorophores. Alternatively, the concatamers can contain multiple types of aptamers that bind to a several different fluorophores, and collectively achieve a blended emission profile.

According to another embodiment, the nucleic acid aptamer molecules can include one or more first domains that bind specifically to multiple identical fluorophore compounds per molecule, and one or more second domains that bind specifically to a target molecule of interest (i.e., one that is distinct of the fluorophore). Also contemplated herein are concatamers of these dual domain aptamer molecules, having the structure (first domain-second domain)$_m$, where m is an integer greater than 1. In these concatamers, the first domain of each functional two-domain sensor can be the same or different. Likewise, the second domain of each functional two-domain sensor can be the same or different. In another embodiment, the concatamer includes a plurality of first domains, which can be the same or different but bind specifically to the same fluorophore, and a single second domain that binds specifically to the target molecule of interest.

The target molecule of interest can be any biomaterial or small molecule including, without limitation, proteins, nucleic acids (RNA or DNA), lipids, oligosaccharides, carbohydrates, small molecules, hormones, cytokines, chemokines, cell signaling molecules, metabolites, organic molecules, and metal ions. The target molecule of interest can be one that is associated with a disease state or pathogen infection.

In one embodiment, the second domain is itself an aptamer that binds specifically to the target molecule.

In another embodiment, the second domain binds specifically to a target nucleic acid via hybridization (e.g., Watson-Crick base-pairing). Thus, the second domain has a nucleotide sequence that is sufficiently complementary to its target nucleic acid so as to hybridize under appropriate conditions with a target nucleic acid molecule that is physiologically found within a cell or within a biological sample. Upon hybridization between the second domain and the target, and the binding of the first domain to a fluorophore (introduced to the sample or cell), the target nucleic acid molecule is effectively labeled by the fluorophore. Presence of the target nucleic acid therefore can be detected based on the presence of fluorescence by the particular fluorophore employed.

Protein or polypeptide targets can be any length, and can include, without limitation, phosphoproteins, lipid-modified proteins, nitrosylated proteins, sulfenated proteins, acylated proteins, methylated proteins, demethylated proteins, C-terminal amidated proteins, biotinylated proteins, formylated proteins, gamma-carboxylated proteins, glutamylated proteins, glycylated proteins, iodinated proteins, hydroxylated proteins, isoprenylated proteins, lipoylated proteins (including prenylation, myristoylation, farnesylation, palmitoylation, or geranylation), proteins covalently linked to nucleotides such as ADP ribose (ADP-ribosylated) or flavin, oxidated proteins, proteins modified with phosphatidylinositol groups, proteins modified with pyroglutamate, sulfated proteins, selenoylated proteins, proteins covalently linked to another protein (including sumoylation, neddylation, ubiquitination, or ISGylation), citrullinated proteins, deamidated proteins, eliminylated proteins, disulfide bridged proteins, proteolytically cleaved proteins, proteins in which proline residues have been racemized, any peptides sequences that undergo the above mentioned modifications, and proteins which undergo one or more conformational changes. In addition, proteins or peptides that possess a mutation can be distinguished from wildtype forms. Complexes of two or more molecules include, without limitation, complexes have the following interactions: protein-protein, protein-cofactor, protein-inhibiting small molecules, protein-activating small molecules, protein-small molecules, protein-ion, protein-RNA, protein-DNA, DNA-DNA, RNA-DNA, RNA-RNA, modified nucleic acids-DNA or RNA, aptamer-aptamer. In addition, nucleic acids that possess a mutation can be distinguished from wildtype forms.

Nucleic acid targets can be any type of nucleic acid including, without limitation, DNA, RNA, LNA, PNA, genomic DNA, viral DNA, synthetic DNA, DNA with modified bases or backbone, mRNA, noncoding RNA, PIWI RNA, termini-associated RNA, promoter-associated RNA, tRNA, rRNA, microRNA, siRNA, post-transcriptionally modified RNA, synthetic RNA, RNA with modified bases or backbone, viral RNA, bacteria RNA, RNA aptamers, DNA aptamers, ribozymes, and DNAzymes.

Lipid targets include, without limitation, phospholipids, glycolipids, mono-, di-, tri-glycerides, sterols, fatty acyl lipids, glycerolipids, glycerophospholipids, sphingolipids, sterol lipids, prenol lipids, saccharolipids, polyketides, eicosanoids, prostaglandins, leukotrienes, thromboxanes, N-acyl ethanolamine lipids, cannabinoids, anandamides, terpenes, and lipopolysaccharides.

Small molecule targets include, without limitation, carbohydrates, monosaccharides, polysaccharides, galactose, fructose, glucose, amino acids, peptides, nucleic acids, nucleotides, nucleosides, cyclic nucleotides, polynucleotides, vitamins, drugs, inhibitors, single atom ions (such as magnesium, potassium, sodium, zinc, cobalt, lead, cadmium, etc.), multiple atom ions (such as phosphate), radicals (such as oxygen or hydrogen peroxide), and carbon-based gases (carbon dioxide, carbon monoxide, etc.).

Targets can also be whole cells or molecules expressed on the surface of whole cells. Exemplary cells include, without limitation, cancer cells, bacterial cells, or normal cells. Targets can also be viral particles.

A number of aptamers for these classes of target biomolecules have been identified previously, and can be incorporated into the multivalent nucleic acid aptamer constructs of the present invention. For example, other known RNA aptamers include, without limitation, RNA ligands of T4 DNA polymerase, RNA ligands of HIV reverse transcriptase, RNA ligands of bacteriophage R17 coat protein, RNA ligands for nerve growth factor, RNA ligands of HSV-1 DNA polymerase, RNA ligands of *Escherichia coli* ribosomal protein 51, and RNA ligands of HIV-1 Rev protein (U.S. Pat. No. 5,270,163 to Gold et al., which is hereby incorporated by reference in its entirety); RNA ligands of *Bacillus subtilis* ribonuclease P (U.S. Pat. No. 5,792,613 to Schmidt et al., which is hereby incorporated by reference); RNA ligands of ATP and RNA ligands of biotin (U.S. Pat. No. 5,688,670 to Szostak et al., which is hereby incorporated by reference in its entirety); RNA ligands of prion protein (Weiss et al., "RNA Aptamers Specifically Interact with the Prion Protein PrP," *J. Virol.* 71(11):8790-8797 (1997), which is hereby incorporated by reference in its entirety); RNA ligands of hepatitis C virus protein NS3 (Kumar et al., "Isolation of RNA Aptamers Specific to the NS3 Protein of Hepatitis C Virus from a Pool of Completely Random RNA," *Virol.* 237(2):270-282 (1997); Urvil et al., "Selection of RNA Aptamers that Bind Specifically to the NS3 Protein of Hepatitis C Virus," *Eur. J. Biochem.* 248(1): 130-138 (1997); Fukuda et al., "Specific RNA Aptamers to NS3 Protease Domain of Hepatitis C Virus," *Nucleic Acids Symp. Ser.* 37:237-238 (1997), each of which is hereby incorporated by reference in its entirety); RNA ligands of chloramphenicol (Burke et al., "RNA Aptamers to the Peptidyl Transferase Inhibitor Chloramphenicol," *Chem. Biol.* 4(11):833-843 (1997), which is hereby incorporated by reference in its entirety); RNA ligands of the adenosine moiety of S-adenosyl methionine (Burke and Gold, "RNA Aptamers to the Adenosine Moiety of S-Adenosyl Methionine: Structural Inferences from Variations on a Theme and the Reproducibility of SELEX," *Nucleic Acids Res.* 25(10): 2020-2024 (1997), which is hereby incorporated by reference in its entirety); RNA ligands of protein kinase C (Conrad et al., "Isozyme-Specific Inhibition of Protein Kinase C by RNA Aptamers," *J. Biol. Chem.* 269(51): 32051-32054 (1994); Conrad and Ellington, "Detecting Immobilized Protein Kinase C Isozymes with RNA Aptamers," *Anal. Biochem.* 242(2):261-265 (1996), each which is hereby incorporated by reference in its entirety); RNA ligands of subtilisin (Takeno et al., "RNA Aptamers of a Protease Subtilisin," *Nucleic Acids Symp. Ser.* 37:249-250 (1997), which is hereby incorporated by reference in its entirety); RNA ligands of yeast RNA polymerase II (Thomas et al., "Selective Targeting and Inhibition of Yeast RNA Polymerase II by RNA Aptamers," *J. Biol. Chem.* 272(44): 27980-27986 (1997), which is hereby incorporated by reference in its entirety); RNA ligands of human activated protein C (Gal et al., "Selection of a RNA Aptamer that Binds to Human Activated Protein C and Inhibits its Protein Function," *Eur. J. Biochem.* 252(3):553-562 (1998), which is hereby incorporated by reference in its entirety); and RNA ligands of cyanocobalamin (Lorsch and Szostak, "In vitro Selection of RNA Aptamers Specific for Cyanocobalamin," *Biochem.* 33(4):973-982 (1994), which is hereby incorporated by reference in its entirety). Additional RNA aptamers are continually being identified and isolated by those of ordinary skill in the art, and these, too, can be incorporated into the multivalent aptamer constructs of the present invention.

According to one embodiment, the multivalent nucleic acid aptamer molecules of the invention include a first domain that binds to the fluorophore substantially only after the second domain binds to the target molecule. As demonstrated in the examples, in multivalent nucleic acid aptamer molecules of this type, the second domain possesses a stable structure and is capable of binding to the target molecule, whereas the first domain or regions of the nucleic acid molecule adjacent to the first domain possess a structure that is substantially incapable of binding the fluorophore (or does so with reduced affinity). Upon binding of the target molecule by the second domain, however, the secondary structure of the first domain is altered and adopts a structure that is capable of binding the fluorophore with sufficiently high affinity. As a consequence of target molecule binding, the fluorophore becomes bound by the first domain and upon exposure to radiation of appropriate wavelength emits a fluorescent emission signal. Multivalent aptamers of this type can be used as "turn-on" sensors.

To facilitate the ability of these sensors to "turn-on" in the presence of the target analyte, the aptamer for the target molecule can be coupled at its 5' and 3' ends to the aptamer specific for the fluorophore via a transducer molecule. The transducer molecule includes a pair of antiparallel stem-forming sequences, one coupled by phosphodiester bond between a first portion of the fluorophore-specific aptamer and a 5' end of the target-binding aptamer, and the other coupled by phosphodiester bond between a second portion of the fluorophore-specific aptamer and a 3' end of the target-binding aptamer. The transducer molecule preferably includes one or more mismatched base pairs or an overall low number of base pairs (e.g., one or two base pairs) such that stem formation of the transducer molecule is thermodynamically unfavorable in the absence of target molecule binding to the target-binding aptamer, and thermodynamically favorable after target molecule binding to the target-binding aptamer.

As described in PCT Application Publ. Nos. WO 2010/096584 and WO 2013/016694, both to Jaffrey et al., which are hereby incorporated by reference in their entirety, multivalent aptamer sensors of this embodiment have been developed that are specific for the biomolecules ADP, adenosine, guanine, GTP, SAM, and streptavidin. As demonstrated in the accompanying Examples, the aptamer sequences described above can be similarly modified to form "turn-on" sensors of this type.

According to another embodiment, the multivalent nucleic acid aptamer molecule of the invention includes a first domain that binds to the fluorophore substantially only in the absence of the second domain binding to the target molecule. In multivalent nucleic acid aptamer molecules of this type, the second domain possesses a stable structure and is capable of binding to the target molecule, and the first domain or regions of the nucleic acid molecule adjacent to the first domain possess a structure that is capable of binding the fluorophore with sufficiently high affinity. Upon binding of the target molecule by the second domain, however, the secondary structure of the first domain is altered and adopts a structure that is substantially incapable of binding the fluorophore with high affinity. As a consequence of target molecule binding, the fluorophore dissociates from the first domain and despite exposure to radiation of appropriate wavelength the fluorophore will no longer emit a fluorescent emission signal (or emits only a substantially diminished level of fluorescent emissions). Multivalent aptamers of this type can be used as "turn-off" sensors.

As discussed below, the monovalent aptamers and aptamer constructs of the invention can be used as sensors for tracking the presence, location, or quantity of a fused nucleic acid molecule of interest in a cell or an in vitro sample; for determining the presence, location, or quantity of a target molecule of interest in a cell or an in vitro sample; for high throughput screening assays to assess the ability of an agent to modulate certain cellular functions, such as transcription levels or splicing, or for modulating the activity or availability of a target molecule; for microarray detection of analytes or genes of interest; and de novo screening of sensor molecules for particular targets of interest using a modified SELEX.

In many of these aptamer constructs, where a single fluorophore binding domain is used, the single fluorophore binding domain can be replaced with a concatamer containing multiple fluorophore binding domains. For example, multiple fluorophore binding sequences, e.g., 8, 12, 16, 20, 24, or more, can be linked together in series with adjacent fluorophore binding sequences separated by a spacer sequence that is sufficiently long (e.g., 2 to 100 nucleotides) so as to inhibit interference between adjacent fluorophore binding sequences. In certain embodiments, the fluorophore binding sequences can be slightly different from one another (or at least relative to immediately adjacent fluorophore binding sequences) to ensure that each aptamer sequence self-hybridizes to fold properly rather than hybridize with other aptamer sequences. Because each individual aptamer sequence within the concatamer is capable of binding to its fluorophore, use of the concatamer is expected to increase the fluorescence per aptamer construct. In this way, it is possible to design aptamer constructs where as few as a single molecule can be detected.

The nucleic acid aptamer molecules of the present invention can also be directed to specific cellular locations by creating nucleic acid fusion with a nucleic acid sequence that is targeted to specific domains in the cells due to intrinsic sequence properties, because they bind biomolecules or proteins that are at these cellular locations.

According to another embodiment, a nucleic acid aptamer construct of the invention includes one or more first domains that bind specifically to multiple identical fluorophore compounds per molecule, and a second domain that includes a random nucleotide sequence.

By "random," it is contemplated that the entirety of the second domain, or merely a portion thereof, contains a nucleotide sequence that is not known a priori, but rather is generated randomly. Thus, a portion of the second domain may contain a known sequence, but the entirety of the second domain sequence is not known. Multivalent aptamer constructs of this type are prepared as "turn-on" sensors, as described above, and are useful for de novo screening and identification of aptamers having affinity for a target molecule of interest. These multivalent nucleic acid aptamer constructs can be generated during a modified SELEX process as described hereinafter. Thus, the present invention also encompasses a library of these multivalent nucleic acid aptamer constructs. In the library, each member of the initial library preferably contains a unique or substantially unique random sequence (i.e., shared by few, if any, other initial library members).

Molecular Complexes

A further aspect of the invention relates to molecular complexes that are formed using the fluorescent compounds and nucleic acid aptamers of the present invention, which are specifically bound to the fluorescent compounds such that the fluorophore has substantially enhanced fluorescence (i.e., in comparison to the fluorophore prior to specific binding) upon exposure to radiation of suitable wavelength.

According to one embodiment, the nucleic acid molecule includes one or more first domains, as described above, and the molecular complex is therefore formed by the nucleic acid molecule and one or more fluorescent compounds that are bound to at least one, and optionally all, of the first domains present in the nucleic acid molecule. These molecular complexes can exist in vitro, in isolated form, or in vivo following introduction of the nucleic acid molecule (or a genetic construction or expression system encoding the same) into a host cell.

According to another embodiment, the nucleic acid molecule includes one or more first domains and a second domain that binds specifically to a target molecule of interest. The molecular complex, therefore, can include the nucleic acid molecule, the target molecule (bound specifically by the second domain), and one or more fluorescent compounds that are bound to the first domain(s). These molecular complexes can exist in vitro, in isolated form or tethered to a substrate such as on an arrayed surface, or in vivo following introduction of the nucleic acid molecule (or a genetic construction or expression system encoding the same) into a host cell.

According to another embodiment, the nucleic acid molecule includes a plurality of aptamer sensor concatamers, each monomer including a first domain and a second domain. The molecular complex, therefore, can include the nucleic acid molecule, a plurality of target molecules (bound specifically by the plurality of second domains), and a plurality of fluorescent compounds that are bound to the plurality of first domain(s). These molecular complexes can exist in vitro, in isolated form or tethered to a substrate such as on an arrayed surface, or in vivo following introduction of the nucleic acid molecule (or a genetic construction or expression system encoding the same) into a host cell.

According to another embodiment, the nucleic acid molecule includes an aptamer sequence linked to a hybridization probe sequence that is complementary to a target nucleic acid molecule. The molecular complex, therefore, can include the nucleic acid molecule hybridized to the target nucleic acid molecule, and one or more fluorophores bound specifically to the fluorophore-specific aptamer domain. These molecular complexes can exist in vitro, in isolated form or tethered to a substrate such as on an arrayed surface, or in vivo following introduction of the nucleic acid molecule (or a genetic construction or expression system encoding the same) into a host cell. In certain embodiments, these complexes can exist in fixed cells or on histologic tissue sections in the manner of an in situ hybridization protocol.

Specific examples of these types of molecular complexes, formed in vitro and in vivo, are disclosed in the accompanying Examples. Although in vitro host cells are described in the accompanying Examples, it should be appreciated to skilled artisans that the host cells can be present in a whole organism, preferably a non-human organism.

For formation of the molecular complex inside a cell, the fluorophore is introduced into the cell where it can interact with (and be bound by) the aptamer that specifically binds to it. According to one approach, the cell or the sample is contacted with the fluorophore by incubating the cell or the sample with the fluorophore. The fluorophore will be taken up by the cell, where it may freely diffuse throughout the cell. According to another approach, the fluorophore is injected into the cell or administered to a plant, embryo, mammal, or transgenic animal including the cell.

Genetic Constructs

While the RNA aptamer molecules of the present invention can be synthesized from chemical precursor, they also can be prepared either in vitro or in vivo using recombinant templates or constructs, including transgenes, that encode the RNA aptamer molecules of the present invention. Whether using in vitro transcription or transgenes suitable for expression in vivo, these genetic constructs can be prepared using well known recombinant techniques.

A further aspect of the present invention relates to a constructed DNA molecule that includes a first region encoding one or more RNA aptamer molecules of the invention. Where multiple RNA aptamer molecules are present, they can be separated by a linker sequence.

According to one embodiment, the constructed DNA molecule encodes an RNA fusion product. Such a product is formed by joining together one piece of DNA encoding an RNA molecule of interest and a second piece of DNA encoding an RNA aptamer molecule that binds specifically to a fluorophore of the invention. As described above, the RNA aptamer molecule can be in the form of a concatamer that contains multiple fluorophore-binding domains.

According to another embodiment, the constructed DNA molecule encodes a molecular sensor of the invention, which is formed by joining together one piece of DNA encoding an RNA aptamer molecule that is specific for a target molecule and a second piece of DNA encoding an RNA aptamer molecule that binds specifically to a fluorophore of the invention, and optionally a third piece of DNA encoding the transducer molecule. The conjoined RNA sequences can cooperate in the manner described above, so as to achieve a "turn-on" sensor or "turn-off" sensor.

According to yet another embodiment, an empty construct can be prepared for preparation of an RNA fusion product. Such an empty construct includes a DNA sequence encoding an RNA aptamer molecule that binds specifically to a fluorophore of the invention, along with appropriate regulatory sequences (discussed below), and a restriction enzyme insertion site that can be used for subsequent insertion of a desired DNA molecule (encoding an RNA molecule of interest). As described above, the RNA aptamer molecule can include a concatamer of fluorophore-binding domains. The restriction enzyme insertion site can include one or more enzymatic cleavage sites to facilitate insertion of virtually any DNA coding sequence as desired. The restriction enzyme insertion site is preferably located between the promoter sequence and the aptamer-encoding DNA sequence.

According to a further embodiment, the constructed DNA molecule encodes an RNA aptamer of the invention, however, within the region encoding the RNA aptamer, an intron is positioned therein. This spatially segregates the RNA aptamer-encoding regions, whereby transcription in the absence of a proper spliceosome will not afford a functional aptamer molecule. In the presence of a proper spliceosome, excision of the intron from a transcript of the constructed DNA molecule affords the RNA aptamer molecule of the invention. This will allow the RNA aptamer to bind to the fluorophore to induce fluorescence.

In an alternative embodiment, the sequences within the intron contribute to the fluorophore-binding aptamer, whereby prior to splicing the RNA molecule is capable of exhibiting fluorescence when bound to the fluorophore. However, in the presence of a proper spliceosome, splicing of the RNA molecule destroys the fluorophore-binding aptamer, thereby inhibiting fluorescence.

Preparation of the DNA molecule can be carried out by well-known methods of DNA ligation. DNA ligation utilizes DNA ligase enzymes to covalently link or ligate fragments of DNA together by catalyzing formation of a phosphodiester bond between the 5' phosphate of one strand of DNA and the 3' hydroxyl of another. Typically, ligation reactions require a strong reducing environment and ATP. The commonly used T4 DNA ligase is an exemplary DNA ligase in preparing the DNA molecule of the present invention. Once the DNA molecule of the present invention has been constructed, it can be incorporated into host cells as described infra.

Transcription of the DNA molecule of the present invention is often dependent upon the presence of a promoter, which is a DNA sequence that directs the binding of RNA polymerase and thereby promotes RNA synthesis. Accordingly, the DNA molecule of the present invention may include a promoter operably coupled to the first region to control expression of the RNA aptamer. Because not all polymerases require promoters, the promoter sequence is optional.

The DNA sequences of eukaryotic promoters differ from those of prokaryotic promoters. Furthermore, eukaryotic promoters and accompanying genetic signals may not be recognized in or may not function in a prokaryotic system and, further, prokaryotic promoters are not recognized and do not function in eukaryotic cells.

Promoters vary in their "strength" (i.e., their ability to promote transcription). Depending on the application, it may be desirable to use strong promoters in order to obtain a high level of transcription. For instance, when used simply as a label high expression levels may be preferred, whereas to assess transcript behavior it may be desirable to obtain lower levels of expression that allow the cell to process the transcript.

Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

As described above, one type of regulatory sequence is a promoter located upstream or 5' to the coding sequence of the DNA molecule. Depending upon the desired activity, it is possible to select the promoter for not only in vitro production of the RNA aptamer, but also in vivo production in cultured cells or whole organisms, as described below. Because in vivo production can be regulated genetically, another suitable class of promoters is an inducible promoter which induces transcription of the DNA molecule in response to specific conditions, thereby enabling expression of the RNA aptamer as desired (i.e., expression within specific tissues, or at specific temporal and/or developmental stages). The various promoter types can be driven by RNA polymerases I, II, or III.

Suitable promoters for use with the constructed DNA molecule of the present invention include, without limitation, a T7 promoter, a SUP4 tRNA promoter, an RPR1 promoter, a GPD promoter, a GAL1 promoter, an hsp70 promoter, an Mtn promoter, a UAShs promoter, and functional fragments thereof. The T7 promoter is a well-defined, short DNA sequence that can be recognized and utilized by T7 RNA polymerase of the bacteriophage T7. The T7 RNA polymerase can be purified in large scale and is commercially available. The transcription reaction with T7 promoter can be conducted in vitro to produce a large amount of the molecular complex of the present invention (Milligan et al., "Oligoribonucleotide Synthesis Using T7 RNA Polymerase and Synthetic DNA Templates," *Nucleic Acids Res.* 15(21): 8783-8798 (1987), which is hereby incorporated by reference in its entirety). The T7 RNA polymerase can also be used in mammalian and bacterial cells to produce very high levels of RNA. The SUP4 tRNA promoter and RPR1 promoter are driven by RNA polymerase III of the yeast *Saccharomyces cerevisiae*, and suitable for high level expression of RNA less than 400 nucleotides in length (Kurjan et al., Mutation at the Yeast SUP4 tRNA$^{tyr}$ Locus: DNA Sequence Changes in Mutants Lacking Suppressor Activity," *Cell* 20:701-709 (1980); Lee et al., "Expression of RNase P RNA in *Saccharomyces cerevisiae* is Controlled by an Unusual RNA Polymerase III Promoter," *Proc. Natl. Acad. Sci. USA* 88:6986-6990 (1991), each of which is hereby incorporated by reference in its entirety). The glyceraldehyde-3-phosphate dehydrogenase (GPD) promoter in yeast is a strong constitutive promoter driven by RNA polymerase II (Bitter et al., "Expression of Heterologous Genes in *Saccharomyces cerevisiae* from Vectors Utilizing the Glyceraldehyde-3-phosphate Dehydrogenase Gene Promoter," *Gene* 32:263-274 (1984), which is hereby incorporated by reference in its entirety). The galactokinase (GAL1) promoter in yeast is a highly inducible promoter driven by RNA polymerase II (Johnston and Davis, "Sequences that Regulate the Divergent GAL1-GAL10 Promoter in *Saccharomyces cerevisiae,*" *Mol. Cell. Biol.* 4:1440-1448 (1984), which is hereby incorporated by reference in its entirety). The heat shock promoters are heat inducible promoters driven by the RNA polymerase II in eukaryotes. The frequency with which RNA polymerase II transcribes the major heat shock genes can be increased rapidly in minutes over 100-fold upon heat shock. Another inducible promoter driven by RNA polymerase II that can be used in the present invention is a metallothionine (Mtn) promoter, which is inducible to the similar degree as the heat shock promoter in a time course of hours (Stuart et al., "A 12-Base-Pair Motif that is Repeated Several Times in Metallothionine Gene Promoters Confers Metal Regulation to a Heterologous Gene," *Proc. Natl. Acad. Sci. USA* 81:7318-7322 (1984), which is hereby incorporated by reference in its entirety).

Initiation of transcription in mammalian cells requires a suitable promoter, which may include, without limitation, β-globin, GAPDH, β-actin, actin, Cstf2t, SV40, MMTV, metallothionine-1, adenovirus Ela, CMV immediate early, immunoglobulin heavy chain promoter and enhancer, and RSV-LTR. Termination of transcription in eukaryotic genes involves cleavage at a specific site in the RNA which may precede termination of transcription. Also, eukaryotic termination varies depending on the RNA polymerase that transcribes the gene. However, selection of suitable 3' transcription termination regions is well known in the art and can be performed with routine skill.

Spatial control of an RNA molecule can be achieved by tissue-specific promoters, which have to be driven by the RNA polymerase II. The many types of cells in animals and plants are created largely through mechanisms that cause different genes to be transcribed in different cells, and many specialized animal cells can maintain their unique character when grown in culture. The tissue-specific promoters involved in such special gene switching mechanisms, which are driven by RNA polymerase II, can be used to drive the transcription templates that code for the molecular complex of the present invention, providing a means to restrict the expression of the molecular complex in particular tissues. Any of a variety of tissue-specific promoters can be selected as desired.

For gene expression in plant cells, suitable promoters may include, without limitation, nos promoter, the small subunit ribulose bisphosphate carboxylase genes, the small subunit chlorophyll A/B binding polypeptide, the 35S promoter of cauliflower mosaic virus, and promoters isolated from plant genes, including the Pto promoter itself (See Vallejos et al., "Localization in the Tomato Genome of DNA Restriction Fragments Containing Sequences Homologous to the rRNA (45S), the major chlorophyllivB Binding Polypeptide and the Ribulose Bisphosphate Carboxylase Genes," *Genetics* 112: 93-105 (1986) (disclosing the small subunit materials), which is hereby incorporated by reference in its entirety). The nos promoter and the 35S promoter of cauliflower mosaic virus are well known in the art.

In addition, the constructed DNA molecule may also include an operable 3' regulatory region, selected from among those which are capable of providing correct transcription termination and polyadenylation of mRNA for expression in plant cells. A number of 3' regulatory regions are known to be operable in plants. Exemplary 3' regulatory regions include, without limitation, the nopaline synthase 3' regulatory region (Fraley et al., "Expression of Bacterial Genes in Plant Cells," *Proc. Nat'l. Acad. Sci. USA*, 80:4803-4807 (1983), which is hereby incorporated by reference in its entirety) and the cauliflower mosaic virus 3' regulatory region (Odell et al., "Identification of DNA Sequences Required for Activity of the Cauliflower Mosaic Virus 35S Promoter," *Nature*, 313(6005):810-812 (1985), which is hereby incorporated by reference in its entirety). Virtually any 3' regulatory region known to be operable in plants would suffice for proper expression of the coding sequence of the constructed DNA molecule of the present invention.

Another type of regulatory sequence is known as an enhancer. Enhancer elements do not need to be located immediately upstream of the promoter or the sequence which encodes the transcript that will be made. Enhancers can, in fact, be located very far away. Nevertheless, they can also serve as regulatory elements, and could potentially be regulated by signaling molecules and thereby influence the expression of a target RNA inside a cell. Exemplary enhancer elements include, without limitation, the well-known SV40 enhancer region and the 35S enhancer element.

Once the DNA molecule of the present invention has been constructed, it can be incorporated into cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation. The vector contains the necessary elements for their persistent existence inside cells and for the transcription of an RNA molecule that can be translated into the molecular complex of the present invention.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and transfection, and replicated in cultures including prokaryotic organisms and eukaryotic cells grown in tissue culture.

Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif, which is hereby incorporated by reference in its entirety), pQE, pIH821, pGEX, pET series (see Studier et al., "Use of T7 RNA Polymerase to Direct Expression of Cloned Genes," *Gene Expression Technology*, vol. 185 (1990), which is hereby incorporated by reference in its entirety), pIIIEx426 RPR, pIIIEx426 tRNA (see Good and Engelke, "Yeast Expression Vectors Using RNA Polymerase III Promoters," *Gene* 151:209-214 (1994), which is hereby incorporated by reference in its entirety), p426GPD (see Mumberg et al., "Yeast Vectors for the Controlled Expression of Heterologous Proteins in Different Genetic Background," *Gene* 156: 119-122 (1995), which is hereby incorporated by reference in its entirety), p426GAL1 (see Mumberg et al., "Regulatable Promoters of *Saccharomyces cerevisiae*: Comparison of Transcriptional Activity and Their Use for Heterologous Expression," *Nucl. Acids Res.* 22:5767-5768 (1994), which is hereby incorporated by reference in its entirety), pUAST (see Brand and Perrimon, "Targeted Gene Expression as a Means of Altering Cell Fates and Generating Dominant Phenotypes," *Development* 118:401-415 (1993), which is hereby incorporated by reference in its entirety), and any derivatives thereof. Suitable vectors are continually being developed and identified.

A variety of host-vector systems may be utilized to express the DNA molecule. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, retrovial vectors, etc.); insect cell systems infected with virus (e.g., baculovirus); and plant cells infected by bacteria or transformed via particle bombardment (i.e., biolistics). The expression elements of these vectors vary in their strength and specificities. Depending upon the host-vector system utilized, any one of a number of suitable transcription elements can be used.

Once the constructed DNA molecule has been cloned into an expression system, it is ready to be incorporated into a host cell. Such incorporation can be carried out by the various forms of transformation, depending upon the vector/host cell system such as transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference in its entirety. Suitable host cells include, but are not limited to, bacteria, yeast, mammalian cells, insect cells, plant cells, and the like. The host cell is preferably present either in a cell culture (ex vivo) or in a whole living organism (in vivo).

Mammalian cells suitable for carrying out the present invention include, without limitation, COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), CHOP, NS-1 cells, embryonic stem cells, induced pluripotent stem cells, and primary cells recovered directly from a mammalian organism. With regard to primary cells recovered from a mammalian organism, these cells can optionally be reintroduced into the mammal from which they were harvested or into other animals.

The expression of high levels of functional RNA aptamers within cells can be complicated by several factors including RNA stability, short half-life, and difficulties in cellular targeting. Nonetheless, substantial progress has been achieved over the last several years. The first demonstration of aptamer function in live cells involved nuclear targets (Klug et al., "In Vitro and In Vivo Characterization of Novel mRNA Motifs that Bind Special Elongation Factor SelB," *Proc. Natl. Acad. Sci. U.S.A.* 94:6676-6681 (1997); Shi et al., "RNA Aptamers as Effective Protein Antagonists In a Multicellular Organism," *Proc. Natl. Acad. Sci. U.S.A.* 96:10033-10038 (1999); Thomas et al., "Selective Targeting and Inhibition of Yeast RNA Polymerase II by RNA Aptamers," *J. Biol. Chem.* 272: 27980-27986 (1997), which are hereby incorporated by reference in their entirety). Aptamer function within the nucleus of mammalian cells has also been demonstrated (Symensma et al., "Polyvalent Rev Decoys Act as Artificial Rev-Responsive Elements," *J. Virol.* 73:4341-4349 (1999), which is hereby incorporated by reference in its entirety). More recently, effective strategies for cytoplasmic targeting of aptamer have also been developed. For example, the human tRNA initiator sequence, which mediates highly efficient nuclear export to deliver functional chimeric RNA aptamers to the cytosol has been used (Chaloin et al., "Endogenous Expression of a High-Affinity Pseudoknot RNA Aptamer Suppresses Replication of HIV-1," *Nucl. Acids Res.* 30:4001-4008 (2002), which is hereby incorporated by reference in its entirety). Functional RNA aptamers have also been directly delivered to the cytoplasm by lipofection (Theis et al., "Discriminatory Aptamer Reveals Serum Response Element Transcription Regulated by Cytohesin-2," *Proc. Natl. Acad. Sci. U.S.A.* 101:11221-11226 (2004), which is hereby incorporated by reference in its entirety). Finally, most recently, very high levels of aptamer expression ($1\times10^7$ molecules per cell) have been achieved by fusion with a highly stable transcript (Choi et al., "Intracellular Expression of the T-cell Factor-1 RNA Aptamer as an Intramer," *Mol. Cancer Ther.* 5:2428-2434 (2006), which is hereby incorporated by reference in its entirety).

Plant tissues suitable for transformation include leaf tissue, root tissue, meristems, zygotic and somatic embryos, and anthers. It is particularly preferred to utilize embryos obtained from anther cultures. The expression system of the present invention can be used to transform virtually any plant tissue under suitable conditions, and the transformed cells can be regenerated into whole plants.

One approach to transforming plant cells and/or plant cell cultures, tissues, suspensions, etc. with a DNA molecule of the present invention is particle bombardment (also known as biolistic transformation) of the host cell. This technique is disclosed in U.S. Pat. Nos. 4,945,050, 5,036,006, and 5,100,792, all to Sanford, et al., which are hereby incorporated by reference in their entirety. Another method of introducing DNA molecules into a host cell is fusion of protoplasts with other entities, either minicells, cells, lysosomes, or other fusible lipid-surfaced bodies that contain the DNA molecule (Fraley et al., "Expression of Bacterial Genes in Plant Cells," *Proc. Natl. Acad. Sci. U.S.A.* 80:4803-4807 (1983), which is hereby incorporated by reference in its entirety). The DNA molecule of the present invention may also be introduced into the plant cells and/or plant cell cultures, tissues, suspensions, etc. by electroporation (Fromm et al., "Expression of Genes Transferred into Monocot and Dicot Plant Cells by Electroporation," *Proc. Natl. Acad. Sci. U.S.A.* 82:5824 (1985), which is hereby incorporated by reference in its entirety).

In producing transgenic plants, the DNA construct in a vector described above can be microinjected directly into plant cells by use of micropipettes to transfer mechanically the recombinant DNA (Crossway, "Integration of Foreign DNA Following Microinjection of Tobacco Mesophyll Protoplasts," *Mol. Gen. Genetics* 202:179-85 (1985), which is hereby incorporated by reference in its entirety). The genetic material may also be transferred into the plant cell using polyethylene glycol (Krens et al., "In Vitro Transformation of Plant Protoplasts with Ti-Plasmid DNA," *Nature* 296:72-74 (1982), which is hereby incorporated by reference in its entirety). Alternatively, genetic sequences can be introduced into appropriate plant cells by means of the Ti plasmid of *A. tumefaciens* or the Ri plasmid of *A. rhizogenes*, which is transmitted to plant cells on infection by *Agrobacterium* and is stably integrated into the plant genome (Schell, "Transgenic Plants as Tools to Study the Molecular Organization of Plant Genes," *Science* 237:1176-83 (1987), which is hereby incorporated by reference in its entirety). After transformation, the transformed plant cells must be regenerated, and this can be accomplished using well known techniques as described in Evans et al., *Handbook of Plant Cell Cultures*, Vol. 1, MacMillan Publishing Co., New York (1983); and Vasil (ed.), *Cell Culture and Somatic Cell Genetics of Plants*, Acad. Press, Orlando, Vol. I (1984) and Vol. III (1986), each of which is hereby incorporated by reference in its entirety.

Methods of Use

In the various methods of use, the formation of molecular complexes of the invention (e.g., fluorophore:aptamer complexes or fluorophore:aptamer:target complexes) can be identified, quantified, and monitored for various purposes, as discussed more fully below. Detection of molecular complex formation, through the fluorescent output of the fluorophore or a FRET partner (e.g., donor or acceptor), can be used to detect complex formation in a cell-free sample (e.g., cell extracts, fractions of cell extracts, or cell lysates), histological or fixed samples, tissues or tissue extracts, bodily fluids, serum, blood and blood products, environmental samples, or in whole cells. Thus, detection and quantification can be carried out in vivo by fluorescence microscopy or the like, or detection and quantification can be carried in vitro on any of the above extracts or on a sample obtained via in vitro mixing of sample materials and reagents.

The genetic constructs can be introduced into living cells using infective or non-infective transformation procedures that are well known in the art.

Regardless of the intended use, a suitable radiation source is used to illuminate the fluorophore after exposing the fluorophore and aptamer to one another. The radiation source can be used alone or with optical fibers and any optical waveguide to illuminate the sample. Suitable radiation sources include, without limitation, filtered, wide-spectrum light sources (e.g., tungsten, or xenon arc), laser light sources, such as gas lasers, solid state crystal lasers, semiconductor diode lasers (including multiple quantum well, distributed feedback, and vertical cavity surface emitting lasers), dye lasers, metallic vapor lasers, free electron lasers, and lasers using any other substance as a gain medium. Common gas lasers include Argon-ion, Krypton-ion, and mixed gas (e.g., Ar Kr) ion lasers, emitting at 455, 458, 466, 476, 488, 496, 502, 514, and 528 nm (Ar ion); and 406, 413, 415, 468, 476, 482, 520, 531, 568, 647, and 676 nm (Kr ion). Also included in gas lasers are Helium Neon lasers emitting at 543, 594, 612, and 633 mn. Typical output lines from solid state crystal lasers include 532 nm (doubled Nd:YAG) and 408/816 nm (doubled/primary from Ti:Sapphire). Typical output lines from semiconductor diode lasers are 635, 650, 670, and 780 mm. Infrared radiation sources can also be employed.

Excitation wavelengths and emission detection wavelengths will vary depending on both the fluorophore and the nucleic acid aptamer molecule that are being employed. Examples of different aptamer:fluorophore combinations are described in PCT Application Publ. Nos. WO 2010/096584 and WO 2013/016694, both to Jaffrey et al., which are hereby incorporated by reference in their entirety. As demonstrated therein, several different aptamer molecules can differently affect the emission spectrum of a single fluorophore, affording very distinct emission patterns.

Detection of the emission spectra can be achieved using any suitable detection system. Exemplary detection systems include, without limitation, a cooled CCD camera, a cooled intensified CCD camera, a single-photon-counting detector (e.g., PMT or APD), dual-photon counting detector, spectrometer, fluorescence activated cell sorting (FACS) systems, fluorescence plate readers, fluorescence resonance energy transfer, and other methods that detect photons released upon fluorescence or other resonance energy transfer excitation of molecules.

In one embodiment, the detector is optically coupled to receive the output emissions of the fluorophore:aptamer complex through a lens system, such as in an optical microscope. In another embodiment, a fiber optic coupler is used, where the input to the optical fiber is placed in close proximity to the substrate surface of a biosensor, either above or below the substrate. In yet another embodiment, the optical fiber provides the substrate for the attachment of nucleic acid sensor molecules and the biosensor is an integral part of the optical fiber.

In one embodiment, the interior surface of a glass or plastic capillary tube provides the substrate for the attachment of the fluorophore or the sensor molecule (or molecular complex). The capillary can be either circular or rectangular in cross-section, and of any dimension. The capillary section containing the biosensors can be integrated into a microfluidic liquid-handling system which can inject different wash, buffer, and analyte-containing solutions through the sensor tube. Spatial encoding of the fluorophore or nucleic acid sensor molecules can be accomplished by patterning them longitudinally along the axis of the tube, as well as radially, around the circumference of the tube interior. Excitation can be accomplished by coupling a laser source (e.g., using a shaped output beam, such as from a VCSEL) into the glass or plastic layer forming the capillary tube. The coupled excitation light will undergo TIR at the interior surface/solution interface of the tube, thus selectively exciting fluorescently labeled biosensors attached to the tube walls, but not the bulk solution. In one embodiment, detection can be accomplished using a lens-coupled, or proximity-coupled large area segmented (pixelated) detector, such as a CCD. In a particular embodiment, a scanning (i.e., longitudinal/axial and azimuthal) microscope objective lens/emission filter combination is used to image the biosensor substrate onto a CCD detector. In a different embodiment, a high resolution CCD detector with an emission filter in front of it is placed in extremely close proximity to the capillary to allow direct imaging of the fluorophore:nucleic acid aptamer complexes. In a different embodiment, highly efficient detection is accomplished using a mirrored tubular cavity that is elliptical in cross-section. The sensor tube is placed along one focal axis of the cavity, while a side-window PMT is placed along the other focal axis with an emission filter in front of it. Any light emitted from the biosensor tube in any direction will be collected by the cavity and focused onto the window of the PMT.

In still another embodiment, the optical properties of a molecular complex are analyzed using a spectrometer (e.g., such as a luminescence spectrometer). The spectrometer can perform wavelength discrimination for excitation and detection using either monochromators (i.e., diffraction gratings), or wavelength bandpass filters. In this embodiment, the fluorophores of the molecular complexes are excited at absorption maxima appropriate to the fluorophore being used and fluorescence intensity is measured at emission wavelengths appropriate for the complexes being detected. Given that the intensity of the excitation light is much greater than that of the emitted fluorescence, even a small fraction of the excitation light being detected or amplified by the detection system will obscure a weak biosensor fluorescence emission signal. In one embodiment, the biosensor molecules are in solution and are pipetted (either manually or robotically) into a cuvette or a well in a microtiter plate within the spectrometer. In a further embodiment, the spectrometer is a multifunction plate reader capable of detecting optical changes in fluorescence or luminescence intensity (at one or more wavelengths), time-resolved fluorescence, fluorescence polarization (FP), absorbance (epi and transmitted), etc., such as the Fusion multifunction plate reader system (Packard Biosciences, Meriden, Conn.). Such a system can be used to detect optical changes in biosensors either in solution, bound to the surface of microwells in plates, or immobilized on the surface of solid substrate (e.g., a microarray on a glass substrate). This type of multiplate/multisubstrate detection system, coupled with robotic liquid handling and sample manipulation, is particularly amenable to high-throughput, low-volume assay formats.

In embodiments where the sensor molecules or fluorophores are attached to substrates, such as a glass slide or in microarray format, it is desirable to reject any stray or background light in order to permit the detection of low intensity fluorescence signals. In one embodiment, a small sample volume (about 10 nl) is probed to obtain spatial discrimination by using an appropriate optical configuration, such as evanescent excitation or confocal imaging. Furthermore, background light can be minimized by the use of narrow-bandpass wavelength filters between the sample and the detector and by using opaque shielding to remove any ambient light from the measurement system.

In one embodiment, spatial discrimination of a molecular complex of the invention (fluorophore:nucleic acid aptamer complexes or fluorophore:nucleic acid aptamer:target molecule complexes) attached to a substrate in a direction normal to the interface of the substrate is obtained by evanescent wave excitation. This is illustrated in PCT Application Publ. No. WO 2010/096584 to Jaffrey and Paige, which is hereby incorporated by reference in its entirety. Evanescent wave excitation utilizes electromagnetic energy that propagates into the lower-index of refraction medium when an electromagnetic wave is totally internally reflected at the interface between higher and lower-refractive index materials. In this embodiment a collimated laser beam is incident on the substrate/solution interface (at which the fluorophore:nucleic acid aptamer complexes or fluorophore:nucleic acid aptamer:target molecule complexes are immobilized) at an angle greater than the critical angle for total internal reflection (TIR). This can be accomplished by directing light into a suitably shaped prism or an optical fiber. In the case of a prism, the substrate is optically coupled (via index-matching fluid) to the upper surface of the prism, such that TIR occurs at the substrate/solution interface on which the molecular complexes are immobilized. Using this method, excitation can be localized to within a few hundred nanometers of the substrate/solution interface, thus eliminating autofluorescence background from the bulk analyte solution, optics, or substrate. Target recognition is detected by a change in the fluorescent emission of the molecular complex, whether a change in intensity or polarization. Spatial discrimination in the plane of the interface (i.e., laterally) is achieved by the optical system.

In the embodiment described above, a TIRF evanescent wave excitation optical configuration is implemented using a detection system that includes a universal fluorescence microscope. Any fluorescent microscope compatible with TIRF can be employed. The TIRF excitation light or laser can be set at either an angle above the sample shining down on the sample, or at an angle through the objective shining up at the sample. Effective results can been obtained with immobilization of either the aptamer or the fluorophore using NHS-activated glass slides. The fluorophore containing a free amine (at the $R_1$ position) can be used to react with the NHS-slide. RNA can be modified with a 5' amine for NHS reactions by carrying out T7 synthesis in the presence of an amine modified GTP analog (commercially available).

In the several embodiments described above, the output of the detection system is preferably coupled to a processor for processing optical signals detected by the detector. The processor can be in the form of personal computer, which contains an input/output (I/O) card coupled through a data bus into the processor. CPU/processor receives and processes the digital output signal, and can be coupled to a memory for storage of detected output signals. The memory can be a random access memory (RAM) and/or read only memory (ROM), along with other conventional integrated circuits used on a single board computer as are well known to those of ordinary skill in the art. Alternatively or in addition, the memory may include a floppy disk, a hard disk, CD ROM, or other computer readable medium which is read from and/or written to by a magnetic, optical, or other reading and/or writing system that is coupled to one or more processors. The memory can include instructions written in a software package (for image processing) for carrying out one or more aspects of the present invention as described herein.

In addition to their specificity in binding to fluorophores, a number of the aptamers have demonstrated that their affinity for the target fluorophore can be modulated by environmental conditions.

According to one embodiment, the affinity of the aptamer for the fluorophore is partially or entirely ion dependent, i.e., any mono or divalent ion. For example, PCT Application Publ. No. WO/2010/096584 to Jaffrey and Paige, which is hereby incorporated by reference in its entirety, describes aptamers that are responsive to $Mg^{2+}$ or $K^+$. Others have identified aptamers that bind specifically to other ions, and can be incorporated into the sensors of the present invention. These include, without limitation, aptamers specific to zinc (Rajendran et al., "Selection of Fluorescent Aptamer Beacons that Light Up in the Presence of Zinc," *Anal. Bioanal. Chem.* 390(4):1067-1075 (2008), which is hereby incorporated by reference in its entirety), cobalt (Breaker et al., "Engineered Allosteric Ribozymes as Biosensor Components," *Curr. Op. in Biotech* 13(1):31-39 (2002), which is hereby incorporated by reference in its entirety), and lead (Brown et al., "A Lead-dependent DNAzyme with a Two-step Mechanism," *Biochem.* 42(23):7152-7161 (2003), which is hereby incorporated by reference in its entirety).

According to another embodiment, the affinity of the aptamer for the fluorophore is temperature dependent. Thus, a titration exists where at very high temperatures, no binding will occur, but at lower temperatures the highest degree of binding will occur. Based on the profile of a particular aptamer-fluorophore pair, the temperature within a system can be determined based on the measured fluorescence output. Aptamers that possess this property can be used as a sensor (discussed below) to determine the temperature of the environment.

According to another embodiment, the affinity of the aptamer for the fluorophore is partially pH dependent. The aptamers are fairly stable near neutral pH, but at higher or lower pH, the folding of the aptamer or the interaction between fluorophore/aptamer is disrupted such that changes in fluorescence can be measured as the pH varied away from neutral. Aptamers that possess this property can be used as a sensor (discussed below) to determine the pH of the environment.

The multivalent aptamers having first and second domains can be used for detection of a target molecule in a medium or sample. This is carried out by exposing the nucleic acid aptamer molecule of the invention to a medium suspected to contain the target molecule under conditions effective to allow the second domain to bind specifically to the target molecule, if present, and also exposing the nucleic acid molecule and medium to a fluorophore of the invention under conditions effective to allow the first domain to bind specifically to the fluorophore after binding of the target molecule by the second domain, thereby inducing the fluorophore to adopt a conformation that exhibits enhanced fluorescent emissions. Detection of molecular complex formation is then achieved by exciting the fluorophore (or FRET partner) with radiation of appropriate wavelength and detecting fluorescence by the fluorophore (or FRET partner), whereby the detection of fluorescence emissions by the fluorophore indicates binding of the nucleic acid molecule to the target molecule and, hence, its presence.

This embodiment can be carried out in whole cells either by introducing the nucleic acid aptamer molecule into the whole cell, or by transforming the whole cell with a transgene encoding the nucleic acid aptamer molecule. The fluorophore can be introduced into the environment of the whole cell, where it is readily taken up. This embodiment can also be carried out in vitro, i.e., in a cell free environment. An image of the detection process can also be acquired or generated using the detection systems described above.

This aspect of the invention is particularly adaptable to a microarray format, where the nucleic acid aptamer molecules are tethered at discrete locations on a substrate surface, i.e., solid support. The solid support used to form the microarray surface can include, without limitation, glass, metal, and ceramic supports. Tethering of the nucleic acid aptamer molecules can be carried out using a 5' biotin to streptavidin-coated glass (ArrayIt, Inc). Alternatively, the sensor molecules of the present invention can be provided with an extraneous sequence at its 5' end, where the extraneous sequence allows for tethering the sensor molecule to a hybridization partner tethered to the array surface using standard techniques. The hybridization partners can be printed onto the array surface, and the sensor molecules allowed to hybridize prior to or after exposing the sensor to the sample. In these array systems, fluorophore is in solution and is recruited to the glass surface only if the target molecule binds the second domain of the surface-bound aptamer, thereby creating a fluorophore:aptamer:target complex that can be detected, e.g., using TIRF. The sensors can be spotted in an array format, i.e., an array of microspots, or configured in other shapes or designs on surfaces, so that the sensors are positioned in a spatially defined manner. This will allow one or a series of sensors that are specific to distinct target molecules to be assayed following contact with a mixture that contains one or more of the target molecules at known or unknown concentrations. The fluorescence intensity can be used to determine the concentrations if suitable solutions containing known amounts of target analytes are used to calibrate the fluorescence signals.

Detection assays can also be carried out using the aptamer constructs that include a first domain that contains the fluorophore-binding aptamer and a second domain that is a hybridization probe has a nucleotide sequence complementary to a target nucleic acid molecule. For example, to detect viral RNA present in a sample, the hybridization probe will contain a nucleotide sequence complementary to the viral RNA. After attaching any nucleic acid in a sample to a substrate (e.g., glass surface), the sample is exposed to the fluorophore and the aptamer construct under conditions to allow hybridization to occur. Subsequent detection of the molecular complex (fluorophore:aptamer construct: complementary viral RNA target), as measured by the fluorescent emissions by the fluorophore on the substrate via TIRF, indicates presence of the viral RNA target. This same assay can be carried out using an aptamer construct that possess a second domain, which instead of being a hybridization probe, includes either an aptamer sequence or a non-aptamer sequence that binds to a specific protein (e.g., MS2 sequence binds the MS2 protein or a fusion protein containing the same), in which case binding of the protein to the substrate (e.g., in an ELISA format) will also allow for detection.

Alternatively, detection assays can be carried out using these same types of aptamer constructs using a fixed cell sample or histologic tissue sample. Where ever the target molecule is present in these samples, the aptamer construct can be bound to the sample and the fluorophore will identify its presence.

While microarrays for monitoring the transcriptome are commonplace and have revolutionized biology, similar approaches are not available to study the proteome. The system and method of the invention allow the production of a protein-sensing microarray. This novel platform for protein detection has the potential to dramatically speed up the analysis of proteins for innumerable applications. For example, these arrays can be used to assay a set of specific proteins, such as clinically relevant biomarkers, or large sections of the proteome, such as proteins of specific functional classes. Current microarray technologies that utilize a panel of antibodies requires labeling of the proteins in biological samples with fluorescent dyes, such as Cy5-NHS, in order for the protein to be detected after binding to the antibodies. This is problematic, because this labeling procedure may affect the epitope recognized by the antibody. In contrast, the sensor arrays of the present invention do not require target labeling because the sensor will only bind to the fluorophore (at its first domain) after that target molecule has been bound by its second domain. The microarray format of the present invention also overcomes a number of challenges that plagued antibody arrays due to: (1) the low cost of the aptamer sensor molecule; (2) the ease with which oligonucleotides can be coupled to microarray surfaces; (3) the ability to reliably synthesize homogeneous preparations of oligonucleotides, which is a challenge with antibodies; (4) the increased stability of oligonucleotides compared to antibodies; (5) the highly specific nature of aptamer-protein interactions, which typically involve large surfaces (Stoltenburg et al., "SELEX—A Revolutionary Method to Generate High-affinity Nucleic Acid Ligands," *Biomolecular Engineering* 24:381-403 (2007); Hermann and Patel, "Adaptive Recognition by Nucleic Acid Aptamers," *Science* 287:820-825 (2000), each of which is hereby incorporated by reference in its entirety) rather than short epitopes as with antibodies; and (6) the ease of sample preparation, as the fluorescent signaling obtained using these protein sensors does not require the sample processing step of fluorescent dye tagging. Instead, binding of the target protein to the sensor is sufficient to elicit a fluorescent signal (in the presence of the solution phase fluorophore), thereby dramatically simplifying the analysis of protein mixtures.

Thus, upon exposure to the target and fluorophore, the molecular complex will form and the fluorophore, upon illumination, will exhibit emission patterns from the discrete location on the array surface. Using appropriate mapping software, the presence of the fluorescent emission signal will positively identify the target molecule as being present in the sample being queried. As noted above, quantification can be carried out if reliable calibration is performed.

Yet another aspect of the invention involves a method for detecting nucleic acid molecules using a gel separation technique. RNA or DNA molecules to be detected can be recovered from cells using well known techniques, or collected following in vitro synthesis. First, the recovered nucleic acid molecules are separated on a gel using known procedures and techniques, and thereafter the separated nucleic acid molecules can optionally be transferred to a solid substrate. Regardless, the separated nucleic acid molecules are then exposed to a conditionally fluorescent fluorophore of the type described herein. The gel or substrate (containing the separated nucleic acid molecules and fluorophores, whether present in the form of a molecular complex or not) is illuminated with light of a wavelength suitable to induce fluorescence emissions by the fluorophore that is bound by a nucleic acid molecule (i.e., in the form of a molecular complex). Detection of fluorescent emissions of the fluorophore indicates the location of the nucleic acid molecule on the gel or substrate.

A further aspect of the invention involves using an aptamer construct having a first domain that includes a fluorophore-specific aptamer and a second domain that binds specifically to the target molecule for determining the location of a target molecule, particularly within a whole cell. This aspect of the invention involves forming a molecular complex (fluorophore:aptamer:target molecule), exciting the fluorophore with light of an appropriate wavelength, and then detecting fluorescence by the fluorophore, whereby fluorescence by the fluorophore identifies presence of the target molecule. In whole cells, this embodiment can be carried out by introducing the nucleic acid aptamer molecule into the whole cell, or by transforming the whole cell with a transgene encoding the nucleic acid aptamer molecule. Once inside the cell, the nucleic acid aptamer molecule will bind specifically to the target molecule via its second domain. The fluorophore can be introduced into the environment of the whole cell, where it is readily taken up. An image of the detection process can also be acquired or generated using the detection systems described above.

A DNA construct encoding one or more RNA aptamer molecule can be used to measure the transcription by a promoter of interest in a cell. This can be carried out by introducing a DNA construct or transgene encoding the RNA aptamer molecule into a cell, introducing the fluorophore into the cell, and then determining whether the aptamer:fluorophore complex forms, as measured by the amount of fluorescence detected within the cell.

This aspect of the invention can be used to screen agents for their ability to modulate transcription of the DNA construct and, thus, native genes that contain the same promoter as the DNA construct. When screening an agent, the agent is introduced to the cell, preferably prior to introducing the fluorophore. After a suitable time delay (to allow for transcription of the nucleic acid aptamer to occur, the fluorophore can be introduced to the cell. The detection of an increase or decrease in fluorescence by the fluorophore:aptamer complex within the cell, relative to an otherwise identical but untreated control cell, indicates that the agent altered the level of transcription by the promoter.

In an alternative embodiment, the same DNA construct can be used in an in vitro detection procedure, whereby the DNA construct and agent are both introduced into a cell and the fluorophore may or may not be introduced to the cell. In one approach, RNA transcripts are recovered from the cell (using known cell lysis and RNA collection procedures) after exposure to the fluorophore. In another approach, RNA transcripts are first recovered from the cell, and then the fluorophore is introduced to the recovered RNA transcripts. The fluorophore can be bound to a solid surface of a suitable detection device, such as TIRF system or other detectors of the type described above. The detection of an increase or decrease in fluorescence by the fluorophore:aptamer complex within the recovered RNA transcripts, relative to the RNA transcripts recovered from an otherwise identical but untreated control cell, indicates that the agent altered the level of transcription by the promoter.

As a further alternative, the entire transcription and detection process can be carried out in vitro in the presence of the agent. This can be used to monitor the production of transcripts, and the effects of the agents on those transcripts.

In these embodiments, the agent can be, without limitation, a genetic or transgenic condition unique to a particular cell type, a drug (small molecule), amino acid, protein, peptide, polypeptide, vitamin, metal, carbohydrate, lipid, a polymer, or RNAi that influences transcription levels.

A further aspect of the invention relates to the monitoring an RNA molecule within a cell. This aspect of the invention involves the use of a DNA construct of the invention that expresses an RNA fusion that includes an RNA aptamer of the invention joined to an RNA molecule of interest. After introducing the DNA construct into a cell and allowing for transcription to occur, the fluorophore of the invention can be introduced to the cell. Alternatively, the RNA molecule can be expressed or synthesized in vitro and later introduced into the cell. Regardless of the approach, this will allow the RNA aptamer portion of the RNA fusion molecule to bind specifically to the fluorophore (forming an aptamer:fluorophore complex) and enhance its fluorescence emissions. Detection of the RNA fusion molecule (including its location, its quantitation, or its degradation) can be carried out by exposing the cell to radiation of a wavelength suitable to induce fluorescence emissions by the fluorophore within the molecular complex; and then measuring the fluorescent emissions of the fluorophore or a FRET partner. The (sub) cellular location of the fluorescence emissions indicates the location of the transcript. Also, any decrease in the fluorescence emissions over time indicates degradation of the transcript. The latter can be confirmed by recovering RNA transcripts and measuring for the RNA fusion using, e.g., RT-PCR. Finally, the level of fluorescence correlates to the quantity of the RNA fusion molecule that is present.

In this embodiment, the RNA product to be monitored can be any of a variety of RNA molecules having diverse functions. These include, without limitation, pre-mRNA, mRNA encoded a native or non-native expression product, pre-rRNA, rRNA, tRNA, hnRNA, snRNA, miRNA, siRNA, shRNA, long noncoding RNA, PIWI RNA, termini-associated RNA, noncoding RNAs, promoter-associated RNAs, viral RNAs, ribozyme, a stabilizing RNA molecule, an RNA sequence that binds a protein such as a MS2 protein-binding RNA, a targeting element that can localize the fusion nucleic acid molecule to a specific localization in the cell. The RNA product can be fused to either the 5' end or the 3' end of the aptamer molecule of the present invention.

The monitoring of the RNA can also be carried out by exposing the cell to an extracellular RNA molecule that includes an aptamer of the present invention, and cellular uptake of the RNA molecule can be observed via microscopy or measurement of the fluorescent emissions upon exposure to the fluorophore (either before or after cell uptake).

Thus, this aspect can used to monitor the effects of an experimental treatment on RNA localization, trafficking, expression levels, rate of degradation, etc., where the experimental treatment can be exposing the cell or organism to an agent such as a drug (small molecule), amino acid, protein, peptide, polypeptide, vitamin, metal, carbohydrate, lipid, a polymer, or RNAi that influences the target molecule or the expression level of another protein in a pathway influenced by the target RNA molecule, expression of a native or foreign gene in the cell or organism, or exposing the cell or organism to a change in environmental conditions (e.g., temperature, hypoxic or hyperoxic conditions, atmospheric pressure, pH, etc.). These treatments can be carried out directly on a transformed cell or cell population. Alternatively, these treatments can be performed on an organism that contains one or more cells transformed with a DNA construction encoding the fusion RNA molecule of interest.

To enhance the fluorescent signal, it is possible to tailor the number of fluorophores that can be bound to a single RNA transcript by using a concatamer of RNA aptamers. In addition, this aspect of the invention is particularly adaptable to assessing the trafficking or degradation of multiple RNA molecules simultaneously. This is possible due to the tailored emission spectra of different aptamer:fluorophore complexes. Thus, this aspect can include introducing a second DNA construct into a cell, wherein the second DNA construct encoding a distinct RNA fusion molecule that includes a distinct RNA aptamer of the invention (or a concatamer thereof) joined to a distinct RNA molecule of interest. After introducing the DNA construct into the cell or organism, and allowing for transcription to occur, a second fluorophore of the invention can be introduced to the cell or organism, i.e., one that is bound specifically by the aptamer present in the second RNA fusion molecule but not the first, and vice versa. This will allow the fluorophore-specific aptamer portion of the RNA to bind specifically to the fluorophore (forming an aptamer:fluorophore complex) and enhance its fluorescence emissions. Detection of fluorescence can be carried out as described above. Simultaneous detection of separate emission peaks will allow for detecting localization or co-localization of both complexes.

In a related aspect, the inventive materials can be used to assess RNA folding, unfolding, or folding-unfolding kinetics by monitoring changes in fluorescence after exposing the RNA fusion protein to a fluorophore of the present invention (to form a molecular complex). The unfolding or folding event can be produced by exposing the molecular complex to an agent such as a protein (e.g., enzyme such as helicase), chemical (e.g., a small organic molecule, vitamin, amino acid, antibiotic, protein, lipid, carbohydrate, polymer, nucleotide, RNA-binding protein, or RNA-binding molecule), ribozyme, or environmental changes (e.g., temperature, hypoxic or hyperoxic conditions, atmospheric pressure, pH, etc.). The RNA aptamer can be the target of the folding or unfolding, or the RNA aptamer can be fused to the target of the folding or unfolding and, as such, incidentally be subject to its folding or unfolding. For the fusion RNA molecule, this aspect of the invention can be practiced in vivo in which case the folding or unfolding event can be affected by the expression of a gene within a cell or organism where the gene encodes a protein, an RNA, a non-coding RNA, an RNAi molecule (e.g., siRNAi, shRNA). Detection of unfolding can be measured by a decrease in fluorescence, and detection of folding can be measured by an increase in fluorescence, following exposure of the in vitro system or cell to radiation of a wavelength suitable to induce fluorescence emissions by the fluorophore within the molecular complex; and then measuring the fluorescent emissions of the fluorophore or a FRET partner.

In a related aspect, the inventive materials can be used to assess RNA binding to another moiety by observing the proximity of the fluorescence signal generated by the RNA aptamer (or RNA fusion) to a moiety. The moiety can be an RNA sequence (e.g., mRNA encoding a protein or noncoding RNA of the types described above), DNA or modified nucleic acid molecule. The RNA aptamer can be the target of the binding event, or the RNA aptamer can be fused to the target of the RNA binding event and, as such, incidentally be subject to structural changes following the binding event. For the fusion RNA molecule, this aspect of the invention can be practiced in vivo in which case the RNA binding event can be carried by the expression of a transgene encoding the RNA fusion molecule within a cell or organism. Detection of RNA binding can be measured by a decrease in fluorescence, and a decrease in RNA binding can be measured by an increase in fluorescence, following exposure of the in vitro system or cell to radiation of a wavelength suitable to induce fluorescence emissions by the fluorophore within the molecular complex; and then measuring the fluorescent emissions of the fluorophore or a FRET partner.

A further aspect of the invention relates to monitoring a target molecule in a cell. This aspect of the invention can be carried out using a nucleic acid aptamer molecule that includes first and second domains, as described above, where the first domain binds specifically to the fluorophore only after the second domain binds specifically to the target molecule. Both the nucleic acid aptamer molecule and a fluorophore of the invention are introduced into a cell, allowing the fluorophore:aptamer:target complex to form in the presence of the target molecule and enhancing the fluorescence emissions by the fluorophore. Upon exposure of the cell to radiation of suitable wavelength to induce fluorescence emissions by the fluorophore that is bound in the complex or a FRET partner; and then measuring the fluorescent emissions of the fluorophore or FRET partner to monitor the target molecule. In this manner, the cellular location of the fluorescence emissions indicates the location of the target molecule, a decrease in the fluorescence emissions over time indicates degradation of the target molecule, and an increase in the fluorescence emissions over time indicates accumulation of the target molecule. Quantitation of the target molecule can be correlated to the level of fluorescence measured.

The target molecule in this aspect of the invention can be any protein, lipid, carbohydrate, hormone, cytokine, chemokine, cell signaling molecule, metabolite, organic molecule, or metal ion, as described above.

This aspect of the invention can be carried by introducing the nucleic acid aptamer molecule directly into the cell or, alternatively, by introducing into the cell a gene that encodes the nucleic acid aptamer molecule.

Another aspect of the present invention relates to a method of screening a drug that modifies gene expression. This aspect can be carried out using a transgene that encodes an RNA aptamer molecule of the present invention. The transgene can be provided with a promoter of interest whose activity is being monitored with respect to the drug being screened. After introducing the transgene into a cell, the cell is exposed to the drug and a fluorophore of the invention, effectively introducing these compounds into the cell. Thereafter, the level of RNA aptamer transcription is measured by exposing the cell to radiation of a wavelength suitable to induce fluorescence emissions by the fluorophore that is bound by the RNA aptamer molecule or a FRET partner, and the fluorescent emissions of the fluorophore or FRET partner are measured, as described above. A reduction or absence of fluorescent emissions, relative to an otherwise identical control cell that is not exposed to the drug, indicates that the drug inhibits expression of the transgene. An increase of fluorescent emissions, relative to an otherwise identical control cell that is not exposed to the drug, indicates that the drug promotes expression of the transgene.

Another aspect of the present invention relates to a method of screening a drug that modifies RNA splicing. This aspect can be carried out using a transgene that encodes an RNA aptamer molecule of the present invention, wherein the RNA transcript of the transgene includes an intron that, with proper splicing, will result in a mature RNA molecule that is a functional fluorophore-binding RNA aptamer of the invention. This method is carried out by introducing the transgene into a cell and exposing the cell to a drug, and allowing transcription to occur such that both the immature transcript and the drug will both be present in the cell when splicing is to occur. A fluorophore of the invention is also introduced into the cell, whereby the mature RNA aptamer, if properly spliced, will be able to bind specifically to the fluorophore to enhance its fluorescence emissions. Detection of whether proper splicing occurred (or not) can be carried out by exposing the cell to radiation of a wavelength suitable to induce fluorescence emissions by the fluorophore (that is bound by the mature RNA aptamer molecule), or its FRET partner, and then measuring the fluorescent emissions of the fluorophore or FRET partner. A reduction or absence of fluorescent emissions, relative to an otherwise identical control cell that is not exposed to the drug, indicates that the drug inhibits proper splicing of the transcript. An increase of fluorescent emissions, relative to the otherwise identical control cell that is not exposed to the drug, indicates that the drug promotes proper splicing of the transcript.

This aspect of the invention can also be carried out in vitro. Basically, a medium is provided that contains the immature RNA transcript (with intron), a spliceosome including an appropriate splicing enzyme, a drug to be screened, and the fluorophore. As noted above, the immature RNA transcript includes first and second exons having an intervening intron region, and the first and second exons, upon excision of the intron, form an RNA aptamer molecule of the present invention. Upon exposing the medium to radiation of a wavelength suitable to induce fluorescence emissions by the fluorophore that is bound by the RNA aptamer molecule (or a FRET partner), any fluorescent emissions of the fluorophore (or FRET partner) are measured. A reduction or absence of fluorescent emissions, relative to an otherwise identical medium that lacks the drug, indicates that the drug inhibits proper splicing of the transcript. An increase of fluorescent emissions, relative to an otherwise identical medium that lacks the drug, indicates that the drug promotes proper splicing of the transcript.

In these embodiments, as an alternative to exposing the cell or organism to a drug, the cell or organism can be exposed to a protein or polypeptide, modifying the expression level of a gene with the cell or organism where the gene encodes a protein, an RNA, a non-coding RNA, a shRNA, or other RNA, introducing a transgene into the cell or organism where the transgene expresses and RNAi molecule, or exposing the cell or organism to a change in environmental conditions of the types described above.

Yet another aspect of the invention relates to a method of screening a drug for activity on a target molecule (i.e., either enhancing or diminishing activity of the target molecule). This process is carried out by introducing or expressing within a cell a nucleic acid molecule aptamer molecule of the present invention that includes first and second domains, as described above, where the first domain binds specifically to the fluorophore only after the second domain binds specifically to the target molecule. A fluorophore of the type described above is also introduced into the cell, where the fluorophore is bound specifically to the first domain of the nucleic acid molecule when the target molecule is bound by the second domain, thereby enhancing fluorescent emissions by the first fluorophore. Upon exposure of the cell to radiation of suitable wavelength to induce fluorescence emissions by the fluorophore that is bound in the complex or a FRET partner, and then measuring the fluorescent emissions of the fluorophore or FRET partner, it is possible to determine whether the activity of the target molecule is modified by the drug. Where a difference exists in the fluorescent emissions by the fluorophore or FRET partner, relative to an otherwise identical cell that lacks the drug, then this will indicates that the drug modifies the activity of the target molecule.

A further aspect of the invention relates to the de novo creation of aptamer-based sensor molecules for a particular target, without any prior knowledge of the aptamer for the particular target. This process is achieved using a modified SELEX procedure, where the nucleic acid molecules of the pool each contain a partially destabilized aptamer molecule that contains a first domain that binds specifically to a fluorophore of the present invention, and a second domain that comprises a wholly or partly random sequence. By partially destabilizing the first domain, only after binding of the second domain to the target molecule is first domain capable of binding specifically to the fluorophore. This is effectively the same approach used in FIG. 7C for the Spinach-derived sensor.

SELEX is carried out by exposing the pool of nucleic acid molecules to a target molecule and the fluorophore (whereby fluorescence emissions by the fluorophore are enhanced by the binding of the first domain to the fluorophore). Illuminating the fluorophore with light of a wavelength suitable to induce fluorescence emissions by the fluorophore that is bound by the first domain molecule, and measuring the fluorescent emissions of the fluorophore provide an indication as to whether any members of the pool bound to the target molecule (via their second domain).

RNAs members of the pool can be "precleared" by passing the RNAs over fluorophore-bound to agarose. This will remove all library members that retain constitutive fluorophore-binding activity (i.e., even in the absence of a functional second domain that binds to the target). In the next step, the pool is exposed to the fluorophore-bound agarose, except that this time the target will be added to the incubation buffer. All washes will also contain target. After washing, the elution will occur in the same buffer, except that no target will be present. Thus, any RNAs whose binding to the fluorophore is dependent on target will elute. These RNAs will be recovered and used for subsequent rounds of SELEX to enrich for target-regulated sensors. The fluorescence of each pool will be tested as above in the presence of the fluorophore with or without the target of interest, and individual clones that exhibit target-dependent fluorescence can be isolated.

A negative selection can also be used to ensure that the sensors do not respond to structurally related molecules. To do this, the structurally related molecules can also be introduced in the elution buffer, so that if they promote fluorophore binding they will be retained on the agarose (whereas sensor constructs that are unaltered by these structurally related molecules will elute).

Fundamentally, this same approach can be used to screen drugs for binding to a target nucleic acid molecule of interest. RNA sequences of interest that have no known drug to target the same can be screened against a library, for instance a chemical library, to find new molecules that would bind to this RNA sequence of interest. Because binding of drugs typically stabilizes RNA sequences, the sensor can be a turn-on sensor of the type described above. Rather than using a random nucleotide sequence for the second domain, the RNA sequence of interest is used as the second domain and it is fused to the fluorophore-binding aptamers of the invention (a first domain). Upon drug binding to the second domain, the nucleic acid molecule will adopt a stabilized conformation that allows the first domain to bind and induce fluorescence of a fluorophore. Thus, the chemical library can be screened based on whether or not the test molecule increases the overall fluorescence. This will allow for the rapid screening of chemical libraries for the discovery of new drugs that bind to known RNA sequences of interest.

In a further aspect of the invention, a transgene of the present invention can be inserted into a viral genome and then packaged to form an infective delivery vehicle, or the transgene can be inserted into a virus like particle to form a pseudovirion. Infection of a cell by the virus or pseudovirus can be detected by measuring expression of the transgene encoding the RNA aptamer or RNA fusion. Expression of the transgene can be detected by exposing the cell to the fluorophore and then exposing the cell to radiation of a wavelength suitable to induce fluorescence emissions by the fluorophore that is bound by the RNA aptamer molecule (or a FRET partner). Any fluorescent emissions of the fluorophore (or FRET partner) reflect transgene expression and, hence, viral or pseudoviral infection of the cell. In contrast, the absence of fluorescence indicates that the virus or pseudovirus did not infect the cell. This aspect of the invention can be used to screen putative therapeutic agents for their ability to inhibit viral infection. Additionally, viral particles themselves can be quantified by fluorescence if the viral particle contains single-stranded RNA containing the aptamer sequence and the fluorophore.

Kits

A further aspect of the present invention relates to various kits that can be used for practicing the present invention. The kit components can vary depending upon the intended use, and any reagents identified in this application can be included in the one or more kits. The kits can be packaged with components in separate containers or as mixtures, as noted below. Instructions for use may also be provided.

For example, according to one embodiment, the kit can include one or more fluorophores of the type described above and one or more nucleic acid aptamers or genetic constructs encoding those aptamers. The genetic construct can be designed for RNA trafficking studies, or for expression of multivalent sensor molecules.

In one embodiment, the aptamer component that is responsible for binding to the fluorophore can be selected such that each of a plurality of nucleic acid aptamers causes a different emission profile by a single fluorophore. In this way, a single fluorophore can be used for multiple, simultaneous detections. According to this embodiment, the plurality of nucleic acid aptamers can be supplied separately, e.g., in different containers, or they can be supplied as a mixture or as a range of mixtures, such that each mixture is characterized by a different blended fluorescent emission pattern with the same fluorophore.

According to another embodiment, the kit can include one or more fluorophores that are immobilized on a substrate to allow for SELEX. The substrate can be an FTIR suitable flow cell. The kit can also include one or more "turn-on" sensor molecules, which are matched for each of the one or more fluorophores, i.e., the fluorophore-specific domain of the sensor is specific for only one of the surface-bound fluorophores or elicits distinct emissions by two or more of the surface-bound fluorophores. This will allow for detection of the target molecule in a sample.

According to another embodiment, the kit can include one or more nucleic acid aptamers that are immobilized on a support, which can be a surface of a substrate. Examples of suitable supports include, without limitation, another nucleotide sequence including RNA, DNA, PNA or modifications or mixtures of these oligonucleotides; a macromolecular structure composed of nucleic acid, such as DNA origami; a surface composed of glass, such as a glass slide; a surface formed of a plastic material such as plastic slides; a protein or polypeptide, such as an antibody; an oligosaccharide; a bead or resin. The substrate can be provided with a plurality of the nucleic acid aptamers that are positioned at discrete locations so as to form an array. The spots on the array where the nucleic acid aptamers are retained can have any desired shape or configuration.

According to another embodiment, the kit can include a plurality of distinct fluorophores of the invention, and a plurality of distinct nucleic acid molecules of the invention which bind specifically to at least one of the plurality of fluorophores. Preferably, only a single monovalent or multivalent nucleic acid aptamer molecule is provided for each fluorophore. To enable their use together, each fluorophore:aptamer pair should be characterized by a distinct emission spectrum such that each can be detected independently. As demonstrated by the accompanying examples, a plurality of distinct aptamer/fluorophore complexes can achieve distinguishable emission spectra. The multiple colors will allow imaging of multiple RNAs simultaneously and allow the development of protein-RNA and RNA-RNA FRET systems.

For example, using multiple sensor molecules with distinct fluorophores that are compatible with FRET, detection of interactions of RNA or DNA with fluorescent proteins, RNAs, or other molecules can be achieved. FRET occurs if an appropriate acceptor fluorophore is sufficiently close to the acceptor fluorophore. Therefore, the interaction of a fluorescent protein, RNA, DNA, or other molecule with an RNA-fluorophore complex can be detected by measuring the FRET emission upon photoexcitation of the acceptor. Measurements like this can be used to measure the rate of binding of a fluorescent molecule to an RNA that is tagged with an RNA-fluorophore complex in both in vitro and in vivo settings. In a similar application, the RNA-fluorophore complex can serve as a donor and a fluorescent protein, RNA, DNA, other molecule can serve as the acceptor. In these cases, the RNA-fluorophore complex can be excited, and FRET emission can be detected to confirm an interaction. As used herein, a FRET partner refers to either a FRET acceptor or a FRET donor, which is used in combination with a fluorophore/aptamer complex of the invention.

According to another embodiment, the kit can include an empty genetic construct of the invention, as described above, along with one or more of the following: one or more restriction enzymes, one or more fluorophore compounds of the invention (which are operable with the aptamer sequence encoded by the construct), and instructions for inserting a DNA molecule encoding an RNA molecule of interest into the restriction sites for formation of a genetic construct that encodes a transcript comprising the RNA molecule of interest joined to the RNA aptamer molecule.

EXAMPLES

The following examples are intended to illustrate practice of the invention, and are not intended to limit the scope of the claimed invention.

Materials and Methods for Examples 1-7

Cell Culture Conditions: Cell lines were obtained directly from the American Type Culture Collection (ATCC) for all experiments. COS-7 (ATCC-CRL-1651), HEK-293T (ATCC-CRL-11268) and Hela (ATCC-CRM-CCL-2) cells were grown according to ATCC instructions. Cells were screened for mycoplasma contamination before passaging using Hoechst 33258, according to ATCC recommendations.

```
Spinach2 DNA Sequence:
                                     SEQ ID NO: 41
5'-GAT GTA ACT GAA TGA AAT GGT GAA GGA CGG GTC CAG
TAG GCT GCT TCG GCA GCC TAC TTG TTG AGT AGA GTG TGA
GCT CCG TAA CTA GTT ACA TC-3',.
```

Reagents and Equipment: Unless otherwise stated, all reagents were purchased from Sigma-Aldrich. Commercially available reagents were used without further purification. Absorbance spectra were recorded with a Thermo Scientific NanoDrop 2000 spectrophotometer with cuvette capability. Fluorescence excitation and emission spectra were measured with a PerkinElmer LS-55 fluorescence spectrometer.

Preparation and Analysis of Spinach and Spinach Mutants: RNAs were created by using the appropriate single-stranded DNA templates (Integrated DNA Technologies) and PCR amplification using primers that included a 5' T7 promoter sequence to generate double-stranded DNA templates. PCR products were then purified with PCR purification columns (Qiagen) and used as templates for in vitro T7 transcription reactions (Epicentre) as described previously (Paige et al., "RNA mimics of green fluorescent protein," *Science* 333: 642-646 (2011), which is hereby incorporated by reference in its entirety). RNA was purified using ammonium acetate precipitation, and quantified using both absorbance values and the Riboquant Assay kit (BD Biosciences). Photophysical characterization of Spinach2 was carried out as previously described (Paige et al., "RNA mimics of green fluorescent protein," *Science* 333: 642-646 (2011), which is hereby incorporated by reference in its entirety).

Thermostability Measurements: Spinach or Spinach2 (1 µM) was incubated in 20 mM HEPES pH 7.4, 100 mM KCl, 1 mM $MgCl_2$ and 10 µM DFHBI. Fluorescence values were recorded in 1° C. increments from 20° C. to 60° C., with a 5-min incubation at each temperature to allow for equilibration. Fluorescence measurements were performed using a PerkinElmer LS-55 fluorescence spectrometer using the following instrument parameters: excitation wavelength, 460 nm; emission wavelength, 501 nm; slit widths, 10 nm. Curves were fitted using the Boltzmann sigmoidal equation in GraphPad Prism 5 software. Values presented are mean and s.e.m. from three independent measurements.

Folding Assay: The folding assay involves measurement of fluorescence under two conditions, one in which RNA is in excess relative to DFHBI, and one in which the DFHBI is in excess relative to RNA. As Spinach and DFHBI form a 1:1 stoichiometric complex, the maximum amount of complex that can be formed is determined by the limiting component. In the first condition, the fluorescence was determined by incubation of 0.1 µM DFHBI and 100-fold excess (10 µM) Spinach. This value was used to define the fluorescence of 0.1 µM Spinach-DFHBI complex. It was assumed that even if nearly all Spinach is misfolded or unfolded, there will be enough properly folded Spinach to stoichiometrically bind 0.1 µM DFHBI. This was confirmed by measuring fluorescence after doubling the RNA to 20 µM, which caused no increase in fluorescence. In the second condition, the fluorescence obtained using 10 µM DFHBI and 0.1 µM Spinach was measured. In theory, up to 0.1 µM Spinach-DFHBI can form if all the Spinach is folded. However, if a portion of Spinach is unfolded, the fluorescence will be proportionately less than the fluorescence of 0.1 µM Spinach-DFHBI. Thus, this approach can reveal the fraction of Spinach that is folded under diverse conditions.

Fluorescence was measured for each RNA under the following conditions: (i) 0.1 µM RNA and 10 µM DFHBI, and (ii) 0.1 µM DFHBI and 10 µM RNA. For each condition, the signal from DFHBI without RNA was subtracted from each signal. Fluorescence was measured in 20 mM HEPES pH 7.4, 100 mM KCl and 1 mM $MgCl_2$ at the designated temperature. Fluorescence measurements were performed using a PerkinElmer LS-55 fluorescence spectrometer using the following instrument parameters: excitation wavelength, 460 nm; emission wavelength, 501 nm; slit widths, 10 nm. Signal from the first condition (limiting RNA) was divided by the signal from the second condition (limiting dye) to determine the fraction folded.

Preparation and In Vitro Analysis of Flanked Spinach and Spinach2 Constructs: Spinach and Spinach2 constructs flanked on either side by 50 base pairs were generated by PCR. For Spinach, the following primers were used:

forward primer
(SEQ ID NO: 42)
5'-TAA TAC GAC TCA CTA TAG GGC GGA CTA TGA CTT AGT
TGC GTT ACA CCC TTT CTT GAC AAA ACC TAA CTT GAC
GCA ACT GAA TGA AAT GGT G-3' reverse primer
(SEQ ID NO: 43)
5'-AAA CAA AAA AAA CAA ATA AGC CAT GCA ATC TCA T
CTT GTT TTC TGC GCG ACG CTA GTT ACG GAG-3'.

For Spinach2, the following primers were used:

forward primer
(SEQ ID NO: 44)
5'-TAA TAC GAC TCA CTA TAG GGC GGA CTA TGA CTT
AGT TGC GTT ACA CCC TTT CTT GAC AAA ACC TAA CTT
GAT GTA ACT GAA TGA AAT G-3' reverse primer
(SEQ ID NO: 45)
5'-AAC AAA AAA AAC AAA TAA AGC CAT GCC AAT CTC
ATC TTG TTT TCT GCG CGA TGT AAC TAG TTA CGG AG-3'.

The 50-base-pair sequences were taken from the human β-actin 3' untranslated region. Both forward primers encode the T7 RNA polymerase promoter for in vitro transcription. 5S-Spinach and 5S-Spinach2 were amplified by PCR from pAV-5S-Spinach and pAV-5S-Spinach2, respectively, using the following primers:

forward primer
(SEQ ID NO: 46)
5'-TAA TAC GAC TCA CTA TAG GGT CTA CGG CCA TAC
CAC CCT G-3' reverse primer
(SEQ ID NO: 47)
5'-TGG CGC CCG AAC AGG GAC-3'.

$(CGG)_{60}$-Spinach and $(CGG)_{60}$-Spinach2 were amplified by PCR from pCDNA-60CGG-Spinach and pCDNA-60CGG-Spinach2, respectively, using the following primers:

forward primer
(SEQ ID NO: 48)
5'-TAA TAC GAC TCA CTA TAG G-3' reverse primer
(SEQ ID NO: 49)
5'-GGC AAA CAA CAG ATG GCT GGC AAC TAG-3'.

PCR products were used as templates for in vitro transcription by Ampliscribe T7 RNA polymerase as previously described (Paige et al., "RNA mimics of green fluorescent protein," Science 333: 642-646 (2011), which is hereby incorporated by reference in its entirety). Fluorescence measurements were recorded for 0.1 µM RNA in the presence of 10 µM DFHBI in buffer composed of 20 mM HEPES pH 7.4, 100 mM KCl and 100 µM $MgCl_2$ as described above.

Cloning Spinach2 for Expression in E. coli: Spinach and Spinach2 were PCR-amplified with primers containing the EagI restriction sites on both the 5' and 3' ends of the Spinach sequence. They were then cloned into a pET28c-based plasmid containing a chimera of the human tRNA$^{Lys3}$ scaffold, which was previously used for Spinach and Spinach-based metabolite sensors and which has previously been shown to stabilize heterologous expression of RNA aptamers in E. coli (Ponchon et al., "Recombinant RNA Technology: The tRNA Scaffold," Nat. Methods 4:571-576 (2007), which is hereby incorporated by reference in it's entirety).

Whole-Cell Fluorescence Measurements of E. coli: BL21 cells were transformed to harbor either pET28c-tRNA-Spinach or pET28c-tRNA-Spinach2, and grown in Luria broth with 100 µg/ml kanamycin to $OD_{600}$ 0.4 at room temperature. The cells were then induced with addition of 1 mM IPTG for 2 h at room temperature. After induction, cells were normalized for cell density and split into two aliquots. One aliquot per sample was incubated at room temperature, and the other was incubated for 20 min at 37° C. Cells were then measured for total fluorescence using a Tecan Safirell plate reader with 460±10 nm excitation and emission was recorded at 510±10 nm. Data shown represent mean and s.e.m. values for three independent experiments.

Quantitative Reverse Transcription—PCR Analysis of Spinach and Spinach2 Concentration in E. coli: Total RNA samples were collected from E. coli at both 25° C. and 37°

C. using the RNeasy Protect Bacteria Mini Kit (Qiagen). Reverse transcription was carried out on all samples using a reverse primer that bound in the tRNA portion of the tRNA-Spinach transcripts (5'-TGG CGC CCG AAC AGG GAC-3', SEQ ID NO: 50) and a reverse primer against 16S RNA (5'-GTA TTA CCG CGG CTG CTG-3', SEQ ID NO: 51) according to the SuperscriptIII reverse transcription kit protocol. qRT-PCR was carried out according to the iQ SYBR Green Supermix (Bio-Rad) protocol with the following primers to the tRNA portion of either transcript:

```
forward primer
                                         (SEQ ID NO: 52)
5'-GCC CGG ATA GCT CAG TCG GTA G-3' reverse primer
                                         (SEQ ID NO: 53)
5'-TGG CGC CCG AAC AGG GAC-3'
``` as well as the following primers to 16S RNA:

```
forward primer
                                         (SEQ ID NO: 54)
5'-CTC CTA CGG GAG GCA GCA G-3' reverse primer
                                         (SEQ ID NO: 55)
5'-GTA TTA CCG CGG CTG CTG-3'.
```

In all cases, Spinach transcript levels were normalized to 16S RNA levels. Data represent mean and s.e.m. values for three independent experiments.

Cloning of 5S-Spinach and Spinach2: pAV-5S-Spinach was generated as previously described (Paige et al., "RNA Mimics of Green Fluorescent Proteins," Science 333:642-646 (2011), which is hereby incorporated by reference in its entirety). This construct contained Spinach in the context of the tRNA$^{Lys3}$ scaffold. Sequence encoding tRNA$^{Lys3}$-Spinach was removed from pAV-5S by restriction digest with SalI and XbaI. Sequence encoding tRNA$_{Lys}$-Spinach2 was amplified from pET28c-tRNA-Spinach2 by PCR using the following primers:

```
forward primer
                                         (SEQ ID NO: 56)
5'-TAG GCG TCG ACG CCC GGA TAG CTC AGT CGG TAG AGC
AG-3' reverse primer
                                         (SEQ ID NO: 57)
5'-ATA TAT TCT AGA TGG CGC CCG AAC AGG GAC TTG AAC
CC-3',
``` and digesting the resulting PCR products with XbaI and SalI to clone into pAV-5S.

Imaging 5S-Spinach and 5S-Spinach2: Imaging of 5S-Spinach and 5S-Spinach2 was carried out as previously described for 5S-Spinach (Paige et al., "RNA Mimics of Green Fluorescent Proteins," Science 333:642-646 (2011), which is hereby incorporated by reference in its entirety). Cells were imaged for either 100 ms or 1 s. Background signals from cells expressing pAV-5S incubated with DFHBI were also taken at 100 ms and 1 s and subtracted from the corresponding images using NIS-Elements software.

For brightness quantification, fluorescence signal was measured for 20 background-subtracted cells per sample and normalized for total area using NIS-Elements AR 3.2 (Nikon). 5S-Spinach2 signal was normalized to 1.0.

Cloning of Spinach-7SK and Spinach2-7SK: Spinach or Spinach2 in the context of the tRNA$_{Lys}$ scaffold was amplified by PCR using the following primers:

```
forward primer
                                         (SEQ ID NO: 58)
5'- ATA TAT GGA TCC GCC CGG ATA GCT CAG TCG G-3' reverse primer
                                         (SEQ ID NO: 59)
5'-ATA TAT AGA TCT GGC GCC CGA ACA GGG ACT TG-3'.
```

The resulting PCR product was digested using BamHI and BglII. This digested PCR produced was then ligated into a version of pLPCXU6PT7SK (Addgene plasmid 27549) that was modified as follows. pLPCXU6PT7SK was used as a template with the following primers:

```
forward primer
                                         (SEQ ID NO: 60)
5'-ATA TAT AAG CTT GGA TCC ATC ATC ATC GCA GCA AGA
TCT GGA TGT GAG GCG ATC TGG C-3' reverse primer
                                         (SEQ ID NO: 61)
5'-GTC TTG GAA GCT TGA CTA CCC TAC GTT CTC CTA
C-3'.
```

This PCR product eliminated the 5' coat protein—binding sequences and encoded BamHI and BglII sites. This PCR product was digested with HindIII and ligated into pLPCXU6PT7SK that was digested with HindIII to generate pLPCXU6PT7SK-fixed. Sequencing was used to verify proper orientation of the insertion. The Spinach and Spinach2 PCR products were then ligated into pLPCXU6PT7SK-fixed at BamHI and BglII to generate pLPC-Spinach-7SK and pLPC-Spinach2-7SK, respectively.

pSC35-mCherry was generated by amplifying mCherry with the following primers:

```
forward primer
                                         (SEQ ID NO: 62)
5'-ATA TAT GGA TCC AAT GGT GAG CAA GGG CGA GG-3' reverse primer
                                         (SEQ ID NO: 63)
5'-TAT ATA TAA GCT TTC ACT TGT ACA GCT CGT CC-3',
``` and cloning via BamHI and HindIII digestion downstream of SC35 in pcDNA3.1-SC35-cMyc (Addgene plasmid 44721) to generate pcDNA3.1-SC35-mCherry.

Imaging Spinach-7SK and Spinach2-7SK: HeLa cells (ATCC-CRM-CCL-2) were cultured and passaged in DMEM medium supplemented with 50 units of penicillin and 50 μg of streptomycin per milliliter. For imaging experiments, cells were grown on cells cultured on 24-well glass-bottom dishes and cotransfected with 0.3 μg of pLPC-Spinach-7SK or pLPC-Spinach2-7SK and 0.3 μg of pCDNA3.1-SC35-mCherry using FuGeneHD (Roche) per the manufacturer's instructions in DMEM lacking penicillin and streptomycin. Cells were imaged 24 h after transfection. At 30 mM before imaging, medium was supplemented with 25 mM HEPES, 5 mM MgSO$_4$ and 20 μM DFHBI. Cells were imaged as described below using FITC and Texas Red filter sets.

Cloning of $CGG_{60}$-Spinach and Spinach2: Spinach or Spinach2 in the context of the $tRNA_{Lys}$ scaffold was amplified by PCR using the following primers:

```
forward primer
                                       (SEQ ID NO: 64)
5'-ATA TAT ATC TAG AGC CCG GAT AGC TCA GTC GGT AGA

GCA G-3' reverse primer
                                       (SEQ ID NO: 65)
5'-ATA TAT GGG CCC TGG CGC CCG AAC AGG GAC TTG AAC

CC-3',
``` and digesting the resulting PCR products with XbaI and ApaI to clone downstream of the 60 CGG repeats and upstream of the BGH polyadenylation sequence in pCDNA-60CGG to generate pCDNA-60CGG-Spinach and pCDNA-60CGG-Spinach2. For TET-off experiments, the entire transcript from pCDNA-60CGG-Spinach2 (CGG60-Spinach2-BGH-polyadenylation signal) was excised using NheI and EcoRV and subcloned into pTRE2-Hyg (Clontech) that was cut with NheI and EcoRV.

Transfection of COS-7 Cells and Live Cell Imaging: COS-7 cells (ATCC-CRL-1651) were cultured and passaged in DMEM supplemented with 50 units of penicillin and 50 µg of streptomycin per milliliter. For imaging experiments, cells were grown on cells cultured on 24-well glass-bottom dishes and transfected with 0.6 µg of pCDNA-60CGG-Spinach or pCDNA-60CGG-Spinach2 using FuGeneHD (Roche) per the manufacturer's instructions in DMEM medium lacking penicillin and streptomycin. Cells were imaged in CO2-independent medium (Invitrogen) supplemented with L-glutamine. At 30 min-1 h before imaging, medium was supplemented with 25 mM HEPES, 5 mM $MgSO_4$, 1 µg/ml Hoechst 33342 (when appropriate) and 20 µM DFHBI or vehicle. Live fluorescence images were acquired in a temperature-controlled chamber at 35-37° C. with a CoolSnap HQ2 CCD camera through a 60× oil objective (Plan Apo 1.4 numerical aperture (NA)) mounted on a Nikon TE2000 epifluorescence microscope and analyzed with the NIS-Elements software. Spinach was imaged with a filter cube typically used for fluorescein or EGFP, with a sputter-coated excitation filter 470/40 nm, dichroic mirror 495 nm (long-pass), and emission filter 525/50 (Chroma Technology). DsRed-Max and mCherry were imaged using a filter cube typically used for Texas Red, with a sputter coated excitation filter 560/40 nm and emission filter 630/75 nm (Chroma Technology). Background intensity was subtracted from all pixel intensity measurements. Image analyses were completed with NIS-Elements AR 3.2 (Nikon). Drug treatments were carried out as specified. Tautomycin was used at a final concentration of 5 µM in all cases. 1a was used at a final concentration 20 µM in all cases. DMSO was added to a final concentration of 0.1% for vehicle treatments.

For foci-formation experiments, COS-7 cells were transiently transfected with a plasmid expressing (CGG)60-Spinach2. After 2 h, the transfection medium was replaced with imaging medium containing DFHBI. After a 1-h incubation in imaging medium, cells were imaged every 20 mM for 6 h.

Analysis of DFHBI Cell Permeability: COS-7 cells were transfected with pCDNA-60CGG-Spinach2. 24 h after transfection, cells were imaged in medium supplemented with 25 mM HEPES, 5 mM $MgSO_4$, 1 µg/ml Hoechst 33342 and 20 µM DFHBI. Images were acquired for Hoechst and Spinach2 signals every 5 min for 1 h for 20 cells. All signals were first normalized to area and then normalized to the highest signal for a given nucleus to determine the time for maximal signal to be reached.

Fluorescence In Situ Hybridization of $CGG_{60}$ RNA: COS-7 cells were grown and transfected as described above on glass coverslips. Cells were fixed and stained as previously described (Sellier et al., "Sam68 Sequestration and Partial Loss of Function are Associated with Splicing Alterations in FXTAS Patients," *EMBO J.* 29:1248-1261 (2010), which is hereby incorporated by reference in its entirety). CGG repeats were probed using an $(CCG)_{8x}$—Texas Red DNA oligonucleotide probe (IDT). Spinach was probed using a 3' Texas Red—labeled DNA oligonucleotide (5'-GCA CTG CCG AAG CAG CCA CAC CTG-3', SEQ ID NO: 66) (IDT). DAPI was added in the mounting solution for DNA staining.

Quantitative Reverse Transcription—PCR Analysis of CGG RNA Stability: COS-7 cells were transfected to express either pTet-off alone or pTet-off with either pTRE2-Hyg-$(CGG)_{60}$, pTRE2-Hyg-$(CGG)_{60}$-Spinach, pTRE2-Hyg-$(CGG)_{60}$-Spinach2, pTRE2-Hyg-$(CGG)_{30}$, or pTRE2-Hyg-$(CGG)_{30}$-Spinach2 in 12 wells each in 24-well plates. At 24 h after transfection, the transfection medium was replaced, and doxycycline was added to 1 µg/ml. At 0 h, 6 h, 12 h and 24 h after transfection, total RNA from three wells per sample was extracted using TRIzol (Invitrogen) according to manufacturer's protocol.

Reverse transcription was carried out on all samples using a reverse primer that bound downstream of the CGG repeats in all constructs (5'-CTA GAG ATA TCA GGC TGA TCA GC-3', SEQ ID NO: 67) and a reverse primer against GAPDH mRNA (5'-TCC ACC ACC CTG TTG CTG TA-3', SEQ ID NO: 68) according to the SuperscriptIII reverse transcription kit protocol. qRT-PCR was carried out according to the iQ SYBR Green Supermix (Bio-Rad) protocol with the following primers against CGG transcripts:

```
forward primer
                                       (SEQ ID NO: 69)
5'-GTC AGC TGA CGC GTG CTA GCG-3' reverse primer
                                       (SEQ ID NO: 70)
5'-CTA GAG ATA TCA GGC TGA TCA GC-3',
``` as well as the following primers against GAPDH mRNA:

```
forward primer
                                       (SEQ ID NO: 71)
5'-ACC ACA GTC CAT GCC ATC AC-3' reverse primer
                                       (SEQ ID NO: 72)
5'-TCC ACC ACC CTG TTG CTG TA-3'.
```

In all cases, CGG transcript levels were normalized to GAPDH mRNA levels. Data represent mean and s.e.m. values for three independent experiments. qRT-PCR of sample RNA compared to in vitro-transcribed control RNA was carried out to determine the approximate number of CGG repeat-containing RNA in a cell. Roughly 0.2 ng of $(CGG)_{60}$-Spinach2 RNA was obtained from $0.2 \times 10^6$ transfected cells. The molecular weight of polyadenylated $(CGG)_{60}$-Spinach2 was estimated to be roughly 280 kDa. Using these values, it was calculated that each transfected cell contained roughly 2,000 copies of $(CGG)_{60}$-Spinach2.

On average, each cell contained 10-15 foci, indicating that each aggregate contains roughly 150-200 RNA molecules. It should be noted that foci vary in size in different cells, and foci that are much smaller than the 'average' size are readily detectable in cells. Moreover, some Spinach2 signal was observed in the nucleoplasm that is not in foci. So 150-200 RNA molecules is unlikely to be the limit of detection at 50 ms; however, the precise limit will require more precise quantification methods of these foci that are closer to the limits of detection. Because foci were typically imaged at 50 ms, it is likely that smaller numbers of RNAs would be detectable at longer imaging times such as 500 ms or 1 s.

Example 1

Low Fluorescence of Spinach-Tagged RNAs

To investigate 'toxic RNA' localization', an RNA containing 60 CGG repeats $(CGG)_{60}$ previously shown to form intranuclear foci resembling those in patients with Fragile X-associated tremor/ataxia syndrome (FXTAS) (Sellier et al., "Sam68 Sequestration and Partial Loss of Function are Associated with Splicing Alterations in FXTAS Patients," *EMBO J.* 29:1248-1261 (2010), which is hereby incorporated by reference in its entirety) was expressed with a 3' Spinach tag. However, expression of the $(CGG)_{60}$-Spinach construct did not result in readily detectable nuclear foci in COS-7 cells in the presence of DFHBI (FIG. 1). Although fluorescence was not detectable, Spinach-tagged RNA formed nuclear foci, as measured by fluorescence in situ hybridization (FISH).

To test whether the Spinach tag was unstable or degraded independently from the CGG repeat-containing RNA, FISH was carried out with a probe to Spinach, confirming its presence in these foci. Tagged and untagged versions of $(CGG)_{60}$ RNA were equally stable based on quantitative reverse-transcription PCR (qRT-PCR). The observation that the Spinach-tagged CGG repeat-containing RNA was abundant in foci but was not fluorescent indicated that Spinach was not fluorescent in the context of the CGG repeat-containing RNA and required modifications to enhance its fluorescence in cells.

Several factors that could affect the brightness of Spinach in cells were considered. These include poor ability of DFHBI to permeate into the cell, low intrinsic brightness and poor folding in cells. Poor ability of DFHBI to enter cells is unlikely because it matches that of Hoechst in mammalian cells, with maximal fluorescence achieved in ~30 min. Additionally, in vitro measurements of Spinach-DFHBI fluorescence show that its intrinsic brightness is 80% of that of GFP and 53% of that of eGFP (Paige et al., "RNA Mimics of Green Fluorescent Proteins," *Science* 333:642-646 (2011), which is hereby incorporated by reference in its entirety), which is bright enough for imaging. Therefore the possibility that Spinach misfolds in cells, which decreases the number of Spinach-tagged RNAs that can bind and activate the fluorescence of DFHBI, was considered.

The melting temperature ($T_m$) of Spinach was determined by monitoring the fluorescence of the RNA-DFHBI complex in vitro between 20° C. and 60° C. Spinach had a $T_m$ of 34±0.6° C. (±s.e.m.), indicating that a substantial fraction of Spinach molecules may be unfolded when imaging at 37° C.

Example 2

Mutational Analysis and Development of Spinach2

Figures 2A, 2B, 2C, 2D:
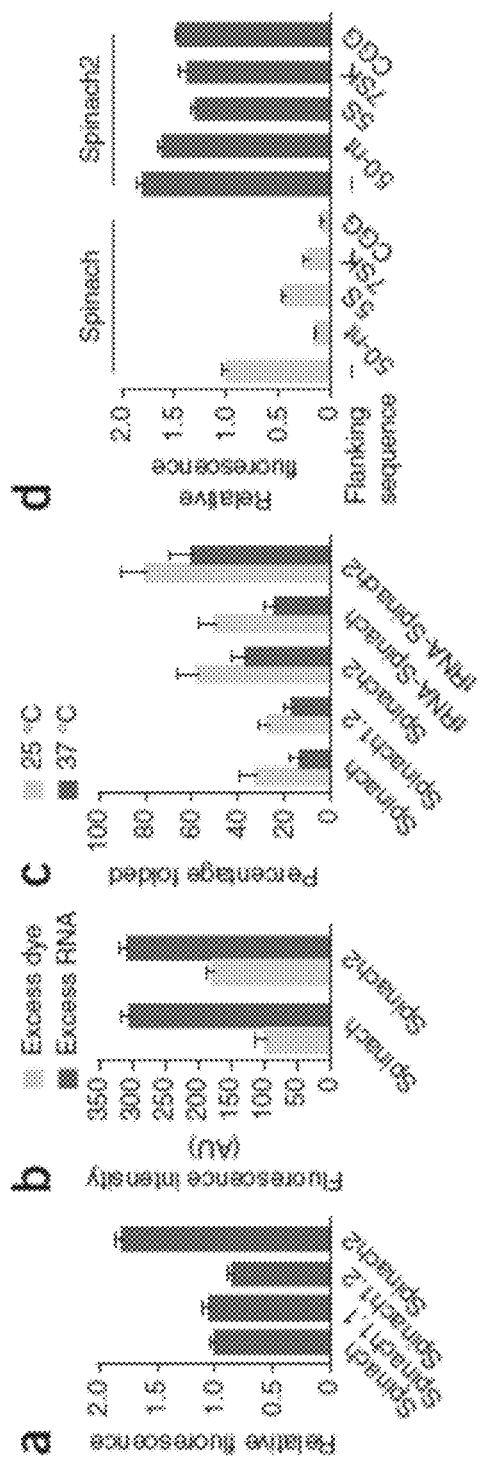
FIGS. 2A-D demonstrate that Spinach2 is brighter than Spinach owing to improved folding.
Figure 18:
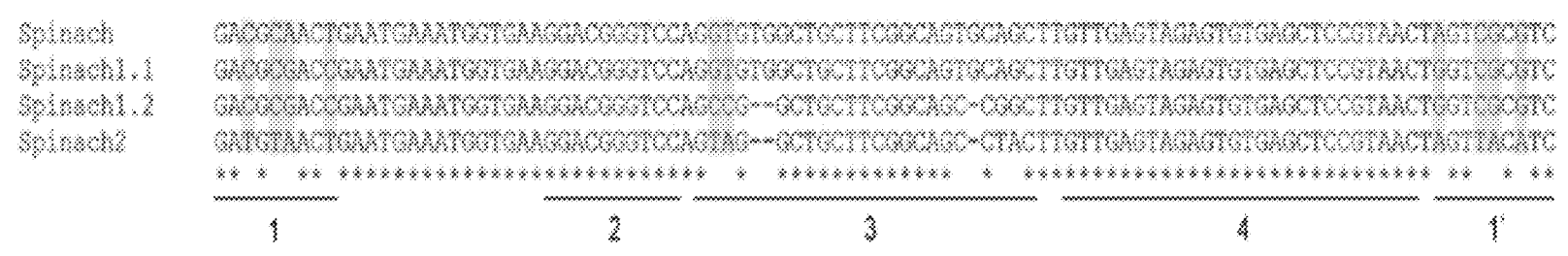

Mutations that could increase the thermostability of Spinach by correcting bulges and mismatches in the predicted structure were identified (FIG. 2B). These results led to the generation of Spinach1.1, which has perfect complementarity in stem 1, and Spinach1.2, which has perfect complementarity in both stem 1 and stem loop 3 (FIG. 18). Spinach1.1 had slightly enhanced thermostability, with a Tm of 35±0.5° C. and was as bright as Spinach (FIG. 2A). Spinach1.2 was more thermostable than Spinach and Spinach1.1, with a Tm of 38±0.3° C.). However, Spinach1.2 was 16% dimmer than Spinach (FIG. 2A), indicating that mutations in stem 1 and stem loop 3 enhance thermostability but do not improve brightness.

Mutations in Spinach1.2 can affect brightness by either reducing the extinction coefficient or quantum yield of Spinach-DFHBI or by increasing the misfolded fraction of Spinach that cannot bind DFHBI. To help distinguish between these alternatives, an assay to measure the fraction of Spinach that is properly folded was developed.

Using this assay with buffers that mimic cytoplasmic ion concentrations, it was found that 32±4.2% and 13±2.8% of Spinach is folded at 25° C. and 37° C., respectively. Spinach1.2 was also largely misfolded, with 27±2.1% and 16±2.3% folded at 25° C. and 37° C., respectively (FIG. 2). Spinach thus folds poorly, and the increased thermostability of Spinach1.2 does not correspond to better folding.

Next, systematic mutagenesis was carried out to identify thermostable Spinach mutants with improved folding. Because elevated G+C content can lead to stable misfolded structures (Kiliszek et al., "Crystal Structures of CGG RNA Repeats with Implications for Fragile X-Associated Tremor Attaxia Syndrome," *Nuc. Acids Res.* 39:7308-7315 (2011); Sobczak et al., "RNA Structure of Trinucleotide Repeats Associated with Human Neurological Diseases," *Nuc. Acids Res.* 31:5469-5482 (2003), each of which is hereby incorporated by reference in its entirety), it was reasoned that decreasing the overall G+C content could promote proper folding. Scanning mutagenesis was carried out, mutating every guanidine and cytosine to adenosine or uracil, respectively. In regions where G and C residues were predicted to form a base pair, both residues were mutated to A and U, to maintain the complementarity. Each of these 35 mutants was synthesized in vitro, and the fraction folded was measured at 25° C. and 42° C. Fluorescence signals that were equal to or greater than Spinach at 25° C. indicated equal or greater percent folded. A higher percentage signal at 42° C. indicated improved thermostability relative to Spinach.

Figure 1B:
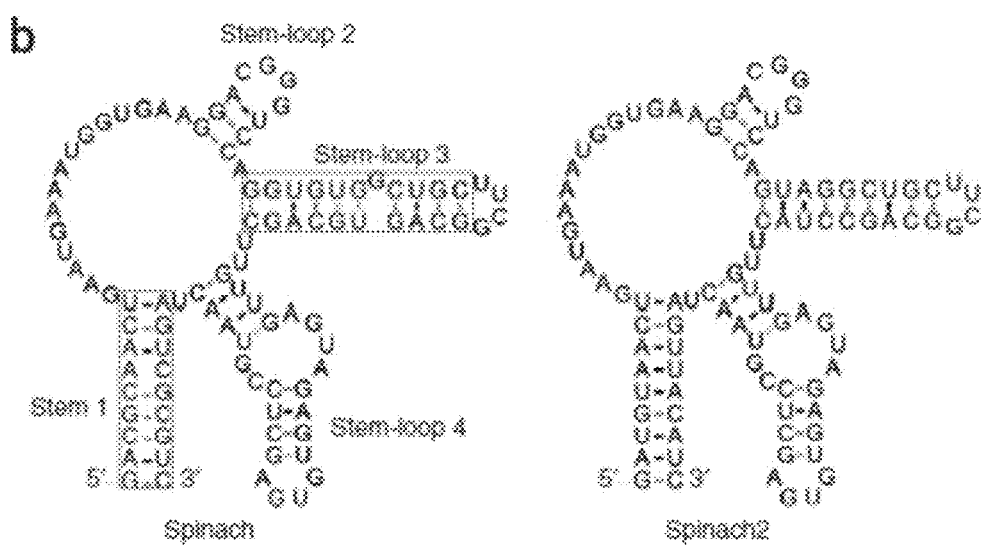

Six positions in Spinach that maintained or enhanced brightness at 25° C. and maintained Spinach1.2 thermostability were identified; mutations in these alone and in combination were tested (Table 1). The best-performing variant from this screen contained all six mutations and was 1.8- and 2.8-fold brighter than Spinach in vitro at 25° C. and 37° C., respectively, with a Tm of 38±0.4° C. (FIG. 3). This mutant was named Spinach2 (FIG. 1B).

TABLE 1

Brightness of Spinach1.2 Mutants at 25 and 42° C.

| Mutations[a] | Relative Brightness[b] (at 25° C.) | Percent Brightness[c] (at 42° C.) |
|---|---|---|
| Spinach | 1.0 | 19 |
| Spinach1.2[a] | 0.8 | 41 |
| G1A, C98T | 0.8 | 35 |
| C3T, G96A | 1.7 | 42 |
| G4A, C95T | 0.7 | 36 |
| *C5T, G94A* | *1.0* | *41* |

TABLE 1-continued

Brightness of Spinach1.2 Mutants at 25 and 42° C.

| Mutations[a] | Relative Brightness[b] (at 25° C.) | Percent Brightness[c] (at 42° C.) |
|---|---|---|
| G6A, C93T | 1.0 | 41 |
| C8T, G91A | 0.8 | 37 |
| *C9T, G90A* | 1.5 | 40 |
| G10A | 0.2 | 5 |
| G14A | 0.1 | 0 |
| G19A | 0.1 | 0 |
| G20A | 0.1 | 0 |
| G22A | 0.1 | 0 |
| G25A, C34T | 0.0 | 0 |
| G26A, C33T | 0.0 | 0 |
| C28T | 0.0 | 0 |
| G29A | 0.0 | 0 |
| G30A | 0.0 | 0 |
| G31A | 0.0 | 0 |
| G36A, C60T | 0.6 | 5 |
| *G37A, C59T* | 1.0 | 41 |
| C38A, G58T | 1.5 | 41 |
| G63A, C88T | 0.5 | 17 |
| G66A | 0.4 | 8 |
| G68A | 0.3 | 5 |
| G71A, C82T | 0.4 | 5 |
| G73A, C80T | 0.4 | 6 |
| G75A | 0.0 | 0 |
| G77A | 0.0 | 0 |
| C83T | 0.1 | 0 |
| G84A | 0.1 | 0 |
| C3T, G96A, C5T, G94A, G6A, C93T, C9T, G90A, G37A, C59T, C38A, G58T | 1.8 | 41 |
| C3T, G96A, G6A, C93T, C9T, G90A, G37A, C59T, C38A, G58T | 1.7 | 41 |
| C3T, G96A, C5T, G94A, C9T, G90A, G37A, C59T, C38A, G58T | 1.6 | 40 |
| C3T, G96A, C5T, G94A, G6A, C93T, G37A, C59T, C38A, G58T | 1.6 | 41 |
| C3T, G96A, C5T, G94A, G6A, C93T, C9T, G90A, C38A, G58T | 1.4 | 40 |
| C3T, G96A, C5T, G94A, G6A, C93T, C38A, G58T | 1.2 | 40 |
| C3T, G96A, C5T, G94A, C9T, G90A, C38A, G58T | 1.3 | 39 |
| C3T, G96A, C5T, G94A, G37A, C59T, C38A, G58T | 1.6 | 41 |
| C3T, G96A, G6A, C93T, C9T, G90A, C38A, G58T | 1.2 | 40 |
| C3T, G96A, G6A, C93T, G37A, C59T, C38A, G58T | 1.5 | 40 |
| C3T, G96A, C9T, G90A, G37A, C59T, C38A, G58T | 1.4 | 41 |
| C3T, G96A, C5T, G94A, C38A, G58T | 1.3 | 40 |
| C3T, G96A, G6A, C93T, C38A, G58T | 1.6 | 39 |
| C3T, G96A, C9T, G90A, C38A, G58T | 1.4 | 40 |
| C3T, G96A, G37A, C59T, C38A, G58T | 1.3 | 40 |
| C3T, G96A, C38A, G58T | 1.5 | 41 |

[a]Mutations are numbered accordig to Spinach nucleotide position. All mutants listed above contain mutations A6C, T9C, A90G, G37C, T38C, AfSG, and Δ40, 41, 56 relative to Spinach unless otherwise noted.
[b]Brightness values are determined relative to Spinach.
[c]Percent brightness values represent the percent of signal remaining at 42° C. for a given mutant.
Mutations in bold improved both brightness and thermostability and were included in subsequent mutagenesis.
Mutations in italics were screend by combinatorial mutagenesis.

Example 3

Characterization of Spinach2 Fluorescence

Figures 3A, 3B, 3C, 3D, 3E:
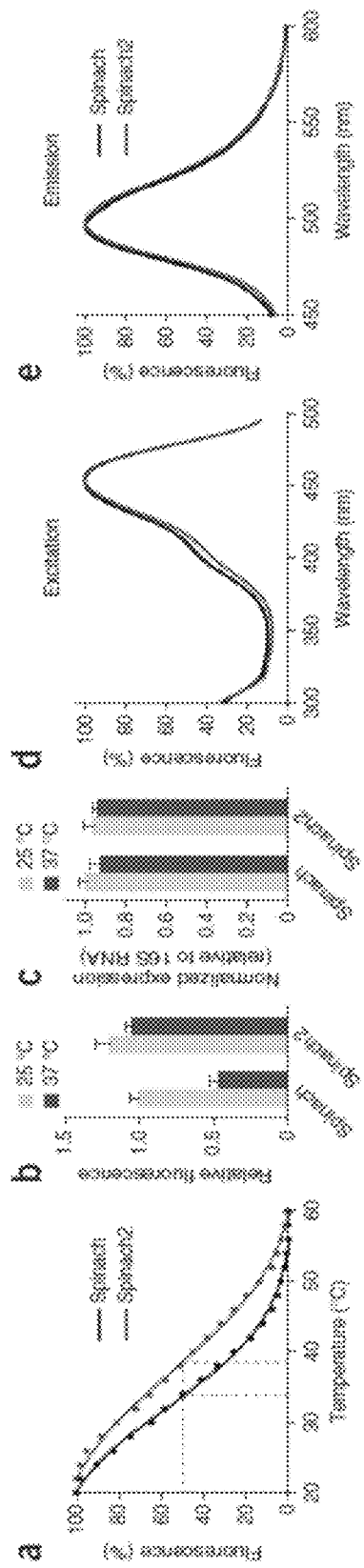
FIGS. 3A-E illustrate the properties of Spinach and Spinach2 in vitro and in bacteria.

In the folding assay, a substantially higher fraction of Spinach2 was folded compared to Spinach; 58±4.8% and 37±3.3% of Spinach2 was folded at 25° C. and 37° C., respectively (FIG. 2C). To determine whether mutations in Spinach2 affect its ability to activate the fluorescence of DFHBI, the extinction coefficient and quantum yield of Spinach2 were calculated. In these experiments, excess RNA and a limiting concentration of 0.1 μM DFHBI was used to compare 0.1 μM Spinach-DFHBI against 0.1 μM Spinach2-DFHBI, regardless of any difference in the percentage of each RNA that is folded. It was found that Spinach and Spinach2 had nearly identical photophysical properties, and that the excitation and emission spectra as well as the dissociation constant (KID) for DFHBI binding were nearly identical (FIGS. 3D, 3E). These data indicate that the enhanced brightness of Spinach2 reflects an increase in its folding efficiency.

Example 4

Spinach2 Retained Fluorescence in Diverse Contexts

RNA folding can be affected by flanking sequences, which may interact with the RNA aptamer. To test whether sequence context affects folding, the fluorescence of Spinach and Spinach2 inserted into different RNAs was monitored. First, it was found that Spinach flanked by 50 nucleotides (nt) of RNA on both the 5' and 3' ends was only 20% as bright as identical concentrations (0.1 μM) of Spinach alone (FIG. 2D). Flanked Spinach2 was 90% as bright as Spinach2 alone and tenfold brighter than flanked Spinach (FIG. 2D), indicating that Spinach2 is relatively insensitive to flanking sequence.

Spinach fluorescence in vivo is improved by inserting Spinach into the tRNA$^{Lys3}$ sequence (Paige et al., "RNA Mimics of Green Fluorescent Proteins," *Science* 333:642-646 (2011); Paige et al., "Fluorescence Imaging of Cellular Metabolites with RNA," *Science* 335:1194 (2012), which are hereby incorporated by reference in their entirety), which acts as a folding scaffold (Ponchon et al., "Recombinant RNA Technology: The tRNA Scaffold," *Nat. Methods* 4:571-576 (2007), which is hereby incorporated by reference in its entirety). In the case of Spinach, folding increased from 32±4.2% to 50±3.9% at 25° C. and from 13±2.8% to 24±2.4% at 37° C. in the presence of the tRNA (FIG. 2C). In the case of Spinach2, folding increased from 58±4.8% to 80±6.1% at 25° C. and from 37±3.3% to 60±5.4% at 37° C. For this reason, tRNA$^{Lys3}$-Spinach and tRNA$^{Lys3}$-Spinach2 was used in all subsequent tagged constructs and imaging experiments.

The brightness of Spinach and Spinach2 in fusions with 5S, 7SK and (CGG)$_{60}$ RNA were compared. The Spinach2 fusions to these RNAs were, respectively, 3-, 6- and 20-fold brighter than the same constructs fused to Spinach (FIG. 2D). Moreover, tagged Spinach2 retained more than 70% of its fluorescence relative to Spinach2 alone in all cases (FIG. 2D).

Example 5

Spinach2 Exhibited Increased Fluorescence in Cells

In *Escherichia coli*, Spinach2 was 1.4-fold brighter at 25° C. and 2.1-fold brighter at 37° C. than Spinach (FIG. 3B). Aptamer abundance was normalized to 16S RNA and found to be essentially identical for all samples (FIG. 3C).

Figures 4A, 4B, 4C:
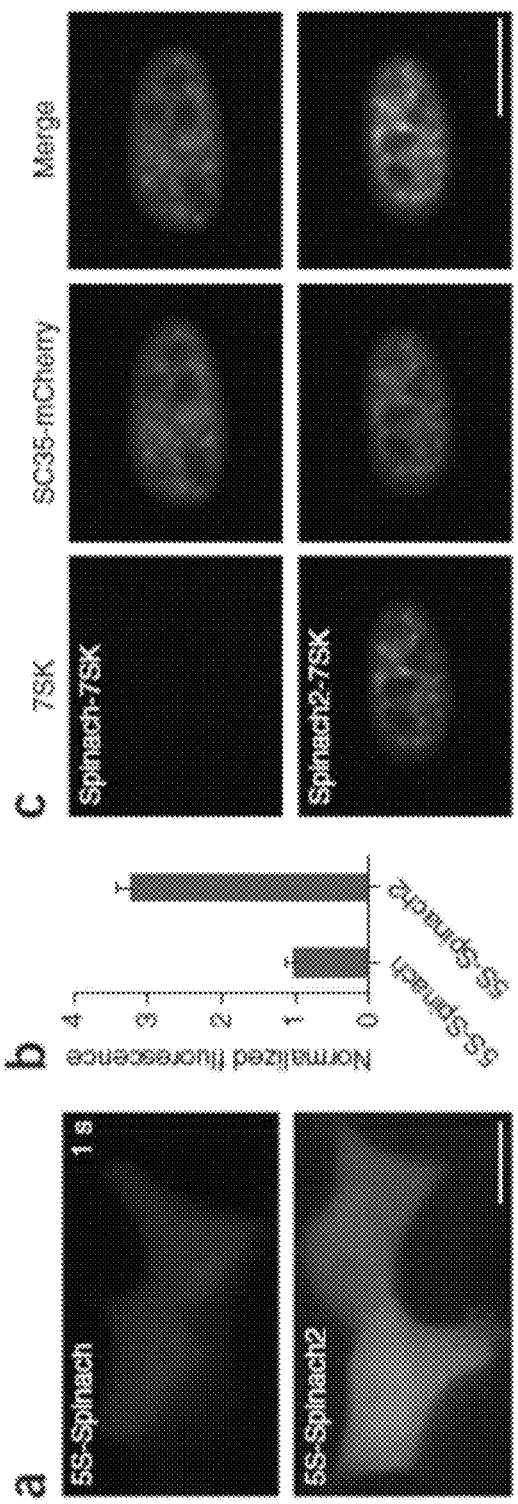
FIGS. 4A-C illustrate that 5S-Spinach2 is brighter than 5S-Spinach in mammalian cells.

Whether 5S-Spinach2 is brighter in mammalian cells was next determined. HEK293T cells expressing 5S-Spinach or 5S-Spinach2 exhibited the expected diffuse nuclear and cytoplasmic distribution (Paige et al., "RNA Mimics of Green Fluorescent Proteins," *Science* 333:642-646 (2011), which is hereby incorporated by reference in its entirety) (FIG. 4A) and 5S-Spinach2 showed 3.2-fold higher signal than 5S-Spinach (FIG. 4B).

The brightness of Spinach-7SK and Spinach2-7SK in HeLa cells was also compared. 7SK localizes to nuclear speckles (Prasanth et al., "Nuclear Organization and Dynamics of 7SK RNA in Regulating Gene Expression," Mol. Biol. Cell 21:4184-4196 (2010), which is hereby incorporated by reference in its entirety). Expression of Spinach-7SK showed no detectable signal, but Spinach2-7SK labeled intranuclear foci that colocalized with mCherry-tagged SC35, a known protein component of nuclear speckles (Prasanth et al., "Nuclear Organization and Dynamics of 7SK RNA in Regulating Gene Expression," Mol. Biol. Cell 21:4184-4196 (2010) and Fu et al., "Factor Required for Mammalian Spliceosome Assembly is Localized to Discrete Regions in the Nucleus," Nature 343:437-441 (1990), which are hereby incorporated by reference in their entirety) (FIG. 4C). These data demonstrate improved RNA imaging in live cells using Spinach2.

Example 6

Imaging $(CGG)_{60}$ RNA with Spinach2

Many 'toxic RNAs' contain extensive trinucleotide repeats (Wojciechowska et al., "Cellular Toxicity of Expanded RNA Repeats: Focus on RNA Foci," Hum. Mol. Genet. 20:3811-3821 (2011), which is hereby incorporated by reference in its entirety). FMR1 transcripts containing 55-200 CGG repeats (Fu et al., "Variation of the CGG Repeat at the Fragile X Site Results in Genetic Instability: Resolution of the Sherman Paradox," Cell 67:1047-108 (1991); Dombrowski et al., "Premutation and Intermediate-Size FMR1 Alleles in 10572 Males from the General Population: Loss of an AGG Interruption is a Late Event in the Generation of Fragile X Syndrome Alleles," Hum. Mol. Genet. 11:371-378 (2002); and Hagerman et al., "Intention Tremor, Parkinsonism, and Generalized Brain Atrophy in Male Carriers of Fragile X," Neurol. 57:127-130 (2001), which are hereby incorporated by reference in their entirety) lead to neurodegeneration associated with FXTAS 13. These transcripts aggregate to form intranuclear foci13 that cause cytotoxicity by sequestering proteins and affecting splicing and microRNA biogenesis (Sellier et al., "Sam68 Sequestration and Partial Loss of Function are Associated with Splicing Alterations in FXTAS Patients," EMBO J. 29:1248-1261 (2010); Iwahashi et al., "Protein Composition of the Intranuclear Inclusions of FXTAS," Brain 129:256-271 (2006); and Sellier et al., "Sequestration of DROSHA and DGCR8 by Expanded CGG RNA Repeats Alters MicroRNA Processing in Fragile X-Associated Tremor/Ataxia Syndrome," Cell Rep. 3:869-880 (2013) which are hereby incorporated by reference in their entirety), although the translation of these RNAs may also contribute to disease phenotypes (Todd et al., "CGG Repeat-Associated Translation Mediates Neurodegeneration in Fragile X Tremor Ataxia Syndrome," Neuron 78:440-455 (2013), which is hereby incorporated by reference in is entirety).

Little is known about the dynamics of CGG repeat-containing RNA localization in the nucleus. Because these RNA complexes are highly (G+C)-rich, it has been proposed that they form highly stable hairpins that may be difficult to disrupt (Sellier et al., "Sam68 Sequestration and Partial Loss of Function are Associated with Splicing Alterations in FXTAS Patients," EMBO J. 29:1248-1261 (2010); Iwahashi et al., "Protein Composition of the Intranuclear Inclusions of FXTAS," Brain 129:256-271 (2006); and Kiliszek et al., "Crystal Structures of CGG RNA Repeats with Implications for Fragile X-Associated Tremor Attaxia Syndrome," Nuc. Acids Res. 39:7308-7315 (2011), which are hereby incorporated by reference in their entirety). Previous studies have shown that the splicing factor Sam68 dynamically associates with nuclear foci of CGG repeats (Sellier et al., "Sam68 Sequestration and Partial Loss of Function are Associated with Splicing Alterations in FXTAS Patients," EMBO J. 29:1248-1261 (2010) and Stoss et al., "The STAR/GSG Family Protein rSLM-2 Regulates the Selection of Alternative Splice Sites," J. Biol. Chem. 276:8665-8673 (2001), which are hereby incorporated by reference in their entirety). However, these studies do not address whether the RNAs themselves are dynamic or immobile in nuclei.

Spinach2 was tested for imaging CGG repeat-containing RNA. Although $(CGG)_{60}$-Spinach was not detected (FIG. 1A), expression of $(CGG)_{60}$-Spinach2 resulted in bright intranuclear foci that was readily detected using widefield microscopy with exposures of 50-100 ms (FIG. 1A). These foci colocalized with mCherry-Sam68, a marker of CGG repeat-containing nuclear foci (Sellier et al., "Sam68 Sequestration and Partial Loss of Function are Associated with Splicing Alterations in FXTAS Patients," EMBO J. 29:1248-1261 (2010), which is hereby incorporated by reference in its entirety) (FIG. 1A). The foci were highly heterogeneous in appearance. Thus $(CGG)_{60}$-Spinach2 can be used to study the dynamics of toxic RNA aggregates.

Example 7

Live-Cell Imaging of CGG Repeat-Containing RNA Aggregates

Figures 5A, 5B, 5C, 5D, 5E:
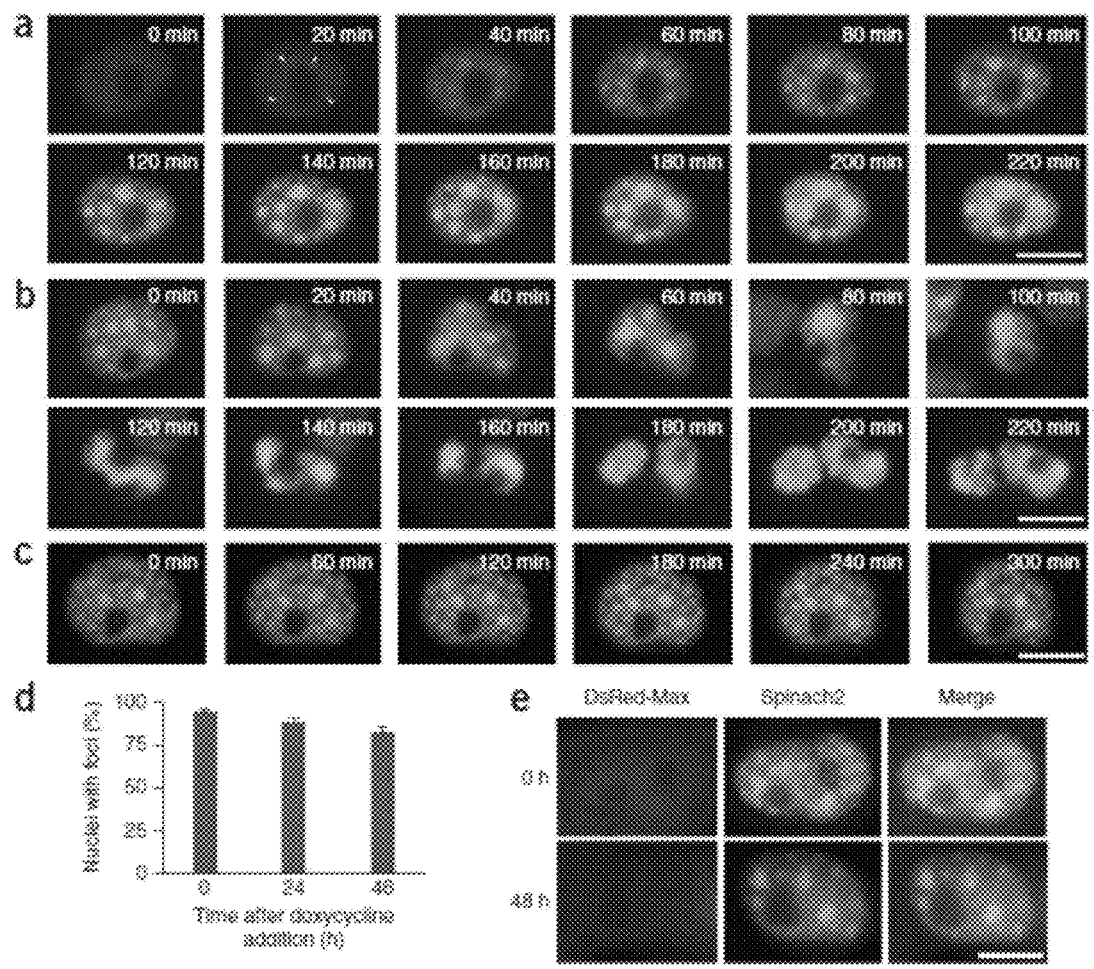
FIGS. 5A-E illustrate the imaging of RNA foci in COS-7 cells.

The formation of $(CGG)_{60}$-Spinach2 foci in transiently transfected COS-7 cells was monitored. Spinach2 fluorescence was detectable as early as 3 h after transfection. $(CGG)_{60}$-Spinach2 signal was initially diffusely nucleoplasmic, with formation of foci evident within 1 h after transfection (FIG. 5A). Number, size and brightness of foci increased over the course of the experiment. These data indicate that CGG repeat-containing RNA aggregates rapidly after expression.

To examine the stability of $(CGG)_{60}$-Spinach2 RNA, fluorescence after treating cells with actinomycin D, a potent transcription inhibitor, was measured. Spinach2 signal was stable and remained unchanged for up to 8 h (FIG. 5C), at which point actinomycin D-mediated cytotoxicity was observed.

To test the stability of $(CGG)_{60}$-Spinach2 foci over longer periods, $(CGG)_{60}$-Spinach2 transcription was controlled using the TET-off system (Gossen et al., "Tight Control of Gene Expression in Mammalian Cells by Tetracycline-Responsive Promoters," Proc. Natl. Acad. Sci. U.S.A. 89:5547-5551 (1992), which is hereby incorporated by reference in its entirety). Immediately after inhibition of transcription, 94±1.7% of transfected cells contained foci. These foci were long-lived: after 24 h and 48 h, 88±5.6% and 82±6.5% of cells retained foci, respectively (FIGS. 5D, E). These results were supported by qRT-PCR results, which demonstrate that $(CGG)_{60}$ and $(CGG)_{60}$-Spinach2 RNA are highly stable. The stability of these RNAs is most likely due to their incorporation into nuclear foci, since $(CGG)_{30}$ RNAs, which do not form foci, are markedly less stable.

As these repeat-containing RNAs are relatively resistant to degradation and form thermodynamically stable duplexes (Kiliszek et al., "Crystal Structures of CGG RNA Repeats with Implications for Fragile X-Associated Tremor Attaxia Syndrome," *Nuc. Acids Res.* 39:7308-7315 (2011) and Sobczak et al., "RNA Structure of Trinucleotide Repeats Associated with Human Neurological Diseases," *Nuc. Acids Res.* 31:5469-5482 (2003), which are hereby incorporated by reference in their entirety), whether they form static foci was tested. Time-lapse imaging revealed that foci were mobile and could merge to form larger foci (FIG. 5A). This dynamic behavior was also apparent in dividing cells (FIG. 5B). During division, the multiple foci typically present in the cell coalesced to form a large single aggregate that subsequently extended into a long linear structure. This long aggregate was divided between daughter cells. The RNA then became diffusely nucleoplasmic before reaggregating into foci. These results indicate that CGG repeat-containing RNA aggregate into foci and disaggregate during the cell cycle.

Example 8

A Small Molecule can Disrupt RNA Aggregates

Whether small molecules can induce disaggregation of foci of CGG repeat-containing RNA was investigated. No molecules have been shown to disrupt existing aggregates, although two drugs prevent the formation of CGG repeat-containing RNA foci in transfected cells. These are tautomycin (Sellier et al., "Sam68 Sequestration and Partial Loss of Function are Associated with Splicing Alterations in FXTAS Patients," *EMBO J.* 29:1248-1261 (2010), which is hereby incorporated by reference in its entirety) and 1a, a small molecule that binds CGG repeat-containing RNA and disrupts its binding to a CGG-binding protein, DGCR8 (Sellier et al., "Sam68 Sequestration and Partial Loss of Function are Associated with Splicing Alterations in FXTAS Patients," *EMBO J.* 29:1248-1261 (2010) and Disney et al., "A Small Molecule that Targets r(CGG)$^{exp}$ and Improves Defects in Fragile X-Associated Tremor Attaxia Syndrome," *ACS Chem. Biol.* 7:1711-1718 (2012), which are hereby incorporated by reference in their entirety). That both drugs prevented formation of (CGG)$_{60}$-Spinach2 foci was confirmed (FIGS. 6A, B).

To determine whether 1a can disrupt existing foci, COS-7 cells expressing (CGG)$_{60}$-Spinach2 were treated with the drug. No change in foci upon imaging every 5 min for 2 h (FIG. 6C) was observed. After 48 h of treatment, the number of cells with foci only changed slightly, from 94±2.8% to 86±3.5%. Furthermore, 48 h of treatment with 1a did not induce the dissociation of Sam68 from (CGG)$_{60}$-Spinach2 foci. These results show that 1a can prevent formation of foci, but does not readily disrupt existing foci, even after long treatments.

Figures 6A, 6B, 6C:
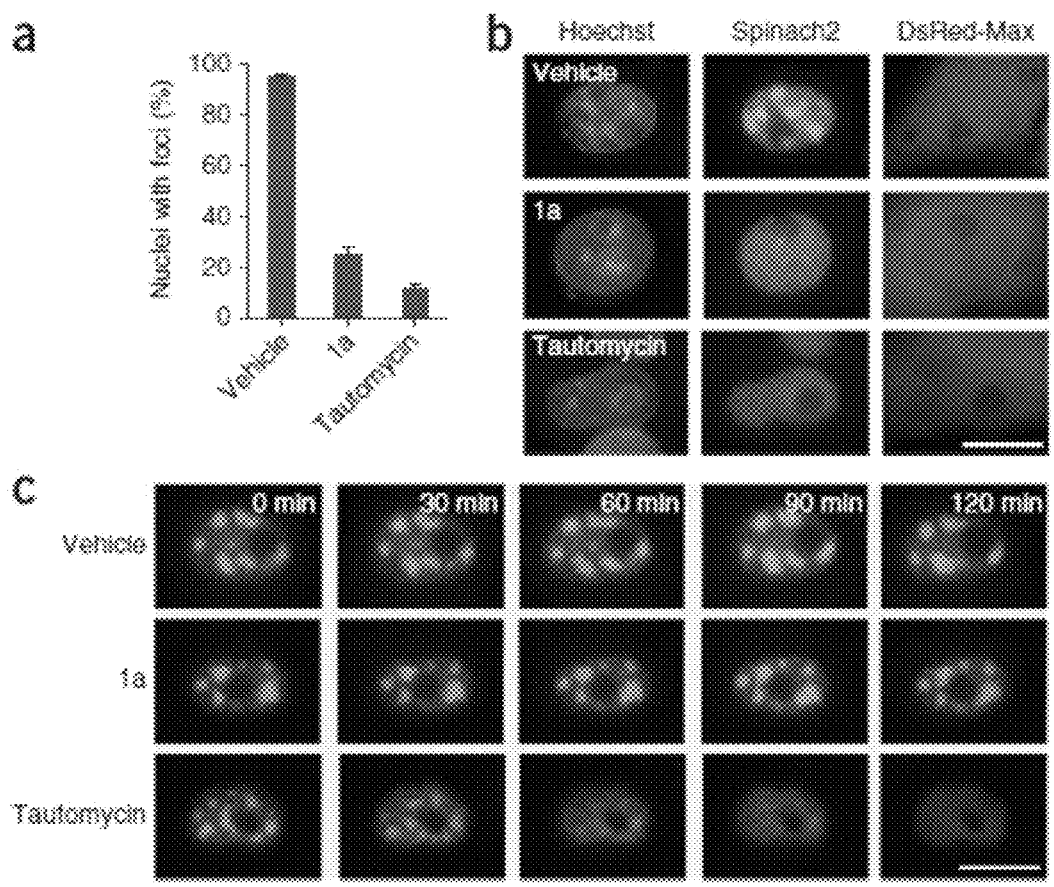
FIGS. 6A-C illustrate the effects of tautomycin and 1a on CGG RNA foci.

In contrast, tautomycin induced disaggregation of foci in as little as 1 h (FIG. 6C). The disaggregated (CGG)$_{60}$-Spinach2 remained as diffuse nucleoplasmic staining in cells (FIG. 6C). Removal of tautomycin after a 2-h treatment was not sufficient to restore foci, indicating that tautomycin induces cellular changes that prevent reaggregation.

To test whether the effect of tautomycin on (CGG)$_{60}$-Spinach2 foci was due to inhibition of its known targets protein phosphatase-1 (PP1) or protein phosphatase-2A (PP2A) (Suganuma et al., "Tautomycin: An Inhibitor of Protein Phosphatases 1 and 2A but Not a Tumor Promoter on Mouse Skin and in Rat Glandular Stomach," *J. Cancer Res. Clin. Oncol.* 121:621-627 (1995), which is hereby incorporated by reference in its entirety), cells were treated with okadaic acid at a concentration that also inhibits both PP1 and PP2A (Cohen et al., "An Improved Procedure for Identifying and Quantitating Protein Phosphatases in Mammalian Tissues," *FEBS Lett.* 250:596-600 (1989), which is hereby incorporated by reference in its entirety). No disruption of foci over 4 h was observed, indicating that the disaggregation effect of tautomycin is due to a different target than PP1 or PP2A.

Discussion of Examples 1-8

As Spinach exhibited poor thermal stability and folding when fused to other RNAs, Spinach2 was developed. Spinach2 has nearly identical photophysical properties to Spinach yet displays enhanced folding both alone and in the context of flanking RNA, at 25° C. and 37° C. The improved folding is more apparent when Spinach2 is fused to other RNAs. For example, Spinach2 retained 80% of its fluorescence when fused to the CGG repeat-containing RNA, whereas Spinach is essentially nonfluorescent in this context. However, it is possible that other flanking sequences will affect fluorescence of Spinach2, so first, fluorescence of in vitro-transcribed Spinach2-tagged RNA should be compared with that of untagged Spinach2. If the tagged RNA lacks fluorescence in vitro, inserting Spinach2 at other sites may restore fluorescence by providing flanking sequences that are more compatible with folding of Spinach2.

Both (CGG)$_{60}$-Spinach2 and Spinach2-7SK formed RNA-enriched foci in the cell, which makes imaging straightforward. However, imaging RNAs that are present at lower concentrations may require longer imaging times. As multimerization of fluorescent proteins has been used to enhance the imaging of low-abundance proteins (Genova et al., "Brighter Reporter Genes from Multimerized Fluorescent Proteins," *Biotechniques* 39:814-818 (2005), which is hereby incorporated by reference in its entirety), an analogous strategy could be adapted to label RNAs with multiple Spinach2 sequences.

The utility of Spinach2 was demonstrated in diverse imaging experiments by imaging the localization of CGG repeat-containing RNAs in living cells. These RNAs had been thought to form stable (G+C)-rich aggregates (Kiliszek et al., "Crystal Structures of CGG RNA Repeats with Implications for Fragile X-Associated Tremor Attaxia Syndrome," *Nuc. Acids Res.* 39:7308-7315 (2011) and Sobczak et al., "RNA Structure of Trinucleotide Repeats Associated with Human Neurological Diseases," *Nuc. Acids Res.* 31:5469-5482 (2003), which are hereby incorporated by reference in their entirety). Studies show that the RNA component of these foci is highly dynamic and undergoes considerable morphologic rearrangements, especially during cell division. These results demonstrate that CGG repeat-containing RNAs bind to preexisting nuclear structures that are normally partitioned during cell division. This idea is supported by previous studies demonstrating colocalization of CGG repeat-containing RNAs with various intranuclear markers (Sellier et al., "Sam68 Sequestration and Partial Loss of Function are Associated with Splicing Alterations in FXTAS Patients," *EMBO J.* 29:1248-1261 (2010), which is hereby incorporated by reference in its entirety).

Imaging (CGG)$_{60}$-Spinach2 identified the first known compound able to induce disaggregation of toxic RNAs. Previous studies have relied on imaging foci-associated RNA-binding proteins, such as Sam68 (Sellier et al., "Sam68 Sequestration and Partial Loss of Function are Associated with Splicing Alterations in FXTAS Patients," *EMBO J.* 29:1248-1261 (2010) and Sellier et al., "Sequestration of DROSHA and DGCR8 by Expanded CGG RNA Repeats Alters MicroRNA Processing in Fragile X-Associated Tremor/Ataxia Syndrome," *Cell Rep.* 3:869-880 (2013), which are hereby incorporated by reference in their entirety). Direct imaging of toxic RNA provides opportunities to identify small molecules and signaling pathways that affect localization dynamics of CGG repeat-containing RNA in living cells. Assays using $(CGG)_{60}$-Spinach2 may enable the identification of additional compounds that can disrupt foci and potentially serve as therapeutics for FXTAS.

Materials and Methods for Examples 9-19

Reagents and Equipment: Unless otherwise stated, all reagents were purchased from Sigma-Aldrich. Commercially available reagents were used without further purification. Absorbance spectra were recorded with a Thermo Scientific NanoDrop 2000 spectrophotometer with cuvette capability. Fluorescence excitation and emission spectra were measured with a PerkinElmer LS-55 fluorescence spectrometer. ChemiDoc MP imager (BioRad) was used to record fluorescence in bacterial colonies on agar plates. Fluorescence also was measured on Safire II or Genios Pro plate readers (Tecan). FACS experiments were performed using FACSAria III instrument (BD Biosciences).

SELEX Procedure: The random library used for SELEX was generated before and already utilized to isolate Spinach aptamer (Paige et al., "RNA Mimics of Green Fluorescent Protein," *Science* 333(6042): 642-6 (2011), which is hereby incorporated by reference in its entirety). Briefly, this library contained two 26-base random stretches separated by a 12-base fixed sequence and flanked from 5' and 3' ends with constant regions used for PCR amplification and in vitro transcription. This ssDNA library was purified and amplified as described previously (Paige et al., "RNA Mimics of Green Fluorescent Protein," *Science* 333(6042): 642-6 (2011), which is hereby incorporated by reference in its entirety).

Doped libraries were created in way that each encoded aptamer resembles the parent aptamer, except that there are on average seven mutations per sequence. In order to obtain this library, to make the doped library, every position is chemically synthesized with a phosphoramidite nucleotide mixture that contains primarily the nucleotide that is found at that position in the parent aptamer, but also contains each of the other nucleotides at a lower concentration. For example, if a C is present at a certain position, a phosphoramidite mixture containing 88.2% C, 3.2% G, 4.8% A, and 3.8% T is used. Unequal concentrations for the non-parent nucleotides are used to take into account the different chemical activity of the respective phosphoramidites. Using these synthesis conditions, most strands will incorporate a C at that position, but some will incorporate one of the other nucleotides. dsDNA encoding doped libraries were designed with 14% mutagenesis efficiency and were ordered from Protein and Nucleic Acid Facility, Stanford University Medical Center.

Affinity matrix for SELEX (DFHBI-sepharose) was prepared as described previously (Paige et al., "RNA Mimics of Green Fluorescent Protein," *Science* 333(6042): 642-6 (2011), which is hereby incorporated by reference in its entirety).

$1 \times 10^{14}$ different sequences of double stranded DNA were transcribed in a 250 µl T7 RNA polymerase transcription reaction using AmpliScribe T7-Flash Transcription Kit (Epicenter) (Epicentre Biotechnologies). After treatment with DNase (Epicentre Biotechnologies) for 1 h, RNAs were purified using RNeasy Mini Kit (Qiagen) following manufacture's recommendations.

For random library SELEX rounds 1-3 RNA was then diluted in selection buffer containing 40 mM HEPES pH 7.4, 100 mM KCl, 1 mM $MgCl_2$, and 0.1% DMSO. Starting round five and onwards RNA was diluted in the same buffer but containing 0.1 mM $MgCl_2$ to preferentially select for aptamers with low magnesium dependence.

SELEX procedure was conducted essentially as described before (Paige et al., "RNA Mimics of Green Fluorescent Protein," *Science* 333(6042): 642-6 (2011), which is hereby incorporated by reference in its entirety). Briefly, during the first step RNA species capable of binding to the sepharose matrix were removed by incubation with "mock" resin consisting of aminohexyl linker bound to sepharose. The resulting RNA solution was then incubated with DFHBI-coupled matrix. RNA bound to DFHBI resin was then washed with 3×0.5 ml of selection buffer during rounds 1-2, 4×0.5 ml during rounds 3-6 and 6×0.5 ml during round 7. Finally, specifically bound RNA was eluted with free DFHBI.

Doped library SELEX was conducted essentially the same way. Magnesium concentration in selection buffer was decreased from 1 mM to 0.1 mM on the second round of SELEX and maintained low during the third round as well.

The eluted RNAs were then ethanol precipitated, reverse-transcribed, PCR amplified and in vitro transcribed to yield the pool for the next round. Presence of fluorescent RNA species in each pool was assessed by mixing 20 µM RNA and 10 µM DFHBI and measuring fluorescence emission of this solution on a fluorometer in comparison with the dye alone.

Bacterial Expression Plasmids: To engineer pETDuet-1-based vector allowing insertion of SELEX library and bearing the gene of a fluorescent protein used for expression normalization the following was done. First, Spinach sequence with flanking human $tRNA_{Lys}$ scaffold regions and downstream T7 terminator was PCR amplified, digested with XbaI and BsiWI restriction enzymes and inserted into pETDuet-1 vector (EMD Biosciences) cut with XbaI and BsrGI. This placed Spinach in tRNA scaffold (tSpinach) after the first T7 promoter and also introduced terminator sequence not present in the first expression cassette in the original vector. The resulting plasmid was further modified to eliminate EagI site in the vector backbone. That was performed using QuickChange site-directed mutagenesis kit (Stratagene) according to the manufacture's protocol. The next step was to remove lac operator sequence after the first T7 promoter so that no additional sequences were present between the promoter and 5' tRNA scaffold sequence. Again, that was done using QuickChange site-directed mutagenesis kit mentioned above. Finally, eqFP670 fluorescent protein gene was PCR amplified from pNirFP-N plasmid (Evrogen), digested with NdeI and XhoI restriction enzymes and inserted into the plasmid generated on the previous step cut with the same enzymes. This resulted in pETDuet-5-tSpinach-eqFP670 plasmid which was used as a vector for library insertion via SacII and EagI sites.

To produce RNA aptamers in arabinose induced LMG194 cells an expression vector was engineered following these steps. tSpinach with T7 terminator on its 5' end was PCR amplified and cut with NcoI and HindIII and then inserted into pBAD/His A vector (Life Technologies) cut with the same enzymes. Then the region between araBAD promoter and 5' tRNA region was removed by means of QuickChange mutagenesis which finally resulted in pBAD E tSpinach plasmid. All RNA aptamers studied or sorted in LMG194 cells were later cloned into this vector using SacII and EagI sites. To express final mutants tested with shortened stem between tRNA scaffold and the aptamer part pBAD F plasmid was engineered by the following procedure. pBAD E plasmid was modified by using QuickChange approach so a short fragment bearing two BbsI sites was inserted between araBAD and T7 terminator sequences. All tRNA scaffold based aptamers lacking EagI and SacII sites, including tBroccoli, were cloned into pBAD F plasmid using BbsI sites having different overhanging sequences.

For the highest expression level of aptamers in bacterial cells pET28c plasmid backbone (EMD Biosciences) was used. Aptamers in tRNA scaffold were PCR amplified to have BglII and T7 promoter on 5' end and T7 terminator and XhoI on 3' end and then were cloned into pET28c-tSpinach2 (see Examples 1-8; Strack et al., "A Superfolding Spinach2 Reveals the Dynamic Nature of Trinucleotide Repeat-Containing RNA," Nat Methods 10(12): 1219-24 (2013), which is hereby incorporated by reference in its entirety) using BglII and XhoI restriction enzymes.

Bacterial Library Generation and FACS Sorting: Radom library SELEX RNA pool 5 or doped library SELEX RNA pool 3 were reverse transcribed and PCR amplified. Then these PCR products were cloned into pETDuet-5-tSpinach2-eqFP570 or pBAD E tSpinach using EagI and SacII sites.

The resulting ligation mixtures were purified and electroporated into Acella strain (Edgebio) or LMG194 (ATCC). LMG194 cells then were grown in LB media overnight in presence of 0.2% arabinose and then collected for sorting. Acella cells were grown overnight with antibiotic only and then were diluted in the morning 1 to 10 with fresh LB and with addition of 1 mM IPTG. Then expression was allowed to proceed for four hours followed by collecting these cells for sorting. Typical bacterial libraries contain $10\text{-}30 \times 10^6$ individual members.

Cells were pre-incubated with 40 µM of 1T dye and then sorted on FACSAria III instrument (BD Biosciences). Sample compartment of the sorter was maintained at 37° C. to facilitate sorting of the most thermostable aptamers. DFHBI or 1T-binding aptamers were excited with 488 nm laser and their emission was collected using 525/50 emission filter. eqFP670 fluorescent protein was monitored in PE-Cy5 channel (561 nm excitation and 660/20 nm emission).

Typically one thousand brightest cells were sorted, rescued in 1 ml SOC at 37° C. for 1 h and then plated on LB/agar supplemented with carbenicillin, DFHBI (or 1T) and, in case of LMG194 cells, 0.2% arabinose. When Acella strain was used 1 mM IPTG was added to dishes the next morning and cells were allowed to express aptamers for four to six more hours.

Dishes were photographed on a ChemiDoc MP imager (Bio-Rad). Aptamer library fluorescence was collected in a channel with 470/30 nm excitation and 532/28 nm emission. eqFP670 fluorescent protein signal was collected with 630/30 nm excitation and 697/55 nm emission. The same channel was used in case of LMG194 cells to collect autofluorescence signal from bacterial colonies which allowed normalizing for their size. Images were processed and normalized in ImageJ software (NIH).

In Vitro Characterization of Aptamers: dsDNA from the brightest bacterial cells in a library was PCR amplified from eluted plasmids. Truncation, deletion and point mutation mutants were generated from dsDNAs PCR amplified based on respective ssDNA templates (Protein and Nucleic Acid Facility, Stanford University Medical Center). Primers were designed so the PCR product contained T7 promoter sequence. When indicated, dsDNA or ssDNA also contained tRNA scaffold part. PCR products were then purified with PCR purification columns (Qiagen) and in vitro transcribed utilizing AmpliScribe T7-Flash Transcription Kit (Epicenter). RNA was purified using Bio-Spin columns (Bio-Rad), and quantified using both absorbance values and the Quant-iT RiboGreen RNA Assay Kit (Life Technologies).

All in vitro RNA properties were measured in 40 mM HEPES pH 7.4, 100 mM KCl, 1 mM $MgCl_2$ buffer unless specified separately. All values presented are averaging of at least three independent experiments, error bars are standard deviations.

Absorption, excitation and emission spectra were measured for solutions with excess RNA and limiting amount of dye to ensure no free dye contribution. RNA concentration used was 30 µM (fluorescence measurements) and 50 µM (absorption measurements) while 1T dye concentration was 1 µM and 5 µM respectively.

Extinction coefficient was calculated based on absorbance spectrum and Beer-Lambert-Bouguer law. For quantum yield calculations fluorescence signal of Broccoli-1T complex was compared at different dilutions to that of equally absorbing Spinach2-1T (quantum yield 0.94, Song et al., "Imaging Bacterial Protein Expression Using Genetically Encoded RNASensors," Nat Methods 10(9): 873-5 (2013), which is hereby incorporated by reference in its entirety).

To calculate dissociation constant titration of 50 nM RNA with increasing concentration of 1T was performed; the resulting data points were then fitted with the curve based on the Hill equation.

To measure thermostability 1 µM of RNA was incubated with 10 µM 1T. Then fluorescence values were recorded in 1° C. increments from 20° C. to 70° C., with 5-min incubation at each temperature to allow for equilibration.

Folding measurements were performed essentially as thoroughly described in Examples 1-8 (see also Strack et al., "A Superfolding Spinach2 Reveals the Dynamic Nature of Trinucleotide Repeat-Containing RNA," Nat. Methods 10(12): 1219-24 (2013), which is hereby incorporated by reference in its entirety). Briefly, fluorescence intensity of two solutions were compared: the one having excess of the dye and limiting amount of RNA and the other with excess of RNA and limiting amount of the dye. 1 µM of 1T (or RNA) and 20 µM of RNA (or 1T) was used. Signal from the first condition (limiting RNA) was divided by the signal from the second condition (limiting dye) to determine the fraction folded. To measure folding in a context of different flanking sequences RNA was generated from separate dsDNA fragments. These fragments were PCR amplified to have β-actin, 5S rRNA and 7SK RNA sequences on either or both sides of Broccoli. The folding assay then proceeded as described above.

To measure magnesium dependence 1 µM RNA was incubated with 10 µM 1T in 40 mM HEPES pH 7.4, 100 mM KCl buffer with different concentrations of $MgCl_2$ and then fluorescence emission was measured on a plate reader.

In Vitro Characterization of tBroccoli-Based Sensor: c-diGMP sensor based on tBroccoli aptamer was generated basically following the strategy used previously (Paige et al., "Fluorescence Imaging of Cellular Metabolites with RNA," Science 335(6073): 1194 (2012) and Kellenberger et al., "RNA-Based Fluorescent Biosensors for Live Cell Imaging of Second Messengers Cyclic di-GMP and Cyclic AMP-GMP," J. Am. Chem. Soc. 135(13): 4906-9 (2013), which are hereby incorporated by reference in their entirety). RNA was in vitro transcribed from PCR fragments generated from ssDNA (Protein and Nucleic Acid Facility, Stanford University Medical Center). To test such sensor functionality, 1 µM of c-diGMP Broccoli-based sensor RNA was -premixed with 10 µM of DFHBI and then treated with 500 nM of c-diGMP. Fluorescence emission increase was recorded on a fluorometer.

Fluorescence Measurements of *E. coli*: Fluorescence measurements of *E. coli* were done in two general ways. To assess fluorescence brightness of bacterial colonies on a plate Acella or LMG194 strains cells were transferred to a new LB/agar dish with respective antibiotic and allowed to grow overnight at 37° C. Typically four to six colonies for the same aptamer were grown on the same plate to provide statistical data. These plates already contained 40 µM DFHBI-1T (or DFHBI) and 0.2% arabinose (in case of LMG194 strain). When Acella strain was used, 1 mM IPTG was added the next morning and incubation was continued for four to six hours more at 37° C. Bacterial colonies were then imaged under ChemiDoc MP imager as described above and images were processed in ImageJ program.

To measure fluorescence of bacterial cell suspensions BL21 Star (DE3) (Life Technologies) strain and pET28c-based expression plasmids were used. This combination provided the strongest signal. Fresh colony was inoculated into LB media with kanamycin and allowed to grow overnight at 37° C. to $OD_{600}$ 0.4. The cells were then induced with addition of 1 mM IPTG for 2-4 h at 37° C. After induction, cells were normalized for cell density and incubated with 400 µM DFHBI-1T. Cells were then measured for total fluorescence using a Genios Pro plate reader at 465 nm excitation and 535 nm emission. All values were normalized for slightly different excitation and emission spectra of Spinach2 and Broccoli.

In-Gel Imaging of Spinach-Containing RNAs: Total bacterial RNA was purified using Trizol LS reagent (Life Technologies) following the manufacturer's protocol. Typically, 200-500 ng of total RNA or 50-100 ng of in vitro transcribed RNA was loaded into a well of precast 6% TBE-Urea Gel (Life Technologies) and ran at 270-300 V in 1×TBE buffer. RiboRuler Low Range RNA Ladder (Thermo Scientific) was used as band size standard.

After the gel was run to completion, the gel was washed 3×5 min with water and then stained for 30 min in 10 µM DFHBI or DFHBI-1T in buffer containing 40 mM HEPES pH 7.4, 100 mM KCl, 1 mM $MgCl_2$. Then gel was imaged using a ChemiDoc MP with 470/30 nm excitation and 532/28 nm emission. Next, to see all the RNA in the sample, the gel was again washed 3×5 min with water followed by staining for 30 min with SYBR Gold (or Green) dye (Life Technologies) diluted 1/10000 in TBE buffer. Then gel was imaged under the same instrument using preset SYBR Gold (or Green) channel (302 nm excitation and 590/110 nm emission). Gel bands intensities were quantified in Image Lab 5.0 software (Bio-Rad). The bacterial 5S rRNA band was used for loading normalization.

Aptamer Imaging in Bacteria: BL21 Star (DE3) (Life Technologies) strain was transformed with pET28c-1-based expression vectors encoding RNA aptamers in tRNA scaffold. Negative cells were transformed with the original pET28c plasmid. Cells were plated, grown overnight and single colonies were picked for inoculation overnight in LB broth with kanamycin. At OD600=0.4 1 mM IPTG was added to the media. After 2-4 more hours at 37° C. culture was pelleted, resuspended in PBS and transferred to poly-d-lysine coated 3.5 cm dishes (MatTek Corporation). Cells were allowed to attached to the dish for 45 min at 37° C., then washed with PBS and incubated with 200 µM 1T in PBS at 37° C. for another 45 min.

Live fluorescence images were taken with a CoolSnap HQ2 CCD camera through a 60× oil objective mounted on a Nikon Eclipse TE2000-E microscope and analyzed with the NIS-Elements software. The filter set used was a sputter coated filter cube with excitation filter 470/40, dichroic mirror 495 (long pass), and emission filter 525/50 (Chroma Technology).

Cloning of 5S-Broccoli and 5S-t-tdBroccoli: Plasmids encoding 5S rRNA fusions with tBroccoli or t-tdBroccoli were engineered using previously described pAV-5S-Spinach plasmid (Paige et al., "RNA Mimics of Green Fluorescent Protein," *Science* 333(6042): 642-6 (2011), which is hereby incorporated by reference in its entirety). This construct contained Spinach in the context of the $tRNA_{Lys}$ scaffold. Sequence encoding $tRNA_{Lys}$-Spinach was removed from pAV-5S by restriction digest with SalI and XbaI. Sequence encoding tBroccoli or t-tdBroccoli were amplified from pET28c-based plasmids by PCR and then digested with XbaI and SalI to finally insert them into pAV-5S.

Cell Culture Conditions: Cell lines were obtained directly from the American Type Culture Collection (ATCC) for all experiments. HEK-293T (ATCC-CRL-11268) were grown according to ATCC instructions. Cells were screened for mycoplasma contamination before passaging using Hoechst 33258, according to ATCC recommendations.

Imaging 5S-tBroccoli and 5S-t-tdBroccoli: Plasmids were transfected into HEK293T cell using FuGENE HD reagent (Promega) following manufacture's protocol. Cell imaging was carried out as previously described for 5S-Spinach (Paige et al., "RNA Mimics of Green Fluorescent Protein," *Science* 333(6042): 642-6 (2011), which is hereby incorporated by reference in its entirety) with DFHBI-1T instead of DFHBI. Background signals from cells expressing pAV-5S-lambda (Paige et al., "RNA Mimics of Green Fluorescent Protein," *Science* 333(6042): 642-6 (2011), which is hereby incorporated by reference in its entirety) incubated with DFHBI-1T were subtracted from the corresponding images using NIS-Elements software (Nikon).

Example 9

Rapid Identification of Novel RNA-Fluorophore Complexes Using FACS

A challenge with developing RNA-fluorophore complexes is that they are selected based on their ability to bind fluorophores, not based on their ability to activate their fluorescence. SELEX was previously performed to identify RNA aptamers that bind DFHBI (Paige et al., "RNA Mimics of Green Fluorescent Protein," *Science* 333(6042): 642-6 (2011), which is hereby incorporated by reference in its entirety). In this screen, many aptamers were found that could bind to DFHBI and other related fluorophores with high affinity, but were unable to activate their fluorescence (Paige et al., "RNA Mimics of Green Fluorescent Protein," *Science* 333(6042): 642-6 (2011), which is hereby incorporated by reference in its entirety). Only a few were able to switch on the fluorescence of this fluorophore. This likely reflects a requirement for a specific binding mode, rather than high affinity, in order to induce fluorescence.

An additional problem with selecting aptamers based on binding is that an aptamer that is highly efficient at activating fluorescence may be lost during selection. This can occur because the aptamer might have a lower binding affinity than another aptamer, which may be inefficient at activating fluorescence. Studies that have characterized aptamer populations during SELEX have shown that certain aptamers begin to predominate during later rounds, largely based on their affinity for the ligand, as well as their ability to be reverse transcribed and PCR amplified (Ameta et al., "Next Generation Sequencing Reveals How RNA Catalysts Evolve from Random Space," *Nuc. Acids Res.* 42(2): 1303-10 (2014), which is hereby incorporated by reference in its entirety). Other aptamers with equal or lower affinity are lost during earlier rounds of selection (Schutze et al., "Probing the SELEX Process with Next-Generation Sequencing," *PloS One* 6:e29604 (2011), which is hereby incorporated by reference in its entirety). Since many of these RNAs may be highly effective at activating fluorescence, desirable aptamers can be lost during the multiple rounds of SELEX.

Figures 7A, 7B, 7C, 7D:
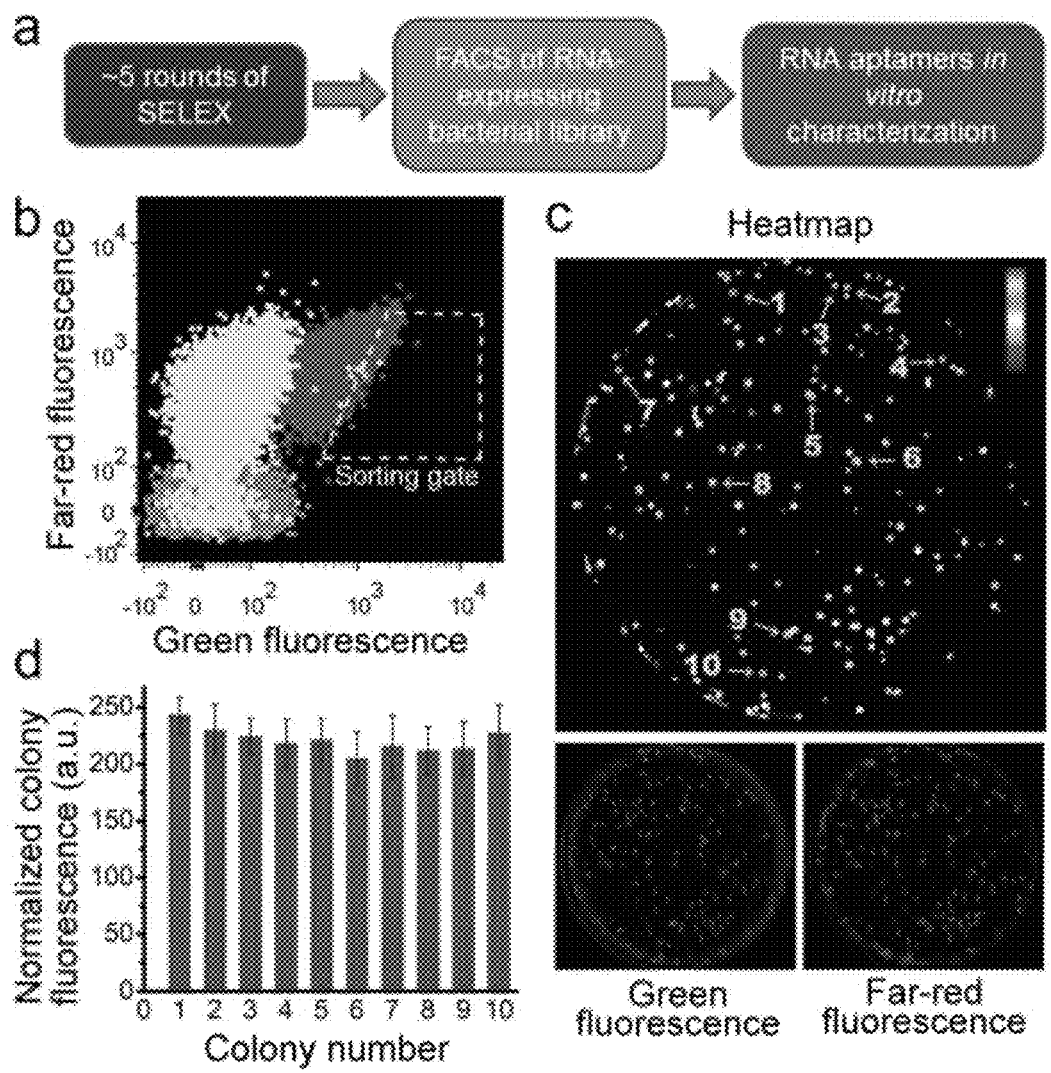
FIGS. 7A-D illustrate a combined SELEX-FACS approach for rapid selection of RNA-fluorophore complexes from random libraries.

To overcome these problems, a selection approach based both on binding and fluorescence activation was developed (FIG. 7A). In this approach, 4-6 rounds of SELEX are performed using a random library containing $\sim 10^{14}$ library members. After each round, the RNA pool is tested for RNA-induced fluorescence.

As described previously, this is typically seen after the fourth or sixth round of SELEX (Paige et al., "RNA Mimics of Green Fluorescent Protein," *Science* 333(6042): 642-6 (2011), which is hereby incorporated by reference in its entirety). Previous studies of combinatorial SELEX libraries have shown that the library pools typically retain considerable diversity at these early rounds of SELEX (Ameta et al., "Next Generation Sequencing Reveals How RNA Catalysts Evolve from Random Space," *Nuc. Acids Res.* 42(2): 1303-10 (2014)). At this point, the RNA pool is reverse transcribed and cloned into a bacterial expression plasmid to prepare an aptamer expression library. In this library, the aptamer is cloned so that it is transcribed fused to the aptamer-folding scaffold tRNA$^{Lys}{}_3$ (Ponchon et al., "Recombinant RNA Technology: the tRNA Scaffold," *Nat. Methods* 4(7): 571-6 (2007), which is hereby incorporated by reference in its entirety) previously used with Spinach and Spinach2 (see Examples 1-8; Paige et al, "RNA Mimics of Green Fluorescent Protein," *Science* 333(6042): 642-6 (2011); and Strack et al., "A Superfolding Spinach2 Reveals the Dynamic Nature of Trinucleotide Repeat-Containing RNA," *Nat. Methods* 10(12): 1219-24 (2013), which are hereby incorporated by reference in their entirety).

After transformation of the library into *E. coli* and transcription induction, bacteria are then sorted by FACS in presence of fluorophore in order to identify the aptamers that exhibit the highest fluorescence. The plasmid also contains a separate promoter for expressing a far-red fluorescent protein which allows the aptamer fluorescence to be normalized to cell volume. Sorted bacteria are grown on agar dishes and imaged in presence of the fluorophore. Plasmid DNA from the brightest colonies is isolated, sequenced and transcribed into RNA for further characterization (FIG. 7A).

Overall, the protocol described above offers a rapid and efficient way to isolate fluorescent aptamers from the large initial random library.

Example 10

Selection of Fluorescent RNA-DFHBI Complexes in *E. coli*

This combined SELEX-FACS protocol was applied using a library containing 52 random nucleotides (Paige et al., "RNA Mimics of Green Fluorescent Protein," *Science* 333 (6042): 642-6 (2011), which is hereby incorporated by reference in its entirety). Fluorescence was detected after the sixth round of SELEX, and the RNA pool was then screened in *E. coli* by FACS, as described above. Sorting was performed at 37° C. to ensure that aptamers that are thermostable at this temperature are selected. *E. coli* expressing Spinach was used as a positive control. As evidenced from the FACS dot plot (FIG. 7B), the vast majority of transformants had minimal green fluorescence, similar to the control-transfected *E. coli*. However, a small number of transformants exhibited similar or higher fluorescence than the mean fluorescence of the Spinach-expressing population (FIG. 7B). Analysis of the sorted bacterial colonies on agar plates showed that more than 80% of them exhibited fluorescence higher than the background level (FIG. 7C).

Sequencing analysis revealed numerous aptamers that conferred fluorescence to *E. coli*, with most aptamers falling into a few distinct families. The brightest clones (FIG. 7D) belonged to one family, each being different by only few mutations. Alignment and mFold predicted secondary structures of three of them, 29-1, 29-2 and 29-3, are presented in FIGS. 19A-B. Other aptamers, including 30-1 and 31-1, were dimmer in vivo and did not exhibit obvious sequence or predicted structural similarity to the 29-n family. Thus, this screening approach can identify distinct aptamers capable of switching on DFHBI fluorescence after only a few rounds of selection.

Example 11

Initial Characterization of 29-1 and Comparison with Spinach

Figure 19A:
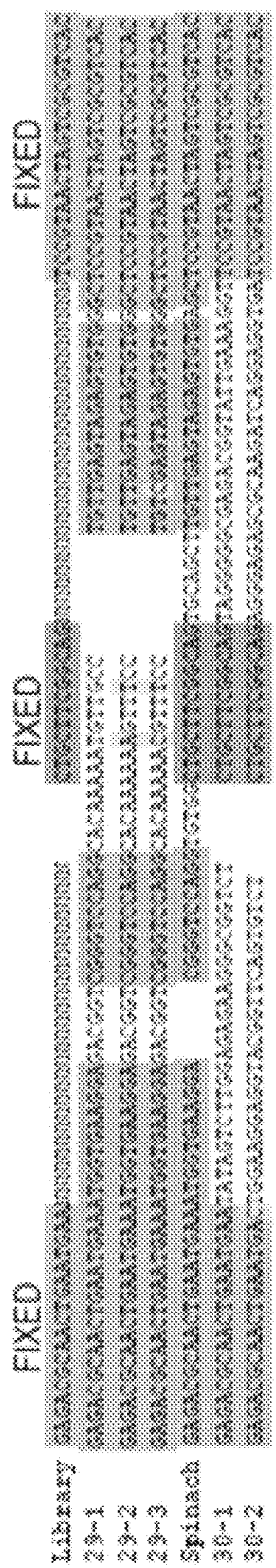
FIGS. 19A-B illustrate SELEX-FACS identification of diverse fluorescence "light up" aptamers.
Figure 19B:
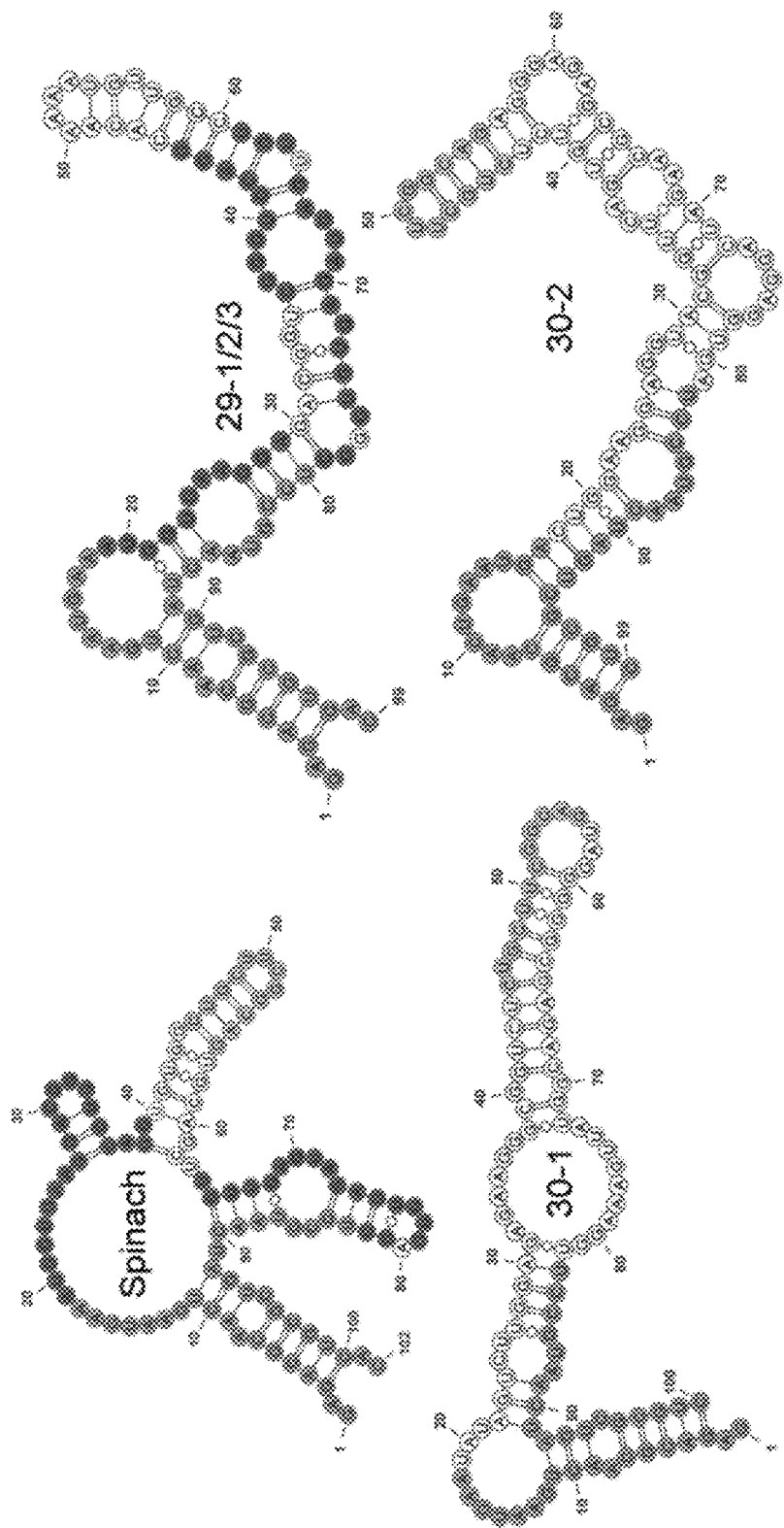

Since 29-1 exhibited the highest colony fluorescence (FIG. 7D), it was further characterized. Sequence analysis of this clone indicated that it is a 99-nucleotide long RNA. As with Spinach, 30-1 and 31-1, all the 29-n family contains the constant regions that are present in the parent library and used for library amplification. However, a fixed stem loop that was inserted in the middle of the library (FIGS. 19A-B) was lost in the 29-n clones, but is present in Spinach, 30-1, and 31-1. Interesting, portions of the 29-n random domain have regions of similarity to Spinach, while other regions do not (FIGS. 19A-B). Thus, 29-1 appears to have exhibited convergent evolution of certain Spinach-like sequences. Such convergent evolution has been previously demonstrated for adenosine RNA aptamers. Numerous independent SELEX screenings resulted in a very similar motif indicating that it may be an optimal sequence for binding to this small molecule (Vu et al., "Convergent Evolution of Adenosine Aptamers Spanning Bacterial, Human, and Random Sequences Revealed by Structure-Based Bioinformatics and Genomic SELEX," *Chem. Biol.* 19(10): 1247-54 (2012), which is hereby incorporated by reference in its entirety).

To measure the fluorescence of aptamer-fluorophore complexes, an approach that overcomes potential confounding effects of incomplete RNA folding was used. The fluorescence of RNA-fluorophore complexes can be measured in either of two ways: using "excess RNA" or "excess fluorophore" (Ponchon et al., "Recombinant RNA Technology: the tRNA Scaffold," *Nat. Methods* 4(7): 571-6 (2007), which is hereby incorporated by reference in its entirety). In an "excess RNA" experiment enough RNA was added to ensure that all the fluorophore (e.g. 1 μM) is bound to the RNA even if a sizeable portion of the RNA is unfolded. As a result, one can be confident that a 1 μM RNA-fluorophore complex is present, and one can therefore calculate the "molar brightness," the fluorescence of a specific concentration of RNA-fluorophore complex independent of RNA folding. In the case of excess fluorophore experimental conditions were reversed and 1 μM of RNA was used with a vast excess of the fluorophore. In this case, the amount of RNA-fluorophore complex is highly dependent on the amount of RNA that is folded. Indeed, by comparing the fluorescence measured using excess RNA and excess fluorophore, the percent of RNA that is folded can be estimated (Strack et al., "A Superfolding Spinach2 Reveals the Dynamic Nature of Trinucleotide Repeat-Containing RNA," *Nat. Methods* 10(12): 1219-24 (2013), which is hereby incorporated by reference in its entirety).

The fluorescence of 29-1 bound to fluorophores was calculated. 29-1 induced the fluorescence of both DFHBI (ex=450 nm; em=501 nm) and DFHBI-1T (ex=472 nm; em=507 nm). Relative to DFHBI, DFHBI-1T exhibits a higher extinction coefficient and lower background fluorescence in cells, as well as a red-shifted excitation and emission spectra that matches commonly used filter cubes (Song et al., "Plug-and-Play Fluorophores Extend the Spectral Properties of Spinach," *J Am Chem Soc.* 136(4): 1198-201 (2014), which is hereby incorporated by reference in its entirety). 29-1-induced fluorescence activation of DFHBI or DFHBI-1T was measured by incubating them with excess RNA. Comparing 29-1-fluorophore to Spinach2-fluorophore complexes showed that their molar brightness is similar.

Overall 29-1 demonstrated high fluorescence activation both in vivo and in vitro and thus was chosen as an initial point for the brighter green fluorescent RNA probe development.

Example 12

Figure 8:
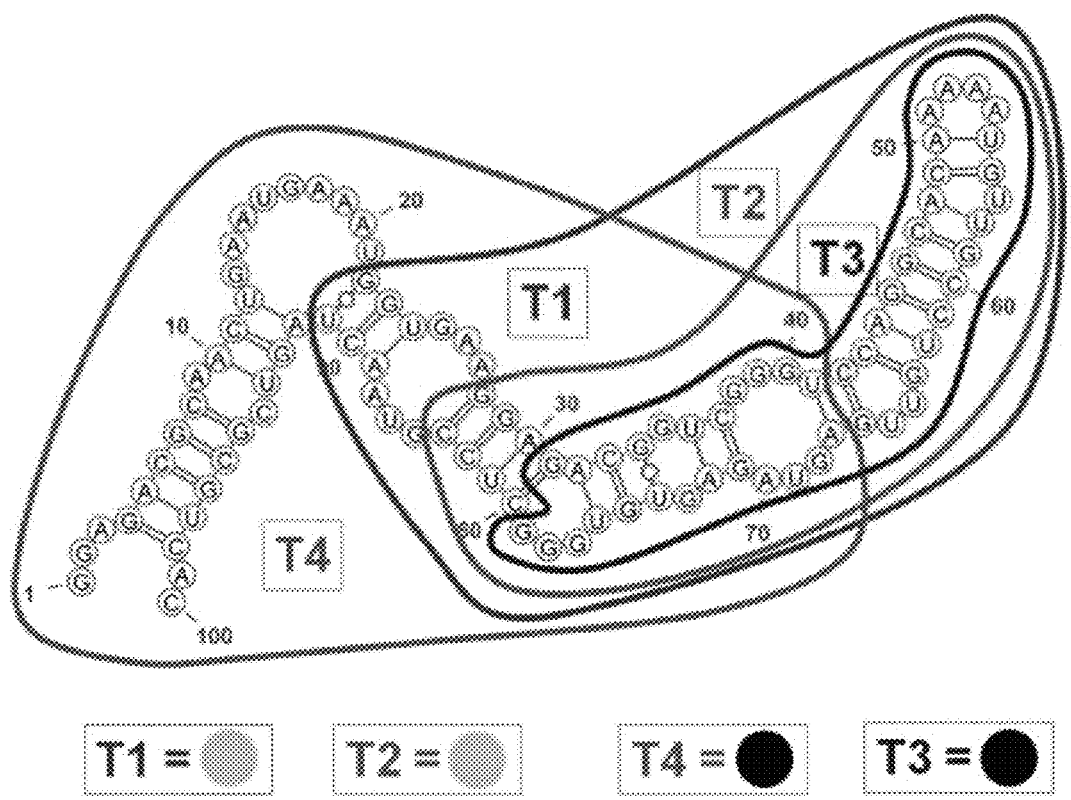
FIG. 8 shows that truncation analysis of 29-1 (SEQ ID NO: 3) identifies core domain responsible for fluorescence activation. mFold-predicted secondary structure of 29-1 is presented. The borders of three truncations (T1, T2, T3 and T4) are indicated. Only T1 and T2 were able to induce fluorescence of DFHBI-1T as measured under excess RNA conditions.

Identification of a Core Sequence in 29-1 that Binds and Induces DFHBI Fluorescence A minimal sequence element that mediates the ability of 29-1 to induce DFHBI-1T fluorescence was next investigated. The structure of 29-1 predicted by mFold (Zucker et al., "Mfold Web Server for Nucleic Acid Folding and Hybridization Prediction," *Nuc. Acids Res.* 31(13): 3406-15 (2003), which is hereby incorporated by reference in its entirety) is a long hairpin structure interrupted by several loops and bulges (FIG. 8A). The first truncation mutant (29-1-T1) lacking the first eight predicted base pairs in the first large loop retained fluorescence. Further reduction of the stem generated 29-1-T2, which also retained the ability to induce DFHBI-1T fluorescence. Subsequent removal of additional base pairs (29-1-T3) abolished the ability of the aptamer to induce DFHBI fluorescence. An additional aptamer missing the terminal hairpin (29-1-T4) was also incapable of inducing DFHBI-1T fluorescence, indicating that this terminal structure was required for fluorescence. Thus, truncation analysis identified 29-1-T2, a 56-nucleotide long aptamer that retains the ability to induce DFHBI fluorescence (FIG. 8).

The folding of T2 and 29-1 was compared. Using the folding assay described above, it was found that T2 was 45% folded, while 29-1 was 81% folded. Therefore 29-1-T2 folding is impaired, although its molar brightness remained the same.

Because 29-1-T2 has impaired folding in vitro, whether 29-1-T2 has impaired fluorescence in cells was investigated. To test this, the fluorescence of colonies expressing 29-1 and 29-1-T2 grown on LB-DFHBI-1T agar plates was compared. In these experiments, it was found that colonies expressing 29-1-T2 were significantly less bright than colonies expressing 29-1 despite the fact that this truncation mutant was expressed within a tRNA scaffold. This confirms that 29-1-T2 folds poorly, which leads to low fluorescence in cells.

Example 13

Directed Evolution of 29-1-T2 Generates Broccoli, an RNA-Fluorophore Complex Optimized for Cellular Performance Although 29-1-T2 has reduced overall fluorescence in cells, its small size is potentially advantageous. Smaller aptamers may be less likely to impair the function of the RNA to which it is attached. Therefore, the use of a directed evolution approach to improve the cellular performance of 29-1-T2 was investigated.

A strategy for directed evolution of aptamers that exhibit fluorescence in *E. coli* (FIG. 9A) was developed. For these experiments, a library of 29-1-T2 mutants was created using a "doping" strategy similar to the mutagenesis approach originally described by Hesselberth et al., "In Vitro Selection of RNA Molecules that Inhibit the Activity of Ricin A-Chain," *J. Biol. Chem.* 275(7): 4937-42, which is hereby incorporated by reference in its entirety. Briefly, a DNA library is synthesized so that each encoded aptamer resembles the parent aptamer, however every nucleotide has a certain and controlled probability of been converted into one of other three nucleotides. This probability is mathematically predicted initially so that the DNA library can have all the combinations of mutations that differ from the parent aptamer by 1, 2, 3, 4, 5, 6, 7 or 8 mutations. This allows optimal utilization of the physical library space and creates a diversity which makes it possible to identify mutants with improved properties.

After the RNA library is reverse transcribed from the doped DNA library, it is subjected to three rounds of SELEX to remove mutant aptamers that do not bind the fluorophore. The RNA pool after SELEX is then converted into a bacterial expression library, transformed into *E. coli*, and screened by FACS as described above.

Figures 9A, 9B, 9C, 9D:
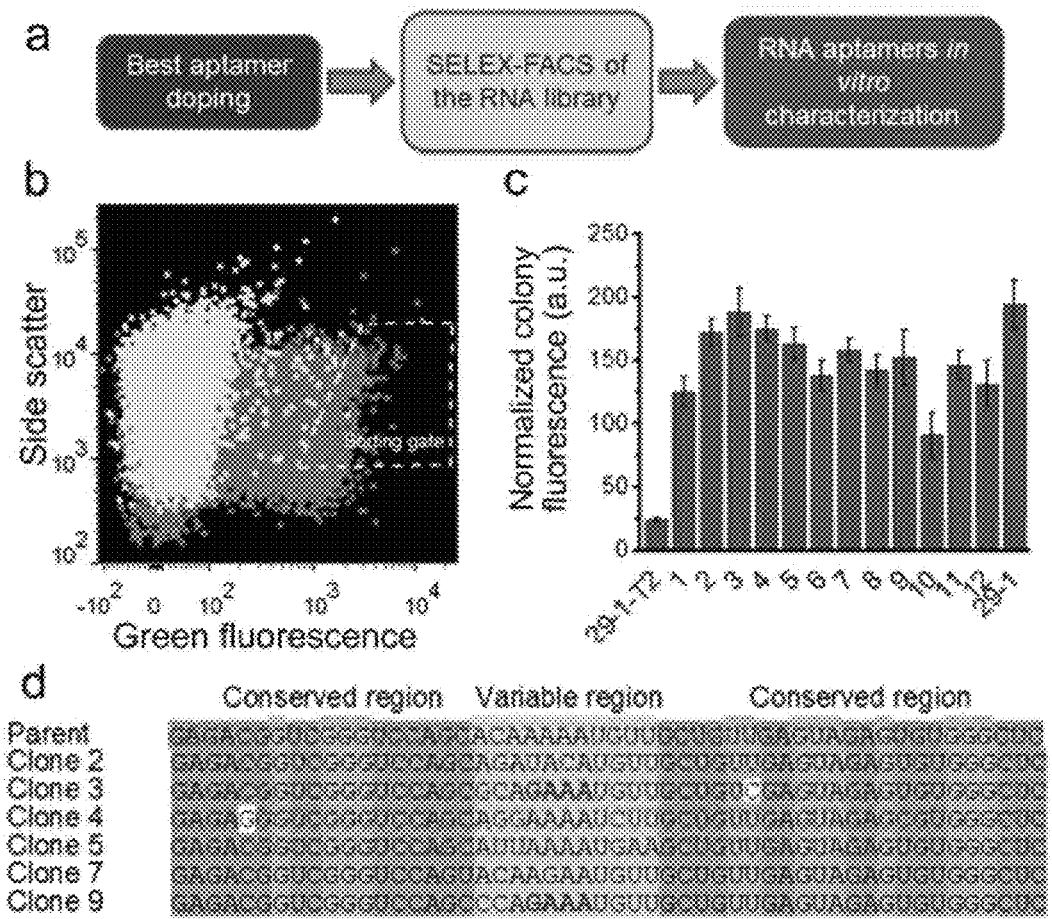
FIGS. 9A-D illustrate that an additional round of directed evolution rescues diminished fluorescence.

After the first round of directed evolution, several clones were identified that exhibited markedly improved colony brightness (FIGS. 9B, C). Many of these clones exhibited brightness that approached the level of the parent aptamer, 29-1 (FIG. 9C). Comparison of the sequences identified distinct domains that appeared to be either intolerant or tolerant of mutations (FIG. 9D). The majority of the sequence was the same in all the clones, except for an 11-nucleotide domain which constitutes the terminal stem-loop (see structure on FIG. 8). Analysis of this region revealed that most of the improved variants acquired mutations stabilizing this terminal stem-loop either by enhanced base-pairing or by introduction of the stable tetraloop GAAA (Heus et al., "Structural Features that Give rise to the Unusual Stability of RNA Hairpins Containing GNRA Loops," *Science* 253(5016): 191-4 (1991), which is hereby incorporated by reference in its entirety). This suggests that the terminal stem-loop is not directly involved in the fluorophore binding but instead improves aptamer in vivo folding.

Figure 20A:
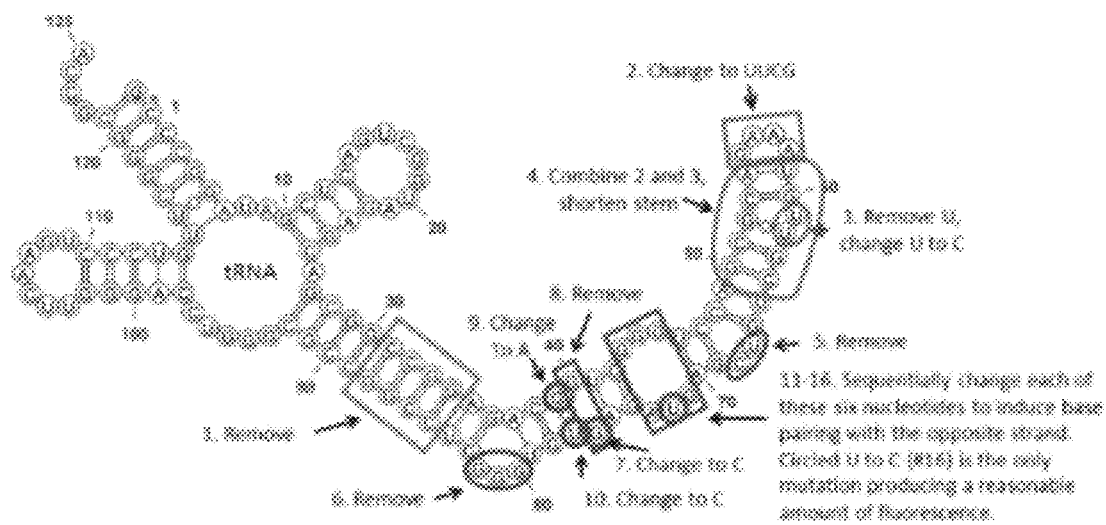
FIGS. 20A-C illustrate the characterization of the structure of 29-1-3 mutant.

Next, the predicted mutation-tolerant and mutation-intolerant domains were tested. The clone designated 29-1-3, which showed in vivo brightness compared to 29-1 (FIGS. 9C, 20A), was selected for further characterization. To test the prediction that the terminal loop was tolerant of mutations, mutations were introduced into this region (FIG. 20A). These were highly tolerated (FIGS. 20A, B). To confirm the predicted terminal four-nucleotide loop, this was converted to UUCG, a tetraloop that confers stability to hairpin structures. An adjacent bulged U was removed in order to form an uninterrupted stem and the stem itself was shortened. These mutations had minimal impact on fluorescence. Similarly, removal of the 4-bp long stem at the base of the aptamer did not impair its fluorescence, presumably because the tRNA scaffold used for aptamer expression conferred the structural stability needed for aptamer function (FIGS. 20A, B). Thus, the directed evolution experiment accurately identified domains that could be modified or mutated without impairing fluorescence of the aptamer-fluorophore complex.

Figure 20B:
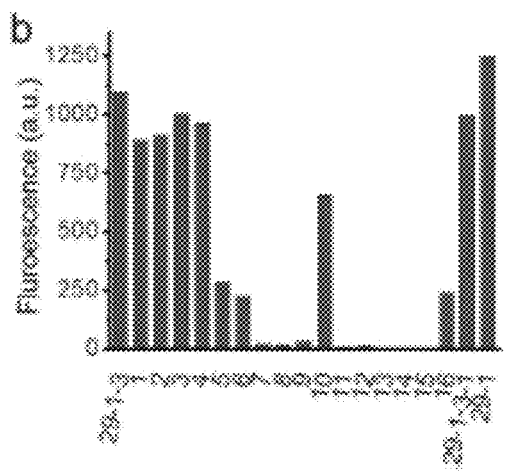

Next whether the regions that were conserved among the different directed evolution clones were intolerant of mutation was investigated. Indeed, mutations elsewhere in the sequence typically exhibited markedly reduced fluorescence, including mutation of a series of G residues (FIGS. 20A, B). The vast majority of cases, these mutations were not tolerated. Thus, these residues likely have an essential role in aptamer holding for binding to the fluorophore. Thus, analysis of the clones from directed evolution can predict functionally important domains in the aptamers (FIG. 20B).

Figure 20C:
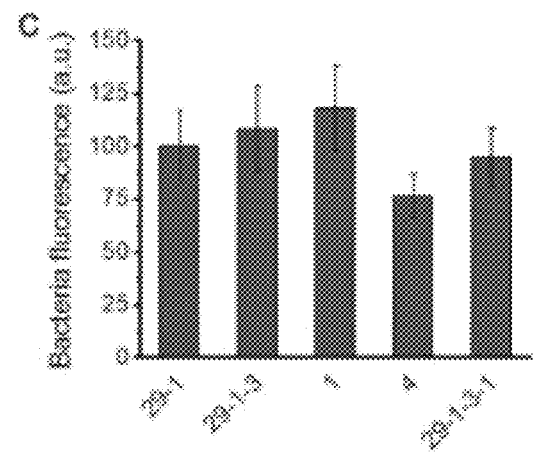

The mutations that shorten the aptamer while preserving its fluorescence were combined. This generated 29-1-3-1. This aptamer exhibited similar overall colony fluorescence as 29-1 (FIG. 20C). Comparison of in vitro folding of 29-3-1 indicates that it exhibits 80% folding relative to 29-1 (FIG. 20B).

Figure 10:
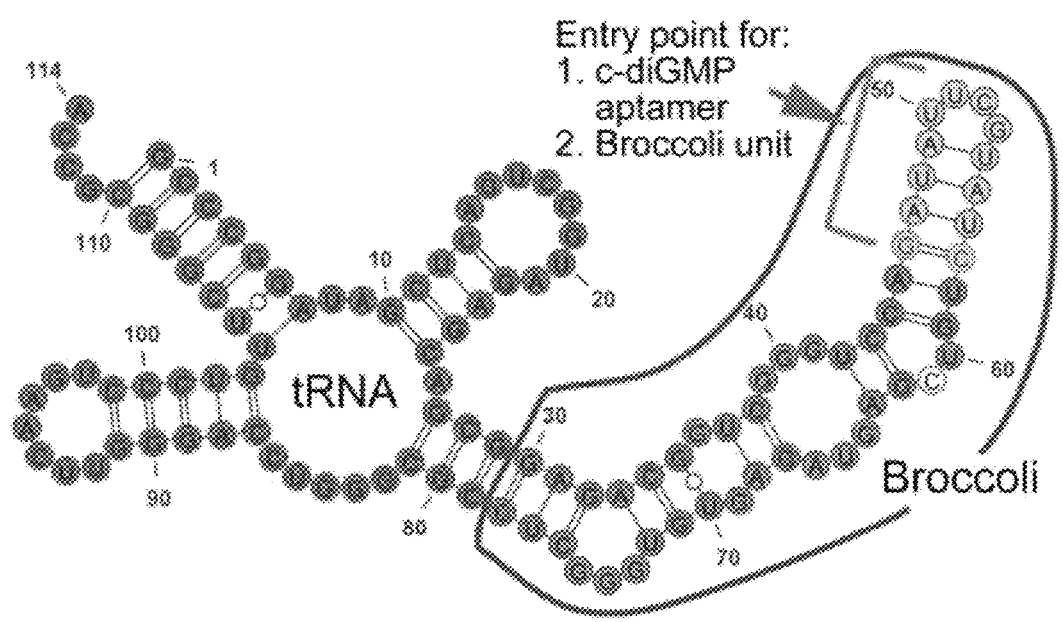
FIG. 10 illustrates the mFold prediction of the secondary structure of Broccoli (circled with green) fused to tRNA (violet), SEQ ID NO: 11. For comparison purposes the color coding of nucleotides is the same as on the FIG. 9D. Green—conservative bases (or equivalent substitutions) participating in base pairing. Blue—conservative bases in bulges. Yellow—re-engineered terminal stem-loop. Non-colored base is a mutation in a conservative bulge. Either a small molecule aptamer or another Broccoli unit (without tRNA) or can be inserted instead of the stem-loop indicated.
Figure 21:
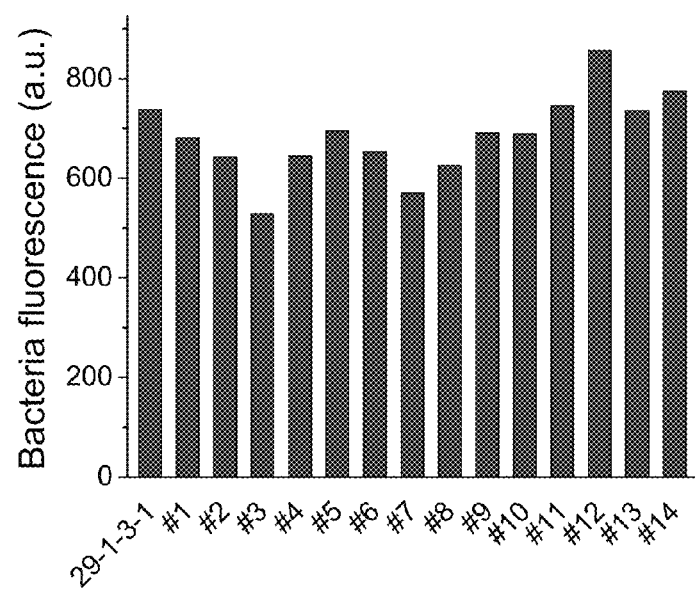
FIG. 21 illustrates that an additional round of directed evolution improved in vivo brightness of 29-3-1 insignificantly. After another round of doping, three rounds of SELEX and FACS sorting, the brightest selected colonies exhibited similar or only slightly (~15%) brighter fluorescence intensity compared to the parental 29-3-1 when measured in bacterial colonies.

Next, 29-1-3-1 was subjected to an additional round of directed evolution and compared in vivo brightness of the top sorted clones (FIG. 21). Among them, none showed significantly increased colony fluorescence compared to 29-1-3-1, which was therefore designated Broccoli (FIGS. 10, 22A).

Example 14

Development of Dimeric Broccoli by Modification of the Terminal Step Loop of Broccoli Analysis of the predicted secondary structure of tBroccoli (Broccoli with tRNA scaffold) (FIG. 10), the directed evolution experiments, and the mutagenesis experiments suggest that the terminal stem-loop, marked in yellow, serves a structural role. To further test this, whether a small molecule-binding aptamer can be inserted into this site was investigated. Small molecule- and protein-binding aptamers have been previously inserted into structural domains in Spinach, which resulted in Spinach aptamers with sensor functionality (Paige et al., "RNA Mimics of Green Fluorescent Protein," *Science* 333(6042): 642-6 (2011) and Kellenberger et al., "RNA-Based Fluorescent Biosensors for Live Cell Imaging of Second Messengers Cyclic di-GMP and Cyclic AMP-GMP," *J. Am. Chem. Soc.* 135(13): 4906-9 (2013), which are hereby incorporated by reference in their entirety).

To test this idea, the cyclic diGMP-binding aptamer (Kellenberger et al., "RNA-Based Fluorescent Biosensors for Live Cell Imaging of Second Messengers Cyclic di-GMP and Cyclic AMP-GMP," *J. Am. Chem. Soc.* 135(13): 4906-9 (2013), which is hereby incorporated by reference in its entirety) was inserted into the stem region of tBroccoli (FIGS. 10A, 22B). The resulting construct exhibited significantly increased fluorescence upon addition of 500 nM c-diGMP.

Figures 11A, 11B, 11C:
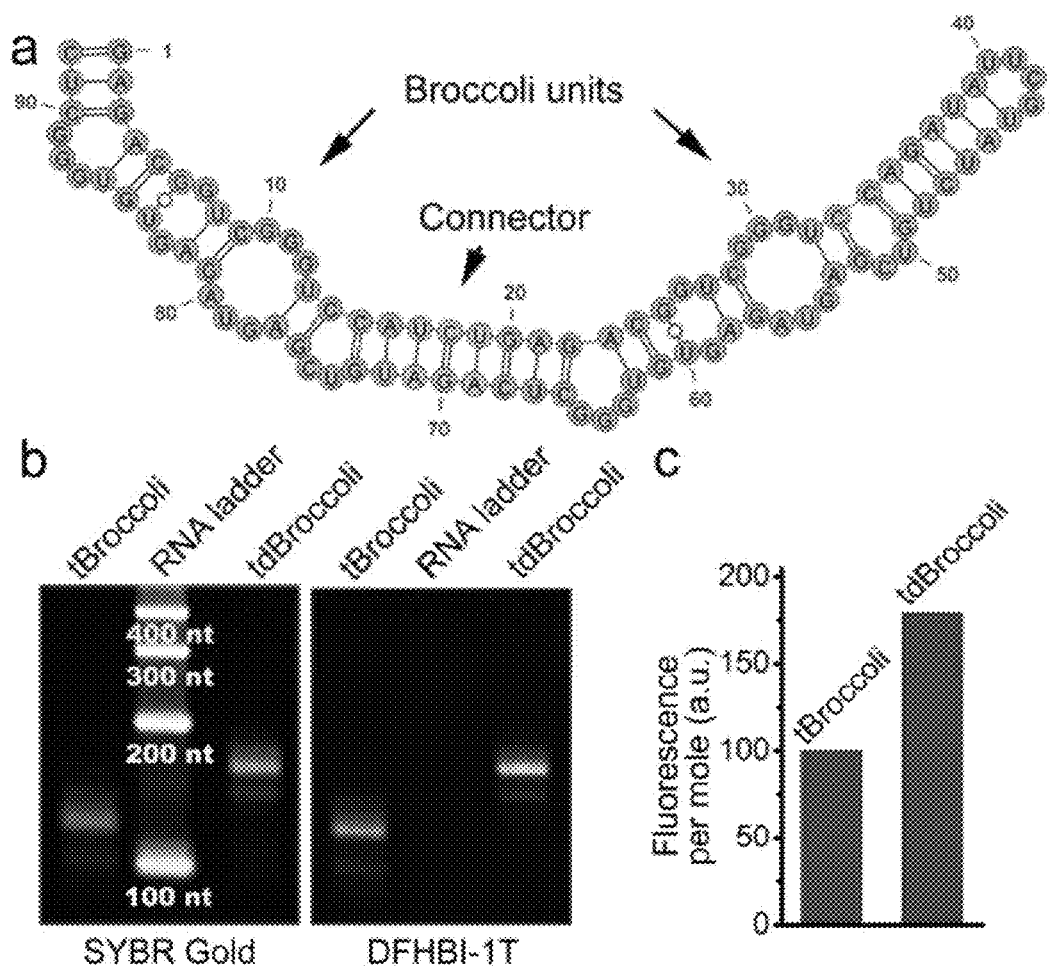
FIGS. 11A-C illustrate the designing of dimeric Broccoli.

Next, whether a second Broccoli aptamer could be inserted into the Broccoli terminal stem was investigated (FIGS. 11A, 22C). This dimeric Broccoli (dBroccoli) exhibits almost twice the fluorescence as the monomeric Broccoli, as demonstrated by comparing 1 μmole of in vitro transcribed tBroccoli and tdBroccoli (dBroccoli in tRNA scaffold) in PAGE gel (FIG. 11B). In these experiments, the gel is first stained with DFHBI-1T to detect the size and fluorescence of RNA-DFHBI-1T complexes, and next with SYBR Gold to detect all RNA.

These experiments indicate that dBroccoli provides nearly twice the fluorescence as Broccoli (FIG. 11C) and that dBroccoli can potentially serve as an enhanced tag for in vivo imaging.

Example 15

Characterization of Spectral Properties and Folding of Broccoli-DFHBI-1T

Figures 12A, 12B, 12C, 12D, 12E, 12F:
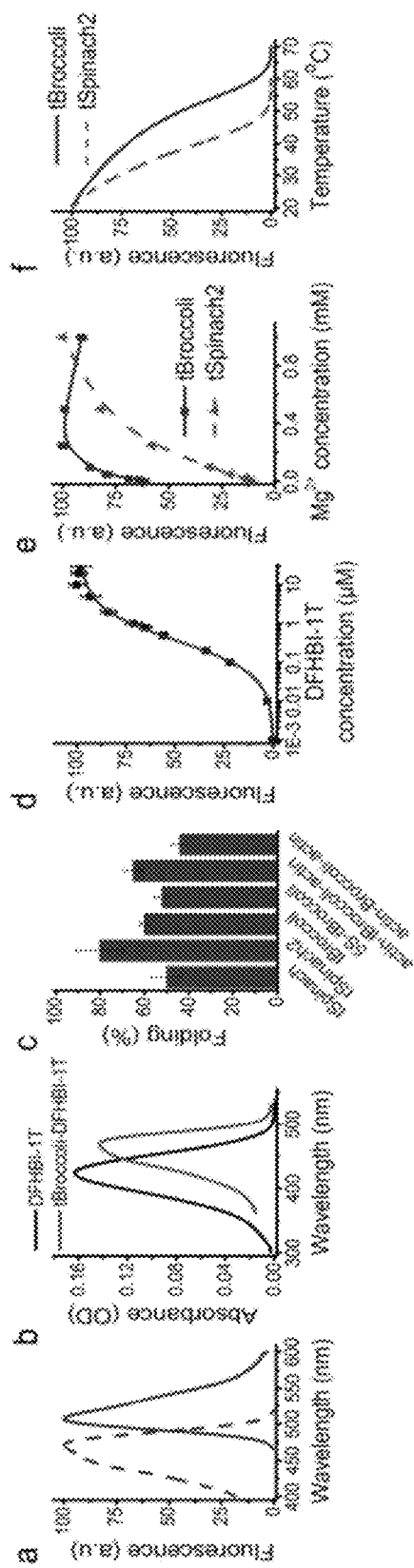
FIGS. 12A-F show that the in vitro comparison of Broccoli and Spinach2 reveals key differences.

Next, the fluorescence properties of Broccoli-DFHBI-1T and Spinach2-DFHBI-1T were compared. The overall spectral properties and fluorophore-binding characteristics were nearly identical (FIGS. 12A, B and summarized in Table 2).

TABLE 2

Photophysical and biochemical properties of Broccoli-DFHBI-1T compared to DFHBI-1T-Spinach2

| | Abs max (nm) | Ex max (nm) | Em max (nm) | Ext. coeff. ($M^{-1}cm^{-1}$) | Quantum yield | Brightness | $K_D$ (nM) | $T_m$ (° C.) |
|---|---|---|---|---|---|---|---|---|
| DFHBI-1T[†] | 423 | 426 | 495 | 35,400 | 0.00098 | 0.12 | — | — |
| Broccoli-DFHBI-1T | 469 | 472 | 507 | 29,600 | 0.94 | 96 | 360 | 45 |
| Spinach2-DFHBI-1T[†] | 470 | 482 | 505 | 31,000 | 0.94 | 100 | 560 | 37 |

[†]Properties are taken from Song et al., "Plug-and-Play Fluorophores Extend the Spectral Properties of Spinach," *J. Am. Chem. Soc.* 136(4): 1198-201 (2014), which is hereby incorporated by reference in its entirety It has been previously shown that increased in vitro folding, especially folding in the presence of flanking sequences, correlates with improved performance in vivo (Strack et al., "A Superfolding Spinach2 Reveals the Dynamic Nature of Trinucleotide Repeat-Containing RNA," *Nat. Methods* 10(12): 1219-24 (2013) and Martell et al., "Optimizing Aptamer Activity for Gene Therapy Applications Using Expression Cassette SELEX," *Mol. Ther.* 6(1): 30-4 (2002), which are hereby incorporated by reference in their entirety). Therefore, the percentage of folded Broccoli alone and in the context of various flanking sequences was measured (FIG. 12C). tBroccoli demonstrated folding efficiency of ~60%, which is similar to tSpinach2 (Hesselberth et al., "In Vitro Selection of RNA Molecules that Inhibit the Activity of Ricin A-Chain," *J. Biol. Chem.* 275(7): 4937-42, which is hereby incorporated by reference in its entirety). Importantly, tBroccoli folding was unaffected by fusing it to the 3' end of the 5S RNA, or by placing it between 50 nt-long flanking sequences derived from the human β-actin 3' untranslated region.

Next, whether Broccoli without the tRNA scaffold can fold and tolerate flanking sequences was tested. Indeed, adding human fi-actin flanking sequences to Broccoli does not prevent Broccoli from folding (FIG. 12D). This indicates that Broccoli can be used without tRNA in vivo.

Example 16

Broccoli Demonstrates Improved Affinity to DFHBI-1T, Higher Thermostability and Lower Fluorescence Dependence on Magnesium The Broccoli-DFHBI-1T dissociation constant was measured (FIG. 12D). Broccoli demonstrates higher affinity to DFHBI-1T compared to Spinach2 (Table 2) which should allow suing lower concentration of DFHBI-1T for imaging and thus to decrease non-specific background.

Next, the magnesium dependence of Broccoli- and Spinach2-induced fluorescence were compared. The total intracellular magnesium concentration has been measured in diverse cell types to be between 17 to 20 mM (Romani et al., "Magnesium Homeostasis in Mammalian Cells," *Met. Ions Life Sci.* 12: 69-118 (2013), which is hereby incorporated by reference in its entirety). However, the majority of cellular magnesium is bound to phospholipids, nucleotides, proteins, and nucleic acids (Romani et al., "Magnesium Homeostasis in Mammalian Cells," *Met. Ions Life Sci.* 12: 69-118 (2013), which is hereby incorporated by reference in its entirety). Indeed, the amount of free magnesium was estimated to be in the range of 0.25-1 mM (Grubbs et al., "Intracellular Magnesium and Magnesium Buffering," *Biometals* 15(3): 251-9 (2002), which is hereby incorporated by reference in its entirety). Thus, it is desirable to have aptamers that are not dependent on high concentrations of magnesium for fluorescence. In these experiments, magnesium levels were reduced during later stages of SELEX, and FACS was performed in media lacking magnesium to bias selection towards aptamers with low magnesium dependence for folding. Thus combined SELEX-FACS selection protocol performed at low magnesium concentration is predicted to produce aptamers with lower fluorescence dependence on this ion.

Indeed, in magnesium-free buffers, Broccoli-DFHBI-1T exhibits 61% of its maximal fluorescence. In contrast, Spinach2 exhibits only 11% of its maximal fluorescence in magnesium-free conditions. A magnesium titration shows that Broccoli is markedly less dependent on magnesium, and exhibits maximal fluorescence at ~300 μM, while Spinach2 exhibits 50% maximal fluorescence at ~300 μM, with maximal fluorescence at ~1 mM (FIG. 11E). Thus, Broccoli exhibits markedly reduced magnesium dependence than Spinach2, which could result in enhanced performance in vivo.

Next, the thermal stability of Broccoli was measured. As shown in Example 1-8, improved aptamer thermostability correlates with better performance for imaging at 37° C. Spinach2 contains a series of mutations that increase its thermal stability and contribute to its overall improve of performance in cells (see Example 2). Consistent with previous studies, Spinach2-DFHBI-1T exhibited a $T_m$ of ~37° C. However, thermal denaturation of Broccoli-DFHBI-1T showed a noticeably increased $T_m$ of ~48° C. Taken together, these data suggest that Broccoli exhibits several improved characteristics that may be useful for cellular imaging.

Example 17

Enhanced Fluorescence of Broccoli-Tagged RNA in Bacteria

Next, Broccoli fluorescence was monitored in living cells. Broccoli was first imaged in *E. coli*. Broccoli, dBroccoli, and Spinach2 were expressed in *E. coli* as tRNA fusions. tSpinach2-expressing cells exhibited significantly increased fluorescence above the level seen in control transformed cells (FIG. 13A,B) Importantly, Broccoli-expressing cells were more than twice as fluorescent as Spinach2-expressing cells. Cells expressing the dimeric Broccoli were approximately twice as fluorescent as cells expressing Broccoli.

Figures 13A, 13B, 13C, 13D:
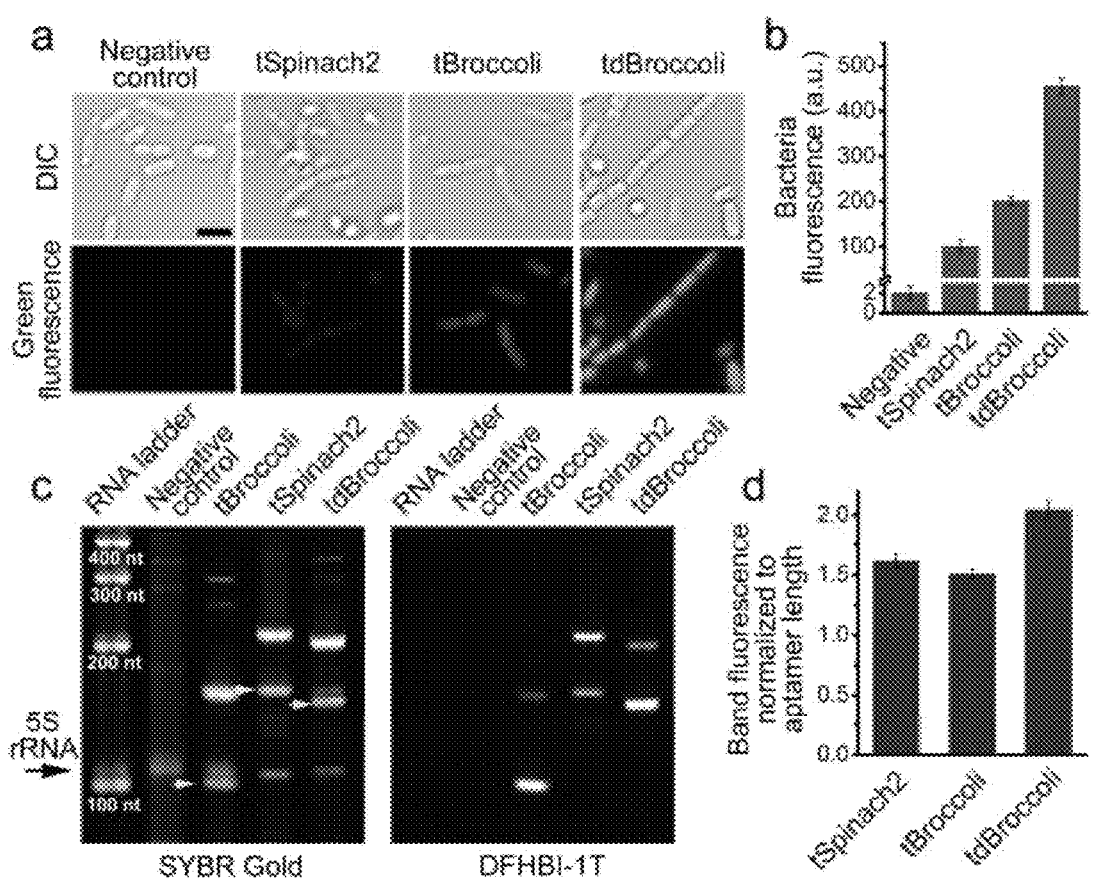
FIGS. 13A-D illustrate that tBroccoli and tdBroccoli show substantially improved performance in bacteria compared to tSpinach2.

Next, the fluorescence intensity was normalized to aptamer expression in cells. To quantify RNA expression, cellular RNA was harvested and fractionated using a 6% polyacrylamide denaturing gel. Gels were stained with SYBR Gold, which specifically stains RNA (Tuma et al., "Characterization of SYBR Gold Nucleic Acid Gel Stain: a Dye Optimized for use with 300-nm Ultraviolet Transilluminators," *Anal. Biochem.* 268(2): 278-88 (1999), which is hereby incorporated by reference in its entirety). The identity of the Broccoli and Spinach2 bands could be inferred because they are uniquely seen in transfected cells and not control cells (FIG. 12C). Bacterial tRNA has been reported to undergo extensive processing upon transcription (Morl et al., "The Final Cut. The Importance of tRNA 3'-Processing," *EMBO Rep.* 2(1): 17-20 (2001), which is hereby incorporated by reference in its entirety). Thus two bands observed for each tRNA-fused aptamer on a gel are likely fully processed and unprocessed species. To confirm that these bands were indeed Broccoli and Spinach2, the gels were stained with DFHBI-1T. Gel staining with DFHBI-1T resulted in selective staining of Broccoli and Spinach2, with minimal background fluorescence of DFHBI-1T (FIG. 13C, yellow arrows). Staining with SYBR Gold is more accurate than DFHBI-1T for quantifying the absolute amounts of different aptamers since the folding efficiency can be different between different aptamers.

Quantification of SYBR Gold-stained total bands intensity for both processed and unprocessed tRNA-aptamers showed that overall RNA expression was highly similar in tSpinach, tBroccoli, and tdBroccoli-expressing cells (FIG. 13D). Thus the increase in fluorescence seen in tBroccoli-expressing cells is unlikely to derive from increased Broccoli expression.

Since in vitro studies showed a large difference in magnesium sensitivity, the possibility that this could account for the reduced brightness of tSpinach2 in *E. coli* was investigated. To test this, the fluorescence of the *E. coli* incubated in LB culture media with or without 20 mM $MgCl_2$ was compared. After 1 hr, the fluorescence of *E. coli* expressing tBroccoli increased by 36%, while the fluorescence of tSpinach-expressing cells increased by 125%. This substantially larger increase in Spinach2 fluorescence suggests that the magnesium levels are insufficient for maximal tSpinach fluorescence in bacterial cells. Taken together, these experiments suggest that the reduced magnesium requirement for tBroccoli likely contributes to its improved performance in E. coli.

Example 18

Broccoli is an Enhanced Tag for Imaging RNA in Mammalian Cells

Next, tBroccoli was imaged in mammalian cells. 5S, a noncoding RNA that associates with the ribosome and has additional functions in the cell was previously imaged (Paige et al., "RNA Mimics of Green Fluorescent Protein," Science 333(6042): 642-6 (2011), which is hereby incorporated by reference in its entirety). Following the same strategy, tBroccoli or tdBroccoli was fused to the 3' terminus of 5S expressed from the pAV5S plasmid. The performance of these aptamers was compared to 5S-tSpinach2 in HEK293T cells.

Figure 23:
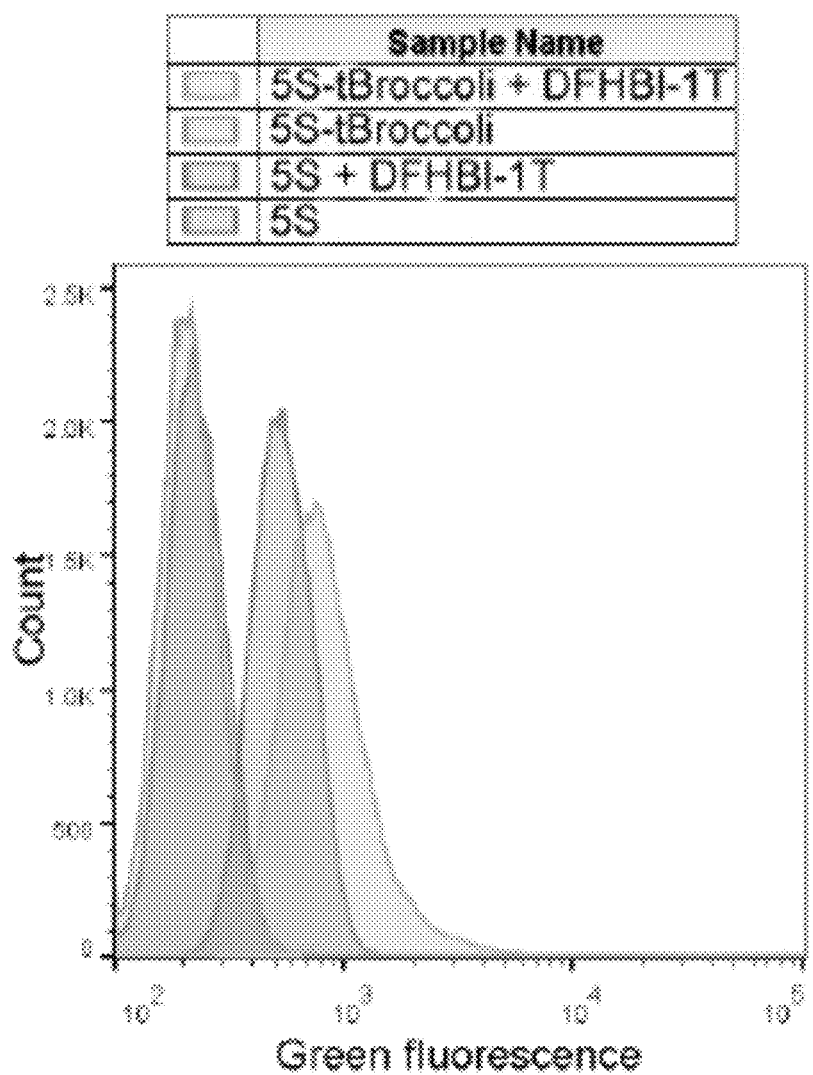
FIG. 23 illustrates that aptamer-specific fluorescent signal appears only after addition of DFHBI-1T. HEK293T cells were transfected with either 5S or 5S-tBroccoli expressing plasmids and then analyzed using flow cytometry on FACSAria III instrument. Half of the cells were treated with 40 µM DFHBI-1T. Though 5S expressing cells treated with DFHBI-1T show some level of dye-induced autofluorescence their average signal is noticeably dimmer than the signal of 5S-tBroccoli cells with the dye. Moreover, only 5S-tBroccoli cells treated with DFHBI-1T show a characteristic bright cells population shoulder (right side of the green histogram).
Figure 24:
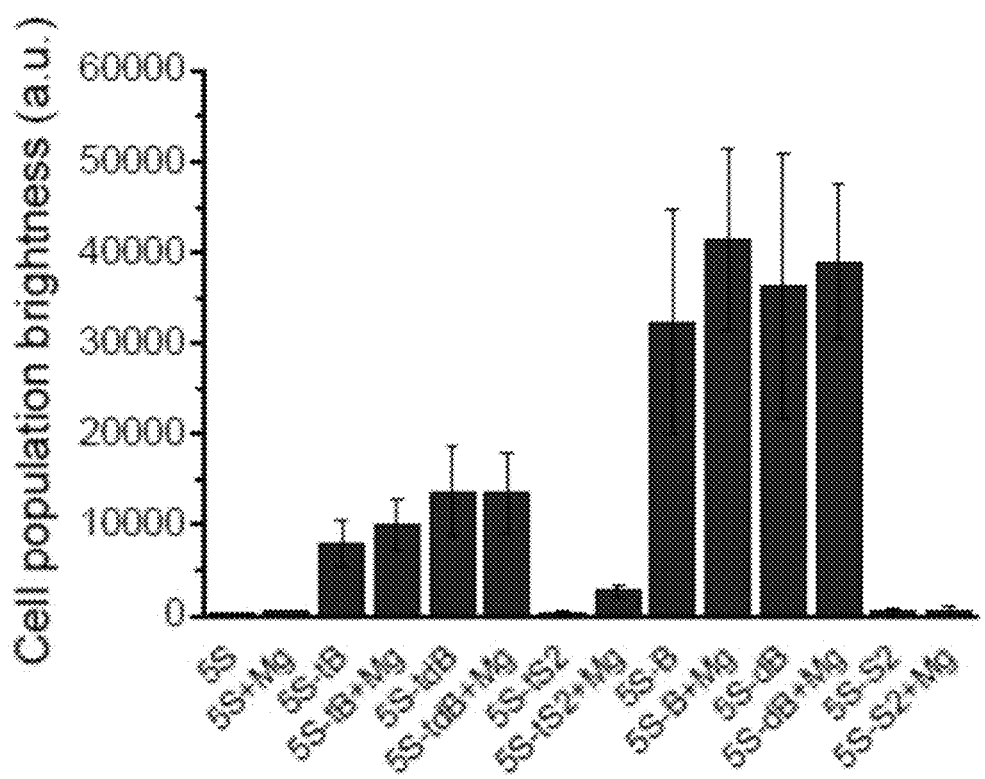
FIG. 24 illustrates the quantification of the flow cytometry analysis of aptamers expression in mammalian cells. To compare specific aptamers' brightness in mammalian cells, HEK293T cells were transfected with two plasmids: one expressing aptamer (with or without tRNA) fused to 5S rRNA and another expressing mCherry fluorescent protein. Cells were then treated with 40 µM DFHBI-1T and analyzed on FACSAria III instrument in two channels: green (ex=488 nm; em=525±50 nm) and red (ex=561 nm and em=610±20). For quantification, mean fluorescent signal of the non-negative population was calculated and then mean fluorescent signal of the negative population was subtracted from it to assess specific, not background fluorescent signal. Finally, this number was multiplied by the percentage of the non-negative population to provide the total fluorescent signal of the non-negative population. These numbers are plotted on the bar graph above. Where indicated, cells were also pre-treated with 5 mM $MgSO_4$. Error bar indicates robust SD calculated by FlowJo program, used for data analysis.

Flow cytometry was used to quantify average brightness of tRNA. Transfected cells were analyzed in two channels: green (ex=488 nm; em=525±50 nm) and red (ex=561 nm; em=610±20). The latter channel was used to detect mCherry, which was used as a transfection control. As evidenced from FIG. 14A, 5S-tBroccoli and 5S-tdBroccoli are clearly detectable in the green fluorescence channel and this specific signal appears only upon cells treatment with DFHBI-1T (FIG. 23). Calculation of the mean fluorescence intensity of the green population indicates that tdBroccoli is 70% brighter than tBroccoli (FIG. 24).

Figures 14A, 14B, 14C, 14D, 14E:
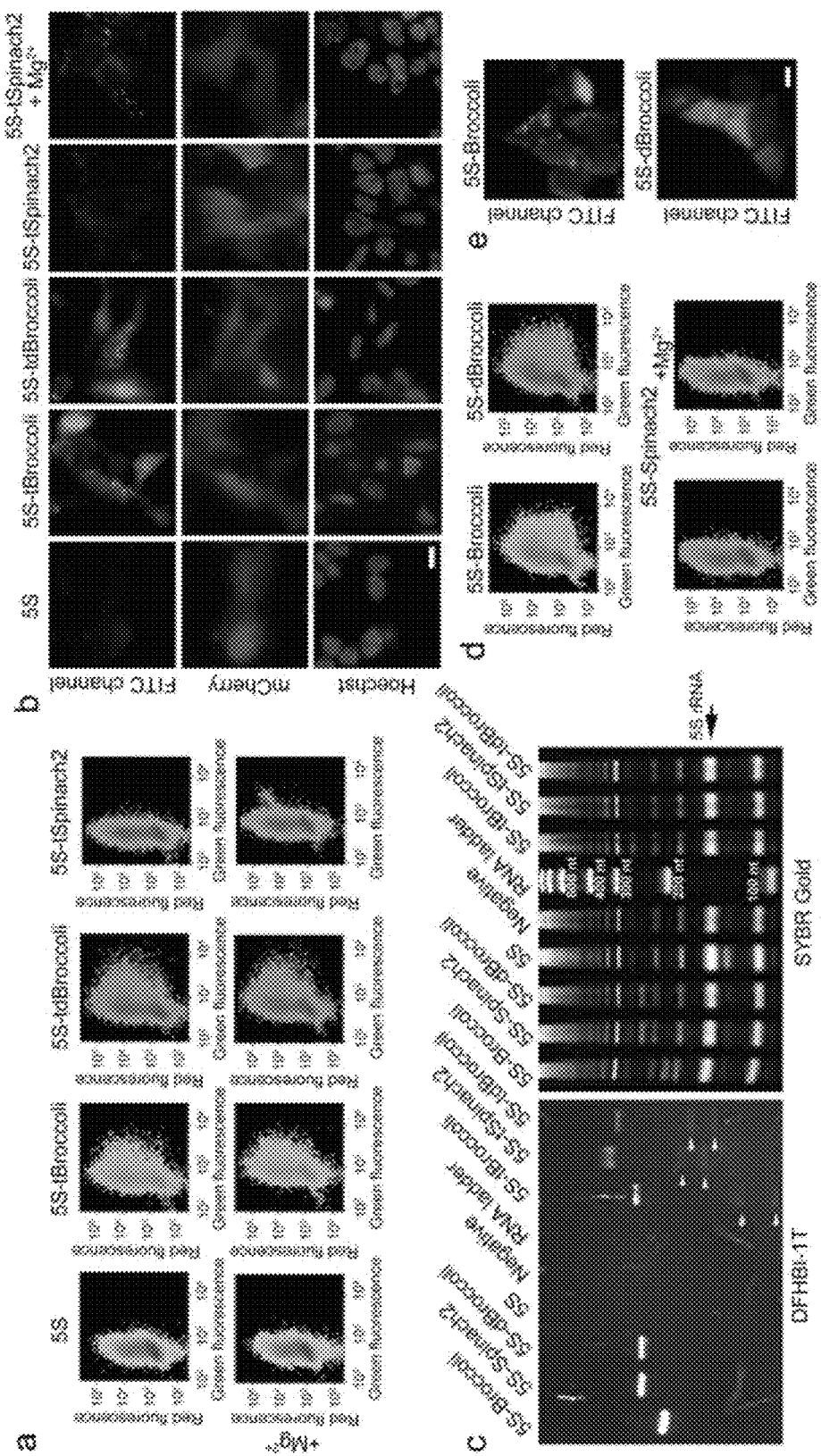
FIGS. 14A-E illustrate that Broccoli serves an enhanced and tRNA independent tag for mammalian cell imaging.

The fluorescence of tBroccoli-expressing cells was compared to tSpinach2-expressing cells. The standard mammalian imaging protocol for Spinach2 uses magnesium-supplemented media (Paige et al., "RNA Mimics of Green Fluorescent Protein," Science 333(6042): 642-6 (2011) and Strack et al., "A Superfolding Spinach2 Reveals the Dynamic Nature of Trinucleotide Repeat-Containing RNA," Nat. Methods 10(12): 1219-24 (2013), which are hereby incorporated by reference in their entirety). Indeed, in the absence of additional magnesium, few fluorescent cells are seen (FIG. 13A). Inclusion of 5 mM MgSO$_4$ resulted in a population of green fluorescent cells, although the number of cells was noticeably smaller than Broccoli-expressing cells (FIGS. 13A, 24). Notably, magnesium did not induce a substantial effect on the fluorescence of tBroccoli- and tdBroccoli-expressing cells (FIG. 14A). Taken together, these results confirm the belief that Broccoli does not require magnesium supplementation for imaging.

To confirm the flow cytometry data on a single cell level the same cells were imaged using widefield fluorescence microscopy. To unambiguously detect aptamer-tagged 5S-RNA the cells were treated with 0.3 M sucrose, which induces RNA 5S granule formation (Paige et al., "RNA Mimics of Green Fluorescent Protein," Science 333(6042): 642-6 (2011), which is hereby incorporated by reference in its entirety). Sucrose treatment resulted in clearly visible cytoplasmic RNA foci in case of 5S-tBroccoli and 5S-tdBroccoli using media that had no added magnesium (FIG. 13B). These foci were brighter than those detected in 5S-tSpinach2-expressing cells imaged in the presence of magnesium (FIG. 13B).

Example 19

Broccoli can be Imaged without tRNA

Although the tRNA scaffold is often used to promote the folding of aptamers in vitro (Iioka et al., "Efficient Detection of RNA-Protein Interactions Using Tethered RNAs," Nuc. Acids Res. 39(8): e53 (2011), which is hereby incorporated by reference in its entirety) and in vivo (Ponchon et al., "Recombinant RNA Technology: the tRNA Scaffold," Nat. Methods 4(7): 571-6 (2007), which is hereby incorporated by reference in its entirety), tRNA-fused aptamers are recognized by cellular enzymes (Ponchon et al., "Recombinant RNA Technology: the tRNA Scaffold," Nat. Methods 4(7): 571-6 (2007), which is hereby incorporated by reference in its entirety) which in turn can lead to undesirable processing.

To test this, aptamer processing in mammalian cells was monitored. Cellular RNA was extracted from HEK293T cells expressing 5S-tSpinach2, 5S-tBroccoli, or 5S-tdBroccoli, and aptamer-tagged RNAs were detected by gel staining with DFHBI-1T. Each of the aptamers was readily detected in the gel, with 5S-tBroccoli being expressed at highest levels Importantly, each of these tRNA-aptamers exhibited two additional distinct lower-molecular weight bands (indicated with arrows on FIG. 14C, left panel), indicating that the RNAs were processed.

Since Broccoli demonstrated high folding efficiency without a tRNA scaffold in vitro (FIG. 12C), whether tRNA was required for imaging Broccoli in mammalian cells was investigated. To test this, Broccoli and dBroccoli were fused to the 3' terminus of 5S without tRNA and the resulting plasmids were transfected into HEK293T cells. Using flow cytometry, it was found that both Broccoli and dBroccoli can be detected in cells (FIG. 14D). Moreover, the average cellular brightness was higher than for 5S fused to tRNA-aptamer constructs (FIG. 24). This supports the idea that the tRNA scaffold has a negative impact on RNA expression. Notably, the 5S-Spinach2 lacking the tRNA scaffold did not show any bright events even at higher magnesium concentrations indicating that this aptamer is likely dependent on the tRNA scaffold for folding (FIG. 14D).

Next, the fluorescence of Broccoli-tagged RNA was confirmed by fluorescence microscopy. As with the tRNA-tagged Broccoli constructs, the constructs lacking tRNA were readily detectable in sucrose-treated cells (FIG. 13E).

As a control, aptamer expression levels were monitored by harvesting cellular RNA and staining the PAGE-separated RNA with SYBR-Gold and DFHBI-1T. These data showed that the 5S-aptamer fusions are expressed at comparable levels and exhibit no evidence of RNA processing (FIG. 14C). Taken together, these data show that Broccoli does not require the tRNA scaffold for folding or cellular fluorescence.

Discussion of Examples 9-19

Examples 9-19 present both a novel platform for isolating fluorescent "light up" aptamers that are compatible for intracellular imaging, and Broccoli, a new RNA imaging probe, which shows improved fluorescence in living cells compared to previous probes.

Unlike Spinach, Broccoli was identified using a mixed SELEX-FACS approach in which SELEX was terminated early and the RNA pool was screened using FACS. The best aptamer found in this screen was then subjected to directed evolution, which involves random mutagenesis and further FACS in E. coli to identify aptamers that exhibit improved performance in living cells. Directed evolution resulted in Broccoli, which has the high folding efficiency, but is substantially shorter than Spinach or Spinach2, does not require tRNA for imaging, and exhibits substantially improved fluorescence magnesium dependence and thermostability.

The FACS-based screening approach provides a markedly simplified method for screening aptamer libraries. Although SELEX is a straightforward protocol, it typically requires 6-20 rounds with many aptamers found between rounds 9-14 (Stoltenburg et al., "SELEX—a (R)Evolutionary Method to Generate High-Affinity Nucleic Acid Ligands," *Biomol. Eng.* 24(4) 381-403 (2207), which is hereby incorporated by reference in its entirety). The selection of fluorophore-activating aptamers is a special case since the desired aptamers exhibit fluorescence activation, which can be detected by FACS. As a result, SELEX can be terminated after only a few rounds, which markedly accelerates the pace of aptamer discovery.

In addition to simplifying SELEX, FACS based screening provides an approach for directed evolution. Directed evolution allowed the investigation of a short 29-1 core sequence with reduced fluorescence to identify mutations that improve its folding so that it exhibits nearly identical fluorescence as the parent 29-1 aptamer. It was notable that subsequent rounds of directed evolution did not substantially improve Broccoli. This may indicate that the high folding, extinction coefficient and quantum yield of Broccoli brought it nearly to its brightness limit. Conceivably FACS may not be sensitive enough to detect further subtle improvements in these parameters.

Apart from providing the ability to select aptamers based on not binding but fluorescent properties, cell based screening has another critical advantage. Cell-based screening favors aptamers which can fold and function in the intracellular environment. Aptamer misfolding is a major challenge that limits the effectiveness of endogenously expressed aptamers, such as protein-inhibiting RNA aptamers developed by SELEX (Martell et al., "Optimizing Aptamer Activity for Gene Therapy Applications Using Expression Cassette SELEX," *Mol. Ther.* 6(1): 30-4 (2002), which is hereby incorporated by reference in its entirety). In the case of aptamer-fluorophore complexes, the fluorescence is an indicator, in part, of folding, allowing selection for in vivo folding. Another advantage of cell-based screening is that RNAs that are capable of resisting intracellular RNA degradation are selected. These aptamers are likely to accumulate to a higher level and therefore be preferentially selected in this screen. Lastly, aptamers that fold in the presence of cellular ions will be selected. The cell contains complex ionic constituents beyond potassium, sodium, and magnesium. By screening aptamers in living cells, aptamers that may be positively or negatively influenced by these other cellular components can be isolated. Overall, cell-based fluorescence screening overcomes the key challenges that limit the development of fluorescent aptamers for cellular RNA imaging.

Data suggests that Broccoli has numerous advantages over Spinach2 for cellular imaging. Although both Spinach2 and Broccoli share common sequence elements, the other domains appear to confer improved imaging properties to Broccoli. This improvement mostly comes from the low magnesium dependence of Broccoli. Imaging with Spinach2 requires pre-incubation of cells in 5 mM magnesium. Since adding exogenous magnesium could influence cellular function, the use of Broccoli overcomes this imaging requirement. Notably, dBroccoli shares the same enhanced cellular performance as Broccoli and shows nearly twice the fluorescence. Thus dBroccoli and Broccoli are valuable imaging tags.

An additional advantage of Broccoli is its short size. Broccoli is 49 nt, which is shorter than the 96-nt long Spinach2 and the 168-nt long tSpinach2. The short size of Broccoli may improve its versatility for some RNAs that might not tolerate a large tag.

Another important property of Broccoli is its ability to fold without a tRNA scaffold. Even though the tRNA scaffold promotes folding in vivo (Ponchon et al., "Recombinant RNA Technology: the tRNA Scaffold," *Nat. Methods* 4(7): 571-6 (2007), which is hereby incorporated by reference in its entirety), its similarity to cellular tRNAs makes it prone to processing (Morl et al., "The Final Cut. The Importance of tRNA 3'-Processing," *EMBO Rep.* 2(1): 17-20 (2001), which is hereby incorporated by reference in its entirety) and thus can reduce cellular aptamer levels.

Although flow cytometry was used in Examples 9-19 to quantify cellular fluorescence, it is noteworthy that FACS is often used to study gene expression in cell populations (Ducrest et al., "Detection of Promoter Activity by Flow Cytometric Analysis of GFP Reporter Expression," *Nuc. Acids Res.* 30(14): e65 (2002), which is hereby incorporated by reference in its entirety). However, these experiments often rely on quantifying GFP, which is detected 10-30 min after gene transcription. The use of Broccoli and related RNA tags can be useful to obtain more direct and temporally accurate measures of RNA levels.

Overall, a novel platform for selecting fluorescent aptamers, and Broccoli, an advanced probe with superior in vivo properties than Spinach2 has been presented. Spinach/Spinach2 have been used in diverse applications, such as the development of novel sensors, imaging transcription and detecting various cytoplasmic and nuclear RNAs (Paige et al., "RNA Mimics of Green Fluorescent Protein," *Science* 333(6042): 642-6 (2011); Strack et al., "A Superfolding Spinach2 Reveals the Dynamic Nature of Trinucleotide Repeat-Containing RNA," *Nat. Methods* 10(12): 1219-24 (2013); Paige et al., "Fluorescence Imaging of Cellular Metabolites with RNA," *Science* 335(6073): 1194 (2012); Song et al., "Imaging Bacterial Protein Expression Using Genetically Encoded RNASensors," *Nat. Methods* 10(9): 873-5 (2013); Kellenberger et al., "RNA-Based Fluorescent Biosensors for Live Cell Imaging of Second Messengers Cyclic di-GMP and Cyclic AMP-GMP," *J. Am. Chem. Soc.* 135(13): 4906-9 (2013); and Pothoulakis et al., "The Spinach RNA Aptamer as a Characterization Tool for Synthetic Biology," *ACS Synth. Bl.* 3(3): 182-7 (2014), which are hereby incorporated by reference in their entirety). Therefore, Broccoli provides the opportunity for improved imaging for these diverse applications.

Example 20

The Core Sequence of Broccoli is the Minimal Sequence Element Capable of Binding to and Switching on the Fluorescence of DFHBI and DFHBI-1T The core sequence of Broccoli describes the minimal sequence element that is capable of binding to and switching on the fluorescence of the DFHBI fluorophore. The core sequence of Broccoli also activates the fluorescence of DFHBI containing a trifluoroethyl substituent at the 1 position (DFHBI-1T).

To identify the core sequence of Broccoli, parent aptamer 29-1 was first investigated. The sequence of 29-1 is, as follows: GAG ACG CAA CUG AAU GAA AUG GUG AAG GAG ACG GUC GGG UCC AGG CAC AAA AAU GUU GCC UGU UGA GUA GAG UGU GGG CUC CGU AAC UAG UCG CGU CAC (SEQ ID NO: 3).

Figure 15A:
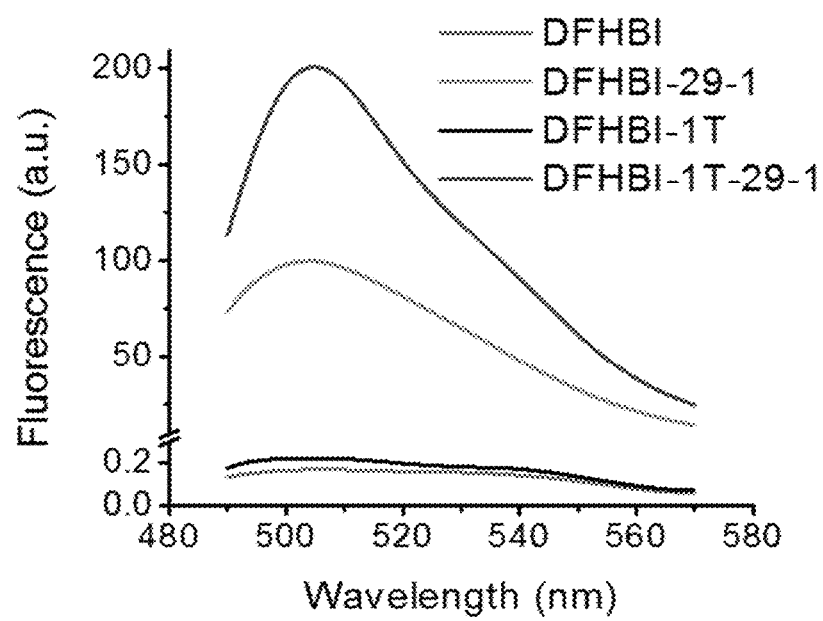
FIGS. 15A-B demonstrate that aptamers comprising the core sequence elements of Broccoli are capable of binding to and switching on the fluorescence of DFHBI and DFHBI-1T.

Analysis of truncation mutants of parent aptamer 29-1 allowed the identification of a shorter sequence which was still capable of inducing fluorescence of DFHBI, 29-1-T2: GGA GAC GGU CGG GUC CAG GCA CAA AAA UGU UGC CUG UUG AGU AGA GUG UGG GCU CC (SEQ ID NO: 4). These aptamers turn on the fluorescence of DFHBI and DFHBI-1T (FIG. 15A).

As can be seen, aptamers that have mutations or sequence alterations in the domain designated "variable domains" are still capable of finding the fluorophore DFHBI-1T. These experiments started to point to the idea that there is a core sequence element that is sufficient for binding the fluorophore DFHBI-1T.

To more precisely define the core sequence, a library containing over 10 million mutants of the sequence designated 29-1-T2 was prepared. Each of the sequences was individually expressed in E. coli bacteria. Bacteria were incubated with the fluorophore DFHBI-1T and sorted based on their fluorescent signal in a fluorescence-activated cell sorting (FACS) instrument. The sequences of different 29-1-T2 mutants that were capable of exhibiting fluorescence in the presence of the fluorophore DFHBI-1T were then examined. By comparing many of the sequences, the specific residues that were not essential for aptamer-induced fluorescence were found. Residues that were either completely invariant, or limited in the potential nucleotides that were allowed order to see fluorescence were also found. Thus, the sequence elements that are necessary, and the sequence that is not necessary for inducing the fluorescence of the fluorophore DFHBI-1T were precisely defined.

FIG. 9B is a sequence alignment of 6 representative 29-1-T2 mutants (i.e., clones) identified in the FACS experiment. The core sequence and variable domains are indicated. As can be seen by comparing different clones, there are different nucleotides present at positions in the variable domains, confirming the idea that the nucleotide identity at those positions is not strictly conserved. However, when looking at the domains that are labeled "core sequence," is clear that there is highly strict sequence conservation.

Based on these data, the core sequence element of an aptamer that induces the fluorescence of the fluorophore DFHBI-1T has been identified as to be, as follows: GAGANGGUCGGGUCCAGN-N-GCUGUNGAGUA-GAGUGUGGGCUC, SEQ ID NO: 74, where N at each of positions 5, 18, and 25 can be any single nucleotide base (A, U, G, or C), and N at position 19 can be any single nucleotide base (A, U, G, or C) or an insertion of any length of various nucleotide bases. Numerous sequences of different lengths have been placed at position 19 and the resulting aptamer retained fluorescence. The core can also be preceded or followed by any arbitrary sequence, but the core is needed for fluorescence.

Example 21

Using Core Broccoli Aptamer Sequences to Image Promoter Activity Using FACS

For many research applications it is desirable to monitor the activity of a gene promoter. Typically, downstream of the gene promoter is a reporter, such as green fluorescent protein. The fluorescence that is seen as a result of the synthesis of this reporter produces a signal that can be detected on the FACS machine. This can allow the activity of a cell, and typically millions of cells, to be rapidly quantified using FACS. The major drawback is that there is a time lag between the time when the reporter RNA is made and the encoded protein is synthesized and exhibits fluorescence. Thus, the core aptamer sequences described here can be used to directly image the RNA which is the immediate product of the gene from there, rather than imaging protein.

Figure 15B:
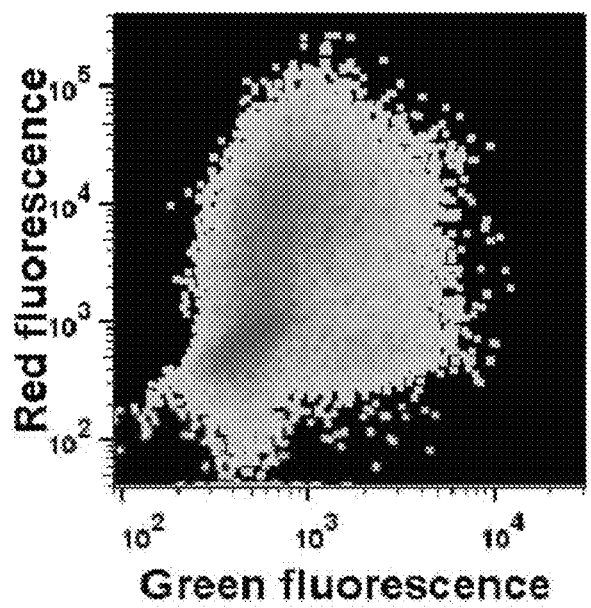

FIG. 15B illustrates a representative experiment in which core aptamer sequences have been expressed in bacterial or mammalian cells, and fluorescence activity has been monitored using FACS. As can be seen, the expression level of fluorescence is suitable for use in FACS experiments.

Example 22

The Core Sequences of Orange and Red Aptamers Describe the Minimal Sequence Elements Capable of Binding to and Switching on Fluorescence DFHO The core sequences of Orange and Red aptamers describe the minimal sequence element that is capable of binding to and switching on the fluorescence of the fluorophore DFHO.

It was previously discovered that parent aptamer 29-1 binds to the fluorophores DFHBI and its derivative DFHBI-1T. Aptamer 29-1 was also found to bind to DFHO, significantly enhancing its fluorescence. When 29-1 binds to DFHO, the fluorescence is not green—it is orange. This early experiment showed that the 29-1 RNA could bind to DFHO and give a new color.

To explore this phenomenon further, a library containing over 10 million mutants of this sequence was prepared. Each of the sequences was individually expressed in E. coli bacteria. The bacteria was incubated with the fluorophore DFHO and then sorted based on their fluorescent signal on a fluorescence-activated cell sorting (FACS) instrument. Analysis of the mutations introduced into the 29-1 aptamer allowed prediction of the core sequence necessary for binding DFHO. The possibility that the core binding sequence for DFHO fluorophore is the same as for the DFHBI fluorophore was also considered. The core binding sequence for DFHBI fluorophore is identified in preceding Example 21.

Figure 16A:
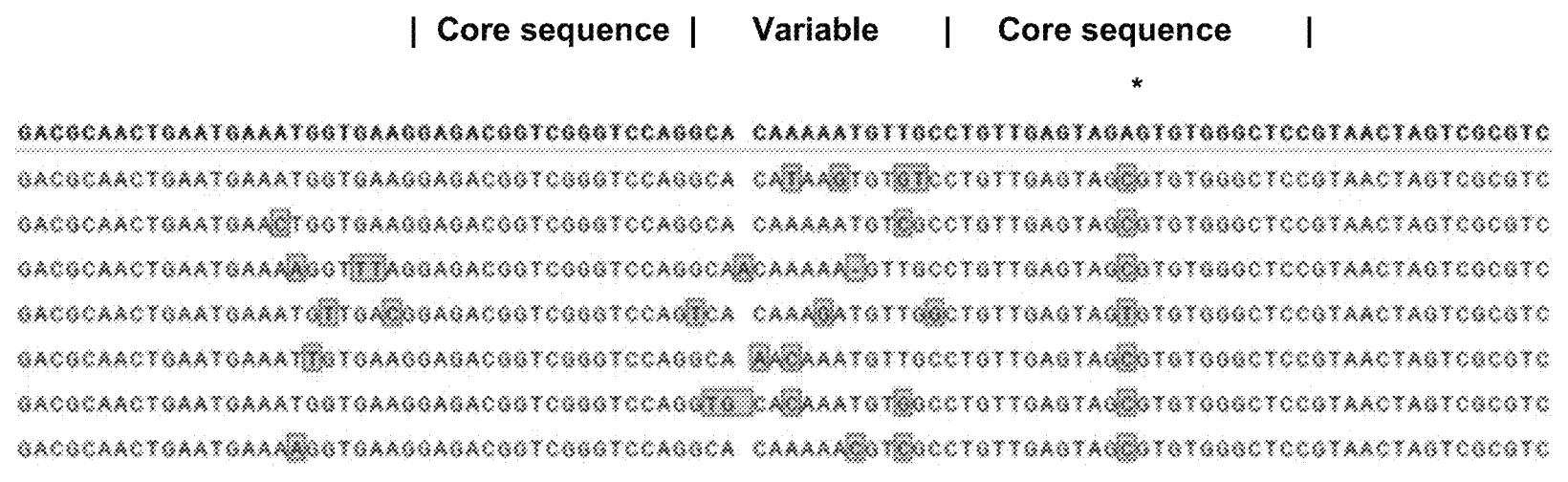

FIG. 16A illustrates a representative example of sequences identified in the 29-1 mutagenesis experiment. While only some sequence variants are shown, all demonstrate the ability to bind to and induce the fluorescence of DFHO. As shown in FIG. 16A, a core sequence for DFHBI binding is seen since it is mostly preserved in all the mutants presented, with the vast majority of mutations falling outside this core sequence. Importantly, it was found that this core sequence was very similar to the core sequence for binding to DFHBI. Therefore, the core sequence elements required for binding DFHO and DFHBI are very similar.

Figure 16B:
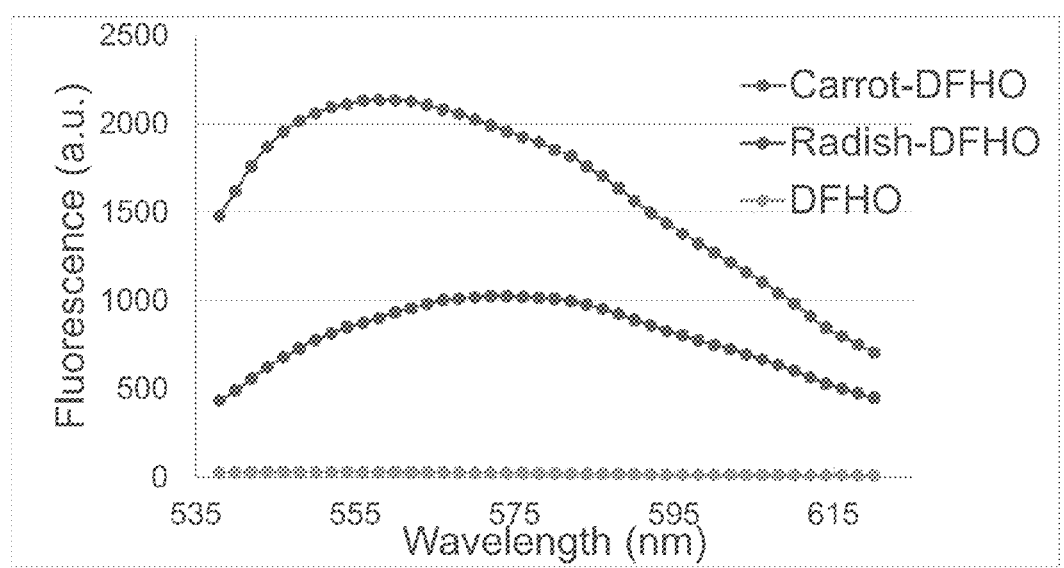

The only consistent mutation observed in the proposed core sequence is indicated by the asterisk in FIG. 16A. The mutation at this position leads to a profound color change. All sequences having C at this position have an excitation maximum at 509 nm and an emission maximum at 559 nm when bound to DFHO. These sequences were designated to belong to Orange family of aptamers. The sequence which has T (U) at this position has an excitation maximum at 512 nm and an emission maximum at 579 nm when bound to DFHO. FIG. 16B illustrates that fluorescence is enhanced markedly upon binding of Orange or Red aptamers to DFHO.

Testing of the G substitution in the position labeled with the asterisk revealed that the resulting aptamer is also capable of binding to DFHO and has excitation and emission spectra similar to those of 29-1 bound to DFHO.

Based on these data and based on the data about the core sequence for DFHBI binding, the core sequence element of an aptamer that induces the fluorescence of the fluorophore DFHO has been identified, as follows:

(SEQ ID NO: 77)
GAGACGGUCGGGUCCAG-N-CUGUUGAGUAGNGUGUGGGCUC, where N at position 18 can be any single nucleotide base (A, U, G, or C) or an insertion of any length of various nucleotide bases, and the bold N at position 30 in the core sequence determines the aptamer-fluorophore phenotype (color). When N at position 30 is C the color is orange, whereas when N at position 30 is U the color is red. The core can also be preceded or followed by any arbitrary sequence, but the core is needed for fluorescence. Any sequence which is compatible with the core sequence indicated above should potentially be able to bind and induce fluorescence of DFHO.

Example 23

Expression of Orange and Red Aptamers in Living Cells

Figure 16C:
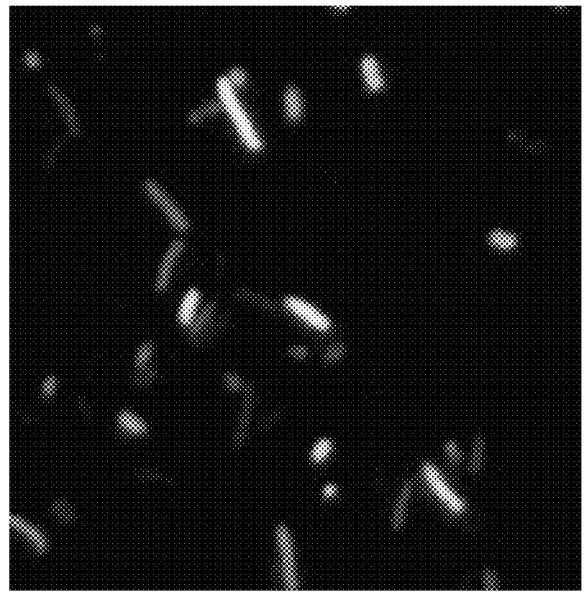
Figure 16D:
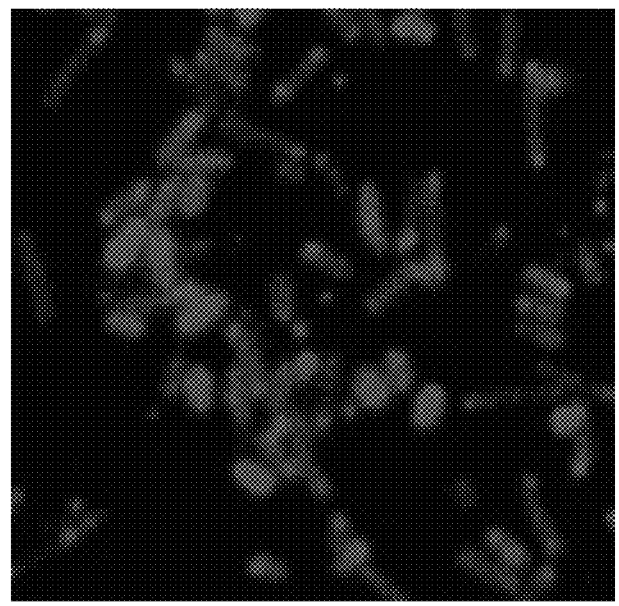

The aptamers described above can be expressed by themselves, or fused to another RNA molecule. Examples of the expression an RNA aptamer of Example 22 fused with a nascent RNA strand in bacterial cells are illustrated in FIGS. 16C, D.

Example 24

Identification of the Core Sequence of Aptamers that Bind DFHO to Induce Yellow Fluorescence The core sequence refers to the minimal sequence element that is capable of binding to and switching on the fluorescence of DFHO and related fluorophores.

Figure 17A:
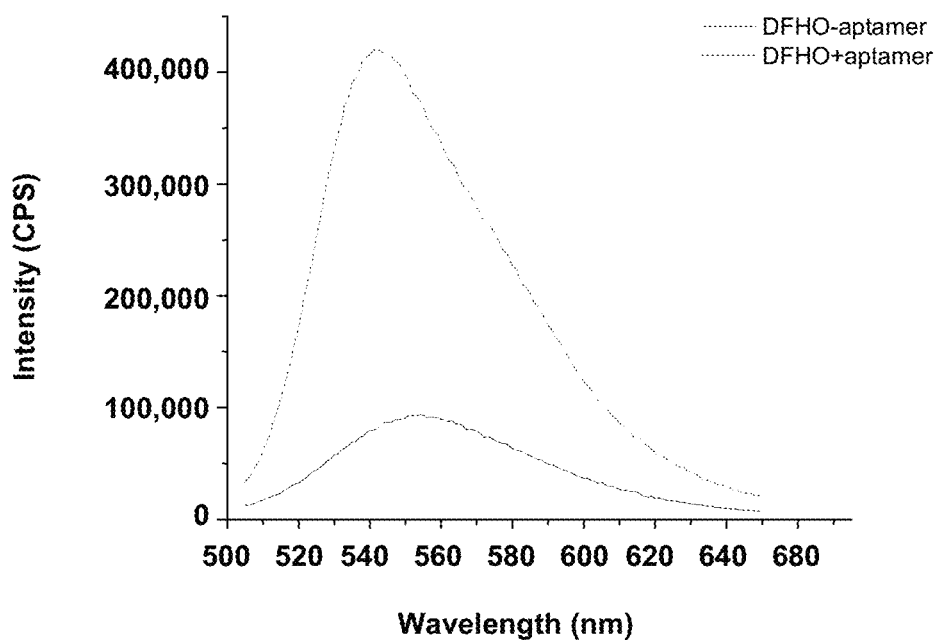
FIGS. 17A-H illustrate that aptamers comprising core sequence elements are capable of binding to and switching on the fluorescence of DFHBO and related fluorophores.

To identify the core sequence, the parent aptamer TAG GGA GAC GCA ACT GAA TGG CGC GAA GAA GGA GGT CTG AGG AGG TCA CTG CGC CGG CAG TGG GGC GTC TCC CTG (SEQ ID NO: 80) was first tested. FIG. 17A illustrates an increase in fluorescence of DFHO upon addition of this aptamer.

Figure 17B:
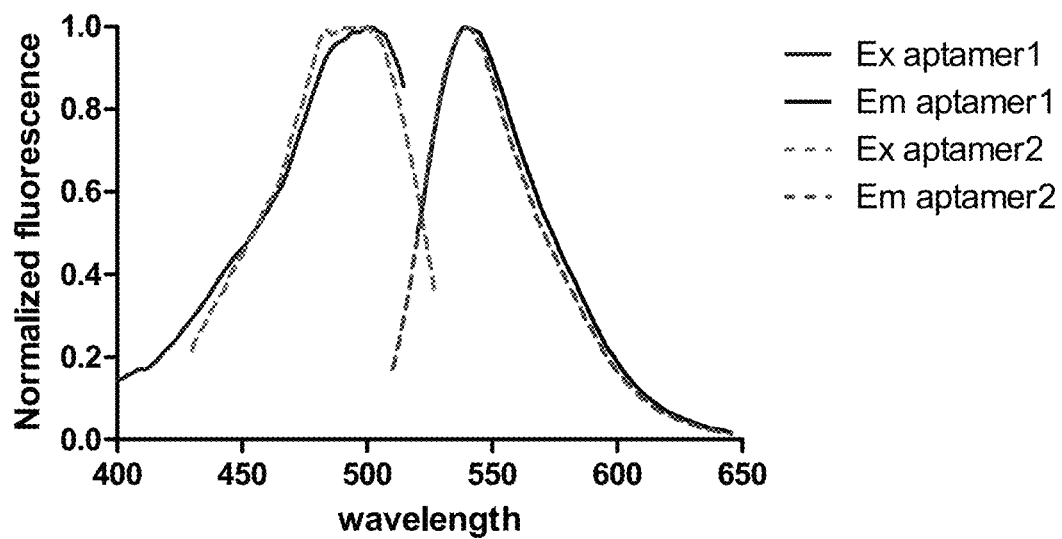

Other related aptamer sequences and mutations were found that also bind and switch on the fluorescence of DFHO. One such sequence is, as follows: GGC CGG TGA CGC AAC TGA ATG AAT CGA GGA AGG AGG TCG GAG GAG GTC ACT GAT TCT ACA GGC TGC GTA CTC CAG TGC TGT GTG TAT ACG TAA CTA GTC GCG TCA CCG GCC GC (SEQ ID NO: 81). FIG. 17B shows that the fluorescence of the fluorophore is markedly enhanced by these aptamers.

Experiments indicated that aptamers that have mutations or sequence alterations in "variable domains" are still capable of binding the fluorophore DFHO. Other mutations were not tolerated—the RNAs could not activate the fluorescence of DFHO. These experiments demonstrated the presence of a central core sequence element that is sufficient for binding the fluorophore DFHO.

To more precisely define the core sequence, a library containing over 10 million mutants of a shortened core sequence was prepared. Each of the sequences was individually expressed in *E. coli* bacteria. The bacteria were incubated with the fluorophore DFHO, and the bacteria were sorted based on their fluorescence signal in a fluorescence-activated cell sorting (FACS) instrument. The sequences of different mutants that were capable of exhibiting fluorescence in the presence of the fluorophore DFHO were then examined. By comparing many of the sequences, the specific residues that were not essential for aptamer-induced fluorescence were found. Residues that were either completely invariant, or limited in the potential nucleotides that were allowed in order to see fluorescence were also identified. Thus, the sequence elements that are absolutely necessary, and the sequences that are not necessary for inducing the fluorescence of the fluorophore DFHO were precisely defined.

Figure 17C:
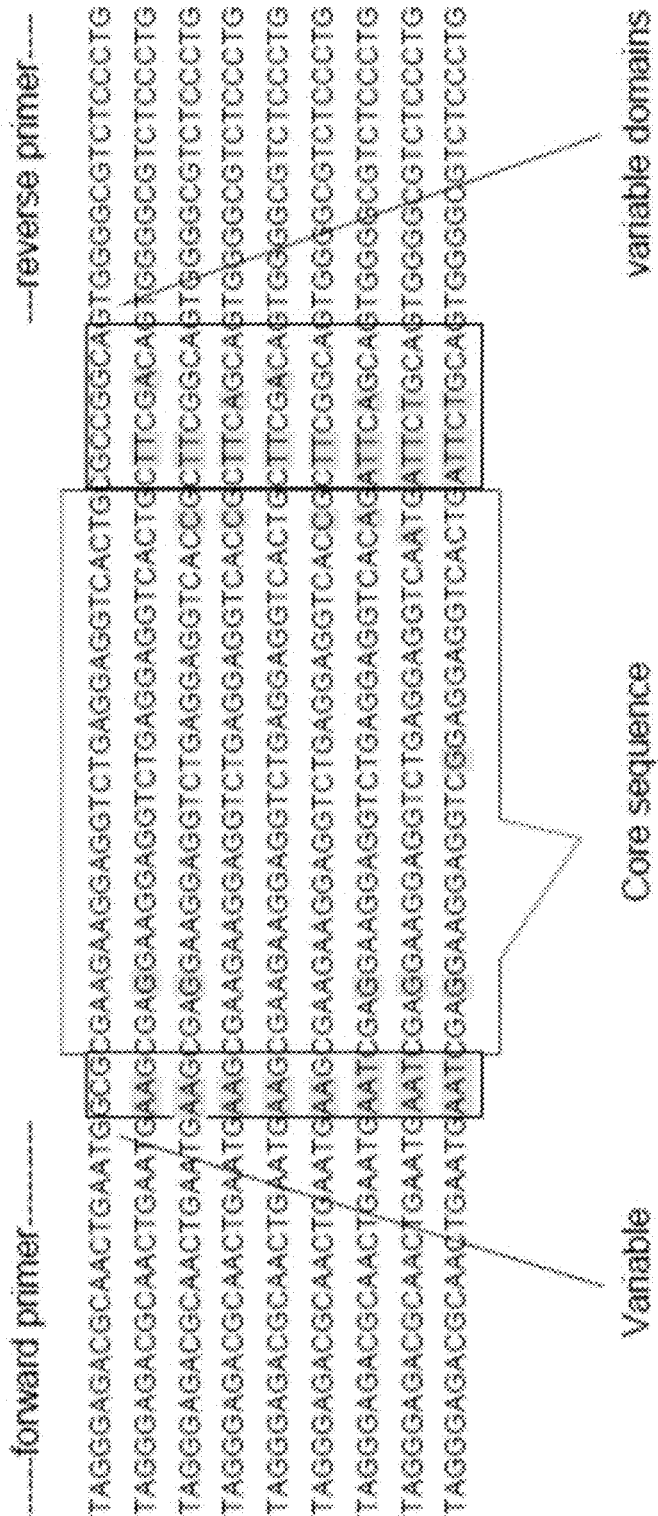

FIG. 17C illustrates some examples of mutants that were identified in the FACS experiment. The domains that are variable are indicated (indicated "variable domains"). As can be seen by comparing different clones, there are different nucleotides present at positions in the variable domains, confirming the idea that the nucleotide identity at those positions is not strictly conserved. However, when looking at the domains that are labeled "core sequence," is clear that there is highly strict sequence conservation.

Based on these data, the core sequence element of an aptamer that induces the fluorescence of the fluorophore DFHO has been identified, as follows:

SEQ ID NO: 76
CGANGAAGGAGGUCUNAGGAGGUCANNG, where N at each of positions 4, 16, 26, and 27 can be any single nucleotide base (A, U, G, or C). Any of these variants can be used interchangeably to induce the fluorescence of fluorophore DFHO.

This core RNA can be attached to other RNAs or be placed within sequences that confer structural stabilization, such as a tRNA sequence (Ponchon et al., "Recombinant RNA Technology: the tRNA Scaffold," *Nat. Methods* 4(7): 571-6 (2007), which is hereby incorporated by reference in its entirety) as was done for Spinach and Spinach2 before. Any structural element would be sufficient to stabilize the structure of the core when it is used in vitro and in vivo.

Although this is the main core sequence of a series of aptamers that bind and induce the fluorescence of DFHO, it should be noted that subtle changes could still be introduced that maintain the overall structure of the core (which has not yet been solved), but which change the sequence by just a few nucleotides. These future mutations would also be considered within a family these core sequences.

Example 25

Figure 17D:
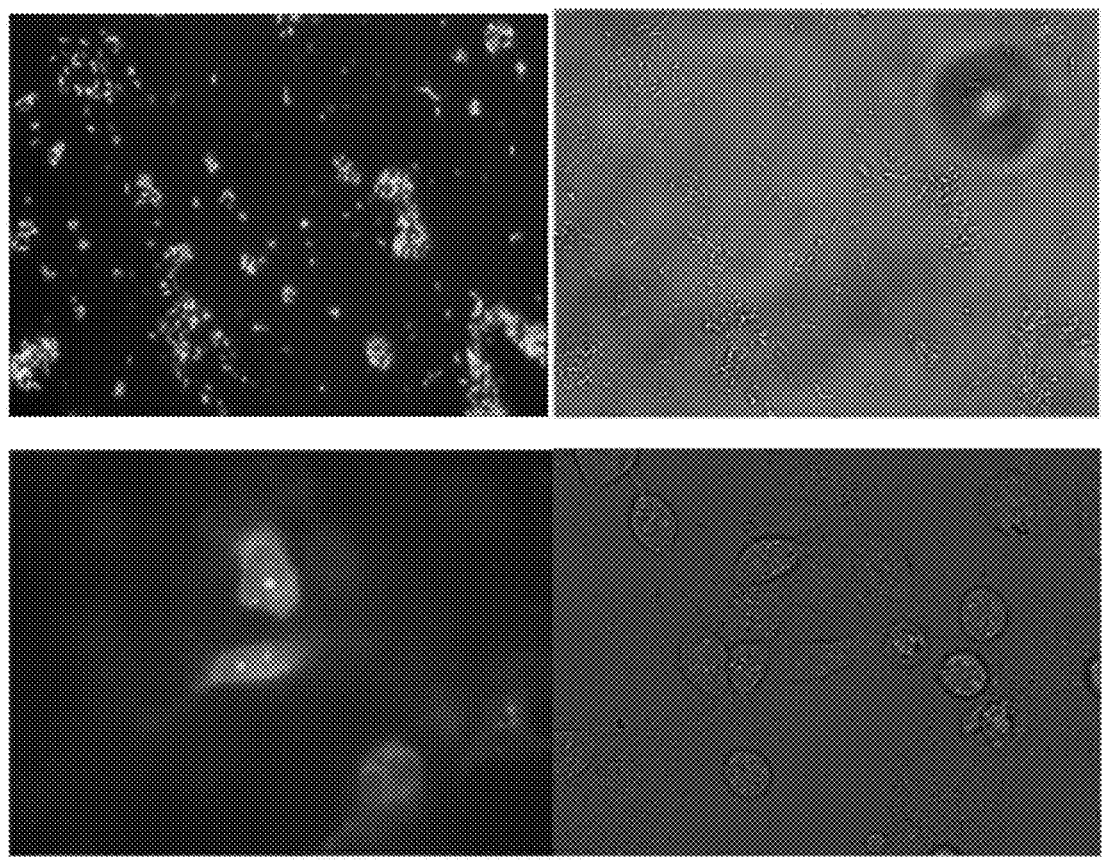
Figure 17E:
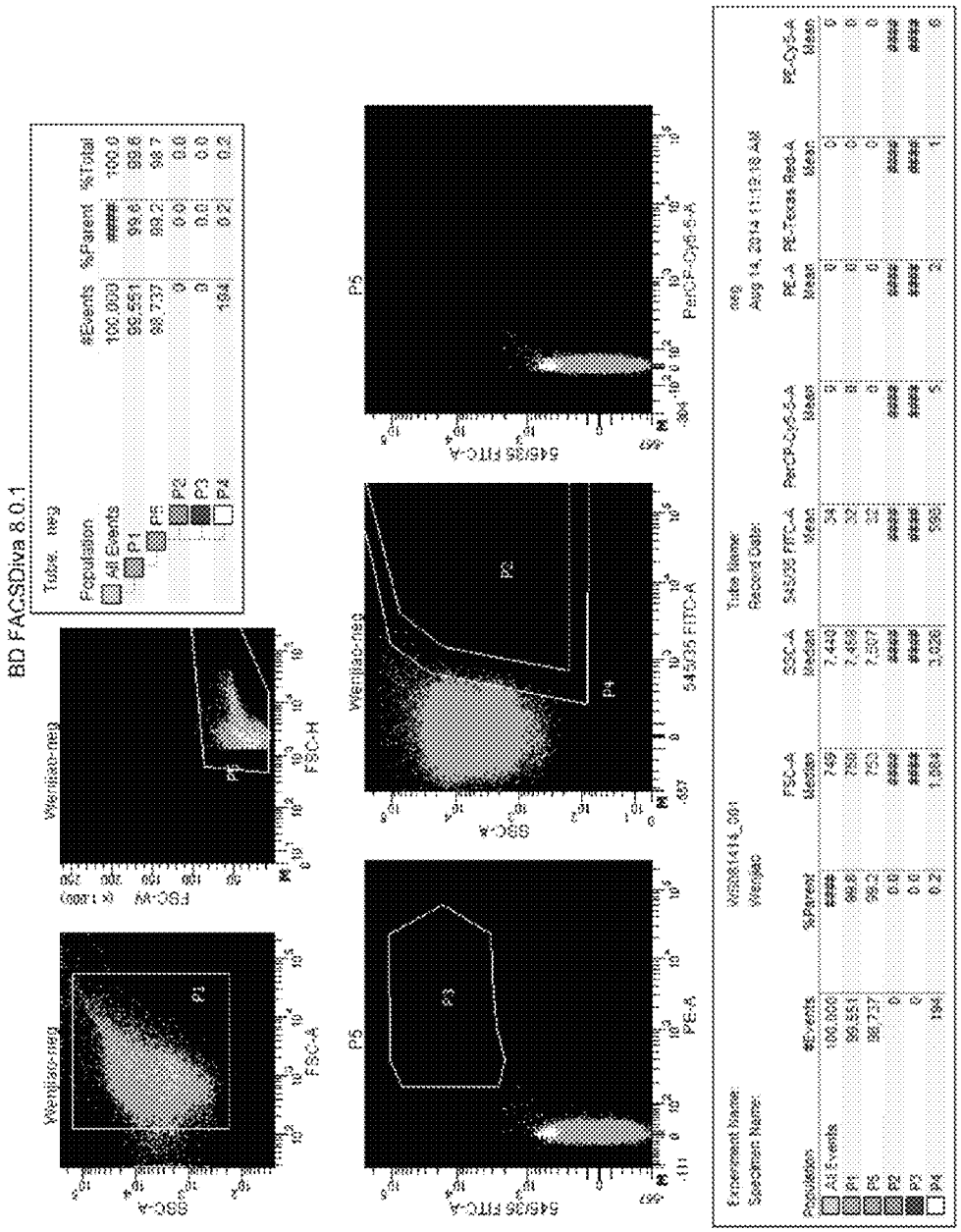
Figure 17F:
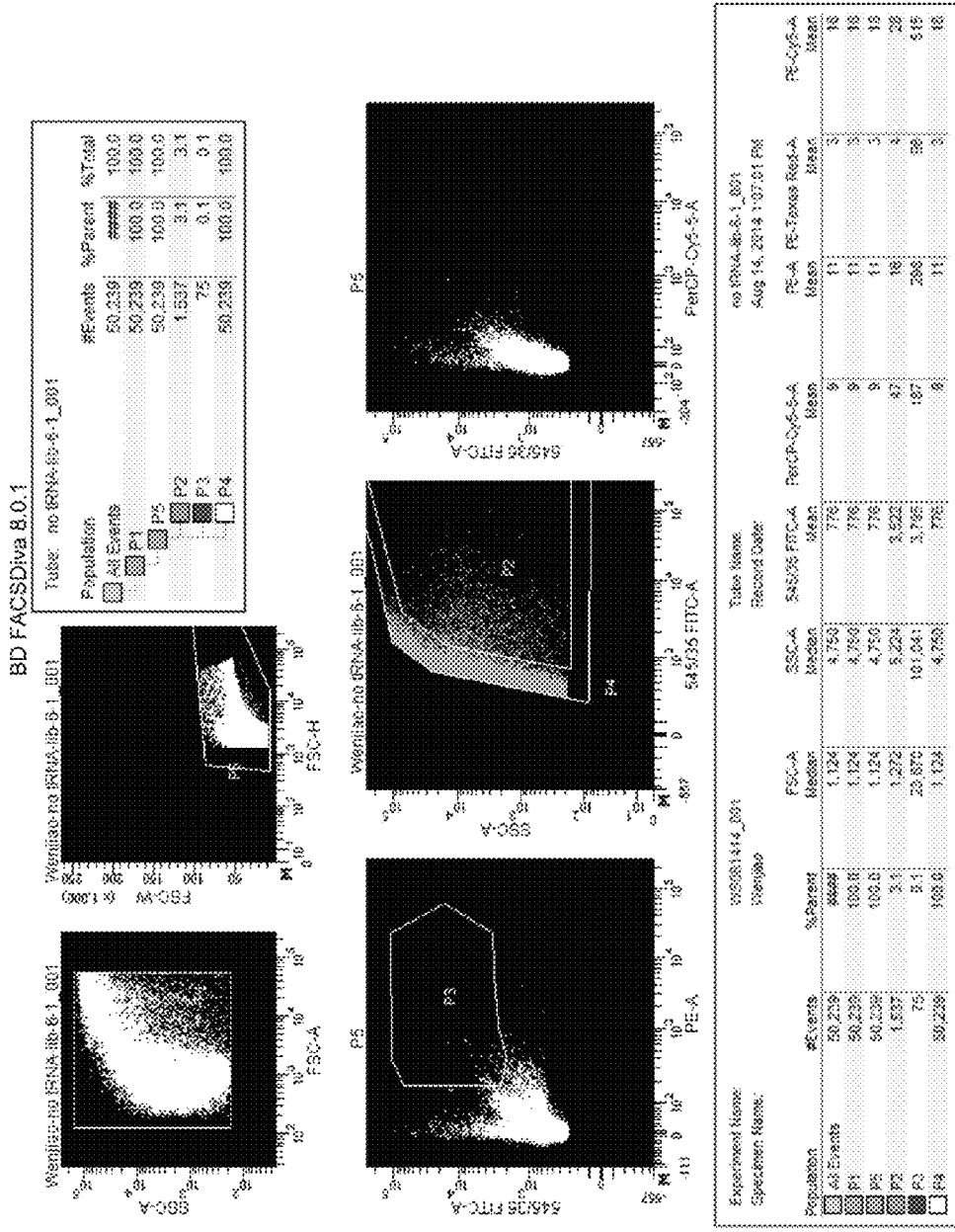
Figure 17G:
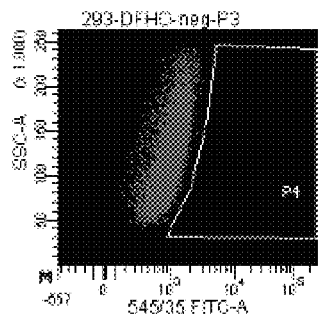
Figure 17H:
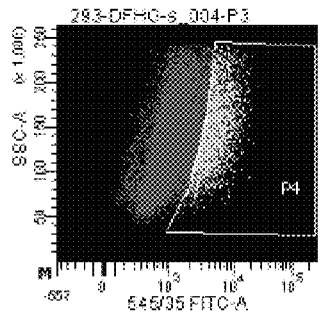

Expression of DFHO-Binding Aptamers that Induce Yellow Fluorescence in Living Cells The aptamers described above can be expressed by themselves, or fused to another RNA molecule. Examples of the expression an RNA aptamer of Example 24 fused with a nascent RNA strand in bacterial and/or mammalian cells are illustrated in FIG. 17D.

Example 26

Using Aptamers that Bind DFHO to Induce Yellow Fluorescence to Image Promoter Activity Using FACS For many research applications it is desirable to monitor the activity of a gene promoter. Typically, downstream of the gene promoter is a reporter, such as green fluorescent protein. The fluorescence that is seen as a result of the synthesis of this reporter produces a signal that can be detected on the FACS machine. This can allow the activity of a cell, and typically millions of cells, to be rapidly quantified using FACS. The major drawback is that there is a time lag between the time when the reporter RNA is made and the encoded protein is synthesized and exhibits fluorescence. Thus, the core aptamer sequences that described here can be used to directly image the RNA which is the immediate product of the gene from there, rather than imaging protein. FIGS. 17E-H illustrate examples of experiments in which aptamer sequences have been expressed in bacterial (FIG. 17E, F) or mammalian (FIG. 17G, H) cells, and in which the activity was monitored using FACS. As can be seen, the expression level of fluorescence is suitable for use in FACS experiments.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed is:

1. A nucleic acid molecule comprising the nucleotide sequence of:

SEQ ID NO: 74
(i) GAGANGGUCGGGUCCAGN-N-GCUGUNGAGUAGAGUGUGGGCUC, where N at each of positions 5, 18, and 25 can be any single nucleotide base, and N at position 19 can be any single nucleotide base or an insertion of any length of various nucleotide bases; or SEQ ID NO: 76
(ii) CGANGAAGGAGGUCUNAGGAGGUCANNG, where N at each of positions 4, 16, 26, and 27 can be any single nucleotide base; or SEQ ID NO: 77
(iii) GAGACGGUCGGGUCCAG-N-CUGUUGAGUAGNGUGUGGGCUC, where N at position 18 can be any single nucleotide base (A, U, G, or C) or an insertion of any length of various nucleotide bases, and N at position 30 can be G or A; and wherein the nucleic acid molecule binds to a conditionally fluorescent fluorophore molecule.

2. The nucleic acid molecule according to claim 1, wherein the nucleotide sequence is

SEQ ID NO: 75
GAGACGGUCGGGUCCAGAUAUUCGUAUCUGUCGAGUAGAGUGUGGGCUC, .

3. The nucleic acid molecule according to claim 1, further comprising an additional nucleotide sequence inserted at position 19 of SEQ ID NO: 75 or position 18 of SEQ ID NO: 77 which comprises a pair of antiparallel stem-forming sequences and an analyte-binding domain that comprises a nucleotide sequence that adopts a conformation to allow the analyte-binding domain to bind specifically to an analyte.

4. The nucleic acid molecule according to claim 3, wherein the portion binds the fluorophore molecule with low affinity, and the fluorophore exhibits low fluorescence, in the absence of analyte binding to the analyte-binding domain.

5. The nucleic acid molecule according to claim 3, wherein the analyte is a small molecule, cellular signaling molecule, a protein, a lipid, a carbohydrate, a hormone, a cytokine, a chemokine, a metabolite, or a metal ion.

6. A detection array comprising one or more nucleic acid molecules according to claim 1 tethered to a discrete location on a surface of the array.

7. A molecular complex comprising:
a fluorophore molecule comprising a methyne bridge between a substituted aromatic ring system and a substituted imidazol(thi)one, oxazol(thi)one, pyrrolin(thi)one, or furan(thi)one; and
the nucleotide molecule according to claim 1 bound specifically to the fluorophore molecule;
wherein the fluorophore molecule has substantially enhanced fluorescence, in comparison to the fluorophore molecule prior to specific binding, upon exposure to radiation of suitable wavelength.

8. The molecular complex according to claim 7, wherein the fluorophore molecule is 4-(3,5-difluoro-4-hydroxybenzylidene)-1,2-dimethyl-imidazol-5-one ("DFHBI"); (Z)-4-(3,5-difluoro-4-hydroxybenzylidene)-2-methyl-1-(2,2,2-trifluoroethyl)-1H-imidazol-5(4H)-one) ("DFHBI-1T"); or 4-(3,5-difluoro-4-hydroxybenzylidene)-1-methyl-5-oxo-4,5-dihydro-1H-imidazole-2-carbaldehyde oxime ("DFHO").

9. An isolated host cell containing the molecular complex according to claim 7.

10. A kit comprising:
a fluorophore comprising a methyne bridge between a substituted aromatic ring system and a substituted imidazol(thi)one, oxazol(thi)one, pyrrolin(thi)one, or furan(thi)one ring; and
a nucleic acid molecule according to claim 1.

11. A constructed DNA molecule encoding an RNA molecule according to claim 1.

12. An expression system comprising an expression vector into which is inserted a DNA molecule according to claim 11.

13. A transgenic host cell comprising the expression system of claim 12, wherein the transgenic host cell is either isolated, non-human, or both isolated and non-human.

14. A genetic construct comprising a promoter sequence operably linked to a first DNA sequence that encodes an RNA molecule according claim 1 and a second DNA sequence that contains one or more enzymatic cleavage sites.

15. A method of detecting a target molecule comprising:
forming a molecular complex according to claim 7;
exciting the fluorophore with radiation of appropriate wavelength; and
detecting fluorescence by the fluorophore, whereby fluorescence by the fluorophore identifies presence of the target molecule.

16. The method according to claim 15, wherein said forming is carried out in a cell.

* * * * *

```
                         SEQUENCE LISTING

<160> NUMBER OF SEQ ID NOS: 84

<210> SEQ ID NO 1
    <211> LENGTH: 98
    <212> TYPE: RNA
    <213> ORGANISM: Artificial
    <220> FEATURE:
    <223> OTHER INFORMATION: Aptamer Spinach

<400> SEQUENCE: 1
gacgcaacug aaugaaaugg ugaaggacgg guccaggugu ggcugcuucg gcagugcagc      60
uuguugagua gagugugagc uccguaacua gucgcguc                             98

<210> SEQ ID NO 2
    <211> LENGTH: 95
    <212> TYPE: RNA
    <213> ORGANISM: Artificial
    <220> FEATURE:
    <223> OTHER INFORMATION: Aptamer Spinach2

<400> SEQUENCE: 2
gauguaacug aaugaaaugg ugaaggacgg guccaguagg cugcuucggc agccuacuug      60
uugaguagag ugugagcucc guaacuaguu acauc                                95

<210> SEQ ID NO 3
    <211> LENGTH: 100
    <212> TYPE: RNA
    <213> ORGANISM: Artificial
    <220> FEATURE:
    <223> OTHER INFORMATION: Aptamer 29-1

<400> SEQUENCE: 3
ggagacgcaa cugaaugaaa uggugaagga gacggucggg uccaggcaca aaaauguugc      60
cuguugagua gagugugggc uccguaacua gucgcgucac                           100

<210> SEQ ID NO 4
    <211> LENGTH: 52
    <212> TYPE: RNA
    <213> ORGANISM: Artificial
    <220> FEATURE:
    <223> OTHER INFORMATION: Aptamer 29-1-T2

<400> SEQUENCE: 4
gagacggucg gguccagcac aaaauguug cuguugagua gagugugggc uc               52

<210> SEQ ID NO 5
```

```
<211> LENGTH: 52
<212> TYPE: RNA
<213> ORGANISM: Artificial
<220> FEATURE:
<223> OTHER INFORMATION: Aptamer 29-1-T2 Clone 2

<400> SEQUENCE: 5
gagacggucg gguccagcag auacauguug cuguugagua gagugugggc uc          52

<210> SEQ ID NO 6
<211> LENGTH: 52
<212> TYPE: RNA
<213> ORGANISM: Artificial
<220> FEATURE:
<223> OTHER INFORMATION: Apamer 29-1-T2 Clone 3

<400> SEQUENCE: 6
gagacggucg gguccagcgc agaaauguug cgucgagua gagugugggc uc           52

<210> SEQ ID NO 7
<211> LENGTH: 52
<212> TYPE: RNA
<213> ORGANISM: Artificial
<220> FEATURE:
<223> OTHER INFORMATION: Aptamer 29-1-T2 Clone 4

<400> SEQUENCE: 7
gagagggucg gguccagcag gaaaaucuug cuguugagua gagcgugggc uc          52

<210> SEQ ID NO 8
<211> LENGTH: 52
<212> TYPE: RNA
<213> ORGANISM: Artificial
<220> FEATURE:
<223> OTHER INFORMATION: Aptamer 29-1-T2 Clone 5

<400> SEQUENCE: 8
gagacggucg gguccagcau uaaaaugaag cuguugagua gagugugggc uc          52

<210> SEQ ID NO 9
<211> LENGTH: 52
<212> TYPE: RNA
<213> ORGANISM: Artificial
<220> FEATURE:
<223> OTHER INFORMATION: Aptamer 29-1-T2 Clone 7

<400> SEQUENCE: 9
gagacggucg gguccaguac aagaauguug cuguugagua gagugugggc uc          52

<210> SEQ ID NO 10
<211> LENGTH: 52
<212> TYPE: RNA
<213> ORGANISM: Artificial
<220> FEATURE:
<223> OTHER INFORMATION: Aptamer 29-1-T2 Clone 9

<400> SEQUENCE: 10
gagacggucg gguccagccc agaaauguug cuguugagua gagugugggc uc          52

<210> SEQ ID NO 11
<211> LENGTH: 114
<212> TYPE: RNA
<213> ORGANISM: Artificial
<220> FEATURE:
<223> OTHER INFORMATION: tRNA-Broccoli Aptamer Fusion

<400> SEQUENCE: 11
```

-continued gcccggauag cucagucggu agagcagcgg agacggucgg guccagauau ucguaucugu    60
cgaguagagu gugggcuccg cggguccagg guucaaguco cuguucgggc gcca    114

<210> SEQ ID NO 12
<211> LENGTH: 92
<212> TYPE: RNA
<213> ORGANISM: Artificial
<220> FEATURE:
<223> OTHER INFORMATION: dBroccoli

<400> SEQUENCE: 12
gagacggucg gguccaucug agacggucgg guccagauau ucguaucugu cgaguagagu    60
gugggcucag augucgagua gagugugggc uc    92

<210> SEQ ID NO 13
<211> LENGTH: 95
<212> TYPE: DNA
<213> ORGANISM: Artificial
<220> FEATURE:
<223> OTHER INFORMATION: Aptamer 29-1

<400> SEQUENCE: 13
gacgcaactg aatgaaatgg tgaaggagac ggtcgggtcc aggcacaaaa atgttgcctg    60
ttgagtagag tgtgggctcc gtaactagtc gcgtc    95

<210> SEQ ID NO 14
<211> LENGTH: 95
<212> TYPE: DNA
<213> ORGANISM: Artificial
<220> FEATURE:
<223> OTHER INFORMATION: Aptamer 29-1 derivative clone

<400> SEQUENCE: 14
gacgcaactg aatgaaatgg tgaaggagac ggtcgggtcc aggcacataa gtgtgtcctg    60
ttgagtagcg tgtgggctcc gtaactagtc gcgtc    95

<210> SEQ ID NO 15
<211> LENGTH: 95
<212> TYPE: DNA
<213> ORGANISM: Artificial
<220> FEATURE:
<223> OTHER INFORMATION: Aptamer 29-1 derivative clone

<400> SEQUENCE: 15
gacgcaactg aatgaactgg tgaaggagac ggtcgggtcc aggcacaaaa atgtcgcctg    60
ttgagtagcg tgtgggctcc gtaactagtc gcgtc    95

<210> SEQ ID NO 16
<211> LENGTH: 95
<212> TYPE: DNA
<213> ORGANISM: Artificial
<220> FEATURE:
<223> OTHER INFORMATION: Aptamer 29-1 derivative clone

<400> SEQUENCE: 16
gacgcaactg aatgaaaagg tttaggagac ggtcgggtcc aggcaacaaa aagttgcctg    60
ttgagtagcg tgtgggctcc gtaactagtc gcgtc    95

<210> SEQ ID NO 17
<211> LENGTH: 95
<212> TYPE: DNA

```
<213> ORGANISM: Artificial
<220> FEATURE:
<223> OTHER INFORMATION: Aptamer 29-1 derivative clone

<400> SEQUENCE: 17
gacgcaactg aatgaaatgt tgacggagac ggtcgggtcc agtcacaaag atgttggctg    60
ttgagtagtg tgtgggctcc gtaactagtc gcgtc                              95

<210> SEQ ID NO 18
<211> LENGTH: 95
<212> TYPE: DNA
<213> ORGANISM: Artificial
<220> FEATURE:
<223> OTHER INFORMATION: Aptamer 29-1 derivative clone

<400> SEQUENCE: 18
gacgcaactg aatgaaattg tgaaggagac ggtcgggtcc aggcaaacaa atgttgcctg    60
ttgagtagcg tgtgggctcc gtaactagtc gcgtc                              95

<210> SEQ ID NO 19
<211> LENGTH: 95
<212> TYPE: DNA
<213> ORGANISM: Artificial
<220> FEATURE:
<223> OTHER INFORMATION: Aptamer 29-1 derivative clone

<400> SEQUENCE: 19
gacgcaactg aatgaaatgg tgaaggagac ggtcgggtcc aggtgcacaa atgtggcctg    60
ttgagtagcg tgtgggctcc gtaactagtc gcgtc                              95

<210> SEQ ID NO 20
<211> LENGTH: 95
<212> TYPE: DNA
<213> ORGANISM: Artificial
<220> FEATURE:
<223> OTHER INFORMATION: Aptamer 29-1 derivative clone

<400> SEQUENCE: 20
gacgcaactg aatgaaaagg tgaaggagac ggtcgggtcc aggcacaaaa acgtcgcctg    60
ttgagtagcg tgtgggctcc gtaactagtc gcgtc                              95

<210> SEQ ID NO 21
<211> LENGTH: 75
<212> TYPE: DNA
<213> ORGANISM: Artificial
<220> FEATURE:
<223> OTHER INFORMATION: parent aptamer

<400> SEQUENCE: 21
tagggagacg caactgaatg gcgcgaagaa ggaggtctga ggaggtcact gcgccggcag    60
tggggcgtct ccctg                                                    75

<210> SEQ ID NO 22
<211> LENGTH: 75
<212> TYPE: DNA
<213> ORGANISM: Artificial
<220> FEATURE:
<223> OTHER INFORMATION: derivative aptamer clone

<400> SEQUENCE: 22
tagggagacg caactgaatg aagcgaggaa ggaggtctga ggaggtcact gcttcgacag    60
tggggcgtct ccctg                                                    75
```

<210> SEQ ID NO 23
<211> LENGTH: 75
<212> TYPE: DNA
<213> ORGANISM: Artificial
<220> FEATURE:
<223> OTHER INFORMATION: derivative aptamer clone

<400> SEQUENCE: 23
tagggagacg caactgaatg aagcgaggaa ggaggtctga ggaggtcacc gcttcggcag       60
tggggcgtct ccctg                                                       75

<210> SEQ ID NO 24
<211> LENGTH: 75
<212> TYPE: DNA
<213> ORGANISM: Artificial
<220> FEATURE:
<223> OTHER INFORMATION: derivative aptamer clone

<400> SEQUENCE: 24
tagggagacg caactgaatg aagcgaagaa ggaggtctga ggaggtcacc gcttcagcag       60
tggggcgtct ccctg                                                       75

<210> SEQ ID NO 25
<211> LENGTH: 75
<212> TYPE: DNA
<213> ORGANISM: Artificial
<220> FEATURE:
<223> OTHER INFORMATION: derivative aptamer clone

<400> SEQUENCE: 25
tagggagacg caactgaatg aagcgaagaa ggaggtctga ggaggtcact gcttcgacag       60
tggggcgtct ccctg                                                       75

<210> SEQ ID NO 26
<211> LENGTH: 75
<212> TYPE: DNA
<213> ORGANISM: Artificial
<220> FEATURE:
<223> OTHER INFORMATION: derivative aptamer clone

<400> SEQUENCE: 26
tagggagacg caactgaatg aagcgaagaa ggaggtctga ggaggtcacc gcttcggcag       60
tggggcgtct ccctg                                                       75

<210> SEQ ID NO 27
<211> LENGTH: 75
<212> TYPE: DNA
<213> ORGANISM: Artificial
<220> FEATURE:
<223> OTHER INFORMATION: derivative aptamer clone

<400> SEQUENCE: 27
tagggagacg caactgaatg aatcgaggaa ggaggtctga ggaggtcaca gattcagcag       60
tggggcgtct ccctg                                                       75

<210> SEQ ID NO 28
<211> LENGTH: 75
<212> TYPE: DNA
<213> ORGANISM: Artificial
<220> FEATURE:
<223> OTHER INFORMATION: derivative aptamer clone -continued

```
<400> SEQUENCE: 28
tagggagacg caactgaatg aatcgaggaa ggaggtctga ggaggtcaat gattctgcag    60
tggggcgtct ccctg                                                    75

<210> SEQ ID NO 29
<211> LENGTH: 75
<212> TYPE: DNA
<213> ORGANISM: Artificial
<220> FEATURE:
<223> OTHER INFORMATION: derivative aptamer clone

<400> SEQUENCE: 29
tagggagacg caactgaatg aatcgaggaa ggaggtcgga ggaggtcact gattctgcag    60
tggggcgtct ccctg                                                    75

<210> SEQ ID NO 30
<211> LENGTH: 98
<212> TYPE: DNA
<213> ORGANISM: Artificial
<220> FEATURE:
<223> OTHER INFORMATION: Spinach 1.1 aptamer

<400> SEQUENCE: 30
gacgcgaccg aatgaaatgg tgaaggacgg gtccaggtgt ggctgcttcg gcagtgcagc    60
ttgttgagta gagtgtgagc tccgtaactg gtcgcgtc                           98

<210> SEQ ID NO 31
<211> LENGTH: 95
<212> TYPE: DNA
<213> ORGANISM: Artificial
<220> FEATURE:
<223> OTHER INFORMATION: Spinach 1.2 aptamer

<400> SEQUENCE: 31
gacgcgaccg aatgaaatgg tgaaggacgg gtccagccgg ctgcttcggc agccggcttg    60
ttgagtagag tgtgagctcc gtaactggtc gcgtc                              95

<210> SEQ ID NO 32
<211> LENGTH: 102
<212> TYPE: DNA
<213> ORGANISM: Artificial
<220> FEATURE:
<223> OTHER INFORMATION: aptamer library member
<220> FEATURE:
<221> NAME/KEY: misc_feature
<222> LOCATION: (19)..(44)
<223> OTHER INFORMATION: N can be any nucleotide
<220> FEATURE:
<221> NAME/KEY: misc_feature
<222> LOCATION: (57)..(82)
<223> OTHER INFORMATION: N can be any nucleotide

<400> SEQUENCE: 32
gagacgcaac tgaatgaann nnnnnnnnnn nnnnnnnnnn nnnctgctt cggcagnnnn     60 nnnnnnnnnn nnnnnnnnnn nntccgtaac tagtcgcgtc ac                     102

<210> SEQ ID NO 33
<211> LENGTH: 99
<212> TYPE: DNA
<213> ORGANISM: Artificial
<220> FEATURE:
<223> OTHER INFORMATION: 29-2

<400> SEQUENCE: 33
```

```
gagacgcaac tgaatgaaat ggtgaaggag acggtcgggt ccaggcacaa aaaagtttcc    60
tgttgagtag agtgtgggct ccgtaactag tcgcgtcac                          99
```

<210> SEQ ID NO 34
<211> LENGTH: 99
<212> TYPE: DNA
<213> ORGANISM: Artificial
<220> FEATURE:
<223> OTHER INFORMATION: 29-3

<400> SEQUENCE: 34

```
gagacgcaac tgaatgaaat ggtgaaggag acggtcgggt ccaggcacaa aaacgtttcc    60
tgtcgagtag agtgtgggct ccgtaactag tcgcgtcac                          99
```

<210> SEQ ID NO 35
<211> LENGTH: 102
<212> TYPE: DNA
<213> ORGANISM: Artificial
<220> FEATURE:
<223> OTHER INFORMATION: 30-1

<400> SEQUENCE: 35

```
gagacgcaac tgaatgaata tagtcttgga gagaagggcg gtctctgctt cggcagtagg    60
gggcgagacg gtattgaaag gttccgtaac tagtcgcgtc ac                      102
```

<210> SEQ ID NO 36
<211> LENGTH: 101
<212> TYPE: DNA
<213> ORGANISM: Artificial
<220> FEATURE:
<223> OTHER INFORMATION: 30-2

<400> SEQUENCE: 36

```
gagacgcaac tgaatgactg gaaggaggta cggttcagtg tctctgcttc ggcagaggga    60
gagcgcaaga tcaggaggtg atccgtaact agtcgcgtca c                       101
```

<210> SEQ ID NO 37
<211> LENGTH: 125
<212> TYPE: RNA
<213> ORGANISM: Artificial
<220> FEATURE:
<223> OTHER INFORMATION: tRNA-Aptamer 29-1-3 fusion

<400> SEQUENCE: 37

```
gcccggauag cucagucggu agagcagcgg ccggagacgg ucggguccag cgcagaaaug    60
uugcugucga guagagugug ggcuccggcc gcgggccagg gguucaaguc ccuguucggg   120
cgcca                                                              125
```

<210> SEQ ID NO 38
<211> LENGTH: 114
<212> TYPE: DNA
<213> ORGANISM: Artificial
<220> FEATURE:
<223> OTHER INFORMATION: tBroccoli Aptamer

<400> SEQUENCE: 38

```
gcccggatag ctcagtcggt agagcagcgg agacggtcgg gtccagatat tcgtatctgt    60
cgagtagagt gtgggctccg cgggtccagg gttcaagtcc ctgttcgggc gcca         114
```

<210> SEQ ID NO 39

```
<211> LENGTH: 179
<212> TYPE: DNA
<213> ORGANISM: Artificial
<220> FEATURE:
<223> OTHER INFORMATION: tRNA-Broccoli-c-diGMP Sensor

<400> SEQUENCE: 39
gcccggatag ctcagtcggt agagcagcgg agacggtcgg gtacgcacag ggcaaaccat    60
tcgaaagagt gggacgcaaa gcctccggcc taaaccagaa gacatggtag gtagcggggt   120
taccgatagt agagtgtggg ctccgcgggt ccagggttca agtccctgtt cgggcgcca    179

<210> SEQ ID NO 40
<211> LENGTH: 157
<212> TYPE: DNA
<213> ORGANISM: Artificial
<220> FEATURE:
<223> OTHER INFORMATION: tdBroccoli

<400> SEQUENCE: 40
gcccggatag ctcagtcggt agagcagcgg agacggtcgg gtccatctga gacggtcggg    60
tccagatatt cgtatctgtc gagtagagtg tgggctcaga tgtcgagtag agtgtgggct   120
ccgcgggtcc agggttcaag tccctgttcg ggcgcca                            157

<210> SEQ ID NO 41
<211> LENGTH: 95
<212> TYPE: DNA
<213> ORGANISM: Artificial
<220> FEATURE:
<223> OTHER INFORMATION: Spinach2

<400> SEQUENCE: 41
gatgtaactg aatgaaatgg tgaaggacgg gtccagtagg ctgcttcggc agcctacttg    60
ttgagtagag tgtgagctcc gtaactagtt acatc                              95

<210> SEQ ID NO 42
<211> LENGTH: 91
<212> TYPE: DNA
<213> ORGANISM: Artificial
<220> FEATURE:
<223> OTHER INFORMATION: Spinach forward primer

<400> SEQUENCE: 42
taatacgact cactataggg cggactatga cttagttgcg ttacacccct tcttgacaaa    60
acctaacttg acgcaactga atgaaatggt g                                  91

<210> SEQ ID NO 43
<211> LENGTH: 69
<212> TYPE: DNA
<213> ORGANISM: Artificial
<220> FEATURE:
<223> OTHER INFORMATION: Spinach reverse primer

<400> SEQUENCE: 43
aaacaaaaaa aacaaataaa gccatgccaa tctcatcttg ttttctgcgc gacgcgacta    60
gttacggag                                                           69

<210> SEQ ID NO 44
<211> LENGTH: 88
<212> TYPE: DNA
<213> ORGANISM: Artificial
<220> FEATURE:
<223> OTHER INFORMATION: Spinach2 forward primer
```

<400> SEQUENCE: 44
taatacgact cactataggg cggactatga cttagttgcg ttacaccctt tcttgacaaa    60
acctaacttg atgtaactga atgaaatg                                       88

<210> SEQ ID NO 45
<211> LENGTH: 68
<212> TYPE: DNA
<213> ORGANISM: Artificial
<220> FEATURE:
<223> OTHER INFORMATION: Spinach2 reverse primer

<400> SEQUENCE: 45
aacaaaaaaa acaaataaag ccatgccaat ctcatcttgt tttctgcgcg atgtaactag    60
ttacggag                                                             68

<210> SEQ ID NO 46
<211> LENGTH: 40
<212> TYPE: DNA
<213> ORGANISM: Artificial
<220> FEATURE:
<223> OTHER INFORMATION: 5S-Spinach and 5S-Spinach2 forward primer

<400> SEQUENCE: 46
taatacgact cactataggg tctacggcca taccaccctg                          40

<210> SEQ ID NO 47
<211> LENGTH: 18
<212> TYPE: DNA
<213> ORGANISM: Artificial Sequence
<220> FEATURE:
<223> OTHER INFORMATION: 5S-Spinach and 5S-Spinach2 reverse primer

<400> SEQUENCE: 47
tggcgcccga acagggac                                                  18

<210> SEQ ID NO 48
<211> LENGTH: 19
<212> TYPE: DNA
<213> ORGANISM: Artificial
<220> FEATURE:
<223> OTHER INFORMATION: (CGG)60-Spinach and (CGG)60-Spinach2 forward
      primer

<400> SEQUENCE: 48
taatacgact cactatagg                                                 19

<210> SEQ ID NO 49
<211> LENGTH: 27
<212> TYPE: DNA
<213> ORGANISM: Artificial
<220> FEATURE:
<223> OTHER INFORMATION: (CGG)60-Spinach and (CGG)60-Spinach2 reverse
      primer

<400> SEQUENCE: 49
ggcaaacaac agatggctgg caactag                                        27

<210> SEQ ID NO 50
<211> LENGTH: 18
<212> TYPE: DNA
<213> ORGANISM: Artificial
<220> FEATURE:
<223> OTHER INFORMATION: tRNA-Spinach transcript, tRNA RT-PCR reverse
      primer

```
<400> SEQUENCE: 50
tggcgcccga acagggac                                                   18

<210> SEQ ID NO 51
<211> LENGTH: 18
<212> TYPE: DNA
<213> ORGANISM: Artificial
<220> FEATURE:
<223> OTHER INFORMATION: 16S RT-PCR reverse primer

<400> SEQUENCE: 51
gtattaccgc ggctgctg                                                   18

<210> SEQ ID NO 52
<211> LENGTH: 22
<212> TYPE: DNA
<213> ORGANISM: Artificial
<220> FEATURE:
<223> OTHER INFORMATION: tRNA RT-PCR forward primer

<400> SEQUENCE: 52
gcccggatag ctcagtcggt ag                                              22

<210> SEQ ID NO 53
<211> LENGTH: 18
<212> TYPE: DNA
<213> ORGANISM: Artificial
<220> FEATURE:
<223> OTHER INFORMATION: tRNA RT-PCR reverse primer

<400> SEQUENCE: 53
tggcgcccga acagggac                                                   18

<210> SEQ ID NO 54
<211> LENGTH: 19
<212> TYPE: DNA
<213> ORGANISM: Artificial
<220> FEATURE:
<223> OTHER INFORMATION: 16S RT-PCR forward primer

<400> SEQUENCE: 54
ctcctacggg aggcagcag                                                  19

<210> SEQ ID NO 55
<211> LENGTH: 18
<212> TYPE: DNA
<213> ORGANISM: Artificial
<220> FEATURE:
<223> OTHER INFORMATION: 16S RT-PCR reverse primer

<400> SEQUENCE: 55
gtattaccgc ggctgctg                                                   18

<210> SEQ ID NO 56
<211> LENGTH: 38
<212> TYPE: DNA
<213> ORGANISM: Artificial
<220> FEATURE:
<223> OTHER INFORMATION: tRNA(Lys)-Spinach2 PCR forward primer

<400> SEQUENCE: 56
taggcgtcga cgcccggata gctcagtcgg tagagcag                             38

<210> SEQ ID NO 57
```

```
<211> LENGTH: 38
<212> TYPE: DNA
<213> ORGANISM: Artificial
<220> FEATURE:
<223> OTHER INFORMATION: tRNA(Lys)-Spinach2 PCR reverse primer

<400> SEQUENCE: 57
atatattcta gatggcgccc gaacagggac ttgaaccc                          38

<210> SEQ ID NO 58
<211> LENGTH: 31
<212> TYPE: DNA
<213> ORGANISM: Artificial
<220> FEATURE:
<223> OTHER INFORMATION: tRNA(Lys)-Spinach-7SK and -Spinach2-7SK PCR
      forward primer

<400> SEQUENCE: 58
atatatggat ccgcccggat agctcagtcg g                                 31

<210> SEQ ID NO 59
<211> LENGTH: 32
<212> TYPE: DNA
<213> ORGANISM: Artificial
<220> FEATURE:
<223> OTHER INFORMATION: tRNA(Lys)-Spinach-7SK and -Spinach2-7SK PCR
      reverse primer

<400> SEQUENCE: 59
atatatagat ctggcgcccg aacagggact tg                                32

<210> SEQ ID NO 60
<211> LENGTH: 58
<212> TYPE: DNA
<213> ORGANISM: Artificial
<220> FEATURE:
<223> OTHER INFORMATION: pLPCXU6PT7SK forward primer

<400> SEQUENCE: 60
atatataagc ttggatccat catcatcgca gcaagatctg gatgtgaggc gatctggc    58

<210> SEQ ID NO 61
<211> LENGTH: 34
<212> TYPE: DNA
<213> ORGANISM: Artificial
<220> FEATURE:
<223> OTHER INFORMATION: pLPCXU6PT7SK reverse primer

<400> SEQUENCE: 61
gtcttggaag cttgactacc ctacgttctc ctac                              34

<210> SEQ ID NO 62
<211> LENGTH: 32
<212> TYPE: DNA
<213> ORGANISM: Artificial
<220> FEATURE:
<223> OTHER INFORMATION: pSC35-mCherry forward primer

<400> SEQUENCE: 62
atatatggat ccaatggtga gcaagggcga gg                                32

<210> SEQ ID NO 63
<211> LENGTH: 32
<212> TYPE: DNA
<213> ORGANISM: Artificial
<220> FEATURE:
<223> OTHER INFORMATION: pSC35-mCherry reverse primer
```

-continued

```
<400> SEQUENCE: 63
tatatataag ctttcacttg tacagctcgt cc                                     32

<210> SEQ ID NO 64
<211> LENGTH: 40
<212> TYPE: DNA
<213> ORGANISM: Artificial
<220> FEATURE:
<223> OTHER INFORMATION: CGG60-Spinach and Spinach2 forward primer

<400> SEQUENCE: 64
atatatatct agagcccgga tagctcagtc ggtagagcag                             40

<210> SEQ ID NO 65
<211> LENGTH: 38
<212> TYPE: DNA
<213> ORGANISM: Artificial
<220> FEATURE:
<223> OTHER INFORMATION: CGG60-Spinach and Spinach2 reverse primer

<400> SEQUENCE: 65
atatatgggc cctggcgccc gaacagggac ttgaaccc                               38

<210> SEQ ID NO 66
<211> LENGTH: 24
<212> TYPE: DNA
<213> ORGANISM: Artificial
<220> FEATURE:
<223> OTHER INFORMATION: Spinach 3' hybridization probe

<400> SEQUENCE: 66
gcactgccga agcagccaca cctg                                              24

<210> SEQ ID NO 67
<211> LENGTH: 23
<212> TYPE: DNA
<213> ORGANISM: Artificial
<220> FEATURE:
<223> OTHER INFORMATION: CGG repeat reverse primer

<400> SEQUENCE: 67
ctagagatat caggctgatc agc                                               23

<210> SEQ ID NO 68
<211> LENGTH: 20
<212> TYPE: DNA
<213> ORGANISM: Artificial
<220> FEATURE:
<223> OTHER INFORMATION: GAPDH reverse primer

<400> SEQUENCE: 68
tccaccaccc tgttgctgta                                                   20

<210> SEQ ID NO 69
<211> LENGTH: 21
<212> TYPE: DNA
<213> ORGANISM: Artificial
<220> FEATURE:
<223> OTHER INFORMATION: CGG repeat RT-PCR forward primer

<400> SEQUENCE: 69
gtcagctgac gcgtgctagc g                                                 21

<210> SEQ ID NO 70
```

```
<211> LENGTH: 23
<212> TYPE: DNA
<213> ORGANISM: Artificial
<220> FEATURE:
<223> OTHER INFORMATION: CGG repeat RT-PCR reverse primer

<400> SEQUENCE: 70
ctagagatat caggctgatc agc                                              23

<210> SEQ ID NO 71
<211> LENGTH: 20
<212> TYPE: DNA
<213> ORGANISM: Artificial
<220> FEATURE:
<223> OTHER INFORMATION: GAPDH RT-PCR forward primer

<400> SEQUENCE: 71
accacagtcc atgccatcac                                                  20

<210> SEQ ID NO 72
<211> LENGTH: 20
<212> TYPE: DNA
<213> ORGANISM: Artificial
<220> FEATURE:
<223> OTHER INFORMATION: GAPDH RT-PCR reverse primer

<400> SEQUENCE: 72
tccaccaccc tgttgctgta                                                  20

<210> SEQ ID NO 73
<211> LENGTH: 45
<212> TYPE: RNA
<213> ORGANISM: Artificial
<220> FEATURE:
<223> OTHER INFORMATION: Aptamer
<220> FEATURE:
<221> NAME/KEY: misc_feature
<222> LOCATION: (20)..(20)
<223> OTHER INFORMATION: n is a, c, g, or u

<400> SEQUENCE: 73
auggugaagg acggguccan uuguugagua gagugugagc uccgu                      45

<210> SEQ ID NO 74
<211> LENGTH: 42
<212> TYPE: RNA
<213> ORGANISM: Artificial
<220> FEATURE:
<223> OTHER INFORMATION: Aptamer
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (18)..(19)
<223> OTHER INFORMATION: n is a, c, g, or u
<220> FEATURE:
<221> NAME/KEY: misc_feature
<222> LOCATION: (25)..(25)
<223> OTHER INFORMATION: n is a, c, g, or u

<400> SEQUENCE: 74
gaganggucg gguccagnng cugungagua gaguguggc uc                          42

<210> SEQ ID NO 75
<211> LENGTH: 49
<212> TYPE: RNA
<213> ORGANISM: Artificial
```

```
<220> FEATURE:
<223> OTHER INFORMATION: Aptamer

<400> SEQUENCE: 75
gagacggucg gguccagaua uucguaucug ucgaguagag ugugggcuc      49

<210> SEQ ID NO 76
<211> LENGTH: 28
<212> TYPE: RNA
<213> ORGANISM: Artificial
<220> FEATURE:
<223> OTHER INFORMATION: Aptamer
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (16)..(16)
<223> OTHER INFORMATION: n is a, c, g, or u
<220> FEATURE:
<221> NAME/KEY: misc_feature
<222> LOCATION: (26)..(27)
<223> OTHER INFORMATION: n is a, c, g, or u

<400> SEQUENCE: 76
cgangaagga ggucunagga ggucanng                             28

<210> SEQ ID NO 77
<211> LENGTH: 40
<212> TYPE: RNA
<213> ORGANISM: Artificial
<220> FEATURE:
<223> OTHER INFORMATION: DFHO aptamer core sequence element
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (30)..(30)
<223> OTHER INFORMATION: n is c or u

<400> SEQUENCE: 77
gagacggucg gguccagncu guugaguagn gugugggcuc                40

<210> SEQ ID NO 78
<211> LENGTH: 40
<212> TYPE: RNA
<213> ORGANISM: Artificial
<220> FEATURE:
<223> OTHER INFORMATION: Aptamer
<220> FEATURE:
<221> NAME/KEY: misc_feature
<222> LOCATION: (18)..(18)
<223> OTHER INFORMATION: n is a, c, g, or u

<400> SEQUENCE: 78
gagacggucg gguccagncu guugaguagc gugugggcuc                40

<210> SEQ ID NO 79
<211> LENGTH: 40
<212> TYPE: RNA
<213> ORGANISM: Artificial
<220> FEATURE:
<223> OTHER INFORMATION: Aptamer
<220> FEATURE:
<221> NAME/KEY: misc_feature
<222> LOCATION: (18)..(18)
<223> OTHER INFORMATION: n is a, c, g, or u
```

<400> SEQUENCE: 79
gagacggucg gguccagncu guugaguagu guguggcuc                                40

<210> SEQ ID NO 80
<211> LENGTH: 75
<212> TYPE: DNA
<213> ORGANISM: Artificial
<220> FEATURE:
<223> OTHER INFORMATION: DFHO Parent Aptamer

<400> SEQUENCE: 80
tagggagacg caactgaatg gcgcgaagaa ggaggtctga ggaggtcact gcgccggcag          60
tggggcgtct ccctg                                                          75

<210> SEQ ID NO 81
<211> LENGTH: 113
<212> TYPE: DNA
<213> ORGANISM: Artificial
<220> FEATURE:
<223> OTHER INFORMATION: DFHO Aptamer

<400> SEQUENCE: 81
ggccggtgac gcaactgaat gaatcgagga aggaggtcgg aggaggtcac tgattctaca         60
ggctgcgtac tccagtgctg tgtgtatacg taactagtcg cgtcaccggc cgc               113

<210> SEQ ID NO 82
<211> LENGTH: 71
<212> TYPE: DNA
<213> ORGANISM: Artificial
<220> FEATURE:
<223> OTHER INFORMATION: DFHO aptamer

<400> SEQUENCE: 82
gggagacgca actgaatggc gcgaagaagg aggtctgagg aggtcactgc gccggcagtg         60
gggcgtctcc c                                                              71

<210> SEQ ID NO 83
<211> LENGTH: 95
<212> TYPE: DNA
<213> ORGANISM: Artificial
<220> FEATURE:
<223> OTHER INFORMATION: DFHO aptamer

<400> SEQUENCE: 83
gacgcaactg aatgaaattg ttaaggagac ggtcgggtcc aggtgcacaa atgtggcctg         60
ttgagtagcg tgtgggctcc gtaactagtc gcgtc                                    95

<210> SEQ ID NO 84
<211> LENGTH: 95
<212> TYPE: DNA
<213> ORGANISM: Artificial
<220> FEATURE:
<223> OTHER INFORMATION: DFHO aptamer

<400> SEQUENCE: 84
gacgcaactg aatgaaatgt tttcggagac ggtcgggtcc agtcccaacg atgttggctg         60
ttgagtagtg tgtgggctcc gtaactagtc gcgtc                                    95

UNITED STATES PATENT AND TRADEMARK OFFICE
CERTIFICATE OF CORRECTION

| | | |
|---|---|---|
| PATENT NO. | : 9,664,676 B2 | Page 1 of 1 |
| APPLICATION NO. | : 14/480130 | |
| DATED | : May 30, 2017 | |
| INVENTOR(S) | : Jaffrey et al. | |

It is certified that error appears in the above-identified patent and that said Letters Patent is hereby corrected as shown below:

In the Claims

In Claim 1, at Column 123, Line 35, delete "," immediately preceding the ".".

Signed and Sealed this
Thirtieth Day of October, 2018

Andrei Iancu
*Director of the United States Patent and Trademark Office*